(12) United States Patent
Gurnett-Bander et al.

(10) Patent No.: US 9,399,674 B2
(45) Date of Patent: Jul. 26, 2016

(54) **HUMAN ANTIBODIES TO *CLOSTRIDIUM DIFFICILE* TOXINS**

(71) Applicant: Regeneron Pharmaceuticals, Inc., Tarrytown, NY (US)

(72) Inventors: Anne Gurnett-Bander, Carmel, NY (US); Carlos Arrecubieta, New York, NY (US); Israel Lowy, Dobbs Ferry, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 13/782,444

(22) Filed: Mar. 1, 2013

(65) Prior Publication Data

US 2013/0230531 A1 Sep. 5, 2013

Related U.S. Application Data

(60) Provisional application No. 61/717,404, filed on Oct. 23, 2012, provisional application No. 61/608,255, filed on Mar. 8, 2012, provisional application No. 61/605,914, filed on Mar. 2, 2012.

(51) Int. Cl.
   *C07K 16/12* (2006.01)
   *A61K 39/40* (2006.01)
   *A61K 39/00* (2006.01)

(52) U.S. Cl.
   CPC ............. *C07K 16/1282* (2013.01); *A61K 39/40* (2013.01); *A61K 2039/505* (2013.01); *A61K 2039/507* (2013.01); *C07K 2317/21* (2013.01); *C07K 2317/31* (2013.01); *C07K 2317/34* (2013.01); *C07K 2317/565* (2013.01); *C07K 2317/76* (2013.01); *C07K 2317/92* (2013.01)

(58) Field of Classification Search
   CPC ..................... C07K 2039/34; C07K 2039/565; C07K 2039/72; C07K 2039/92; C07K 2039/31; C07K 16/1282; A61K 2039/505; A61K 2039/507; A61K 39/08; A61K 39/40
   See application file for complete search history.

(56) References Cited

U.S. PATENT DOCUMENTS

| | | | |
|---|---|---|---|
| 5,085,862 A | 2/1992 | Klein et al. | |
| 5,221,618 A | 6/1993 | Klein et al. | |
| 5,224,657 A | 7/1993 | Kuriyama et al. | |
| 5,332,583 A | 7/1994 | Klein et al. | |
| 5,358,868 A | 10/1994 | Klein et al. | |
| 5,433,945 A | 7/1995 | Klein et al. | |
| 6,596,541 B2 | 7/2003 | Murphy et al. | |
| 7,151,159 B2 | 12/2006 | Von Eichel-Streiber et al. | |
| 7,582,298 B2 | 9/2009 | Stevens et al. | |
| 7,625,559 B2 | 12/2009 | Ambrosino et al. | |
| 8,236,311 B2 | 8/2012 | Ambrosino et al. | |
| 8,257,709 B2 | 9/2012 | Ambrosino et al. | |
| 2004/0101920 A1 | 5/2004 | Radziejewski et al. | |
| 2004/0137601 A1 | 7/2004 | Von-Eichel-Streiber et al. | |
| 2005/0287150 A1 | 12/2005 | Ambrosino et al. | |
| 2007/0280945 A1 | 12/2007 | Stevens et al. | |
| 2009/0087478 A1 | 4/2009 | Hansen et al. | |
| 2010/0233181 A1 | 9/2010 | Ambrosino et al. | |
| 2010/0233182 A1 | 9/2010 | Ambrosino et al. | |
| 2010/0331527 A1 | 12/2010 | Davis et al. | |
| 2011/0020356 A1 | 1/2011 | Fang et al. | |
| 2011/0195454 A1 | 8/2011 | McWhirter et al. | |
| 2012/0121607 A1 | 5/2012 | Shone et al. | |
| 2012/0288508 A1 | 11/2012 | Ambrosino et al. | |

FOREIGN PATENT DOCUMENTS

| | | |
|---|---|---|
| EP | 1024826 B1 | 3/2005 |
| EP | 1568378 A1 | 8/2005 |
| EP | 2261253 A2 | 12/2010 |
| EP | 2305293 A2 | 4/2011 |
| EP | 2305303 A2 | 4/2011 |
| EP | 2270045 A1 | 5/2011 |
| EP | 1766093 B1 | 6/2011 |
| WO | WO 91/18293 | 11/1991 |
| WO | WO 2005/058353 | 6/2005 |
| WO | WO 2005/103081 | 12/2005 |
| WO | WO 2006/121422 | 11/2006 |
| WO | WO 2009/108652 | 9/2009 |
| WO | WO 2010/094970 | 8/2010 |
| WO | WO 2011/063346 | 5/2011 |
| WO | WO 2011/130650 | 10/2011 |

OTHER PUBLICATIONS

Skolnick et al. (Trends in Biotechnology 18: 34-39, 2000).*
Greenspan et al. (Nature Biotechnology 7: 936-937, 1999).*
Casadevall et al. (PNAS vol. 109 No. 31, pp. 12272-12273).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS, vol. 109 No. 31, pp. 12272-12273).*

(Continued)

*Primary Examiner* — Robert A Zeman
(74) *Attorney, Agent, or Firm* — Veronica Mallon; Brownstein Hyatt Farber Schreck, LLP; Cara L. Crowley-Weber

(57) ABSTRACT

The present invention provides fully human antibodies that bind to either toxin A or toxin B of *Clostridium difficile*, or to both toxin A and toxin B, compositions comprising the antibodies and methods of use. The antibodies of the invention are useful for neutralizing the toxins from *C. difficile*, thus providing a means of treating the disease and symptoms associated with a *C. difficile* infection, including the treatment of diarrhea, or pseudomembranous colitis caused by *C. difficile*. The antibodies may also prevent the severity and/or duration of the primary disease, or may prevent the number, duration, and/or the severity of recurrences, or relapses of the disease attributed to the presence of *C. difficile*. The antibodies of the invention may also be useful for diagnosis of an infection by *C. difficile*.

7 Claims, 5 Drawing Sheets

(56) References Cited

OTHER PUBLICATIONS

Al-Lazikani et al. (1997) "Standard Conformations for the Canonical Structures of Immunoglobulins" J. Mol. Biol. 273:927-948.
Alonso et al. (2012) "Epidemiology and Outcomes of *Clostridium difficile* Infections in Hematopoietic Stem Cell Transplant Recipients" Clin Inf. Dis. 54(8):1053-1063.
Altschul et al. (1990) "Basic Local Alignment Search Tool" J. Mol. Biol. 215:403-410.
Altschul et al. (1997) "Gapped BLAST and PSI-BLAST: a new generation of protein database search programs" Nucleic Acids Res. 25(17):3389-3402.
Anand et al. (1993) "*Clostridium difficile* Infection Associated with Antineoplastic Chemotherapy: A Review" Clin. Infect. Dis. 17:109-113.
Babcock et al. (2006) "Human Monoclonal Antibodies Directed against Toxins A and B Prevent *Clostridium difficile*-Induced Mortality in Hamsters" Infect. Immun. 74(11):6339-6347.
Bartlett et al. (1978) "Antibiotic-Associated Pseudomembranous Colitis Due to Toxin-Producing Clostridia" N. Engl. J. Med. 298(10):531-534.
Clabots et al. (1993) "Development of a Rapid and Efficient Restriction Endonuclease Analysis Typing System for *Clostridium difficile* and Correlation with Other Typing Systems" J. Clin. Microbiol. 31(7): 1870-1875.
Cohen et al., (2000) "Analysis of the Pathogenicity Locus in *Clostridium difficile* Strains" J. Infect. Dis. 181:659-663.
Corthier et al. (1991) "Protection against Experimental Pseudomembranous Colitis in Gnotobiotic Mice by Use of Monoclonal Antibodies against *Clostridium difficile* Toxin A" Infection and Immunity 59(3):1192-1195.
Coughlin et al. (1994) "Characterization of Six Murine Monoclonal Antibodies Specific for Toxin B of *Clostridium difficile*" Hybridoma; 13(2):147-152.
Davies et al. (2011) "Super toxins from a super bug: structure and function of *Clostridium difficile* toxins" Biochem. J. 436:517-526.
Demarest et al. (2010) "Neutralization of *Clostridium difficile* toxin A using antibody combinations" MABS; 2(2):190-198.
Dworczynski et al. (1991) "Antibiotic resistance of *Clostridium difficile* isolates" 65:149-153.
Ehring (1999) "Hydrogen Exchange/Electrospray Ionization Mass Spectrometry Studies of Structural Features of Proteins and Protein/Protein Interactions" Analytical Biochemistry 267:252-259.
Engen and Smith (2001) "A powerful new approach . . . " Anal. Chem. 256A-265A.
Fawley and Wilcox (2002) "Pulsed-Field Gel Electrophoresis Can Yield DNA Fingerprints of Degradation-Susceptible *Clostridium difficile* Strains" J. Clin. Microbiol. 40(9):3546-3547.
Fekety and Shah (1993) "Diagnosis and Treatment of *Clostridium difficile* Colitis" JAMA, 269(1):71-75.
Fekety (1997) "Guidelines for the Diagnosis and Management of *Clostridium difficile*-Associated Diarrhea and Colitis" Am. J. Gastroenterology, 92(5):739-750.
Genth et al. (2000) "New Method to Generate Enzymatically Deficient *Clostridium difficile* Toxin B as an Antigen for Immunization" Infection and Immunity 68(3):1094-1101.
Giannasca et al. (1999) "Serum Antitoxin Antibodies Mediate Systemic and Mucosal Protection from *Clostridium difficile* Disease in Hamsters" Infection and Immunity 67(2):527-538.
Gonçalves et al. (2004) "Prevalence and Characterization of a Binary Toxin (Actin-Specific ADP-Ribosyltransferase) from *Clostridium difficile*" J. Clin. Microbiol. 42(5):1933-1939.
Gonnet et al. (1992) "Exhaustive Matching of the Entire Protein Sequence Database" Science 256:1443-1445.
Hochleitner et al. (2000) "Characterization of a discontinuous epitope of the human immunodeficiency virus (HIV) core protein p24 by epitope excision and differential chemical modification followed by mass spectrometric peptide mapping analysis" Protein Science 9:487-496.
Hussack et al. (2011) "Neutralization of *Clostridium difficile* Toxin A with Single-domain Antibodies Targeting the Cell Receptor Binding Domain" J. Biological Chemistry 286(11):8961-8976.
International Search Report with respect to PCT/US2013/028630, mailed Aug. 2, 2013.
Johnson et al. (1990) "Nosocomial *Clostridium difficile* colonization and disease" The Lancet 336:97-100.
Junghans et al. (1990) "Anti-Tac-H, a Humanized Antibody to the Interleukin 2 Receptor with New Features for Immunotherapy in Malignant and Immune Disorders" Cancer Research 50:1495-1502.
Karlström et al. (1998) "A Prospective Nationwide Study of *Clostridium difficile*-Associated Diarrhea in Sweden" Clin. Infect. Dis. 26:141-145.
Kelly and Lamont (1998) "*Clostridium difficile* Infection" Annu. Rev. Med. 49:375-390.
Kelly and Lamont (2008) "*Clostridium difficile*—More Difficult Than Ever" N. Engl. J. Med. 359:1932-1940.
Kink and Williams (1998) "Antibodies to Recombinant *Clostridium difficile* Toxins A and B are an Effective Treatment and Prevent Relapse of *C. difficile*—Associated Disease in a Hamster Model of Infection" Infection and Immunity 66(5):2018-2025.
Kuehne et al. (2010) "The role of toxin A and toxin B in *Clostridium difficile* infection" Nature 467:711-713.
Kufer et al. ( 2004) "A revival of bispecific antibodies" Trends Biotechnol. 22(5):238-244.
Kyne et al. (2000) "Asymptomatic Carriage of *Clostridium difficile* and Serum Levels of IgG Antibody Against Toxin A" N. Engl. J. Med. 342(6), 390-397.
Kyne et al. (2001) "*Clostridium difficile*" Gastroenterology Clin. N. Am. 30(3):753-777.
Kyne et al. (2001) "Association between antibody response to toxin A and protection against recurrent *Clostridium difficile* diarrhoea" Lancet 357:189-193.
Langer (1990) "New Methods of Drug Delivery" Science 249:1527-1533.
Leav et al. (2010) "Serum anti-toxin B antibody correlates with protection from recurrent *Clostridium difficile* infection (CDI)" Vaccine 28:965-969.
Loo et al. (2005) "A Predominantly Clonal Multi-Institutional Outbreak of *Clostridium difficile*-Associated Diarrhea with High Morbidity and Mortality" N. Engl. J. Med. 353(23):2442-2449.
Lowe et al. (2006) "Proton Pump Inhibitors and Hospitalization for *Clostridium difficile*-Associated Disease: A Population-Based Study" Clin. Infect. Dis. 43:1272-1276.
Lowy et al. (2010) "Treatment with Monoclonal Antibodies against *Clostridium difficile* Toxins" N. Engl. J. Med. 362(3):197-205.
Lyras et al. (2009) "Toxin B is essential for virulence of *Clostridium difficile*" Nature 458:1176-1179.
Marozsan et al. (2012) "Protection Against *Clostridium difficile* Infection with Broadly Neutralizing Antitoxin Monoclonal Antibodies" JID 206:706-713.
Marozsan et al. (2011) "Humanized mAbs Against *Clostridium difficile* Toxins A and B Demonstrate Potent Neutralizing Activity In Vitro and Durable Protection from Lethal Disease In Vivo" Abstracts of the Interscience Conference of Antimicrobial Agents of Chemotherapy 51:B-1188.
Marozsan et al. (2010) "Mechanistic Studies of Novel Monoclonal Antibodies against *Clostridium difficile* Toxins" Abstracts of the Interscience Conference of Antimicrobial Agents of Chemotherapy 50:F2-881.
Martin et al. (1989) "Modeling antibody hypervariable loops: A combined algorithm" Proc. Natl. Acad. Sci. USA 86:9268-9272.
McDonald, et al. (2005) "An Epidemic, Toxin Gene—Variant Strain of *Clostridium difficile*" N. Engl. J. Med. 353(23):2433-2441.
McDonald et al. (2006) "*Clostridium difficile* Infection in Patients Discharged from US Short-stay Hospitals, 1996-2003" Emerg. Infect. Dis. 12(3):409-415.
Padlan et al. (1995) "Identification of specificity-determining residues in antibodies" FASEB J. 9:133-139.
Pearson (1994) "Using the FASTA Program to Search Protein and DNA Sequence Databases" Methods in Molecular Biology 24:307-331.

(56) References Cited

OTHER PUBLICATIONS

Petrella et al. (2012) "Decreased Cure and Increased Recurrence Rates for *Clostridium difficile* Infection Caused by the Epidemic *C. difficile* BI Strain" Clinical Infectious Diseases 55(3):351-357.

Powell et al. (1998) "Compendium of Excipients for Parenteral Formulations" PDA Journal Pharm. Science & Tech. 52(5):238-311.

Reddy et al. (2000) "Elimination of Fc Receptor-Dependent Effector Functions of a Modified IgG4 Monoclonal Antibody to Human CD4" J. Immunol. 164:1925-1933.

Redelings et al. (2004) "Increase in *Clostridium difficile*-related Mortality Rates, United States 1999-2004" Emerging Infection Diseases 13(9):1417-1419.

Reineke (2004) "Antibody Epitope Mapping Using Arrays of Synthetic Peptides" Methods in Molecular Biology 248: 443-463.

Relyveld and Ben-Efraim (1983) "Preparation of Vaccines by the Action of Glutaraldehyde on Toxins, Bacteria, Viruses, Allergens, and Cells" Methods of Enzymology 93:24-60.

Rothman et al. (1988) "Immunochemical and Structural Similarities in Toxin A and Toxin B of *Clostridium difficile* Shown by Binding to Monoclonal Antibodies" Toxicon 26(6), 583-597.

Shields et al. (2002) "Lack of Fucose on Human IgG1 *N*-Linked Oligosaccharide Improves Binding to Human FcγRIII and Antibody-dependent Cellular Toxicity" J. of Bio. Chem. 277(30): 26733-26740.

Thibault et al. (1991) "Risk Factors for the Development of *Clostridium difficile*-Associated Diarrhea During a Hospital Outbreak" Infect. Control Hosp. Epidemiol 12(6):345-348.

Tiller (2011) "Single B cell antibody technologies" New Biotechnology 28(5):453-457.

Tutt et al. (1991) "Trispecific F(ab')$_3$ Derivatives that Use Cooperative Signaling Via the TCR/CD3 Complex and CD2 to Activate and Redirect Resting Cytotoxic T Cells" J. Immuno. 147(1):60-69.

Vajdos et al.(2002) "Comprehensive Functional Maps of the Antigen-binding Site of an Anti-ErbB2 Antibody Obtained with Shotgun Scanning Mutagenesis" J. Mol. Biol. 320:415-428.

Warny et al. (1994) "Human Antibody Response to *Clostridium difficile* Toxin A in Relation to Clinical Course of Infection" Infection and Immunity 62(2):384-389.

Warny et al. (2005) "Toxin production by an emerging strain of *Clostridium difficile* associated with outbreaks of severe disease in North America and Europe" Lancet 366:1079-1084.

Wu and Wu (1987) "Receptor-mediated in Vitro Gene Transformation by a Soluble DNA Carrier System" J. Biological Chemistry 262(10):4429-4432.

Yearsley et al. (2006) "Proton pump inhibitor therapy is a risk factor for *Clostridium difficile*-associated diarrhoea" Aliment. Pharmacol. Ther. 24:613-619.

\* cited by examiner

HUMAN ANTIBODIES TO *CLOSTRIDIUM DIFFICILE* TOXINS

CROSS-REFERENCE TO RELATED APPLICATIONS

This application claims the benefit under 35 U.S.C. §119(e) of U.S. provisional application Nos. 61/605,914, filed Mar. 2, 2012; 61/608,255, filed Mar. 8, 2012, and 61/717,404, filed Oct. 23, 2012, all of which are herein specifically incorporated by reference in their entirety.

FIELD OF THE INVENTION

The present invention is related to human antibodies and antigen-binding fragments of human antibodies that specifically bind to toxin A and/or toxin B of *Clostridium difficile*, compositions comprising these antibodies and therapeutic methods of using these antibodies.

STATEMENT OF RELATED ART

*Clostridium difficile* (*C. difficile*) is a gram positive, anaerobic, spore forming bacterium, which is a major cause of hospital-acquired gastrointestinal disease in humans, resulting in symptoms ranging from mild to severe diarrhea and colitis. It is believed that treatment with broad spectrum antibiotics, such as ampicillin, amoxicillin, cephalosporins, fluoroquinolones and clindamycin, may result in disruption of normal intestinal flora, which then allows for colonization of the gut with *C. difficile* (Kelly and Lamont, (1998), Ann. Rev. Med. 49:375-90). Treatment of *C. difficile* infections may involve stopping or modifying the use of broad spectrum antibiotics and requires commencing treatment with specific anticlostridial antibiotics, such as, for example, vancomycin, metronidazole, or fidaxomicin.

The diarrhea and inflammation observed in patients suffering from a *C. difficile* infection is believed to be due to the production of two toxins by the bacterium, enterotoxin (toxin A) and cytotoxin (toxin B). *C. difficile* toxins A and B are high molecular weight glucosyltransferases that inhibit members of the Rho family of GTPases. Toxin A has a molecular weight of 308 kDa and Toxin B has a molecular weight of 270 kDa. Both toxin A and toxin B deactivate small GTPases such as Rho, Rac and Cdc42 by glucosylation of a threonine residue. Inhibition of these GTPases causes the shutdown of signal transduction cascades leading to: depolymerization of the cytoskeleton, gene transcription of certain stress-activated protein kinases, a drop in synthesis of phosphatidylinositol bisphosphate, and possibly even the loss of cell polarity. Loss of cytoskeletal structure results in cell rounding, and this loss of structure may account for the host reactions to *C. difficile*. Toxin B is at least 1,000 times more cytotoxic than toxin A in cell rounding assays.

*C. difficile* toxins A and B are 63% homologous in amino acid content and have a similar three-dimensional structure (Davies, A H, (2011), Biochem. J., 436:517-526). The C-terminal third of each toxin is made up of sequences called clostridial repetitive oligopeptides (CROPs), which are highly antigenic. The remaining N-terminal two-thirds of toxins A and B are less similar to each other with respect to sequence homology; however, it is this portion of each protein that contains the glucosyltransferase activity.

Support for the role of toxin A and/or toxin B in the onset of diarrhea and inflammation following infection with *C. difficile* stems from observations in animal models. For example, oral dosing with the toxins mimics the disease (Kelly and Lamont, (1998), Ann. Rev. Med. 49:375-90). Mutant strains lacking toxin A and B have reduced or altered virulence (Lyras D, O'Connor J R, Howarth P K et al., Nature 458(7242), 1176-1179 (2009); Kuehne S A, Cartman S T, Heap J T, Kelly M L, Cockayne A, Minton N P, Nature 15, 467(7316), 711-713 (2010).). Furthermore, administration of polyclonal antibodies to the toxins has been shown to protect hamsters from the disease (Gianasca et al., (1999), Infect. Immun. 66(2): 527-38). In the clinic, studies have shown that there is a correlation between the presence of anti-toxin A or anti-toxin B antibodies and protection against *C. difficile* associated diarrhea and disease recurrence (Warny, M. et al., (1994), Inf. Immun. 62(2): 384-389; Kyne, L. et al. (2001), Lancet 357:189-193; Leav, B. A., (2010), Vaccine 28(4):965-969). Development of anti-toxin antibody is associated with asymptomatic carriers (Kyne, L. et al. (2000), NEJM 342(6), 390-397). Furthermore, a clinical trial using a combination of *C. difficile* anti-toxin A and anti-toxin B antibodies in conjunction with metronidazole or vancomycin resulted in a reduction in the rate of recurrent infection with *C. difficile* (Lowy, I. et al., (2010), NEJM 362(3):197-205).

Monoclonal antibodies to *C. difficile* toxin A have been described by Wilkins, et al. in U.S. Pat. No. 4,879,218. In addition, Rothman et al. described a murine monoclonal antibody that cross-reacts with *C. difficile* toxins A and B. Furthermore, Coughlin et al. described a monoclonal antibody specific for *C. difficile* toxin B, which did not cross-react with toxin A. Other antibodies to the *C. difficile* toxins have been described (See, for example, U.S. Pat. No. 7,151,159; U.S. Pat. No. 7,625,559; U.S. Pat. No. 8,236,311; U.S. Pat. No. 8,257,709; US publication Nos. 2009/0087478; US2010/0233182; US2010/0233181; US2012/0288508; US2012/012160; US2011/0020356; US2012/0121607; EP1766093B1; EP1024826B1; EP1568378A1; EP2305303A2; EP2305293A2; EP2405940A1; EP2261253A2; WO2006/121422; WO2011/130650; WO2010/094970; WO2009/108652; WO2011/063346 and WO2005/058353).

BRIEF SUMMARY OF THE INVENTION

The invention provides fully human monoclonal antibodies (mAbs) and antigen-binding fragments thereof that bind specifically to either toxin A or to toxin B produced by *Clostridium difficile* (*C. difficile*), or which bind to both toxin A and toxin B of *C. difficile* (ie. human monoclonal antibodies that cross react with both toxin A and toxin B). Such antibodies may be useful to neutralize the toxicity associated with either toxin A or toxin B, or both, and as such, may act to lessen the severity of the primary *C. difficile*-associated condition or disease, or reduce the number, the duration, or the severity of disease recurrence, or ameliorate at least one symptom associated with the *C. difficile*-associated condition or disease. Such antibodies may be used alone or in conjunction with a second agent useful for treating a *C. difficile*-associated condition or disease. In certain embodiments, the antibodies specific for toxin A, toxin B, or both, may be given therapeutically in conjunction with a second agent to lessen the severity of the primary *C. difficile*-associated condition or disease, or to reduce the number, the duration, or the severity of disease recurrence, or ameliorate at least one symptom associated with the *C. difficile*-associated condition or disease. In certain embodiments, the antibodies may be used prophylactically as stand-alone therapy to protect patients who are at risk for developing a *C. difficile*-associated condition or disease. For example, certain patient populations may be at risk for developing a *C. difficile* condition or disease, including elderly patients, or patients who have chronic and/or concomitant underlying medical conditions that may predispose them to a *C. difficile* infection. Other at-risk patient populations include patients who are hospitalized for extended periods of time and who are taking broad spectrum antibiotics that may disrupt the normal intestinal flora and which may predispose them to infection with *C. difficile*. More recent data suggest that patients taking proton pump inhibitors (PPIs) are at risk for developing *C. difficile*-associated diarrhea (Yearsley, K. et al. (2006), Aliment. Pharmacol. Ther. 24(4):613-619; Lowe, D O, et al. Clin. Infect. Dis. (2006), 43(10):1272-1276). Other patient populations at risk for developing a *C. difficile* infection include patients who are undergoing any type of immunosuppressive therapy, such as, but not limited to an anti-cancer drug, general radiotherapy to treat certain cancers, or a drug or drug regimen to prevent tissue or organ graft rejection following a transplant. Patients who receive a hematopoietic stem cell transplant (HSCT) may be at particularly high risk for developing a *C. difficile* infection because of long hospitalizations, receipt of broad-spectrum antibiotics and chemotherapy-related disruption of enteric mucosal barriers (Thibault, A. et al., ((1991), Infect. Control Hosp. Epidemiol. 12:345-8; Anand, A. et al. (1993), Clin. Infect. Dis. 17:109-13). Patients who receive a solid organ transplant may also be at risk for developing a *C. difficile* infection. Included in the at-risk population are patients suffering from an autoimmune disease, or patients on dialysis. More recent studies demonstrated that patients who received either an autologous or allogeneic HSCT were not only at greater risk for developing a *C. difficile* infection, but these patients were also at higher risk of developing gastrointestinal graft versus host disease (GI-GVHD) (Alonso, C. D., et. al. (2012), Clin Inf. Dis, 54:1053-1063). While this study clearly demonstrated that *C. difficile* infections were a frequent early complication following HSCT, the exact relationship or interplay between *C. difficile* infections (CD) and GVHD involving the GI tract needs to be explored in greater detail. Any of these patient populations may benefit from treatment with the antibodies of the invention, when given alone or in conjunction with a second agent, such as metronidazole, vancomycin or fidaxomicin.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., (2000), J. Immunol. 164:1925-1933).

Accordingly, in a first aspect, the invention provides an isolated fully human monoclonal antibody or antigen-binding fragment thereof that binds to either toxin A, or to toxin B, or that binds to or cross reacts with both toxin A and toxin B of *Clostridium difficile*, wherein:

a) the isolated antibody or antigen-binding fragment thereof that specifically binds toxin A of *Clostridium difficile* comprises the three heavy chain complementarity determining regions (HCDR1, HCDR2 and HCDR3) contained within a heavy chain variable region (HCVR) amino acid sequence selected from the group consisting of SEQ ID NOs: 2, 98, 114, 130, 146 and 162; and the three light chain complementarity determining regions (LCDR1, LCDR2 and LCDR3) contained within a light chain variable region (LCVR) amino acid sequence selected from the group consisting of SEQ ID NOs: 10, 106, 122, 138, 154 and 170;

b) the isolated antibody or antigen-binding fragment thereof that specifically binds toxin B of *Clostridium difficile* comprises the HCDR1, HCDR2 and HCDR3 contained within a HCVR amino acid sequence selected from the group consisting of SEQ ID NOs: 178, 194, 210, 226, 242, 258, 274, 290, 306, 322, 338 and 354; and the LCDR1, LCDR2 and LCDR3 contained within a LCVR amino acid sequence selected from the group consisting of SEQ ID NOs: 186, 202, 218, 234, 250, 266, 282, 298, 314, 330, 346 and 362; and c) the isolated antibody or antigen-binding fragment that binds to, or cross reacts with both toxin A and toxin B of *Clostridium difficile* comprises the HCDR1, HCDR2 and HCDR3 contained within a HCVR amino acid sequence selected from the group consisting of SEQ ID NOs: 18, 34, 50, 66 and 82; and the LCDR1, LCDR2 and LCDR3 contained within a LCVR amino acid sequence selected from the group consisting of SEQ ID NOs: 26, 42, 58, 74 and 90.

In one embodiment, the human monoclonal antibody that binds to/cross reacts with both toxin A and toxin B of *C. difficile* specifically binds to the carboxy terminal receptor binding domain (CBD) of both toxin A (CBD-A: SEQ ID NO: 375) and toxin B (CBD-B: SEQ ID NO: 376) of *C. difficile*.

In one embodiment, the isolated human antibody or antigen-binding fragment thereof which binds to/cross reacts with both toxin A and toxin B of *C. difficile* binds to toxin A and toxin B with a $K_D$ equal to or less than $10^{-7}$ M.

In one embodiment, the isolated human antibody or antigen-binding fragment thereof which binds to/cross reacts with both toxin A and toxin B of *C. difficile* comprises the three heavy chain CDRs (HCDR1, HCDR2 and HCDR3) contained within any one of the heavy chain variable region (HCVR) sequences selected from the group consisting of SEQ ID NOs: 18, 34, 50, 66 and 82; and the three light chain CDRs (LCDR1, LCDR2 and LCDR3) contained within any one of the light chain variable region (LCVR) sequences selected from the group consisting of SEQ ID NOs: 26, 42, 58, 74 and 90. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., (1997), *J. Mol. Biol.* 273:927-948; and Martin et al., (1989), *Proc. Natl. Acad. Sci. USA* 86:9268-9272. Public databases are also available for identifying CDR sequences within an antibody.

In one embodiment, the isolated human antibody or antigen-binding fragment thereof which binds to/cross reacts with both toxin A and toxin B of *C. difficile* comprises a HCVR having an amino acid sequence selected from the group consisting of SEQ ID NOs: 18, 34, 50, 66 and 82.

In one embodiment, the isolated human antibody or antigen-binding fragment thereof which binds to/cross reacts with both toxin A and toxin B of *C. difficile* comprises a LCVR having an amino acid sequence selected from the group consisting of SEQ ID NOs: 26, 42, 58, 74 and 90.

In one embodiment, the isolated human antibody or antigen-binding fragment thereof which binds to/cross reacts with both toxin A and toxin B of *C. difficile* comprises (a) a HCVR having an amino acid sequence selected from the group consisting of SEQ ID NOs: 18, 34, 50, 66 and 82; and (b) a LCVR having an amino acid sequence selected from the group consisting of SEQ ID NO: 26, 42, 58, 74 and 90.

In one embodiment, the isolated human antibody or antigen-binding fragment thereof which binds to/cross reacts with both toxin A and toxin B of *C. difficile* comprises:
- (a) a HCDR1 domain having an amino acid sequence selected from the group consisting of SEQ ID NOs: 20, 36, 52, 68, and 84;
- (b) a HCDR2 domain having an amino acid sequence selected from the group consisting of SEQ ID NOs: 22, 38, 54, 70 and 86;
- (c) a HCDR3 domain having an amino acid sequence selected from the group consisting of SEQ ID NOs: 24, 40, 56, 72 and 88;
- (d) a LCDR1 domain having an amino acid sequence selected from the group consisting of SEQ ID NOs: 28, 44, 60, 76 and 92;
- (f) a LCDR2 domain having an amino acid sequence selected from the group consisting of SEQ ID NOs: 30, 46, 62, 78 and 94; and
- (g) a LCDR3 domain having an amino acid sequence selected from the group consisting of SEQ ID NOs: 32, 48, 64, 80 and 96.

In one embodiment, the human antibody or antigen binding fragment thereof that binds to/cross reacts with both toxin A and toxin B of *C. difficile* comprises the HCDR1, HCDR2 and HCDR3 amino acid sequences of SEQ ID NO: 20, 22 and 24, respectively and LCDR1, LCDR2 and LCDR3 amino acid sequences of SEQ ID NO: 28, 30 and 32, respectively.

In one embodiment, the human antibody or antigen binding fragment thereof that binds to/cross reacts with both toxin A and toxin B of *C. difficile* comprises the HCDR1, HCDR2 and HCDR3 amino acid sequences of SEQ ID NO: 36, 38 and 40, respectively and LCDR1, LCDR2 and LCDR3 amino acid sequences of SEQ ID NO: 44, 46 and 48, respectively.

In one embodiment, the isolated human antibody or antigen-binding fragment thereof which binds to/cross reacts with both toxin A and toxin B of *C. difficile* comprises a HCVR/LCVR amino acid sequence pair selected from the group consisting of SEQ ID NOs: 18/26, 34/42, 50/58, 66/74 and 82/90.

In one embodiment, the isolated human antibody or antigen-binding fragment thereof which binds to/cross reacts with both toxin A and toxin B of *C. difficile* comprises the HCVR/LCVR amino acid sequence pair of SEQ ID NOs: 18/26 and 34/42.

In one embodiment, the isolated human antibody or antigen-binding fragment thereof that binds to/cross reacts with both toxin A and toxin B binds to:
- an epitope within the carboxy terminal receptor binding domain of both toxin A and toxin B of *Clostridium difficile*, wherein the antibody comprises a HCVR/LCVR amino acid sequence pair selected from the group consisting of SEQ ID NOs: 18/26 and 34/42; or
- an epitope outside of the carboxy terminal receptor binding domain of both toxin A and toxin B of *Clostridium difficile*, wherein the antibody comprises a HCVR/LCVR amino acid sequence pair selected from the group consisting of SEQ ID NOs: 50/58, 66/74 and 82/90.

In one embodiment, the invention provides a fully human monoclonal antibody or antigen-binding fragment thereof that binds to/cross reacts with both toxin A and toxin B of *C. difficile*, wherein the antibody or fragment thereof exhibits one or more of the following characteristics: (i) comprises a HCVR having an amino acid sequence selected from the group consisting of SEQ ID NO: 18, 34, 50, 66 and 82, or a substantially similar sequence thereof having at least 90%, at least 95%, at least 98% or at least 99% sequence identity; (ii) comprises a LCVR having an amino acid sequence selected from the group consisting of SEQ ID NO: 26, 42, 58, 74 and 90, or a substantially similar sequence thereof having at least 90%, at least 95%, at least 98% or at least 99% sequence identity; (iii) comprises a HCDR3 domain having an amino acid sequence selected from the group consisting of SEQ ID NO: 24, 40, 56, 72 and 88, or a substantially similar sequence thereof having at least 90%, at least 95%, at least 98% or at least 99% sequence identity; and a LCDR3 domain having an amino acid sequence selected from the group consisting of SEQ ID NO: 32, 48, 64, 80 and 96, or a substantially similar sequence thereof having at least 90%, at least 95%, at least 98% or at least 99% sequence identity; (iv) comprises a HCDR1 domain having an amino acid sequence selected from the group consisting of SEQ ID NO: 20, 36, 52, 68 and 84, or a substantially similar sequence thereof having at least 90%, at least 95%, at least 98% or at least 99% sequence identity; a HCDR2 domain having an amino acid sequence selected from the group consisting of SEQ ID NO: 22, 38, 54, 70 and 86, or a substantially similar sequence thereof having at least 90%, at least 95%, at least 98% or at least 99% sequence identity; a LCDR1 domain having an amino acid sequence selected from the group consisting of SEQ ID NO: 28, 44, 60, 76 and 92, or a substantially similar sequence thereof having at least 90%, at least 95%, at least 98% or at least 99% sequence identity; and a LCDR2 domain having an amino acid sequence selected from the group consisting of SEQ ID NO: 30, 46, 62, 78 and 94, or a substantially similar sequence thereof having at least 90%, at least 95%, at least 98% or at least 99% sequence identity; (v) binds to toxin A and to toxin B with a $K_D$ equal to or less than $10^{-9}$M.

In one embodiment, the fully human monoclonal antibody or antigen binding fragment thereof that binds to/cross reacts with both toxin A and toxin B of *C. difficile* comprises a HCDR1 sequence comprising the formula $X^1$-$X^2$-$X^3$-$X^4$-$X^5$-$X^6$-$X^7$-$X^8$ (SEQ ID NO: 381), wherein $X^1$ is Gly, $X^2$ is Phe, Val, or Ile, $X^3$ is Thr, Ala, or Ser, $X^4$ is Phe or Leu, $X^5$ is Ser, Arg, or Asn, $X^6$ is Gly, Thr, Asp, or Ser, $X^7$ is His, or Tyr, and $X^8$ is Gly, or Glu; a HCDR2 sequence comprising the formula $X^1$-$X^2$-$X^3$-$X^4$-$X^5$-$X^6$-$X^7$-$X^8$ (SEQ ID NO: 382), wherein $X^1$ is Ile, $X^2$ is Leu, Ser, or Asp, $X^3$ is Tyr, Phe, or Ser, $X^4$ is Asp, or Ser, $X^5$ is Gly, $X^6$ is Ser, Gly, Asp, or Thr, $X^7$ is Ser, His, or Ile, and $X^8$ is Glu, Gln, or Ile; a HCDR3 sequence comprising the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$ (SEQ ID NO: 383), wherein $X^1$ is Ala, or Val, $X^2$ is Lys, or Arg, $X^3$ is Gly, or Glu, $X^4$ is Ser, or Arg, $X^5$ is Ile, Asp, or Tyr, $X^6$ is Leu, Ser, or Asp, $X^7$ is Asn, Ser, Gln, or His, $X^8$ is Arg, Tyr, or Ser, $X^9$ is Pro, or Gly, $X^{10}$ is Phe, or Tyr, $X^{11}$ is Asp, Gly, or Tyr, $X^{12}$ is Tyr, $X^{13}$ is Phe, Leu, or absent, $X^{14}$ is Gly, or absent, $X^{15}$ is Met, or absent, $X^{16}$ is Asp, or absent, $X^{17}$ is Val, or absent; a LCDR1 sequence comprising the formula $X^1$-$X^2$-$X^3$-$X^4$-$X^5$-$X^6$-$X^7$-$X^8$-$X^9$-$X^{10}$-$X^{11}$-$X^{12}$ (SEQ ID NO: 384), wherein $X^1$ is Gln, $X^2$ is Ser, or Glu, $X^3$ is Ile, Val, or Thr, $X^4$ is Leu, or Asp, $X^5$ is Phe, Lys, or Asn, and $X^6$ is Ser, or Trp, $X^7$ is Ser, or absent, $X^8$ is Asn, Asp, or absent, $X^9$ is Asn, or absent, $X^{10}$ is Lys, or absent, $X^{11}$ Ile, Asn, or absent, $X^{12}$ is Tyr, or absent; a LCDR2 sequence comprising the formula $X^1$-$X^2$-$X^3$ (SEQ ID NO: 385), wherein $X^1$ is Trp, Lys, or Arg, $X^2$ is Ala or Thr, and $X^3$ is Ser; and a LCDR3 sequence comprising the formula $X^1$-$X^2$-$X^3$-$X^4$-$X^5$-$X^6$-$X^7$-$X^8$, $X^9$ (SEQ ID NO: 386), wherein $X^1$ is Gln or His, $X^2$ is Gln, or Glu, $X^3$ is Tyr, $X^4$ is Tyr, or Asn, $X^5$ is Thr, or Ser, $X^6$ is Leu, Ala, or Tyr, $X^7$ is Pro, Phe, or Ser, $X^8$ is Leu, Phe, or Arg and $X^9$ is Thr, or Ala.

In one embodiment, the invention provides an isolated human monoclonal antibody or antigen-binding fragment thereof that binds specifically to toxin A of *Clostridium difficile*, wherein the antibody comprises the three heavy chain CDRs (HCDR1, HCDR2 and HCDR3) contained within any one of the HCVR amino acid sequences selected from the group consisting of SEQ ID NOs: 2, 98, 114, 130, 146 and 162; and the three light chain CDRs (LCDR1, LCDR2 and LCDR3) contained within any one of the LCVR amino acid sequences selected from the group consisting of SEQ ID NOs: 10, 106, 122, 138, 154 and 170.

In one embodiment, the isolated human antibody or antigen-binding fragment thereof that binds specifically to toxin A of *Clostridium difficile*, comprises a HCVR having an amino acid sequence selected from the group consisting of SEQ ID NOs: 2, 98, 114, 130, 146 and 162.

In one embodiment, the isolated human antibody or antigen-binding fragment thereof that binds specifically to toxin A of *Clostridium difficile*, comprises a LCVR having an amino acid sequence selected from the group consisting of SEQ ID NOs: 10, 106, 122, 138, 154 and 170.

In one embodiment, the isolated human antibody or antigen-binding fragment thereof that binds specifically to toxin A of *Clostridium difficile*, comprises (a) a HCVR having an amino acid sequence selected from the group consisting of SEQ ID NOs: 2, 98, 114, 130, 146 and 162; and (b) a LCVR having an amino acid sequence selected from the group consisting of SEQ ID NO: 10, 106, 122, 138, 154 and 170.

In one embodiment, the isolated human antibody or antigen-binding fragment thereof that binds specifically to toxin A of *Clostridium difficile*, comprises:

(a) a HCDR1 domain having an amino acid sequence selected from the group consisting of SEQ ID NOs: 4, 100, 116, 132, 148 and 164;

(b) a HCDR2 domain having an amino acid sequence selected from the group consisting of SEQ ID NOs: 6, 102, 118, 134, 150 and 166;

(c) a HCDR3 domain having an amino acid sequence selected from the group consisting of SEQ ID NOs: 8, 104, 120, 136, 152 and 168;

(d) a LCDR1 domain having an amino acid sequence selected from the group consisting of SEQ ID NOs: 12, 108, 124, 140, 156, and 172;

(e) a LCDR2 domain having an amino acid sequence selected from the group consisting of SEQ ID NOs: 14, 110, 126, 142, 158 and 174; and (f) a LCDR3 domain having an amino acid sequence selected from the group consisting of SEQ ID NOs: 16, 112, 128, 144, 160 and 176.

In one embodiment, the isolated human antibody or antigen-binding fragment thereof that binds specifically to toxin A of *Clostridium difficile*, comprises the HCDR1, HCDR2 and HCDR3 amino acid sequences of SEQ ID NO: 148, 150 and 152, respectively and LCDR1, LCDR2 and LCDR3 amino acid sequences of SEQ ID NO: 156, 158 and 160, respectively.

In one embodiment, the isolated human antibody or antigen-binding fragment thereof that binds specifically to toxin A of *Clostridium difficile*, comprises a HCVR/LCVR amino acid sequence pair selected from the group consisting of SEQ ID NOs: 2/10, 98/106, 114/122, 130/138, 146/154 and 162/170.

In one embodiment, the isolated human antibody or antigen-binding fragment thereof that binds specifically to toxin A of *Clostridium difficile*, comprises the HCVR/LCVR amino acid sequence pair of SEQ ID NOs: 146/154.

In one embodiment, the isolated human antibody or antigen-binding fragment thereof that binds specifically to toxin A of *Clostridium difficile* binds to:

an epitope within the carboxy terminal receptor binding domain of toxin A of *Clostridium difficile*, wherein the antibody comprises a HCVR/LCVR amino acid sequence pair selected from the group consisting of SEQ ID NOs: 2/10, 98/106, 130/138, 146/154 and 162/170; or an epitope outside of the carboxy terminal receptor binding domain of toxin A of *Clostridium difficile*, wherein the antibody comprises a HCVR/LCVR amino acid sequence pair of SEQ ID NOs: 114/122.

In one embodiment, the invention provides a fully human monoclonal antibody or antigen-binding fragment thereof that binds specifically to toxin A of *C. difficile*, wherein the antibody or fragment thereof exhibits one or more of the following characteristics: (i) comprises a HCVR having an amino acid sequence selected from the group consisting of SEQ ID NO: 2, 98, 114, 130, 146 and 162, or a substantially similar sequence thereof having at least 90%, at least 95%, at least 98% or at least 99% sequence identity; (ii) comprises a LCVR having an amino acid sequence selected from the group consisting of SEQ ID NO: 10, 106, 122, 138, 154 and 170, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 104, 120, 136, 152 and 168, or a substantially similar sequence thereof having at least 90%, at least 95%, at least 98% or at least 99% sequence identity; and a LCDR3 domain having an amino acid sequence selected from the group consisting of SEQ ID NO: 16, 112, 128, 144, 160 and 176, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 100, 116, 132, 148 and 164, or a substantially similar sequence thereof having at least 90%, at least 95%, at least 98% or at least 99% sequence identity; a HCDR2 domain having an amino acid sequence selected from the group consisting of SEQ ID NO: 6, 102, 118, 134, 150 and 166, or a substantially similar sequence thereof having at least 90%, at least 95%, at least 98% or at least 99% sequence identity; a LCDR1 domain having an amino acid sequence selected from the group consisting of SEQ ID NO: 12, 108, 124, 140, 156 and 172, or a substantially similar sequence thereof having at least 90%, at least 95%, at least 98% or at least 99% sequence identity; and a LCDR2 domain having an amino acid sequence selected from the group consisting of SEQ ID NO: 14, 110, 126, 142, 158 and 174, or a substantially similar sequence thereof having at least 90%, at least 95%, at least 98% or at least 99% sequence identity; (v) demonstrates a $K_D$ equal to or less than $10^{-9}$; (vi) demonstrates neutralization of Toxin A (at a concentration of 32 pM) with an IC50 ranging from about 7 pM to about 65 pM in a cell viability assay.

In one embodiment, the fully human monoclonal antibody or antigen binding fragment thereof that binds specifically to toxin A of *C. difficile* comprises a HCDR1 sequence comprising the formula $X^1$-$X^2$-$X^3$-$X^4$-$X^5$-$X^6$-$X^7$-$X^8$ (SEQ ID NO: 387), wherein $X^1$ is Gly, or Arg, $X^2$ is Phe, $X^3$ is Asn, or Thr, $X^4$ is Phe, $X^5$ is Gly, Ser, Asn, or Thr, $X^6$ is Thr, Ser, Asn, or Asp, $X^7$ is His, Tyr, or Phe and $X^8$ is Asp, Val, Ala, or Tyr; a HCDR2 sequence comprising the formula $X^1$-$X^2$-$X^3$-$X^4$-$X^5$-$X^6$-$X^7$-$X^8$ (SEQ ID NO: 388), wherein $X^1$ is Leu, or Ile, $X^2$ is Thr, Gly, Ser, or Trp, $X^3$ is Ser, Thr, Gly, or Phe, $X^4$ is Thr, Val, Tyr, Val, Asp, or Gly, $X^5$ is Gly, $X^6$ is Gly, Asp, Ser, or Ala, $X^7$ is Ser, Thr, Asn, or Ala, and $X^8$ is Ala, Thr, Glu, Lys, or absent; a HCDR3 sequence comprising the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X^{20}$-$X^{21}$-$X^{22}$-$X^{23}$-$X^{24}$ (SEQ ID NO: 389), wherein $X^1$ is Ala, $X^2$ is Lys, or Arg, $X^3$ is Thr, Asp, or Ser, $X^4$ is Phe, Arg, His, Ala, or Leu, $X^5$ is Asn, Gly, or Lys, $X^6$ is Trp, Gly, Asp, or Ile, $X^7$ is Asn, Ala, or Phe, $X^8$ is Ser, Asn, Tyr, Gly, or Asp, $X^9$ is Tyr, Ile, Ala, Thr, Glu, or Leu, $X^{10}$ is Phe, Tyr, Ser, Gly, or absent, $X^{11}$ is Asp. Ser, Gly, or absent, $X^{12}$ is Tyr, Phe, Ser, Pro, or absent, $X^{13}$ is Tyr, Leu, or absent, $X^{14}$ is Tyr, Phe, or absent, $X^{15}$ Gly, Asn, Asp, or absent, $X^{16}$ is Met, Arg, Tyr, or absent, $X^{17}$ is Asp, or absent, $X^{18}$ is Tyr, Val, or absent, $X^{19}$ is Tyr, or absent, $X^{20}$ is Tyr, or absent, $X^{21}$ is Gly, or absent, $X^{22}$ is Met, or absent, $X^{23}$ is Asp, or absent, $X^{24}$ is Val, or absent; a LCDR1 sequence comprising the formula $X^1$-$X^2$-$X^3$-$X^4$-$X^5$-$X^6$-$X^7$ (SEQ ID NO: 390), wherein $X^1$ is Gln, $X^2$ is Ser, Asp, or Thr, $X^3$ is Ile, or Val, $X^4$ is Ser, $X^5$ is Thr, Asn, or Ser, $X^6$ is Tyr, Trp, Phe, or Ser and $X^7$ is Tyr, or absent; a LCDR2 sequence comprising the formula $X^1$-$X^2$-$X^3$ (SEQ ID NO: 391), wherein $X^1$ is Gly, Ala, Lys, or Thr, $X^2$ is Ala, Thr, or Val and $X^3$ is Ser; and a LCDR3 sequence comprising the formula $X^1$-$X^2$-$X^3$-$X^4$-$X^5$-$X^6$-$X^7$-$X^8$-$X^9$-$X^{10}$ (SEQ ID NO: 392), wherein $X^1$ is Gln or absent, $X^2$ is Gln, Lys, or absent, $X^3$ is Tyr, Asn, or absent, $X^4$ is Gly, Asn, Thr, Tyr, His, or absent, $X^5$ is Asn, Ser, or absent, $X^6$ is Ser, Ala, Tyr, Asp, Trp, or absent, $X^7$ is Leu, Pro, Ser, or absent, $X^8$ is Tyr, Phe, Arg, Pro, or absent, $X^9$ is Thr, Tyr, or absent, and $X^{10}$ is Thr.

In one embodiment, the invention provides an isolated human monoclonal antibody or antigen-binding fragment thereof that binds specifically to toxin B of *Clostridium difficile*, wherein the antibody comprises the three heavy chain CDRs (HCDR1, HCDR2 and HCDR3) contained within any one of the HCVR amino acid sequences selected from the group consisting of SEQ ID NOs: 178, 194, 210, 226, 242, 258, 274, 290, 306, 322, 338 and 354; and the three light chain CDRs (LCDR1, LCDR2 and LCDR3) contained within any one of the LCVR amino acid sequences selected from the group consisting of SEQ ID NOs: 186, 202, 218, 234, 250, 266, 282, 298, 314, 330, 346 and 362.

In one embodiment, the isolated human antibody or antigen-binding fragment thereof that binds specifically to toxin B of *Clostridium difficile* comprises a HCVR having an amino acid sequence selected from the group consisting of SEQ ID NOs: 178, 194, 210, 226, 242, 258, 274, 290, 306, 322, 338 and 354.

In one embodiment, the isolated human antibody or antigen-binding fragment thereof that binds specifically to toxin B of *Clostridium difficile* comprises a LCVR having an amino acid sequence selected from the group consisting of SEQ ID NOs: 186, 202, 218, 234, 250, 266, 282, 298, 314, 330, 346 and 362.

In one embodiment, the isolated human antibody or antigen-binding fragment thereof that binds specifically to toxin B of *Clostridium difficile* comprises (a) a HCVR having an amino acid sequence selected from the group consisting of SEQ ID NOs: 178, 194, 210, 226, 242, 258, 274, 290, 306, 322, 338 and 354; and (b) a LCVR having an amino acid sequence selected from the group consisting of SEQ ID NO: 186, 202, 218, 234, 250, 266, 282, 298, 314, 330, 346 and 362.

In one embodiment, the isolated human antibody or antigen-binding fragment thereof that binds specifically to toxin B of *Clostridium difficile* comprises (a) a HCDR1 domain having an amino acid sequence selected from the group consisting of SEQ ID NOs: 180, 196, 212, 228, 244, 260, 276, 292, 308, 324, 340 and 356;

(b) a HCDR2 domain having an amino acid sequence selected from the group consisting of SEQ ID NOs: 182, 198, 214, 230, 246, 262, 278, 294, 310, 326, 342 and 358;

(c) a HCDR3 domain having an amino acid sequence selected from the group consisting of SEQ ID NOs: 184, 200, 216, 232, 248, 264, 280, 296, 312, 328, 344 and 360;

(d) a LCDR1 domain having an amino acid sequence selected from the group consisting of SEQ ID NOs: 188, 204, 220, 236, 252, 268, 284, 300, 316, 332, 348 and 364;

(e) a LCDR2 domain having an amino acid sequence selected from the group consisting of SEQ ID NOs: 190, 206, 222, 238, 254, 270, 286, 302, 318, 334, 350 and 366; and (f) a LCDR3 domain having an amino acid sequence selected from the group consisting of SEQ ID NOs: 192, 208, 224, 240, 256, 272, 288, 304, 320, 336, 352 and 368.

In one embodiment, the isolated human antibody or antigen-binding fragment thereof that binds specifically to toxin B of *Clostridium difficile*, comprises the HCDR1, HCDR2 and HCDR3 amino acid sequences of SEQ ID NO: 276, 278 and 280, respectively and LCDR1, LCDR2 and LCDR3 amino acid sequences of SEQ ID NO: 284, 286 and 288, respectively.

In one embodiment, the isolated human antibody or antigen-binding fragment thereof that binds specifically to toxin B of *Clostridium difficile* comprises a HCVR/LCVR amino acid sequence pair selected from the group consisting of SEQ ID NOs: 178/186, 194/202, 210/218, 226/234, 242/250, 258/266, 274/282, 290/298, 306/314, 322/330, 338/346 and 354/362.

In one embodiment, the isolated human antibody or antigen-binding fragment thereof that binds specifically to toxin B of *Clostridium difficile* comprises the HCVR/LCVR amino acid sequence pair of SEQ ID NOs: 274/282.

In one embodiment, the isolated human antibody or antigen-binding fragment thereof that binds specifically to toxin B of *Clostridium difficile* binds to:

an epitope within the carboxy terminal receptor binding domain of toxin B of *Clostridium difficile*, wherein the antibody comprises a HCVR/LCVR amino acid sequence pair of SEQ ID NOs: 178/186; or an epitope outside of the carboxy terminal receptor binding domain of toxin B of *Clostridium difficile*, wherein the antibody comprises a HCVR/LCVR amino acid sequence pair selected from the group consisting of SEQ ID NOs: 194/202, 210/218, 226/234, 242/250, 258/266, 274/282 and 290/298.

In one embodiment, the invention provides a fully human monoclonal antibody or antigen-binding fragment thereof that binds specifically to toxin B of *C. difficile*, wherein the antibody or fragment thereof exhibits one or more of the following characteristics: (i) comprises a HCVR having an amino acid sequence selected from the group consisting of SEQ ID NO: 178, 194, 210, 226, 242, 258, 274, 290, 306, 322, 338 and 354, or a substantially similar sequence thereof having at least 90%, at least 95%, at least 98% or at least 99% sequence identity; (ii) comprises a LCVR having an amino acid sequence selected from the group consisting of SEQ ID NO:186, 202, 218, 234, 250, 266, 282, 298, 314, 330, 346 and 362, or a substantially similar sequence thereof having at least 90%, at least 95%, at least 98% or at least 99% sequence identity; (iii) comprises a HCDR3 domain having an amino acid sequence selected from the group consisting of SEQ ID NO:184, 200, 216, 232, 248, 264, 280, 296, 312, 328, 344 and 360, or a substantially similar sequence thereof having at least 90%, at least 95%, at least 98% or at least 99% sequence identity; and a LCDR3 domain having an amino acid sequence selected from the group consisting of SEQ ID NO:192, 208, 224, 240, 256, 272, 288, 304, 320, 336, 352 and 368, or a substantially similar sequence thereof having at least 90%, at least 95%, at least 98% or at least 99% sequence identity; (iv) comprises a HCDR1 domain having an amino acid sequence selected from the group consisting of SEQ ID NO: 180, 196, 212, 228, 244, 260, 276, 292, 308, 324, 340 and 356, or a substantially similar sequence thereof having at least 90%, at least 95%, at least 98% or at least 99% sequence identity; a HCDR2 domain having an amino acid sequence selected from the group consisting of SEQ ID NO: 182, 198, 214, 230, 246, 262, 278, 294, 310, 326, 342 and 358, or a substantially similar sequence thereof having at least 90%, at least 95%, at least 98% or at least 99% sequence identity; a LCDR1 domain having an amino acid sequence selected from the group consisting of SEQ ID NO: 188, 204, 220, 236, 252, 268, 284, 300, 316, 332, 348 and 364, or a substantially similar sequence thereof having at least 90%, at least 95%, at least 98% or at least 99% sequence identity; and a LCDR2 domain having an amino acid sequence selected from the group consisting of SEQ ID NO: 190, 206, 222, 238, 254, 270, 286, 302, 318, 334, 350 and 366, or a substantially similar sequence thereof having at least 90%, at least 95%, at least 98% or at least 99% sequence identity; (v) demonstrates a $K_D$ equal to or less than $10^{-6}$M; (vi) demonstrates neutralization of Toxin B (at a concentration of 0.03 pM) with an IC50 ranging from about 25 pM to about 320 pM in a cell viability assay.

In one embodiment, the fully human monoclonal antibody or antigen binding fragment thereof that binds specifically to toxin B of *C. difficile* comprises a HCDR1 sequence comprising the formula $X^1$-$X^2$-$X^3$-$X^4$-$X^5$-$X^6$-$X^7$-$X^8$-$X^9$-$X^{10}$ (SEQ ID NO: 393), wherein $X^1$ is Gly, $X^2$ is Phe, Asp, or Tyr, $X^3$ is Thr, Asn, Ser, or Val, $X^4$ is Phe, or Val, $X^5$ is Ser, Arg, Lys, Glu, or Thr, $X^6$ is Ser, Ile, Asp, or Arg, $X^7$ is Phe, Tyr, or Asn, $X^8$ is Gly, Ala, Ser, or Tyr; $X^9$ is Ala, or absent and $X^{10}$ is Ala or absent; a HCDR2 sequence comprising the formula $X^1$-$X^2$-$X^3$-$X^4$-$X^5$-$X^6$-$X^7$-$X^8$-$X^9$ (SEQ ID NO: 394), wherein $X^1$ is Ile, or Thr, $X^2$ is Ser, Gly, Tyr, or Asn, $X^3$ is Thr, Gly, Tyr, Trp, Pro, or Ser, $X^4$ is Asp, Ser, Asn, Arg, Lys, or Asp, $X^5$ is Gly, Ser, or Thr, $X^6$ is Ser, Asp, Gly, Lys, or Asn, $X^7$ is Lys, Arg, Asn, Ser, Trp, or Gly, $X^8$ is Lys, Thr, Ile, or Tyr, $X^9$ is His, or absent; a HCDR3 sequence comprising the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$ (SEQ ID NO: 395), wherein $X^1$ is Ala, or Val, $X^2$ is Arg, Lys, Thr, or Ser, $X^3$ is Val, Gly, Asp, Arg, or Tyr, $X^4$ is Gly, Trp, Arg, Lys, or Asn, $X^5$ is Glu, Tyr, Arg, Ser, or Trp, $X^6$ is Leu, Tyr, Ser, Pro, or Asn, $X^7$ Leu, Asp, Tyr, Ser, or Asp, $X^8$ is Asn, Ser, Phe, Lys, Arg, Asp, or Gly, $X^9$ is Tyr, Gly, Phe, Asp, Trp, or Val, $X^{10}$ is Ser, Tyr, Asn, Asp, or absent, $X^{11}$ is Tyr, Leu, Val, Gly, or absent, $X^{12}$ is Tyr, Leu, Phe, Val, or absent, $X^{13}$ is Asn, Gly, Asp, Phe, or absent, $X^{14}$ is Tyr, Met, Asp, or absent, $X^{15}$ Asp, Tyr, or absent, and $X^{16}$ is Val, or absent; a LCDR1 sequence comprising the formula $X^1$-$X^2$-$X^3$-$X^4$-$X^5$-$X^6$-$X^7$ (SEQ ID NO: 396), wherein $X^1$ is Gln, Leu, or Arg, $X^2$ is Gly, Asp, or Ser, $X^3$ is Ile, or Val, $X^4$ is Arg, Ser, Gly, or Tyr, $X^5$ is Ser, or Asn, $X^6$ is Trp, His, Asn, Phe, Ser, or Asp, and $X^7$ is Tyr, or absent; a LCDR2 sequence comprising the formula $X^1$-$X^2$-$X^3$ (SEQ ID NO: 397), wherein $X^1$ is Ala, Ser, Asp, or Gly, $X^2$ is Ala, or Thr, and $X^3$ is Ser; and a LCDR3 sequence comprising the formula $X^1$-$X^2$-$X^3$-$X^4$-$X^5$-$X^6$-$X^7$-$X^8$-$X^9$ (SEQ ID NO: 398), wherein $X^1$ is Gln, His, or Leu, $X^2$ is Gln, $X^3$ is Ala, Tyr, Arg, Asp, His, or Val, $X^4$ is Tyr, Gly, Asn, Ser, Ile, or Lys, $X^5$ is Ser, Leu, Pro, Ile, Asn, Thr, or Gly, $X^6$ is Phe, Tyr, Trp, or Ser, $X^7$ is Pro, $X^8$ is Leu, Pro, Phe, Val, or Tyr and $X^9$ is Thr.

In one embodiment, the invention provides an isolated antibody or antigen-binding fragment thereof that competes for specific binding to *C. difficile* toxin A and/or toxin B with an antibody or antigen-binding fragment comprising the complementarity determining regions (CDRs) of a heavy chain variable region (HCVR), wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338 and 354; and the CDRs of a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346 and 362.

In a related embodiment, the invention provides an isolated antibody or antigen-binding fragment thereof that competes for specific binding to *C. difficile* toxin A and/or toxin B with an antibody or antigen-binding fragment comprising the heavy and light chain CDRs contained within heavy and light chain sequence pairs selected from the group consisting of SEQ ID NOs: 18/26, 34/42, 146/154 and 274/282.

In one embodiment, the invention provides an isolated antibody or antigen-binding fragment thereof that binds the same epitope on *C. difficile* toxin A and/or toxin B as an antibody or antigen-binding fragment comprising the CDRs of a heavy chain variable region (HCVR), wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338 and 354; and the CDRs of a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346 and 362.

In a related embodiment, the invention provides an isolated antibody or antigen-binding fragment thereof that binds the same epitope on *C. difficile* toxin A and/or toxin B as an antibody or antigen-binding fragment comprising the heavy and light chain CDRs contained within heavy and light chain sequence pairs selected from the group consisting of SEQ ID NOs: 18/26, 34/42, 146/154, 274/282.

In certain embodiments of the invention, the antibodies may interact with, or bind to, amino acid residues 468-863 of the carboxy terminal receptor binding domain of toxin A produced by *Clostridium difficile*, the sequence of which is shown in SEQ ID NO: 375. This region corresponds to amino acid residues ranging from residues 2315-2710 of SEQ ID NO: 378 (full length toxin A). In certain embodiments of the invention, the antibodies may interact with, or bind to, an epitope in the carboxy terminal receptor binding domain of toxin A produced by *Clostridium difficile*, wherein the epitope is selected from the group consisting of residues 468-488 of SEQ ID NO: 375, residues 510-530 of SEQ ID NO: 375, residues 602-610 of SEQ ID NO: 375, residues 644-703 of SEQ ID NO: 375, residues 724-794 of SEQ ID NO: 375, residues 799-814 of SEQ ID NO: 375 and residues 858-863 of SEQ ID NO: 375. These residues correspond to the amino acid sequences found in the full length toxin A sequence having SEQ ID NO: 378, with the particular regions identified as residues 2315-2335 of SEQ ID NO: 378, residues 2357-2377 of SEQ ID NO: 378, residues 2449-2457 of SEQ ID NO: 378, residues 2491-2550 of SEQ ID NO: 378, residues 2571-2641 of SEQ ID NO: 378, residues 2646-2661 of SEQ ID NO: 378 and residues 2705-2710 of SEQ ID NO: 378. In one embodiment, the antibody that binds to or interacts with an epitope in the carboxy terminal receptor binding domain of toxin A produced by *Clostridium difficile*, selected from the group consisting of residues 468-488 of SEQ ID NO: 375, residues 510-530 of SEQ ID NO: 375, residues 602-610 of SEQ ID NO: 375, residues 644-703 of SEQ ID NO: 375, residues 724-794 of SEQ ID NO: 375, residues 799-814 of SEQ ID NO: 375 and residues 858-863 of SEQ ID NO: 375 comprises the HCVR/LCVR amino acid sequence pair of SEQ ID NOs: 146/154. In one embodiment, the antibody that binds to or interacts with an epitope in the carboxy terminal receptor binding domain of toxin A produced by *Clostridium difficile*, selected from the group consisting of residues 468-

488 of SEQ ID NO: 375, residues 510-530 of SEQ ID NO: 375, residues 602-610 of SEQ ID NO: 375, residues 644-703 of SEQ ID NO: 375, residues 724-794 of SEQ ID NO: 375, residues 799-814 of SEQ ID NO: 375 and residues 858-863 of SEQ ID NO: 375 is combined with a second antibody that binds specifically to toxin B of *Clostridium difficile* in a pharmaceutical composition. In one embodiment, this second antibody that interacts with or binds to toxin B of *Clostridium difficile* comprises the HCVR/LCVR amino acid sequence pair of SEQ ID NOs: 274/282.

In a second aspect, the invention provides nucleic acid molecules encoding anti-toxin A and/or anti-toxin B antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, 305, 321, 337 and 353 or a substantially identical sequence having at least 90%, at least 95%, at least 98%, or at least 99% homology thereof.

In one embodiment, the HCVR is encoded by a nucleic acid sequence selected from the group consisting of SEQ ID NO: 17, 33, 145 and 273.

In one embodiment, the antibody or fragment thereof further comprises a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, 313, 329, 345 and 361, or a substantially identical sequence having at least 90%, at least 95%, at least 98%, or at least 99% homology thereof.

In one embodiment, the LCVR is encoded by a nucleic acid sequence selected from the group consisting of SEQ ID NO: 25, 41, 153 and 281.

In one embodiment, the invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, 311, 327, 343 and 359 or a substantially similar sequence thereof having at least 90%, at least 95%, at least 98% or at least 99% sequence identity; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, 335, 351 and 367, or a substantially similar sequence thereof having at least 90%, at least 95%, at least 98% or at least 99% sequence identity.

In one embodiment, the invention provides an antibody or fragment thereof further comprising a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, 323, 339 and 355, or a substantially similar sequence thereof having at least 90%, at least 95%, at least 98% or at least 99% sequence identity; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, 309, 325, 341 and 357, or a substantially similar sequence thereof having at least 90%, at least 95%, at least 98% or at least 99% sequence identity; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, 331, 347 and 363, or a substantially similar sequence thereof having at least 90%, at least 95%, at least 98% or at least 99% sequence identity; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, 317, 333, 349 and 365, or a substantially similar sequence thereof having at least 90%, at least 95%, at least 98% or at least 99% sequence identity.

In a third aspect, the invention features a human antibody or antigen-binding fragment specific for toxin A and/or toxin B of *C. difficile* comprising a HCVR encoded by nucleotide sequence segments derived from $V_H$, $D_H$ and $J_H$ germline sequences, and a LCVR encoded by nucleotide sequence segments derived from $V_K$ and $J_K$ germline sequences, with combinations as shown in Table 2.

The invention encompasses antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

In a fourth aspect, the invention provides a pharmaceutical composition comprising at least one isolated fully human monoclonal antibody or antigen-binding fragment thereof that binds to either toxin A or toxin B of *C. difficile*, or that binds to both toxin A and toxin B of *C. difficile* and a pharmaceutically acceptable carrier or diluent. In one embodiment, the invention provides a pharmaceutical composition comprising an isolated fully human monoclonal antibody or antigen-binding fragment thereof that binds specifically to only toxin A of *C. difficile* and a pharmaceutically acceptable carrier or diluent. In one embodiment, the invention provides a pharmaceutical composition comprising an isolated fully human monoclonal antibody or antigen-binding fragment thereof that binds specifically to only toxin B of *C. difficile* and a pharmaceutically acceptable carrier or diluent. In one embodiment, the invention provides a pharmaceutical composition comprising two fully human monoclonal antibodies or antigen-binding fragments thereof, one that binds specifically to toxin A and one that binds specifically to toxin B of *C. difficile* and a pharmaceutically acceptable carrier or diluent. In one embodiment, the invention provides a pharmaceutical composition comprising one dual binding fully human monoclonal antibody (an antibody that binds to both toxin A and toxin B) and a pharmaceutically acceptable carrier or diluent. In one embodiment, the invention provides a pharmaceutical composition comprising two dual binding fully human monoclonal antibodies (an antibody that binds to both toxin A and toxin B) and a pharmaceutically acceptable carrier or diluent. The dual antibodies used in the pharmaceutical composition may recognize and/or bind to the same epitope on toxin A or toxin B, or may recognize and/or bind to different epitopes on toxin A or toxin B. It is to be understood that any combination of antibodies as described herein may be used in a pharmaceutical composition to achieve the desired results in the patient population in need of such therapy. For example, two antibodies that recognize and/or bind only toxin A may be used in a composition. Alternatively, two antibodies that recognize and/or bind only toxin B may be used in a composition. In one embodiment, one antibody that recognizes/binds to only toxin A or toxin B may be combined with a dual binding antibody in a composition. In one embodiment, one antibody that recognizes/binds to only toxin A may be combined with one antibody that recognizes/binds to only toxin B and this combination may be used in a composition.

In one embodiment, the pharmaceutical composition comprises a fully human monoclonal antibody that binds to the carboxy terminal receptor binding domain of both toxin A and toxin B of *C. difficile* having any one or more of the characteristics described herein. The antibody that binds to the carboxy terminal receptor binding domain of both toxin A and toxin B of *C. difficile* binds toxin A and toxin B with a $K_D$ equal to or less than $10^{-7}$M.

In one embodiment, the composition comprises an antibody that binds both toxin A and toxin B of *C. difficile* and has a HCVR/LCVR amino acid sequence pair selected from the group consisting of SEQ ID NOs: 18/26, 34/42, 50/58, 66/74 and 82/90.

In one embodiment, the composition comprises an antibody that binds both toxin A and toxin B of *C. difficile* and has a HCVR/LCVR amino acid sequence pair selected from the group consisting of SEQ ID NOs: 18/26 and 34/42.

In one embodiment, the pharmaceutical composition comprises at least one antibody that binds a *Clostridium difficile* toxin, wherein the antibody is selected from the group consisting of:

a) an isolated antibody or antigen-binding fragment thereof that specifically binds toxin A of *Clostridium difficile*, wherein the antibody comprises the three heavy chain complementarity determining regions (HCDR1, HCDR2 and HCDR3) contained within any one of the heavy chain variable region (HCVR) amino acid sequences selected from the group consisting of SEQ ID NOs: 2, 98, 114, 130, 146 and 162; and the three light chain complementarity determining regions (LCDR1, LCDR2 and LCDR3) contained within any one of the light chain variable region (LCVR) amino acid sequences selected from the group consisting of SEQ ID NOs: 10, 106, 122, 138, 154 and 170;

b) an isolated antibody or antigen-binding fragment thereof that specifically binds toxin B of *Clostridium difficile*, wherein the antibody comprises the three heavy chain CDRs (HCDR1, HCDR2 and HCDR3) contained within any one of the HCVR amino acid sequences selected from the group consisting of SEQ ID NOs: 178, 194, 210, 226, 242, 258, 274, 290, 306, 322, 338 and 354; and the three light chain CDRs (LCDR1, LCDR2 and LCDR3) contained within any one of the LCVR amino acid sequences selected from the group consisting of SEQ ID NOs: 186, 202, 218, 234, 250, 266, 282, 298, 314, 330, 346 and 362; and c) an isolated antibody or antigen-binding fragment that binds to/cross reacts with both toxin A and toxin B of *Clostridium difficile*, wherein the antibody comprises the three heavy chain CDRs (HCDR1, HCDR2 and HCDR3) contained within any one of the HCVR amino acid sequences selected from the group consisting of SEQ ID NOs: 18, 34, 50, 66 and 82; and the three light chain CDRs (LCDR1, LCDR2 and LCDR3) contained within any one of the LCVR amino acid sequences selected from the group consisting of SEQ ID NOs: 26, 42, 58, 74 and 90.

In one embodiment, the pharmaceutical composition comprises an isolated first fully human monoclonal antibody or antigen-binding fragment thereof that specifically binds toxin A of *Clostridium difficile*, as described herein, and an isolated second fully human monoclonal antibody or antigen-binding fragment thereof that specifically binds toxin B of *Clostridium difficile*, as described herein, and a pharmaceutically acceptable carrier or diluent.

In one embodiment, the composition comprises at least one antibody, or an antigen-binding fragment thereof that binds specifically to toxin A of *Clostridium difficile* and at least one antibody, or an antigen-binding fragment thereof that binds specifically to toxin B of *Clostridium difficile*, wherein:

a) the antibody or antigen-binding fragment thereof that binds specifically to toxin A comprises the three heavy chain complementarity determining regions (HCDR1, HCDR2 and HCDR3) contained within any one of the heavy chain variable region (HCVR) amino acid sequences selected from the group consisting of SEQ ID NOs: 2, 98, 114, 130, 146 and 162; and the three light chain complementarity determining regions (LCDR1, LCDR2 and LCDR3) contained within any one of the light chain variable region (LCVR) amino acid sequences selected from the group consisting of SEQ ID NOs: 10, 106, 122, 138, 154 and 170; and wherein b) the antibody or antigen-binding fragment thereof that binds specifically to toxin B comprises the three heavy chain CDRs (HCDR1, HCDR2 and HCDR3) contained within any one of the HCVR amino acid sequences selected from the group consisting of SEQ ID NOs: 178, 194, 210, 226, 242, 258, 274, 290, 306, 322, 338 and 354; and the three light chain CDRs (LCDR1, LCDR2 and LCDR3) contained within any one of the LCVR amino acid sequences selected from the group consisting of SEQ ID NOs: 186, 202, 218, 234, 250, 266, 282, 298, 314, 330, 346 and 362.

In one embodiment, the pharmaceutical composition comprises:

a) an isolated first fully human monoclonal antibody, or antigen-binding fragment thereof that specifically binds toxin A of *Clostridium difficile*, which comprises a HCVR having an amino acid sequence selected from the group consisting of SEQ ID NOs: 2, 98, 114, 130, 146 and 162; and a LCVR having an amino acid sequence selected from the group consisting of SEQ ID NOs: 10, 106, 122, 138, 154 and 170; and b) an isolated second fully human monoclonal antibody, or antigen-binding fragment thereof that specifically binds toxin B of *Clostridium difficile*, which comprises a HCVR having an amino acid sequence selected from the group consisting of SEQ ID NOs: 178, 194, 210, 226, 242, 258, 274, 290, 306, 322, 338 and 354; and a LCVR having an amino acid sequence selected from the group consisting of SEQ ID NOs: 186, 202, 218, 234, 250, 266, 282, 298, 314, 330, 346 and 362.

In one embodiment, the pharmaceutical composition comprises an isolated first fully human monoclonal antibody or antigen-binding fragment thereof that specifically binds toxin A of *C. difficile*, which comprises a HCVR/LCVR amino acid sequence pair selected from the group consisting of SEQ ID NOs: 2/10, 98/106, 114/122, 130/138, 146/154 and 162/170; and an isolated second fully human monoclonal antibody or antigen-binding fragment thereof that specifically binds toxin B of *C. difficile*, which comprises a HCVR/LCVR amino acid sequence pair selected from the group consisting of SEQ ID NOs: 178/186, 194/202, 210/218, 226/234, 242/250, 258/266, 274/282, 290/298, 306/314, 322/330, 338/346 and 354/362.

In another embodiment, the pharmaceutical composition comprises an isolated first fully human monoclonal antibody or antigen-binding fragment thereof that specifically binds toxin A of *C. difficile*, which comprises a HCVR/LCVR amino acid sequence pair of SEQ ID NOs: 146/154; and an isolated second fully human antibody or antigen-binding fragment thereof that specifically binds toxin B of *C. difficile*, which comprises a HCVR/LCVR amino acid sequence pair of SEQ ID NOs: 274/282.

In another related embodiment, the pharmaceutical composition comprises:

a) an isolated first human antibody, or antigen-binding fragment thereof that specifically binds toxin A of *Clostridium difficile*, comprising a HCDR1 having the amino acid sequence of SEQ ID NO: 148, a HCDR2 having the amino acid sequence of SEQ ID NO: 150, a HCDR3 having the amino acid sequence of SEQ ID NO: 152, a LCDR1 having the amino acid sequence of SEQ ID NO: 156, a LCDR2 having the amino acid sequence of SEQ ID NO: 158, a LCDR3 having the amino acid sequence of SEQ ID NO: 160;

b) an isolated second human antibody, or antigen-binding fragment thereof that specifically binds toxin B of *Clostridium difficile*, comprising a HCDR1 having the amino acid sequence of SEQ ID NO: 276, a HCDR2 having the amino acid sequence of SEQ ID NO: 278, a HCDR3 having the amino acid sequence of SEQ ID NO: 280, a LCDR1 having the amino acid sequence of SEQ ID NO: 284, a LCDR2 having the amino acid sequence of SEQ ID NO: 286, a LCDR3 having the amino acid sequence of SEQ ID NO: 288; and c) a pharmaceutically acceptable carrier or diluent.

In one embodiment, the antibodies of the invention, or compositions containing one or more antibodies of the invention may be used to neutralize either toxin A, or toxin B, or both toxin A and B from any strain of *Clostridium difficile*.

In one embodiment, the antibodies of the invention, or compositions containing one or more antibodies of the invention may be used to neutralize toxins A and/or B from a hypervirulent strain of *Clostridium difficile*.

In one embodiment, the antibodies of the invention, or compositions containing one or more antibodies of the invention may be used to neutralize toxins A and/or B from a BI/NAP1/027 strain.

In one embodiment, the antibodies of the invention, or compositions containing one or more antibodies of the invention, may be used to neutralize toxins A and/or B from a BI/NAP1/027 strain, wherein the BI/NAP1/027 strain is selected from the group consisting of VA5, VA17, 6336 and 6443.

In one embodiment, the antibody composition comprising a first antibody that binds specifically to toxin A, may be administered alone as a separate composition and the antibody composition comprising the second antibody that binds specifically to toxin B may also be administered as a separate composition. Each composition may be prepared for delivery to the patient in separate syringes, or delivery devices, or vials. When formulated separately as two compositions, both compositions may be delivered separately, with one antibody composition being given immediately prior to the other antibody composition. Alternatively, the two antibody compositions may be mixed together shortly before administration and given concurrently.

In one embodiment, the invention features a composition, which is a combination of an antibody or antigen-binding fragment of an antibody of the invention, and a second therapeutic agent.

The second therapeutic agent may be a small molecule drug, a protein/polypeptide, an antibody, a nucleic acid molecule, such as an anti-sense molecule, or a siRNA. The second therapeutic agent may be synthetic or naturally derived.

The second therapeutic agent may be any agent that is advantageously combined with the antibody or fragment thereof of the invention, for example, a probiotic, an antibiotic, a toxoid, a vaccine specific for *C. difficile*, or a second different antibody against *C. difficile* toxin A and/or toxin B.

In certain embodiments, the second therapeutic agent may be an agent that helps to counteract or reduce any possible side effect(s) associated with the antibody or antigen-binding fragment of an antibody of the invention, if such side effect(s) should occur.

It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated.

When multiple therapeutics are co-administered, dosages may be adjusted accordingly, as is recognized in the pertinent art.

A fifth aspect of the invention provides a method for treating a patient suffering from a *Clostridium difficile*-associated condition or disease, or for treating at least one symptom or complication associated with the condition or disease, or for preventing the development of a *Clostridium difficile*-associated condition or disease in a patient at risk thereof, the method comprising administering to the patient an effective amount of an antibody or an antigen-binding fragment thereof that binds to *C. difficile* toxin A and/or toxin B; or a pharmaceutical composition comprising an effective amount of an antibody or an antigen-binding fragment thereof that binds to *Clostridium difficile* toxin A and/or toxin B, such that the *Clostridium difficile*-associated condition or disease is either prevented, or lessened in severity and/or duration, or at least one symptom or complication associated with the condition or disease is prevented, or ameliorated, or that the frequency and/or duration of, or the severity of recurrences, or relapses with *Clostridium difficile* is reduced.

In one embodiment, the invention provides for use of one or more antibodies of the invention, or pharmaceutical compositions comprising one or more antibodies of the invention in the manufacture of a medicament for use in treating a patient suffering from a *Clostridium difficile*-associated condition or disease, or for treating at least one symptom or complication associated with the condition or disease, or for preventing the development of a *Clostridium difficile*-associated condition or disease in a patient at risk thereof, wherein the *Clostridium difficile*-associated condition or disease is either prevented, or lessened in severity and/or duration, or at least one symptom or complication associated with the condition or disease is prevented, or ameliorated, or that the frequency and/or duration of, or the severity of recurrences, or relapses with *Clostridium difficile* is reduced. The at least one symptom or complication associated with the *Clostridium difficile*-associated condition or disease may be selected from the group consisting of anorexia, abdominal pain, abdominal bloating, diarrhea with or without bleeding, dehydration, malnutrition, pseudomembranous colitis, complete or segmental colonic resection, fever and systemic infection (sepsis), death, relapse of the *Clostridium difficile* condition or disease, and rejection of a transplanted tissue or organ.

In one embodiment, the patient to be treated with the antibodies of the invention, or with the pharmaceutical compositions comprising one or more antibodies of the invention are infected with a hypervirulent isolate of *Clostridium difficile*, such as one belonging to the BI/NAP1/027 group, or may be at risk for developing an infection with a hypervirulent strain, as described herein.

In a related embodiment, the antibodies of the invention, or a pharmaceutical composition containing one or more antibodies of the invention may be used to neutralize the toxins produced by a hypervirulent strain of *Clostridium difficile*, such as but not limited to any of those belonging to the BI/NAP1/027 group of strains. Included in these hypervirulent strains are clinical isolates noted herein as VA5, VA17, 6336 and 6443, described herein in Example 10.

In one embodiment, the patient at risk of developing a *Clostridium difficile*-associated condition or disease, who may benefit from treatment with the antibodies of the invention, or with a composition comprising one or more antibodies of the invention, may be selected from the group consisting of an elderly 65 years old) patient, a patient who is immunocompromised due to underlying illness or due to administration of immunosuppressive therapeutics, a patient who has some underlying medical condition that may pre-dispose them to acquiring a *Clostridium difficile* infection, a patient hospitalized for an extended period of time (one week or more), a patient who has been treated for an extended period of time 14 days) with broad spectrum antibiotics, a cancer patient, a transplant patient, and a patient on therapy with agents such as but not limited to a proton pump inhibitor, or histamine H2 receptor inhibitor that are used for treatment of gastrointestinal diseases or conditions to reduce or treat gastric acidity, gastroesophageal reflux disease (GERD), stomach and small intestine ulcers, or heartburn.

In one embodiment, the patient at risk of developing a *Clostridium difficile*-associated condition or disease is a cancer patient. In a related embodiment, the cancer patient is undergoing treatment with an anti-cancer drug, or undergoing radiotherapy to treat a cancer.

In one embodiment, the patient at risk of developing a *Clostridium difficile*-associated condition or disease is a transplant patient. In a related embodiment, the transplant patient is a patient receiving a hematopoietic stem cell transplant, or a solid tissue or organ transplant. In certain embodiments, the transplant patient is being treated with an immunosuppressive drug, or any transplant rejection drug, or is a patient who is undergoing treatment with a drug regimen to prevent tissue or organ graft rejection following the transplant.

In one embodiment, the antibody is administered therapeutically (administered after the infection has been established and given throughout the course of the infection) to a patient suffering from a *Clostridium difficile*-associated condition or disease, or suffering from at least one symptom or complication associated with the condition or disease. In one embodiment, the antibody is administered prophylactically (administered prior to development of the infection) to a patient at risk for developing a *Clostridium difficile*-associated condition or disease, or at risk for developing at least one symptom or complication associated with the *Clostridium difficile* condition or disease. For example, such "patients at risk for developing a *Clostridium difficile* infection" include the elderly (65 years of age or older), or patients who may be immunocompromised due to illness or due to administration of immunosuppressive therapeutics, or patients who have some underlying medical condition that may pre-dispose them to acquiring a *Clostridium difficile* infection, or patients hospitalized for long periods of time (generally one week or longer), or patients who have been treated for a long period of time with broad spectrum antibiotics (generally 14 days or longer), or patients on therapy with proton pump inhibitors for treatment of gastrointestinal diseases or conditions. Other patients at risk for developing a *Clostridium difficile* infection are those patients that are in need of a tissue or organ transplant, who would be undergoing treatment with immunosuppressive drugs to prevent tissue or organ rejection. This patient population includes individuals in need of either an autologous or allogeneic hematopoietic stem cell transplant. The long hospitalization required for these patients, in addition to receipt of high doses of antibiotic therapy to prevent other types of infections may pre-dispose these patients to acquiring a primary *C. difficile* infection. Alternatively, if a patient in need of such a transplant already suffers from a *C. difficile* infection, or has exhibited symptoms of a *C. difficile* infection, that patient may be prone to a recurrence, or exacerbation of such infection when placed on high dose antibiotic therapy, then followed by immunosuppressive therapy to prevent graft rejection. Furthermore, these transplant patients may be at risk not only for acquiring a *C. difficile* infection, but also may be at risk for rejection of the transplant due to GI related graft versus host disease (GI-GVHD), which appears to be enhanced in transplant patients suffering from infection with *C. difficile* (See Alonso, C. D. et. al., (2012), Clin. Infect. Dis. 54, 1053-1063. The relationship between *C. difficile* infection and GVHD involving the GI tract is unclear at this time, but it is appears that this patient population would benefit from therapy with the anti-toxin A and/or anti-toxin B antibodies of the invention. While it is envisioned that this patient population may be treated therapeutically (after the start of the infection), it is also contemplated that these patients would benefit from prophylactic (prior to infection) administration of any of the antibodies of the invention. The patients who are candidates for treatment with the antibodies of the invention may be administered the compositions comprising one or more antibodies by any route of delivery suitable for administration, including but not limited to intravenous injection, or subcutaneous injection.

In one embodiment, the pharmaceutical composition comprising the antibodies of the invention is administered to the patient in combination with one or more therapeutic agents useful for treating a *C. difficile* infection.

In one embodiment, the one or more therapeutic agents may be selected from the group consisting of a toxoid, a probiotic, a *C. difficile* vaccine (e.g., inactivated toxins A and B, such as, but not limited to ACAM-CDIFF™), an antibiotic (e.g. metronidazole, vancomycin or fidaxomicin), another different antibody to *C. difficile* toxin A and/or B, and any other palliative therapy useful for reducing the severity of the *C. difficile* disease or for reducing the frequency of recurrence of the *C. difficile* disease or for ameliorating at least one symptom associated with a *C. difficile*-associated condition or disease.

In another embodiment, the one symptom or complication associated with the *C. difficile*-associated condition or disease is selected from the group consisting of diarrhea, pseudomembranous colitis, relapse/recurrence of the *Clostridium difficile* condition or disease, and rejection of a transplanted tissue or organ.

Other embodiments will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

DEFINITIONS

The term "toxin A" (also referred to as "tcdA") refers to the toxin A protein produced by *Clostridium difficile* (also referred to herein as "*C. difficile*"). The amino acid sequence of "toxin A' is provided in GenBank as accession number CAA63564 and is also referred to herein as SEQ ID NO: 378. Toxin A is encoded by the nucleic acid provided herein as SEQ ID NO: 377, and is also found in GenBank as accession number AM180355.

The term "toxin B" (also referred to as "tcdB") refers to the toxin B protein produced by *Clostridium difficile*. The amino acid sequence of "toxin B' is provided in GenBank as accession number CAJ67492 and is also referred to herein as SEQ ID NO: 380. Toxin B is encoded by the nucleic acid provided herein as SEQ ID NO: 379, and is also found in GenBank as accession number AM180355.

Figure 1:
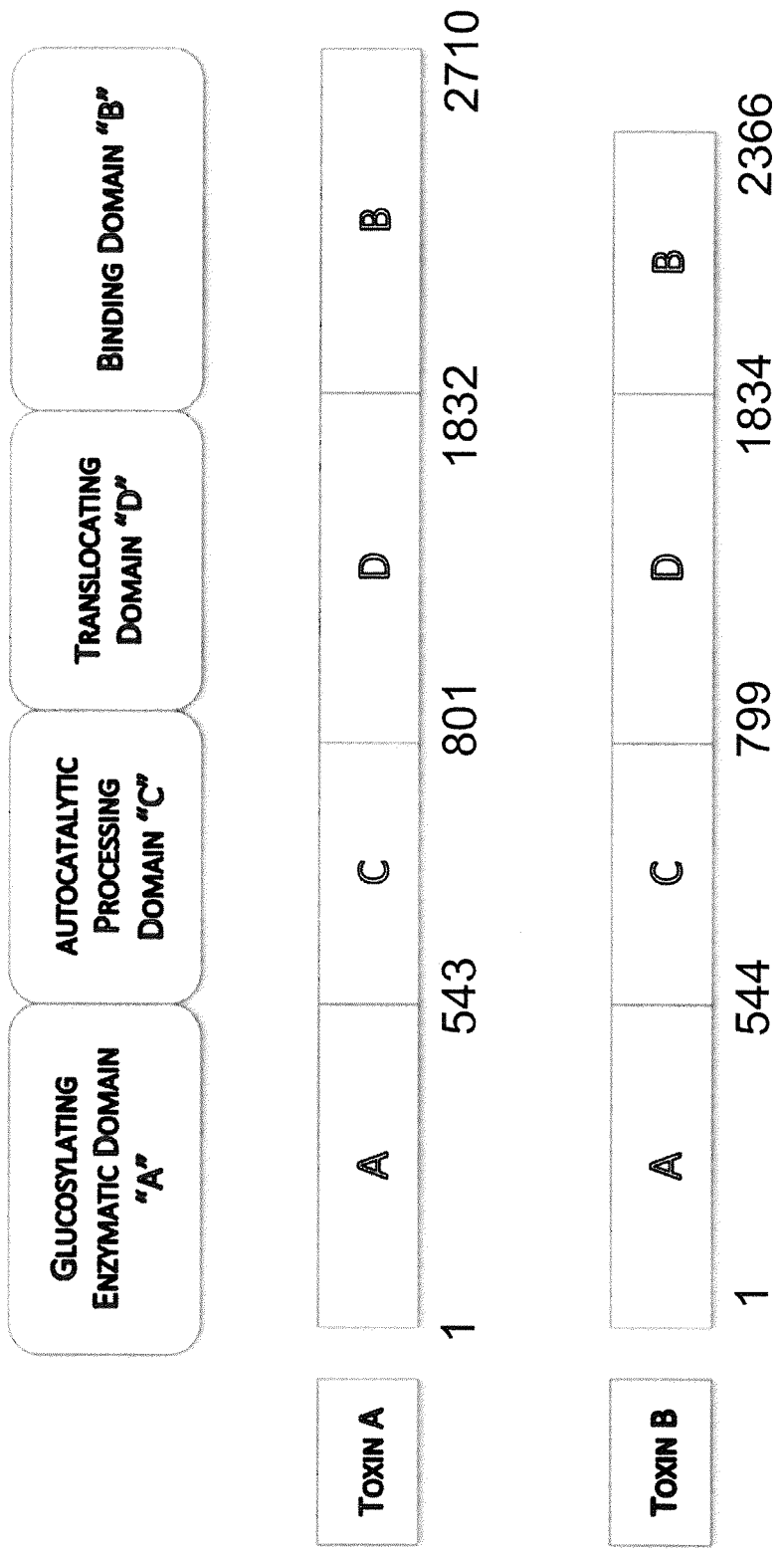
FIG. 1 shows the domain structures of Toxin A and Toxin B from *Clostridium difficile* (See Davies A H, et al., Biochem. J. (2011), 436:517-526).

The "carboxy terminal receptor binding domain of toxin A and toxin B of *Clostridium difficile*" refers to the portion of toxin A and toxin B from *C. difficile* that is responsible for binding to the target cell, thus allowing for subsequent receptor mediated endocytosis. As described herein, the amino acid sequence of the carboxy terminal receptor binding domain of toxin A is shown in SEQ ID NO: 375. The amino acid sequence of the carboxy terminal receptor binding domain of toxin B is shown in SEQ ID NO: 376. The various domains of toxin A and toxin B from *C. difficile* are illustrated in FIG. 1 and further described in Davies et al. (Davies, A H, et al., Biochem. J. (2011), 436:517-526).

The "BI/NAP1/027" designation for *Clostridium difficile* refers to a highly virulent group of isolates of *Clostridium difficile* that has been associated with an increase in morbidity and mortality throughout Europe and North America (Loo, V G, et al., (2005), N Engl J Med, 353:2442-9; McDonald, L C et al. (2006), Emerg Infect Dis, 12:409-15; McDonald, L C, et al., (2005), N Engl J Med, 353:2433-41; Redelings, M D, et al., (2007), Emerg Infect Dis 13:1417-9). The "BI/NAP1/027" designation further refers to North American pulsed-field type I (NAP1), ribotype 027, and group BI by restriction endonuclease analysis. It was originally identified in the 1980s, but was not originally identified as being resistant to the newer fluoroquinolone agents and was not epidemic prior to 2000 (Warny, M. et al., (2005), Lancet 366:1079-84; Kelly, C P, et al., N Engl J Med 359:1932-40). The "BI/NAP1/027" strain of *Clostridium difficile* is also characterized by increased toxin A and toxin B production, by the presence of an additional toxin (binary toxin), and increased resistance to fluoroquinolones (McDonald, L C, et al., (2005), N Engl J Med, 353:2433-41; Warny, M. et al., (2005), Lancet 366: 1079-84).

The term "antibody", as used herein, is intended to refer to immunoglobulin molecules comprised of four polypeptide chains, two heavy (H) chains and two light (L) chains interconnected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-toxin A and/or anti-toxin B monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-toxin A and/or anti-toxin B monoclonal antibodies comprising variants of any of the HCVR, LCVR, and/or CDR amino acid sequences disclosed herein having one or more conservative substitutions. For example, the present invention includes anti-toxin A and anti-toxin B antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to either toxin A, or specifically to toxin B from *C. difficile*, while others have been identified that bind specifically to the carboxy terminal receptor binding domain of both toxin A and B. Moreover, multi-specific antibodies that bind to toxin A or toxin B and one or more additional antigens or a bi-specific that binds to two different regions of toxin A or toxin B are nonetheless considered antibodies that "specifically bind", as used herein.

The term "high affinity" antibody refers to those mAbs having a binding affinity to toxin A or toxin B, expressed as $K_D$, of at least $10^{-8}$ M; preferably $10^{-9}$ M; more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from toxin A or toxin B, or both, with a rate constant of $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to bind to toxin A or toxin B or both.

The specific embodiments, antibody or antibody fragments of the invention may be conjugated to a therapeutic moiety ("immunoconjugate"), such as an antibiotic, a second antitoxin A or B antibody, or a C. difficile vaccine, or a toxoid, or any other therapeutic moiety useful for treating a disease or condition caused by C. difficile.

An "isolated antibody", as used herein, is intended to refer to an antibody that is substantially free of other antibodies (Abs) having different antigenic specificities (e.g., an isolated antibody that specifically binds toxin A or toxin B, or a fragment thereof, is substantially free of Abs that specifically bind antigens other than toxin A or toxin B.

A "blocking antibody" or a "neutralizing antibody", as used herein (or an "antibody that neutralizes toxin A and/or toxin B activity"), is intended to refer to an antibody whose binding to toxin A and/or toxin B results in inhibition of at least one biological activity of toxin A and/or toxin B. For example, an antibody of the invention may aid in preventing the primary disease caused by C. difficile. Alternatively, an antibody of the invention may demonstrate the ability to prevent a recurrence or relapse of the disease caused by C. difficile, or at least one symptom caused by C. difficile infection, including diarrhea or psudomembranous colitis. This inhibition of the biological activity of toxin A and/or toxin B can be assessed by measuring one or more indicators of toxin A and/or toxin B biological activity by one or more of several standard in vitro assays (such as a neutralization assay, as described herein) or in vivo assays known in the art (for example, animal models to look at protection from challenge with C. difficile following administration of one or more of the antibodies described herein).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402, each of which is herein incorporated by reference.

In specific embodiments, the antibody or antibody fragment for use in the method of the invention may be mono-specific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise an Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

General Description

*Clostridium difficile* is a gram-positive, spore-forming, toxin producing bacterium, which is a leading cause of nosocomial antibiotic-associated diarrhea and colitis in humans (Bartlett, J. G. et al. (1978), N. Engl. J. Med. 298:531-534; Kyne, L., et al. (2001), Clin. N. Am. 30:753-777). The perturbation of the colonic environment resulting from administration of broad-spectrum antibiotics leads to colonization of the gut by the bacterium (Johnson, S. C. et al. (1990), Lancet 336:97-100). A large percentage of this patient population that becomes colonized with *C. difficile* develops diarrhea, which in certain instances leads to pseudomembranous colitis, which is believed to be due to the production of two exotoxins by *C. difficile*, toxin A and toxin B. Treatment consists of the discontinuation of the offending antibiotic, or alterations in the dosing of the offending antibiotic, or no change in the offending antibiotic, followed by the administration of metronidazole, vancomycin, or fidaxomicin. While this treatment regimen is usually successful, many patients relapse when therapy is discontinued (Fekety, R., (1997), Am. J. Gastroenterology, 92:739-750). Furthermore, in many instances, the *C. difficile* bacterium becomes resistant to the therapy used, thus leading to treatment failures and in some instances increased mortality rates (Dworczynski, A. et al. (1991), Cytobios. 65:149-153; Fekety, R. et al. (1993), JAMA, 269:71-75). Accordingly, there is a need for more effective therapies to combat this disease and/or to prevent the recurrence of this disease in patients colonized with *C. difficile*. In addition, there is a need to treat patients who are at risk for developing a *C. difficile* infection by prophylactic administration of an effective agent. Included in this at risk patient population are the elderly, in particular, patients 65 years of age and older, although patients younger than 65 may be at greater risk depending on the presence of any underlying disease that may predispose them to infection with *C. difficile*. Patients that have been infected with *C. difficile* previously may be at greater risk of recurrences. Other patients at risk include patients who are pre-disposed to a *C. difficile* infection because of an underlying medical condition, or patients who are hospitalized for long periods of time (at least one week or longer) and/or, who are on long term treatment (≥14 days) with broad spectrum antibiotics, as well as patients who are on proton pump inhibitors to treat gastroesophageal reflux disease (GERD), stomach and small intestine ulcers and inflammation of the esophagus. These agents include dexlansoprazole, esomeprazole, lansoprazole, omeprazole, pantoprazole sodium, or rabeprazole sodium. Other agents that are under study for placing a patient at risk for developing a *C. difficile* infection include histamine-H2 receptor blockers, such as cimetidine, famotidine, nizatidine and ranitidine. Other studies noted an age-specific incidence of *C. difficile*-associated diarrhea, more specifically, an increase in patients after the age of 50 years, and an increase in mortality rate in patients after the age of 60 (Loo, V G, et al., (2005), N Engl J Med 353:2442-9). This study was in fact, consistent with an earlier study that showed an age-related increase in the incidence of positive assays for *C. difficile* toxin (Karlström, O. et al. (1998), Clin Infect Dis 26:141-5).

To address the need for more effective therapies against *C. difficile*, many studies have been conducted to determine if anti-toxin A and/or B antibodies, when used alone, or as adjunct therapy, could be used as a means of treating this disease, or at least as a means of preventing the recurrence of the diarrhea or colitis associated with *C. difficile* infection. (Corthier, et al. (1991), Infect. Immun. 59(3):1192-1195; Kink, J. A. and Willilams, J. A., (1998), Infect. Immun. 66(5): 2018-2025; Lowy, I. et al. (2010), N. Engl. J. Med. 362(3): 197-205; Babcock, G. J., et al.; (2006), Infection and Immunity, 74(11):6339-6347). More particularly, animal models of infection with *C. difficile* have been used to study the effect of antibodies to toxin A and/or toxin B from *C. difficile* on primary infection, as well as on relapse rates in vivo (Corthier, G. et al. (1991), Infect. Immun. 59(3):1192-1195; Kink, J. A.

et al. (1998), Infect. Immun. 66(5):2018-2025; Babcock, G. J. et al. (2006), 74(11):6339-6347). The results in animal models of *C. difficile* showed significant protection, thus prompting further clinical trials using anti-toxin A and anti-toxin B antibodies in human patients with the disease (Lowy, I., et al., (2010), N. Engl. J. Med. 362(3):197-205).

The antibodies described herein demonstrate specific binding to toxin A and/or to toxin B of *C. difficile* and may be useful for treating patients suffering from infection with *C. difficile*. The use of such antibodies may be an effective means of treating patients suffering from a primary infection with *C. difficile*, or they may be used to prevent a relapse or recurrence of the disease and the accompanying symptoms associated with the disease, or may be used to lessen the severity of the diarrhea or colitis associated with a primary infection or with the recurrence of the infection. They may be used alone or as adjunct therapy with other therapeutic moieties or modalities known in the art for treating *C. difficile* infections, such as, but not limited to, antibiotic therapy, for example, with metronidazole, vancomycin, or fidaxomicin. They may be used in conjunction with a *C. difficile* vaccine, or with use of a toxoid, or with a second or third different antibody specific for toxin A and/or B.

In certain embodiments of the invention, combinations of the antibodies of the invention may be used to treat an infection caused by a hypervirulent strain of *C. difficile*. The most notable hypervirulent epidemic isolate group to date is one referred to as "BI/NAP1/027". This has been associated with outbreaks of *C. difficile* infections throughout Europe and North America. Isolates that fall into this designation are characterized by increased toxin A and toxin B production, by the presence of an additional toxin (binary toxin) and by an increased resistance to fluoroquinolones (McDonald, L C, et al., (2005), N Engl J Med 353:2433-41; Warny, M E, et al., (2005), Lancet 366:1079-84). This group of isolates may also be referred to as the North American pulsed-field type 1 (NAP1), ribotype 027, group BI strains. This group of strains contains an 18 base pair tcdC gene deletion and the binary toxin, which it produces is encoded by cdtA and cdtB genes. It has been reported that this group produces toxin A and toxin B in quantities 16 and 23 times, respectively, greater than control strains (Warny, M E, et al., (2005), Lancet 366:1079-84). Since the antibodies of the present invention have been shown to neutralize the toxin produced by four different clinically isolated *C. difficile* BI/NAP1/027 strains (VA5, VA17, 6336 and 6443), it is envisioned that compositions comprising the antibodies of the present invention may be administered therapeutically to patients suffering from an infection with the above-noted hypervirulent strains of *C. difficile*, or may be administered prophylactically to patients who are at risk for developing an infection with the hypervirulent strains noted herein, as well as with any other clinically relevant hypervirulent strains. The means by which to identify these strains are known to those skilled in the art, and these methods may include pulsed-field gel electrophoresis (PFGE) of *C. difficile* isolates (See for example, Fawley, W N, et al., (2002), J. Clin Microbiol 40:3546-7), PCR analyses for binary toxin genes and partial deletions of the tcdC gene (See, for example, Gonsalves, C. et al. (2004), J Clin Microbiol 42:1933-9; and Cohen, S H et al., (2000), J Infect Dis 181: 659-63), and restriction-endonuclease analyses (See, for example, Clabots, C R, et al., (1993), J Clin Microbiol 31:1870-5).

In certain embodiments, the antibodies of the invention are obtained from mice immunized with a primary immunogen, such as a native, inactivated, toxin A (See GenBank accession number CAA63564 (SEQ ID NO: 378)), or toxin B (See GenBank accession number CAJ67492 (SEQ ID NO: 380)) from *C. difficile*, or with a recombinant, but inactivated form of the toxins, or toxin fragments, followed by immunization with a secondary immunogen, or with an immunogenically active fragment of the native toxin. Animals may be immunized with either inactivated toxin A alone or inactivated toxin B alone, or with both inactivated toxin A and inactivated toxin B concurrently. The toxins can be inactivated prior to use as an immunogen using standard procedures for preparing toxoids, including by treatment with formaldehyde, glutaraldehyde, peroxide, or oxygen treatment (Relyveld, et al. *Methods in Enzymology*, 93:24, 1983, Woodrow and Levine, eds. *New Generation Vaccines*, Marcel Dekker, Inc., New York, 1990). Another means of inactivation is by use of UDP-dialdehyde (Genth et al., (2000), Infect. Immun. 68(3):1094-1101), which may act to preserve the native structure of the toxin compared to other inactivation methods, thereby enhancing the likelihood of eliciting antibodies that are more reactive with the native toxin.

Alternatively, mutant toxins from *C. difficile*, which exhibit reduced toxicity, may be produced using standard recombinant techniques and used as immunogens (See, for example, U.S. Pat. Nos. 5,085,862; 5,221,618; 5,244,657; 5,332,583; 5,358,868; and 5,433,945). Such mutants may contain deletions or point mutations in the active site of the toxin.

The immunogen may be a biologically active and/or immunogenic fragment of native toxin A or toxin B, or DNA encoding the active fragment thereof. The fragment may be derived from the N-terminal or C-terminal domain of either toxin A or toxin B. The fragment may be derived from any of the known domains of toxin A or toxin B (See FIG. 1), including the glucosylating enzymatic domain (A), the autocatalytic processing domain (C), the translocating domain (D) or the binding domain (B). In certain embodiments of the invention, the immunogen is the carboxy terminal receptor binding domain of toxin A that ranges from about amino acid residues 1832-2710 of SEQ ID NO: 378. In certain embodiments of the invention, the immunogen is the carboxy terminal receptor binding domain of toxin A that is shown in SEQ ID NO: 375. In certain embodiments of the invention, the immunogen is the carboxy terminal receptor binding domain of toxin B that ranges from about amino acid residues 1834-2366 of SEQ ID NO: 380. In certain embodiments of the invention, the immunogen is the carboxy terminal receptor binding domain of toxin B that is shown in SEQ ID NO: 376.

The full-length amino acid sequence of toxin A from *C. difficile* is shown as SEQ ID NO: 378.

The full-length amino acid sequence of toxin B from *C. difficile* is shown as SEQ ID NO: 380.

In certain embodiments, antibodies that bind specifically to *C. difficile* toxin A or toxin B may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of toxin A or toxin B specific antibodies. In certain embodiments, any one or more of the above-noted regions of toxin A or toxin B, or fragments thereof may be used for preparing monospecific, bispecific, or multispecific antibodies.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to either toxin A and/or toxin B of *C. difficile*. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (V) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to toxin A and/or toxin B of *C. difficile*.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to toxin A and/or toxin B of *C. difficile* are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-toxin A and anti-toxin B antibodies and antibody fragments of the present invention encompass proteins having amino acid sequences that vary from those of the described antibodies, but that retain the ability to bind toxin A or toxin B. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Biological Characteristics of the Antibodies

In general, the antibodies of the present invention may function by binding to either toxin A or to toxin B of *C. difficile*, or to both toxin A and toxin B of *C. difficile* (cross-reactive antibodies), or to a fragment of either A or B.

In certain embodiments, the antibodies of the present invention may bind to an epitope located in at least the C-terminal receptor binding domain of toxin A and/or toxin B of *C. difficile*. In one embodiment, the antibodies may bind to the C-terminal region of toxin A, ranging from amino acid residue 1832-2710 of the carboxy terminal receptor binding domain of toxin A, which spans amino acid residues 1832-2710 of SEQ ID NO: 378. In certain embodiments of the invention, the antibodies may bind the carboxy terminal receptor binding domain of toxin A that is shown in SEQ ID NO: 375. In certain embodiments of the invention, the antibodies may interact with, or bind to, amino acid residues 468-863 of the carboxy terminal receptor binding domain of toxin A produced by *Clostridium difficile*, the sequence of which is shown in SEQ ID NO: 375. In certain embodiments of the invention, the antibodies may interact with, or bind to, an epitope in the carboxy terminal receptor binding domain of toxin A produced by *Clostridium difficile*, wherein the epitope is selected from the group consisting of residues 468-488 of SEQ ID NO: 375, residues 510-530 of SEQ ID NO: 375, residues 602-610 of SEQ ID NO: 375, residues 644-703 of SEQ ID NO: 375, residues 724-794 of SEQ ID NO: 375, residues 799-814 of SEQ ID NO: 375 and residues 858-863 of SEQ ID NO: 375. In one embodiment, the antibody that binds to or interacts with an epitope in the carboxy terminal receptor binding domain of toxin A produced by *Clostridium difficile*, selected from the group consisting of residues 468-488 of SEQ ID NO: 375, residues 510-530 of SEQ ID NO: 375, residues 602-610 of SEQ ID NO: 375, residues 644-703 of SEQ ID NO: 375, residues 724-794 of SEQ ID NO: 375, residues 799-814 of SEQ ID NO: 375 and residues 858-863 of SEQ ID NO: 375 comprises the HCVR/LCVR amino acid sequence pair of SEQ ID NOs: 146/154. In one embodiment, the antibody that binds to or interacts with an epitope in the carboxy terminal receptor binding domain of toxin A produced by *Clostridium difficile*, selected from the group consisting of residues 468-488 of SEQ ID NO: 375, residues 510-530 of SEQ ID NO: 375, residues 602-610 of SEQ ID NO: 375, residues 644-703 of SEQ ID NO: 375, residues 724-794 of SEQ ID NO: 375, residues 799-814 of SEQ ID NO: 375 and residues 858-863 of SEQ ID NO: 375 is combined with a second antibody that binds specifically to toxin B of *Clostridium difficile* in a pharmaceutical composition. In one embodiment, this second antibody that interacts with or binds to toxin B of *Clostridium difficile* comprises the HCVR/LCVR amino acid sequence pair of SEQ ID NOs: 274/282.

In certain embodiments of the invention, the antibodies may bind to the carboxy terminal receptor binding domain of toxin B that ranges from about amino acid residues 1834-2366 of SEQ ID NO: 380. In certain embodiments of the invention, the antibodies may bind to the carboxy terminal receptor binding domain of toxin B that is shown in SEQ ID NO: 376.

In certain embodiments, the antibodies of the present invention may function by blocking or inhibiting the toxicity associated with toxin A of *C. difficile* by binding to any other region or fragment of the full length native toxin A protein, the amino acid sequence of which is shown in SEQ ID NO: 378, which is encoded by the nucleic acid sequence shown in SEQ ID NO: 377.

In certain embodiments, the antibodies of the present invention may function by blocking or inhibiting the toxicity associated with toxin B of *C. difficile* by binding to any other region or fragment of the full length native toxin B protein, the amino acid sequence of which is shown in SEQ ID NO: 380, which is encoded by the nucleic acid sequence shown in SEQ ID NO: 379.

In certain embodiments, the antibodies of the present invention may be bi-specific antibodies. The bi-specific antibodies of the invention may bind one epitope in toxin A and may also bind one epitope in toxin B. In certain embodiments, the bi-specific antibodies of the invention may bind two different epitopes in toxin A. In certain embodiments, the bi-specific antibodies of the invention may bind two different epitopes in toxin B. In certain embodiments, the bi-specific antibodies of the invention may bind to two different sites within the same domain on either one of toxin A or toxin B, or may bind to the same domain on both toxin A and toxin B.

In one embodiment, the invention provides a fully human monoclonal antibody or antigen-binding fragment thereof that binds to the carboxy terminal receptor binding domain of both toxin A and toxin B of *C. difficile*, wherein the antibody or fragment thereof exhibits one or more of the following characteristics: (i) comprises a HCVR having an amino acid sequence selected from the group consisting of SEQ ID NO: 18, 34, 50, 66 and 82, or a substantially similar sequence thereof having at least 90%, at least 95%, at least 98% or at least 99% sequence identity; (ii) comprises a LCVR having an amino acid sequence selected from the group consisting of SEQ ID NO: 26, 42, 58, 74 and 90, or a substantially similar sequence thereof having at least 90%, at least 95%, at least 98% or at least 99% sequence identity; (iii) comprises a HCDR3 domain having an amino acid sequence selected from the group consisting of SEQ ID NO: 24, 40, 56, 72 and 88, or a substantially similar sequence thereof having at least 90%, at least 95%, at least 98% or at least 99% sequence identity; and a LCDR3 domain having an amino acid sequence selected from the group consisting of SEQ ID NO: 32, 48, 64, 80 and 96, or a substantially similar sequence thereof having at least 90%, at least 95%, at least 98% or at least 99% sequence identity; (iv) comprises a HCDR1 domain having an amino acid sequence selected from the group consisting of SEQ ID NO: 20, 36, 52, 68 and 84, or a substantially similar sequence thereof having at least 90%, at least 95%, at least 98% or at least 99% sequence identity; a HCDR2 domain having an amino acid sequence selected from the group consisting of SEQ ID NO: 22, 38, 54, 70 and 86, or a substantially similar sequence thereof having at least 90%, at least 95%, at least 98% or at least 99% sequence identity; a LCDR1 domain having an amino acid sequence selected from the group consisting of SEQ ID NO: 28, 44, 60, 76 and 92, or a substantially similar sequence thereof having at least 90%, at least 95%, at least 98% or at least 99% sequence identity; and a LCDR2 domain having an amino acid sequence selected from the group consisting of SEQ ID NO: 30, 46, 62, 78 and 94, or a substantially similar sequence thereof having at least 90%, at least 95%, at least 98% or at least 99% sequence identity; (v) binds to toxin A and toxin B with a $K_D$ equal to or less than $10^{-9}$M.

In one embodiment, the invention provides a fully human monoclonal antibody or antigen-binding fragment thereof that binds specifically to toxin A (but not to toxin B) of *C. difficile*, wherein the antibody or fragment thereof exhibits one or more of the following characteristics: (i) comprises a HCVR having an amino acid sequence selected from the group consisting of SEQ ID NO: 2, 98, 114, 130, 146 and 162, or a substantially similar sequence thereof having at least 90%, at least 95%, at least 98% or at least 99% sequence identity; (ii) comprises a LCVR having an amino acid sequence selected from the group consisting of SEQ ID NO: 10, 106, 122, 138, 154 and 170, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 104, 120, 136, 152 and 168, or a substantially similar sequence thereof having at least 90%, at least 95%, at least 98% or at least 99% sequence identity; and a LCDR3 domain having an amino acid sequence selected from the group consisting of SEQ ID NO: 16, 112, 128, 144, 160 and 176, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 100, 116, 132, 148 and 164, or a substantially similar sequence thereof having at least 90%, at least 95%, at least 98% or at least 99% sequence identity; a HCDR2 domain having an amino acid sequence selected from the group consisting of SEQ ID NO: 6, 102, 118, 134, 150 and 166, or a substantially similar sequence thereof having at least 90%, at least 95%, at least 98% or at least 99% sequence identity; a LCDR1 domain having an amino acid sequence selected from the group consisting of SEQ ID NO: 12, 108, 124, 140, 156 and 172, or a substantially similar sequence thereof having at least 90%, at least 95%, at least 98% or at least 99% sequence identity; and a LCDR2 domain having an amino acid sequence selected from the group consisting of SEQ ID NO: 14, 110, 126, 142, 158 and 174, or a substantially similar sequence thereof having at least 90%, at least 95%, at least 98% or at least 99% sequence identity; (v) demonstrates a $K_D$ equal to or less than $10^{-9}$M; (vi) demonstrates neutralization of Toxin A (at a concentration of 32 pM) with an IC50 ranging from about 7 pM to about 65 pM in a cell viability assay.

In one embodiment, the invention provides a fully human monoclonal antibody or antigen-binding fragment thereof that binds specifically to toxin B (but not to toxin A) of *C. difficile*, wherein the antibody or fragment thereof exhibits one or more of the following characteristics: (i) comprises a HCVR having an amino acid sequence selected from the group consisting of SEQ ID NO: 178, 194, 210, 226, 242, 258, 274, 290, 306, 322, 338 and 354, or a substantially similar sequence thereof having at least 90%, at least 95%, at least 98% or at least 99% sequence identity; (ii) comprises a LCVR having an amino acid sequence selected from the group consisting of SEQ ID NO:186, 202, 218, 234, 250, 266, 282, 298, 314, 330, 346 and 362, or a substantially similar sequence thereof having at least 90%, at least 95%, at least 98% or at least 99% sequence identity; (iii) comprises a HCDR3 domain having an amino acid sequence selected from the group consisting of SEQ ID NO:184, 200, 216, 232, 248, 264, 280, 296, 312, 328, 344 and 360, or a substantially similar sequence thereof having at least 90%, at least 95%, at least 98% or at least 99% sequence identity; and a LCDR3 domain having an amino acid sequence selected from the group consisting of SEQ ID NO:192, 208, 224, 240, 256, 272, 288, 304, 320, 336, 352 and 368, or a substantially similar sequence thereof having at least 90%, at least 95%, at least 98% or at least 99% sequence identity; (iv) comprises a HCDR1 domain having an amino acid sequence selected from the group consisting of SEQ ID NO: 180, 196, 212, 228, 244, 260, 276, 292, 308, 324, 340 and 356, or a substantially similar sequence thereof having at least 90%, at least 95%, at least 98% or at least 99% sequence identity; a HCDR2 domain having an amino acid sequence selected from the group consisting of SEQ ID NO: 182, 198, 214, 230, 246, 262, 278, 294, 310, 326, 342 and 358, or a substantially similar sequence thereof having at least 90%, at least 95%, at least 98% or at least 99% sequence identity; a LCDR1 domain having an amino acid sequence selected from the group consisting of SEQ ID NO: 188, 204, 220, 236, 252, 268, 284, 300, 316, 332, 348 and 364, or a substantially similar sequence thereof having at least 90%, at least 95%, at least 98% or at least 99% sequence identity; and a LCDR2 domain having an amino acid sequence selected from the group consisting of SEQ ID NO: 190, 206, 222, 238, 254, 270, 286, 302, 318, 334, 350 and 366, or a substantially similar sequence thereof having at least 90%, at least 95%, at least 98% or at least 99% sequence identity; (v) demonstrates a $K_D$ equal to or less than $10^{-9}$M; (vi) demonstrates neutralization of Toxin B (at a concentration of 0.03 pM) with an IC50 ranging from about 25 pM to about 320 pM in a cell viability assay.

Certain anti-toxin A or anti-toxin B antibodies of the present invention are able to bind to and neutralize the toxicity of either toxin A, or toxin B, or both, of *C. difficile*, as determined by in vitro or in vivo assays. The ability of the antibodies of the invention to bind to and neutralize the activity of the toxins may be measured using any standard method known to those skilled in the art, including binding assays, or neutralization of toxicity (protection from cell death) assays, as described herein.

Non-limiting, exemplary in vitro assays for measuring binding activity are illustrated in Examples 4, 5 and 6, herein. In Examples 4 and 5, the binding affinities and kinetic constants of human anti-toxin A or anti-toxin B antibodies were determined by surface plasmon resonance and the measurements were conducted on a T200 Biacore instrument. In Example 6, the binding studies were conducted using size exclusion chromatography. In Example 7, a neutralization bioassay was developed in Vero cells to detect cell viability after treatment with toxin A or B and antibodies to either toxin A or to toxin B.

The present invention also includes anti-toxin A or B antibodies and antigen binding fragments thereof which bind to at least one biologically active fragment of any of the following proteins, or peptides: SEQ ID NO: 378 (full length toxin A), residue numbers 1832-2710 of SEQ ID NO: 378 (C-terminal domain of toxin A); SEQ ID NO: 380 (full length toxin B), residues 1834-2366 of SEQ ID NO: 380; SEQ ID NO: 375 (carboxy terminal receptor binding domain of toxin A); or SEQ ID NO: 376. The present invention also provides for antibodies that interact with or bind to an epitope within the carboxy terminal receptor binding domain of toxin A produced by *Clostridium difficile*, or an antigen binding fragment thereof, wherein the epitope is contained within residues ranging from about residue 468 to about 863 of SEQ ID NO: 375. In one embodiment, the epitope for an antibody that binds toxin A is selected from the group consisting of residues 468-488 of SEQ ID NO: 375, residues 510-530 of SEQ ID NO: 375, residues 602-610 of SEQ ID NO: 375, residues 644-703 of SEQ ID NO: 375, residues 724-794 of SEQ ID NO: 375, residues 799-814 of SEQ ID NO: 375 and residues 858-863 of SEQ ID NO: 375. Any of the toxin A or toxin B peptides described herein, or fragments thereof, may be used to generate anti-toxin A or anti-toxin B antibodies.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization. The antibodies specific for toxin A or toxin B may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Epitope Mapping and Related Technologies

Various techniques known to persons of ordinary skill in the art can be used to determine whether an antibody "interacts with one or more amino acids" within a polypeptide or protein. Exemplary techniques include, for example, a routine cross-blocking assay such as that described *Antibodies*, Harlow and Lane (Cold Spring Harbor Press, Cold Spring Harb., N.Y.) can be performed. Other methods include alanine scanning mutational analysis, peptide blot analysis (Reineke (2004) Methods Mol Biol 248:443-63), peptide cleavage analysis crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) *Analytical Biochemistry* 267(2):252-259; Engen and Smith (2001) *Anal. Chem.* 73:256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-toxin A or anti-toxin B antibody or antigen-binding fragments thereof binds an epitope within any one of the regions exemplified in FIG. 1, or in SEQ ID NOS: 378, or 380, or at least one of the carboxy terminal receptor binding domains of toxin A or toxin B, or to a fragment thereof, wherein the carboxy terminal receptor binding domain of toxin A is shown in SEQ ID NO: 375, and wherein the carboxy terminal receptor binding domain of toxin B is shown as SEQ ID NO: 376.

The present invention includes anti-toxin A or anti-toxin B antibodies that bind to the same epitope as any of the specific exemplary antibodies described herein in Table 1. Likewise, the present invention also includes anti-toxin A or anti-toxin B antibodies that compete for binding to toxin A or B or a toxin A or B fragment with any of the specific exemplary antibodies described herein in Table 1.

One can easily determine whether an antibody binds to the same epitope as, or competes for binding with, a reference anti-toxin A or anti-toxin B antibody by using routine methods known in the art. For example, to determine if a test antibody binds to the same epitope as a reference anti-toxin A or anti-toxin B antibody of the invention, the reference antibody is allowed to bind to a toxin A or B protein or peptide under saturating conditions. Next, the ability of a test antibody to bind to the toxin A or B molecule is assessed. If the test antibody is able to bind to toxin A or B following saturation binding with the reference anti-toxin A or anti-toxin B antibody, it can be concluded that the test antibody binds to a different epitope than the reference anti-toxin A or anti-toxin B antibody. On the other hand, if the test antibody is not able to bind to the toxin A or B molecule following saturation binding with the reference anti-toxin A or anti-toxin B antibody, then the test antibody may bind to the same epitope as the epitope bound by the reference anti-toxin A or anti-toxin B antibody of the invention.

To determine if an antibody competes for binding with a reference anti-toxin A or anti-toxin B antibody, the above-described binding methodology is performed in two orientations: In a first orientation, the reference antibody is allowed to bind to a toxin A or B molecule under saturating conditions followed by assessment of binding of the test antibody to the toxin A or B molecule. In a second orientation, the test antibody is allowed to bind to a toxin A or B molecule under saturating conditions followed by assessment of binding of the reference antibody to the toxin A or B molecule. If, in both orientations, only the first (saturating) antibody is capable of binding to the toxin A or B molecule, then it is concluded that the test antibody and the reference antibody compete for binding to toxin A or B. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-toxin A or anti-toxin B monoclonal antibody conjugated to a therapeutic moiety ("immunoconjugate"), such as an agent that is capable of reducing the severity of primary infection with *C. difficile*, or to ameliorate at least one symptom associated with *C. difficile* infection, including diarrhea or colitis, or the severity thereof. Such an agent may be a second different antibody to either or both toxin A or toxin B of *C. difficile*, or a toxoid, or a *C. difficile* vaccine. The type of therapeutic moiety that may be conjugated to the anti-toxin A or anti-toxin B antibody and will take into account the condition to be treated and the desired therapeutic effect to be achieved. Alternatively, if the desired therapeutic effect is to treat the sequelae or symptoms associated with *C. difficile* infection, or any other condition resulting from such infection, such as, but not limited to, pseudomembranous colitis, it may be advantageous to conjugate an agent appropriate to treat the sequelae or symptoms of the condition, or to alleviate any side effects of the antibodies of the invention. Examples of suitable agents for forming immunoconjugates are known in the art, see for example, WO 05/103081.

Multi-Specific Antibodies

The antibodies of the present invention may be mono-specific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, the present invention includes bi-specific antibodies wherein one arm of an immunoglobulin is specific for toxin A of *C. difficile*, or a fragment thereof, and the other arm of the immunoglobulin is specific for toxin B of

*C. difficile*, or a second therapeutic target, or is conjugated to a therapeutic moiety. In certain embodiments of the invention, one arm of an immunoglobulin is specific for an epitope on the C-terminal domain of toxin A or a fragment thereof, and the other arm of the immunoglobulin is specific for an epitope on the C-terminal domain of toxin B, or a fragment thereof.

An exemplary bi-specific antibody format that can be used in the context of the present invention involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_{H3}$ domain binds Protein A and the second Ig $C_{H3}$ domain contains a mutation that reduces or abolishes Protein A binding such as an H95R modification (by IMGT exon numbering; H435R by EU numbering). The second $C_{H3}$ may further comprise a Y96F modification (by IMGT; Y436F by EU). Further modifications that may be found within the second $C_{H3}$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Administration and Formulations

The invention provides therapeutic compositions comprising the anti-toxin A or anti-toxin B antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of each of the antibodies of the invention may vary depending upon the age and the size of a subject to be administered, target disease, conditions, route of administration, and the like. When the antibodies of the present invention are used for treating a *C. difficile* infection in a patient, or for treating one or more symptoms associated with a *C. difficile* infection, such as the diarrhea or colitis associated with a *C. difficile* infection in a patient, or for preventing a relapse of the disease, or for lessening the severity of the disease, it is advantageous to administer each of the antibodies of the present invention intravenously or subcutaneously normally at a single dose of about 0.01 to about 30 mg/kg body weight, more preferably about 0.1 to about 20 mg/kg body weight, or about 0.1 to about 15 mg/kg body weight, or about 0.02 to about 7 mg/kg body weight, about 0.03 to about 5 mg/kg body weight, or about 0.05 to about 3 mg/kg body weight, or about 1 mg/kg body weight, or about 3.0 mg/kg body weight, or about 10 mg/kg body weight, or about 20 mg/kg body weight. Multiple doses may be administered as necessary. Depending on the severity of the condition, the frequency and the duration of the treatment can be adjusted. In certain embodiments, the antibodies or antigen-binding fragments thereof of the invention can be administered as an initial dose of at least about 0.1 mg to about 800 mg, about 1 to about 600 mg, about 5 to about 300 mg, or about 10 to about 150 mg, to about 100 mg, or to about 50 mg. In certain embodiments, the initial dose may be followed by administration of a second or a plurality of subsequent doses of the antibodies or antigen-binding fragments thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousands Oaks, Calif.), the PENLET™ (Haselmeier, Stuttgart, Germany), the EPIPEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Administration Regimens

According to certain embodiments of the present invention, multiple doses of an antibody to toxin A and/or B of *Clostridium difficile* may be administered to a subject over a defined time course. The methods according to this aspect of the invention comprise sequentially administering to a subject multiple doses of an antibody to toxin A and/or B. As used herein, "sequentially administering" means that each dose of antibody to toxin A and/or B is administered to the subject at a different point in time, e.g., on different days separated by a predetermined interval (e.g., hours, days, weeks or months). The present invention includes methods which comprise sequentially administering to the patient a single initial dose of an antibody to toxin A and/or B, followed by one or more secondary doses of the antibody to toxin A and/or B, and optionally followed by one or more tertiary doses of the antibody to toxin A and/or B.

The terms "initial dose," "secondary doses," and "tertiary doses," refer to the temporal sequence of administration of the antibody to toxin A and/or B. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of antibody to toxin A and/or B, but generally may differ from one another in terms of frequency of administration. In certain embodiments, however, the amount of antibody to toxin A and/or B contained in the initial, secondary and/or tertiary doses vary from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antibody to toxin A and/or B which is administered to a patient prior to the administration of the very next dose in the sequence with no intervening doses.

The methods according to this aspect of the invention may comprise administering to a patient any number of secondary and/or tertiary doses of an antibody to toxin A and/or B. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Therapeutic Uses of the Antibodies

Due to their interaction with toxin A and/or toxin B of *C. difficile*, the present antibodies are useful for treating the primary *C. difficile* disease or condition, or at least one symptom associated with the disease or condition, such as diarrhea or colitis, or for preventing a relapse of the disease, or for lessening the severity, duration, and/or frequency of recurrences of the disease. The antibodies of the invention are also contemplated for prophylactic use in patients at risk for developing or acquiring a *C. difficile* infection. These patients include the elderly (for example, in anyone 65 years of age or older), or patients immunocompromised due to illness or treatment with immunosuppressive therapeutics, or patients who may have an underlying medical condition that predisposes them to a *C. difficile* infection (for example, cancer, inflammatory bowel disease, pre-liver transplant patients with ascites accumulation), or patients that are hospitalized for long periods of time (for example, in some cases this time period may vary from as little as two or three days, but generally can be from one week, to two weeks or longer), making them prone to acquiring nosocomial infections, or patients on long term treatment (≥14 days) with broad spectrum antibiotics (in some instances, patients may acquire the infection within 24 hours if the gut is disregulated, but in other instances this may take much longer, for example, one week or longer), or patients on therapy with proton pump inhibitors for treatment of gastrointestinal disorders. It is contemplated that the antibodies of the invention may be used alone, or in conjunction with a second agent, or third agent for treating the *C. difficile* infection, or for alleviating at least one symptom or complication associated with the *C. difficile* infection, such as the diarrhea or colitis associated with, or resulting from such an infection. The second or third agents may be delivered concurrently with the antibodies of the invention, or they may be administered separately, either before or after the antibodies of the invention.

In yet a further embodiment of the invention the present antibodies are used for the preparation of a pharmaceutical composition for treating patients suffering from a *C. difficile* infection, including those infections caused by a clinically relevant hypervirulent strain of *Clostridium difficile*, or the diarrhea and colitis associated with a *C. difficile* infection. In yet another embodiment of the invention the present antibodies are used for the preparation of a pharmaceutical composition for reducing the severity of a primary infection with *C. difficile*, or for reducing the severity, duration of, and/or number of recurrences with *C. difficile*. In a further embodiment of the invention the present antibodies are used as adjunct therapy with any other agent useful for treating *C. difficile* infections, including probiotics, antibiotics, toxoids, vaccines, or any other palliative therapy known to those skilled in the art.

Combination Therapies

The methods of the present invention, according to certain embodiments, comprise administering to the subject one or more additional therapeutic agents in combination with an antibody to toxin A and/or toxin B of *Clostridium difficile*. As used herein, the expression "in combination with" means that the additional therapeutic agents are administered before, after, or concurrent with the pharmaceutical composition comprising the anti-toxin A and/or B antibodies. The term "in combination with" also includes sequential or concomitant administration of the anti-toxin A and/or B antibodies and a second therapeutic agent.

For example, when administered "before" the pharmaceutical composition comprising the anti-toxin A and/or B antibodies, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the anti-toxin A and/or B antibodies. When administered "after" the pharmaceutical composition comprising the anti-toxin A and/or B antibodies, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the anti-toxin A and/or B antibodies. Administration "concurrent" or with the pharmaceutical composition comprising the anti-toxin A and/or B antibodies means that the additional therapeutic agent is administered to the subject in a separate dosage form within less than 5 minutes (before, after, or at the same time) of administration of the pharmaceutical composition comprising the anti-toxin A and/or B antibodies, or administered to the subject as a single combined dosage formulation comprising both the additional therapeutic agent and the anti-toxin A and/or B antibodies.

Combination therapies may include an anti-toxin A or anti-toxin B antibody of the invention and any additional therapeutic agent that may be advantageously combined with an antibody of the invention, or with a biologically active fragment of an antibody of the invention.

For example, a second or third therapeutic agent may be employed to aid in reducing the bacterial load in the gut, such as an antibiotic that is bacteriostatic or bacteriocidal with respect to *C. difficile*. Exemplary antibiotics include vancomycin, metronidazole, or fidaxomicin. The antibodies may also be used in conjunction with other therapies, such as toxoids, vaccines specific for *C. difficile*, or probiotic agents, such as *Saccharomyces boulardii*.

Diagnostic Uses of the Antibodies

The anti-toxin A or anti-toxin B antibodies of the present invention may also be used to detect and/or measure toxin A or B in a sample, e.g., for diagnostic purposes. It is envisioned that confirmation of an infection thought to be caused by *C. difficile* may be made by measuring the presence of either toxin A or toxin B through use of any one or more of the antibodies of the invention. Exemplary diagnostic assays for toxin A or toxin B may comprise, e.g., contacting a sample, obtained from a patient, with an anti-toxin A or anti-toxin B antibody of the invention, wherein the anti-toxin A or anti-toxin B antibody is labeled with a detectable label or reporter molecule or used as a capture ligand to selectively isolate toxin A or toxin B protein from patient samples. Alternatively, an unlabeled anti-toxin A or anti-toxin B antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure toxin A or toxin B in a sample include enzyme-linked immunosorbent assay (ELISA), radioimmunoassay (RIA), and fluorescence-activated cell sorting (FACS).

Samples that can be used in *C. difficile* diagnostic assays according to the present invention include any tissue or fluid sample obtainable from a patient, which contains detectable quantities of either *C. difficile* toxin A or toxin B protein, or fragments thereof, under normal or pathological conditions. Generally, levels of toxin A or toxin B in a particular sample obtained from a healthy patient (e.g., a patient not afflicted with a disease or condition associated with the presence of *C. difficile*) will be measured to initially establish a baseline, or standard, level of toxin A or toxin B from *C. difficile*. This baseline level of toxin A or toxin B can then be compared against the levels of toxin A or toxin B measured in samples obtained from individuals suspected of having a *C. difficile* related disease or condition, or symptoms associated with such disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to *Clostridium difficile* Toxin A and/or Toxin B An immunogen comprising any one of the following can be used to generate antibodies to *C. difficile* toxin A and/or toxin B. In certain embodiments, the antibodies of the invention are obtained from mice immunized with a primary immunogen, such as a full length, native, inactivated, toxin A (See GenBank accession number CAA63564 (SEQ ID NO: 378)), and/or toxin B (See GenBank accession number CAJ67492 (SEQ ID NO: 380)) from *C. difficile*, or with a recombinant, but inactivated form of the toxins, or toxin fragments, or a toxoid, followed by immunization with a secondary immunogen, or with an immunogenically active fragment of the native toxin. Animals may be immunized with either inactivated toxin A alone or inactivated toxin B alone, or with both inactivated toxin A and inactivated toxin B, concurrently. The toxins can be inactivated prior to use as an immunogen using standard procedures for preparing toxoids, including by treatment with formaldehyde, glutaraldehyde, peroxide, or oxygen treatment (Relyveld, et al. *Methods in Enzymology*, 93:24, 1983, Woodrow and Levine, eds. *New Generation Vaccines*, Marcel Dekker, Inc., New York, 1990). Another means of inactivation is by use of UDP-dialdehyde (Genth et al., (2000), Infect. Immun. 68(3):1094-1101), which may act to preserve the native structure of the toxin compared to other inactivation methods, thereby enhancing the likelihood of eliciting antibodies that are more reactive with the native toxin. Alternatively, mutant toxins from *C. difficile*, which exhibit reduced toxicity, may be produced using standard recombinant techniques and used as immunogens (See, for example, U.S. Pat. Nos. 5,085,862; 5,221,618; 5,244,657; 5,332,583; 5,358,868; and 5,433,945). Such mutants may contain deletions or point mutations in the active site of the toxin.

In certain embodiments, the antibodies of the invention are obtained from mice immunized with a primary immunogen, such as a biologically active and/or immunogenic fragment of native toxin A or toxin B, or DNA encoding the active fragment thereof. In certain embodiments, the immunogen may be a peptide from the N terminal or C terminal end of toxin A and/or toxin B, or a fragment derived from the N or C terminal peptide of toxin A and/or toxin B. In certain embodiments of the invention, the immunogen is the carboxy terminal receptor binding domain of toxin A that ranges from about amino acid residues 1832-2710 of SEQ ID NO: 378. In certain embodiments of the invention, the immunogen is the carboxy terminal receptor binding domain of toxin A that is shown in SEQ ID NO: 375. In certain embodiments of the invention, the immunogen is the carboxy terminal receptor binding domain of toxin B that ranges from about amino acid residues 1834-2366 of SEQ ID NO: 380. In certain embodiments of the invention, the immunogen is the carboxy terminal receptor binding domain of toxin B that is shown in SEQ ID NO: 376.

Accordingly, in one embodiment, the antibodies of the invention were obtained from mice immunized with either an inactivated full length toxin A (toxoid), or an inactivated full length toxin B (toxoid), or both toxoids. Furthermore, in one embodiment, antibodies were obtained from mice immunized with a polypeptide comprising amino acid sequences from the carboxy-terminal receptor binding domain of *C. difficile* toxin A, or with a polypeptide comprising amino acid sequences from the carboxy-terminal receptor binding domain of *C. difficile* toxin B, or both, concurrently.

In certain embodiments, antibodies that bind specifically to *C. difficile* toxin A or toxin B may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of toxin A or toxin B specific antibodies. In certain embodiments, any one or more of the above-noted regions of toxin A or toxin B, or fragments thereof may be used for preparing monospecific, bispecific, or multispecific antibodies.

The full length proteins, or carboxy-terminal fragments thereof, that were used as immunogens, as noted above, were administered directly, with an adjuvant to stimulate the immune response, to a VELOCIMMUNE® mouse comprising DNA encoding human Immunoglobulin heavy and kappa light chain variable regions. The antibody immune response was monitored by a *C. difficile* toxin A and/or toxin B-specific immunoassay. When a desired immune response was achieved splenocytes were harvested and fused with mouse myeloma cells to preserve their viability and form hybridoma cell lines. The hybridoma cell lines were screened and selected to identify cell lines that produce *C. difficile* toxin A and/or toxin B-specific antibodies. Using this technique, and the various immunogens described above, several anti-*C. difficile* toxin A and toxin B, as well as cross-reactive, chimeric antibodies (i.e., antibodies possessing human variable domains and mouse constant domains) were obtained; certain exemplary antibodies generated in this manner were designated as H1H3067N, H1H3134N, H1H3117N, H1M3123N, H1M3121N and H1M3124N.

Anti-*C. difficile* toxin A and toxin B antibodies were also isolated directly from antigen-positive B cells without fusion to myeloma cells, as described in U.S. 2007/0280945A1, herein specifically incorporated by reference in its entirety. Using this method, several fully human anti-*C. difficile* toxin A and toxin B antibodies (i.e., antibodies possessing human variable domains and human constant domains) were obtained; exemplary antibodies generated in this manner were designated as follows: H1H3328P, H1H3324P, H1H3325P, H1H3330P, H1H3350P, H1H3347P, H1H3335P, H1H3344P, H1H3339P, H1H3337P, H1H3343P, H1H3411P, H1H3354P, H1H3317P, H1H3355P, H1H3394P and H1H3401P.

The biological properties of the exemplary antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected antibodies specific for toxin A and/or toxin B from *C. difficile* and their corresponding antibody identifiers. Antibodies are typically referred to herein according to the following nomenclature: Fc prefix (e.g. "H4H", "H1M", "H2M"), followed by a numerical identifier (e.g. "3117" as shown in Table 1), followed by a "P" or "N" suffix. Thus, according to this nomenclature, an antibody may be referred to as, e.g. "H1H3117". The H4H, H1M, and H2M prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs), which are indicated by the numerical identifiers shown in Table 1, will remain the same. Antibodies having the same numerical antibody designation, but differing by a letter suffix of N, B or P refer to antibodies having heavy and light chains with identical CDR sequences but with sequence variations in regions that fall outside of the CDR sequences (i.e., in the framework regions). Thus, N, B and P variants of a particular antibody have identical CDR sequences within their heavy and light chain variable regions but differ from one another within their framework regions.

Antibody Comparators

Anti-toxin A and anti-toxin B antibody controls were included in the following Examples for comparative purposes. Isotype matched negative controls were also used in the Examples. One anti-toxin A control antibody is designated herein as Control I and is an anti-toxin A antibody with heavy and light chain variable domain sequences of the "3D8" antibody as set forth in U.S. Pat. No. 7,625,559 and US2005/0287150. One anti-toxin B antibody is designated herein as Control II and is an anti-toxin B antibody with heavy and light chain variable domain sequences of the "124-152" antibody as set forth in U.S. Pat. No. 7,625,559 and US2005/0287150. Another anti-toxin A antibody is designated herein as Control III and is an anti-toxin A antibody with heavy and light chain variable domain sequences of the "3358" antibody as set forth in US2009/0087478.

Example 3

Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each Heavy Chain Variable Region (HCVR) and Light Chain Variable Region (LCVR). Table 2 sets forth the gene usage for selected antibodies in accordance with the invention.

TABLE 2

| Antibody | Antibody Identifier HCVR/LCVR | HCVR | | | LCVR | |
|---|---|---|---|---|---|---|
| | | $V_H$ | $D_H$ | $J_H$ | $V_K$ | $J_K$ |
| H1H3067N | 34/42 | 3-30 | 6-6 | 4 | 4-1 | 4 |
| H1H3134N | 18/26 | 3-33 | 3-10 | 4 | 4-1 | 3 |
| H1H3117N | 2/10 | 3-23 | 1-7 | 4 | 3-20 | 2 |
| H1H3123N | 66/74 | 3-48 | 4-11 | 6 | 1-5 | 1 |
| H1H3121N | 50/58 | 3-48 | 5-18 | 6 | 1-5 | 1 |
| H1H3124N | 82/90 | 3-48 | 3-22 | 6 | 1-5 | 1 |
| H1H3328P | 130/138 | 3-13 | 3-10 | 6 | 1-27 | 3 |
| H1H3324P | 98/106 | 3-13 | 3-10 | 6 | 1-27 | 3 |
| H1H3325P | 114/122 | 3-23 | 3-10 | 6 | 1-5 | 1 |
| H1H3330P | 146/154 | 3-33 | 1-7 | 4 | 1-39 | 5 |
| H1H3350P | 162/170 | 3-11 | 7-27 | 4 | 3-15 | 2 |
| H1H3347P | 274/282 | 3-23 | 1-26 | 4 | 1-16 | 3 |
| H1H3335P | 194/202 | 3-23 | 1-26 | 4 | 1-16 | 3 |
| H1H3344P | 258/266 | 3-23 | 2-15 | 4 | 1-16 | 3 |
| H1H3339P | 226/234 | 3-23 | 1-26 | 4 | 1-16 | 3 |
| H1H3337P | 210/218 | 3-23 | 1-26 | 5 | 1-16 | 3 |
| H1H3343P | 242/250 | 3-23 | 1-26 | 4 | 1-16 | 3 |
| H1H3411P | 354/362 | 3-23 | 1-1 | 6 | 1D-12 | 2 |
| H1H3354P | 290/298 | 6-1 | 2-8 | 4 | 3-11 | 2 |
| H1H3317P | 178/186 | 3-30 | 3-10 | 4 | 1D-12 | 4 |
| H1H3355P | 306/314 | 3-9 | 1-26 | 6 | 1-6 | 3 |
| H1H3394P | 322/330 | 1-2 | 2-2 | 4 | 3-20 | 4 |
| H1H3401P | 338/346 | 3-30 | 1-1 | 4 | 1D-12 | 2 |

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H3117N | 2 | 4 | 6 | 8 | 10 | 12 | 14 | 16 |
| H1H3134N | 18 | 20 | 22 | 24 | 26 | 28 | 30 | 32 |
| H1H3067N | 34 | 36 | 38 | 40 | 42 | 44 | 46 | 48 |
| H1H3121N | 50 | 52 | 54 | 56 | 58 | 60 | 62 | 64 |
| H1H3123N | 66 | 68 | 70 | 72 | 74 | 76 | 78 | 80 |
| H1H3124N | 82 | 84 | 86 | 88 | 90 | 92 | 94 | 96 |
| H1H3324P | 98 | 100 | 102 | 104 | 106 | 108 | 110 | 112 |
| H1H3325P | 114 | 116 | 118 | 120 | 122 | 124 | 126 | 128 |
| H1H3328P | 130 | 132 | 134 | 136 | 138 | 140 | 142 | 144 |
| H1H3330P | 146 | 148 | 150 | 152 | 154 | 156 | 158 | 160 |
| H1H3350P | 162 | 164 | 166 | 168 | 170 | 172 | 174 | 176 |
| H1H3317P | 178 | 180 | 182 | 184 | 186 | 188 | 190 | 192 |
| H1H3335P | 194 | 196 | 198 | 200 | 202 | 204 | 206 | 208 |
| H1H3337P | 210 | 212 | 214 | 216 | 218 | 220 | 222 | 224 |
| H1H3339P | 226 | 228 | 230 | 232 | 234 | 236 | 238 | 240 |
| H1H3343P | 242 | 244 | 246 | 248 | 250 | 252 | 254 | 256 |
| H1H3344P | 258 | 260 | 262 | 264 | 266 | 268 | 270 | 272 |
| H1H3347P | 274 | 276 | 278 | 280 | 282 | 284 | 286 | 288 |
| H1H3354P | 290 | 292 | 294 | 296 | 298 | 300 | 302 | 304 |
| H1H3355P | 306 | 308 | 310 | 312 | 314 | 316 | 318 | 320 |
| H1H3394P | 322 | 324 | 326 | 328 | 330 | 332 | 334 | 336 |
| H1H3401P | 338 | 340 | 342 | 344 | 346 | 348 | 350 | 352 |
| H1H3411P | 354 | 356 | 358 | 360 | 362 | 364 | 366 | 368 |

Example 4

Antibody Binding to Toxin A and/or Toxin B from *C. difficile* as Determined by Surface Plasmon Resonance Binding affinities and kinetic constants of human monoclonal anti-*Clostridium difficile* toxin A and/or B antibodies were determined by surface plasmon resonance at 37° C. (Tables 3-5). Measurements were conducted on a T200 Biacore instrument.

Antibodies, expressed as human IgG1 Fc (AbPID prefix H1H) or hybridoma (AbPID prefix HxM), were captured onto an anti-human or anti-mouse-Fc sensor surface, respectively (Mab capture format). Soluble full-length toxin A or B (TechLab), ranging from 5 to 10 nM, was injected over the antibody-captured surface. Antibody-antigen association was monitored for 150 seconds while dissociation in buffer was monitored for 480 seconds. Kinetic analysis was performed to calculate $K_D$ and half-life of antigen/antibody complex dissociation using Biacore T200 evaluation software 1.0.

As seen in Tables 3-5, three types of antibodies were isolated: antibodies that bound both toxin A and toxin B ("dual binders", see Table 3), antibodies that bound only toxin A (Table 4), and antibodies that bound only toxin B (Table 5). Several antibodies were identified that bound both toxin A and toxin B, including those designated as H2M3121N, H2M3123N, H2M3124N, H1H3067N and H1H3134N and thus were classified as dual binders. Isolated anti-toxin A antibodies bound toxin in the sub-nanomolar (nM) range similar to the isotype matched comparator Mab (control I; see U.S. Pat. No. 7,625,559 for comparator sequences for clone 3D8 (A toxin Ab) and clone 124-152 (B toxin Ab)), while only a few anti-toxin B binders showed affinities in the range of control II isotype matched comparator Mab (clone 124-152) (~200-300 pM). Binding dissociation equilibrium constants and dissociative half-lives were calculated from the kinetic rate constants as: $K_D = k_d/k_a$; $T_{1/2}$ (min) $= (\ln 2/k_d)/60$

TABLE 3

Biacore affinities of anti-*C. difficile* Dual Binding mAbs at 37° C. Binding at 37° C./Mab Capture Format

| AbPID | Analyte (Toxin) | ka (Ms$^{-1}$) | kd (s$^{-1}$) | $K_D$ (Molar) | T½ (min) |
|---|---|---|---|---|---|
| H2M3121N | Toxin A | 9.69E+05 | 1.66E−04 | 1.72E−10 | 69 |
| | Toxin B | 6.11E+04 | 7.58E−05 | 1.24E−09 | 152 |
| H2M3123N | Toxin A | 1.23E+06 | 5.93E−04 | 4.81E−10 | 19 |
| | Toxin B | 3.97E+04 | 6.54E−05 | 1.65E−09 | 176 |
| H2M3124N | Toxin A | 1.14E+06 | 1.98E−04 | 1.74E−10 | 58 |
| | Toxin B | 3.31E+05 | 1.00E−06 | 3.02E−12 | 11550 |
| H1H3067N | Toxin A | 1.44E+05 | 3.45E−05 | 2.40E−10 | 335 |
| | Toxin B | 2.54E+03 | 6.43E−04 | 2.53E−07 | 18 |
| H1H3134N | Toxin A | 1.02E+05 | 2.82E−06 | 2.78E−11 | 4096 |
| | Toxin B | 2.99E+03 | 9.73E−04 | 3.25E−07 | 12 |

TABLE 4

Biacore affinities of anti-*C. difficile* Toxin A mAbs at 37° C. Binding at 37° C./Mab Capture Format

| AbPID | Analyte | ka (Ms$^{-1}$) | kd (s$^{-1}$) | $K_D$ (Molar) | T½ (min) |
|---|---|---|---|---|---|
| H1H3117N | Toxin A | 4.38E+05 | 3.84E−05 | 7.93E−11 | 332 |
| H1H3324P | Toxin A | 2.51E+05 | 3.50E−06 | 1.39E−11 | 3297 |
| H1H3325P | Toxin A | 5.27E+05 | 5.51E−05 | 1.05E−10 | 209 |
| H1H3328P | Toxin A | 3.82E+05 | 3.66E−05 | 9.57E−11 | 316 |
| H1H3330P | Toxin A | 2.50E+05 | 1.37E−04 | 5.47E−10 | 85 |
| H1H3350P | Toxin A | 4.02E+05 | 4.05E−06 | 1.01E−11 | 2854 |
| Control I | Toxin A | 3.77E+05 | 3.24E−05 | 8.59E−11 | 58 |

TABLE 5

Biacore affinities of anti-*C. difficile* Toxin B mAbs at 37° C.

| AbPID | Analyte | ka (Ms$^{-1}$) | kd (s$^{-1}$) | $K_D$ (Molar) | T½ (min) |
|---|---|---|---|---|---|
| H1H3317P | Toxin B | 6.50E+05 | 7.78E−05 | 1.20E−10 | 149 |
| H1H3335P | Toxin B | 1.77E+05 | 4.14E−04 | 2.34E−09 | 28 |
| H1H3337P | Toxin B | 2.41E+05 | 9.45E−04 | 3.93E−09 | 12 |
| H1H3339P | Toxin B | 2.76E+05 | 5.37E−04 | 1.95E−09 | 22 |
| H1H3343P | Toxin B | 2.84E+05 | 4.48E−04 | 1.58E−09 | 26 |
| H1H3344P | Toxin B | 2.04E+05 | 8.65E−04 | 4.24E−09 | 13 |
| H1H3347P | Toxin B | 3.39E+05 | 8.13E−04 | 2.40E−09 | 14 |
| H1H3354P | Toxin B | NB | NB | NB | |
| H1H3355P | Toxin B | NB | NB | NB | |
| H1H3394P | Toxin B | 4.86E+05 | 1.62E−04 | 3.33E−10 | 72 |
| H1H3401P | Toxin B | 4.20E+05 | 2.41E−04 | 5.74E−10 | 48 |
| H1H3411P | Toxin B | 2.35E+05 | 1.59E−04 | 6.77E−10 | 73 |
| Control II | Toxin B | 2.11E+06 | 4.59E−04 | 2.18E−10 | 25 |

NB = no binding under the conditions tested

Example 5

Determination of the Binding Domain for Anti-*Clostridium difficile* Toxin A and B Antibodies Using Surface Plasmon Resonance Studies were done to determine if anti-*Clostridium difficile* toxin A and/or B antibodies bound to the C-term receptor-Binding Domain (CBD) of each toxin. In these studies, two experimental Biacore formats were employed. The first utilized captured anti-*C. difficile* antibody surfaces in which 100 nM of CBD-toxin A-Fc (SEQ ID NO:375) or CBD-toxin B-Fc (SEQ ID NO:376) was flowed over and the responses (RU) recorded. The CBD-toxin reagents were formatted in both human and mouse Fc to enable both hybridoma and human Fc formatted antibody analysis. The second format employed antigen (CBD-Fc) captured surfaces in which 500 nM of anti-*C. difficile* mAb was flowed over. In this format, hybridoma or human Fc formatted antibodies were flowed over human and mouse Fc captured antigens, respectively. In both formats a response that was significantly above background (>50 RU) was considered binding to the CBD of toxin A or B (see Table 6). For both anti-toxin A and anti-toxin B antibodies, epitopes that were within and outside the CBD were obtained. Both control I (3D8 antibody from U.S. Pat. No. 7,625,559 and US 2005/0287150) and control II (124-152 antibody from U.S. Pat. No. 7,625,559 and US 2005/0287150) were mapped to the CBD of their respective toxins in agreement with previous reports (data not shown; see US 2005/0287150 and U.S. Pat. No. 7,625,559).

TABLE 6

Determination of the domain of binding for *C. difficile* antibodies

| mAb | C-term Toxin A Binding | | C-term Toxin B Binding | | Domain Binding# |
|---|---|---|---|---|---|
| | mAb Capture 100 nM CBD-A binding (RU) | CBD-A Capture 500 nM mAB binding (RU) | mAB Capture 100 nM CBD-B Binding (RU) | CBD-B Capture 500 nM mAb binding (RU) | |
| H2aM3067N | −2 | 237 | 25 | 369 | C-Term |
| H1M3117N | −3 | 350 | −1 | 21 | C-Term A |
| H2aM3121N | 0 | 23 | 2 | 10 | Non CBD |
| H2aM3123N | 1 | 23 | 1 | 14 | Non CBD |
| H2aM3124N | 0 | 29 | 0 | 19 | Non CBD |
| H1M3134N | −1 | 195 | 23 | 394 | C-Term |
| H1H3324P | 269 | 224 | 19 | −8 | C-Term A |
| H1H3325P | 17 | 3 | 7 | −8 | Non CBD |
| H1H3328P | 354 | 227 | 35 | −6 | C-Term A |
| H1H3330P | 441 | 515 | 40 | −4 | C-Term A |
| H1H3335P | 13 | 5 | 13 | −6 | Non CBD |
| H1H3337P | −17 | 8 | −24 | −2 | Non CBD |
| H1H3339P | 19 | 2 | 14 | −2 | Non CBD |
| H1H3343P | 11 | 3 | 9 | −4 | Non CBD |
| H1H3344P | 5 | 5 | 4 | −2 | Non CBD |
| H1H3347P | 42 | −13 | 44 | 7 | Non CBD |
| H1H3354P | −19 | −2 | −24 | −4 | Non CBD |

Non CBD indicates no binding to C-term receptor Binding Domain of Toxin-A or -B.

Example 6

Determination of the Domain of Binding for Anti-*Clostridium difficile* Toxin A and B Antibodies Using Size Exclusion Chromatography As a complimentary method for determining if anti-*Clostridium difficile* toxin A and/or B antibodies bound the C-term receptor Binding Domain (CBD), size exclusion chromatography (SEC) was utilized. Briefly, the CBD of toxin A (SEQ ID NO: 375) or the CBD of toxin B (SEQ ID NO: 376), at ~500 nM was mixed with excess antibody at specified molar ratios (1:5 and 1:20; CBD:Mab) in phosphate buffered saline containing 5% glycerol pH 7.4 (PBS/G) and incubated at room temperature for 1 hour.

Any precipitation visible after 1 hr was recorded as +++ (strong), ++ (moderate), + (minimal), or − (not observed). Following centrifugation (5 min. @ 16,000×g), the mixture of antibody and CBD was subjected to SEC analysis using a Superose 6 column (GE Healthcare) with PBS/G as the mobile phase. Protein peaks corresponding to complexes larger than the antibody or CBD alone were interpreted as binding to the C-terminal domain.

The results demonstrated that CBD binding corresponds well with that predicted from the domain of binding inferred from SPR (Biacore) and CBD studies (see example 5). One notable exception was H1H3134N, where binding to CBD-A was not observed via SEC but $K_D$ values indicated dual binding properties for the antibody.

TABLE 7

Domain of binding for anti-*Clostridium difficile* toxin A and B antibodies

| mAb | Precipitation with CBD-A | Observed CBD-A binding via SEC | Precipitation with CBD-B | Observed CBD-B binding via SEC | Domain Binding Via Biacore |
|---|---|---|---|---|---|
| H2M3067N | +++ | Yes | NT | NT | C-Term A/B |
| H1M3117N | +++ | Yes | NT | NT | C-Term A |
| H2M3121N | − | No | NT | NT | Non CBD |
| H2M3123N | − | No | NT | NT | Non CBD |
| H2M3124N | − | No | NT | NT | Non CBD |
| H1M3134N | − | No | NT | NT | C-Term A/B |
| H1H3317P | NT | NT | − | Yes | NT |
| H1H3324P | + | Yes | NT | NT | C-Term A |
| H1H3325P | − | No | NT | NT | Non CBD |
| H1H3328P | − | Yes | NT | NT | C-Term A |
| H1H3330P | − | Yes | N.D. | N.D. | C-Term A |
| H1H3335P | NT | NT | − | No | Non CBD |
| H1H3337P | NT | NT | − | No | Non CBD |
| H1H3339P | NT | NT | − | No | Non CBD |
| H1H3343P | NT | NT | − | No | Non CBD |
| H1H3344P | NT | NT | − | No | Non CBD |
| H1H3347P | NT | NT | − | No | Non CBD |
| H1H3350P | − | Yes | NT | NT | NT |
| H1H3354P | NT | NT | − | No | Non CBD |

NT = Not Tested.
Non CBD indicates no binding to C-term receptor Binding Domain of Toxin-A or -B.

Example 7

Determination of the Neutralization Potency of Anti-*Clostridium difficile* Toxin A and/or Toxin B Antibodies To determine the neutralization potency ($IC_{50}$) of anti-*C. difficile* antibodies in vitro, a cell viability assay was conducted. Briefly, Vero cells ($1.25 \times 10^3$) cultured in MEM alpha medium, supplemented with 10% FBS, were seeded into 96-well microplates and incubated for 16-18 hours at 37° C., in 5% $CO_2$. Anti-*C. difficile* toxin antibodies, at various concentrations (0-66 nM), were added to the cells and subsequently incubated with *C. difficile* toxin A (32 or 25 pM) or toxin B (0.03 pM or 0.01 pM) for 48 hrs. Controls not containing toxin (100% viability) and controls containing toxin but no antibody (100% relative lethality) were utilized. All dilutions of antibody were conducted in triplicate. Following the 2-day incubation, cell viability was measured by adding tetrazolium salt (WST-1; Roche Biochemicals), waiting for 4 hrs to allow for color development and then recording absorbance at 450 nm. Absorbance values were analyzed by a four-parameter logistic equation over an 11-point response curve (GraphPad Prism).

The results showed that ten antibodies displayed neutralization against toxin A with $IC_{50}$ values ranging from 7 pM to 65 pM at 25-32 pM constant toxin A (Table 8A). Of note, H1H3330P demonstrated neutralization potency equal to that of Control III (isotype matched comparator antibody, clone 3358 as set forth in US2009/0087478) and potency of approximately 20 fold greater than control I (see US2005/0287150 for clone 3D8). Several toxin-B neutralizing antibodies showed significantly greater potency than control II (isotype matched comparator antibody, see clone 124-152 of US2005/0287150) with $IC_{50}$s ranging from 25-120 pM at 0.03 pM constant toxin B (Table 8B). Antibodies H1M3067N and H1M3134N, while able to bind both toxin A and B showed only neutralization activity against toxin A. While the reason for this is not yet known, one possible explanation for this finding may be that while antibodies can bind at many sites in the repetitive regions of the C terminal portion of the toxin, other parts of the same toxin domain may still be capable of interacting with the mammalian membrane, thus allowing entry of the toxin into the cell.

TABLE 8A

Neutralization potency ($IC_{50}$) for selected mAbs against Toxin A

| mAb | Trial 1 ($IC_{50}$) 32 pM Toxin A | Trial 2 ($IC_{50}$) 32 pM Toxin A | Trial 3 ($IC_{50}$) 32 pM Toxin A | Trial4 ($IC_{50}$) 32 pM Toxin A | Trial5 ($IC_{50}$) 25 pM Toxin A |
|---|---|---|---|---|---|
| H1M3067N | 64 pM | 44 pM | NT | NT | NT |
| H1M3117N | 29 pM | 11 pM | NT | NT | NT |
| H2aM3121N | 65 pM | 35 pM | NT | NT | NT |
| H2aM3123N | 65 pM | 24 pM | NT | NT | NT |
| H2aM3124N | 41 pM | 21 pM | NT | NT | NT |
| H1M3134N | NT | NT | NT | 38 pM | NT |
| H1H3324P | NT | NT | NT | 33 pM | NT |
| H1H3325P | NT | NT | NT | 33 pM | NT |
| H1H3328P | NT | NT | 112 pM | NT | NT |
| H1H3330P | NT | NT | 7 pM | NT | 7 pM |
| Control I | NT | NT | NT | NT | 199 pM |
| Control III | 18 pM | 6 pM | 10 pM | 11 pM | 9 pM |

NT: Not tested

TABLE 8B

Neutralization potency ($IC_{50}$) for selected Mabs against Toxin B

| mAb | Trial 1 ($IC_{50}$) 0.1 pM Toxin B | Trial 2 ($IC_{50}$) 0.1 pM Toxin B | Trial3 ($IC_{50}$) 0.03 pM Toxin B |
|---|---|---|---|
| H1M3067N | No Neutralization | | |
| H1M3134N | No Neutralization | | |
| H1H3317P | No Neutralization | NT | NT |
| H1H3335P | 730 pM | 380 pM | 120 pM |
| H1H3337P | 1730 pM | 980 pM | 320 pM |
| H1H3339P | 480 pM | 270 pM | 90 pM |
| H1H3343P | 280 pM | 200 pM | 50 pM |
| H1H3344P | 580 pM | 400 pM | 40 pM |
| H1H3347P | 130 pM | 90 pM | 25 pM |
| H1H3350P | No Neutralization | NT | NT |
| H1H3340P | NT | No Neutralization | NT |

TABLE 8B-continued

Neutralization potency ($IC_{50}$) for selected Mabs against Toxin B

| mAb | Trial 1 ($IC_{50}$) 0.1 pM Toxin B | Trial 2 ($IC_{50}$) 0.1 pM Toxin B | Trial3 ($IC_{50}$) 0.03 pM Toxin B |
|---|---|---|---|
| H1H3411P | NT | 8pM[#] | NT |
| Control II | 1800 pM | 1500 pM | 290 pM |

[#]Antibody only partially protect (40-50%) at highest concentration
NT: Not Tested Example 8

Generation of a Bi-Specific Antibody

Various bi-specific antibodies are generated for use in practicing the methods of the invention. For example, *C. difficile* toxin A or toxin B-specific antibodies are generated in a bi-specific format (a "bi-specific") in which variable regions binding to distinct domains of toxin A and/or B are linked together to confer dual-domain and/or dual toxin specificity within a single binding molecule. Appropriately designed bi-specifics may enhance overall toxin neutralization efficacy through increasing both specificity and binding avidity. Variable regions with specificity for individual domains, as shown in FIG. 1, (e.g., segments of the N-terminal domain, which is the glucosylating enzymatic domain (designated as domain 'A'), or the autocatalytic processing domain (designated as domain 'C'), or the translocating domain (designated as domain D'), or the carboxy terminal receptor binding domain (designated as domain 'B') or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind both toxin A and/or toxin B and a second target, such as, but not limited to, for example, a second different anti-toxin A or anti-toxin B antibody, or a toxoid, or a vaccine, may be prepared in a bi-specific format using techniques described herein, or other techniques known to those skilled in the art. Antibody variable regions binding to distinct toxin A regions may be linked together with variable regions that bind to relevant sites on, for example, toxin B, to confer dual-antigen specificity within a single binding molecule. Appropriately designed bi-specifics of this nature serve a dual function. For example, in the case of a bi-specific antibody that binds both toxin A and toxin B, one may be able to better neutralize both toxin A and toxin B concurrently, without the need for administration of a composition containing two separate antibodies. Variable regions with specificity for toxin A, are combined with a variable region with specificity for toxin B and are paired on a structural scaffold that allows each variable region to bind to the separate antigens.

The bi-specific binders are tested for binding and functional blocking of the target antigens, for example, toxin A and toxin B, in any of the assays described above for antibodies. For example, standard methods to measure soluble protein binding are used to assess the bispecific interaction, such as Biacore, ELISA, size exclusion chromatography, multi-angle laser light scattering, direct scanning calorimetry, and other methods. Binding of bi-specific antibodies to both toxin A and toxin B is determined through use of an ELISA binding assay in which synthetic peptides representing the different toxins are coated onto the wells of microtiter plates, and binding of a bi-specific is determined through use of a secondary detection antibody. Binding experiments can also be conducted using surface plasmon resonance experiments, in which real-time binding interaction of peptide to antibody is measured by flowing a peptide or bi-specific across a sensor surface on which bi-specific or peptide, respectively, is captured. Functional in vitro blocking of both toxin A and toxin B by a bi-specific is determined using any bioassay such as the neutralization assay described herein, or by in vivo protection studies in appropriate animal models, such as those described herein.

Example 9

Evaluation of In Vivo Efficacy of Anti-Toxin a and/or Anti-Toxin B Antibodies Against *C. difficile* Infection (CDI) in a Hamster Relapse Model (A) and in an Acute Hamster Model (B)

The efficacy of antibodies specific for toxin A and/or toxin B from *C. difficile* against infection with *C. difficile* was evaluated in hamsters in two different models, described below. Hamsters, in the presence of clindamycin, are sensitive to *C. difficile* infection and usually die within 2-4 days after infection.

(A) Relapse Model:

Male Syrian Golden Hamsters were given an oral suspension containing a mixture of *C. difficile* spores and vegetative cells ($10^6$ in total) on day −1. Twenty-four hours after infection (day 0), animals received a single subcutaneous injection of clindamycin (10 mg/kg). On days 1-3, hamsters were administered oral vancomycin (10 mg/kg) once per day to ameliorate the infection. The antibiotic vancomycin is used clinically to treat a *C. difficile* infection. After the last vancomycin dose, antibodies were administered subcutaneously q.d. for 4 days (days 3-6), or 1 day (day 3) according to their treatment and dosing group (see Tables 9A and 9B below).

Two different trials (See FIGS. 2 and 3) using the relapse model as a surrogate for clinical efficacy were conducted. Both trials compared two antibody combinations:

1. Antibodies designated H1H3330P and H1H3347P
2. Comparator anti-Toxin A (Control I; See U.S. Pat. No. 7,625,559 for clone 3D8 sequence) and comparator anti-Toxin B antibodies (Control II; See U.S. Pat. No. 7,625,559 for clone 124-152 sequence)

In Trial 1, four doses of antibody were administered at 5 mg/kg of each antibody (a total 10 mg/kg dose). In Trial 2, one dose of antibody was given at either 5 mg/kg or 2 mg/kg of each antibody (a total of either 10 mg/kg or 4 mg/kg).

TABLE 9A

Trial 1 Design: Relapse model: Combination Treatments with H1H3330P + H1H3347P or comparator anti-Toxin A + comparator anti-Toxin B

| Group | Treatment* | Dose (mg/kg × # doses) | n |
|---|---|---|---|
| 1 | Negative Control (irrelevant) antibody | 10 × 4 | 14 |
| 2 | Comparator anti-Toxin A and comparator anti-Toxin B | [5/5] × 4 | 23 |
| 3 | (H1H3330P + H1H3347P combination) | [5/5] × 4 | 23 |
| 4 | No antibody | | 15 |

*All animals received vancomycin as noted above.

TABLE 9B

Trial 2 Design: Relapse model: Combination Treatments with H1H3330P + H1H3347P or comparator anti-Toxin A + comparator anti-Toxin B

| Group | Treatment* | Dose (mg/kg × # doses) | n |
|---|---|---|---|
| 1 | Negative Control (irrelevant) antibody | 10 × 1 | 14 |
| 2 | Comparator anti-Toxin A and comparator anti-Toxin B | [5/5] × 1 | 16 |
| 3 | (H1H3330P + H1H3347P combination) | [5/5] × 1 | 16 |
| 4 | Comparator anti-Toxin A and comparator anti-Toxin B | [2/2] × 1 | 16 |
| 5 | (H1H3330P + H1H3347P combination) | [2/2] × 1 | 16 |

*All animals received vancomycin as noted above.

Animals were observed twice a day for the duration of the experiment. General observations included signs for mortality and morbidity, the presence of diarrhea ("wet tail") and overall appearance (activity, general response to handling, touch, ruffled fur). Animals judged to be in a moribund state were euthanized. Criteria used to assign a moribund state were extended periods (5 days) of weight loss, progression to an emaciated state, prolonged lethargy (more than 3 days), signs of paralysis, skin erosions or trauma, hunched posture, and a distended abdomen. Observations continued, with deaths or euthanasia recorded for a period up to 18 days post-infection for the relapse model.

(B) Acute Model:

Male Syrian Golden Hamsters were treated with clindamycin intraperitoneally at a dose of 10 mg/kg on day −1. On day 0 *C. difficile* spores were diluted with sterile PBS to give 100 spores/300 μl and administered by oral gavage. Antibodies were administered every day for 4 days, beginning on day −3 and continuing to day 0, using a subcutaneous route. The dose of the antibodies is indicated in the figure legend. See also Table 9C below for the study outline.

TABLE 9C

Trial 3: Acute model: Combination Treatments with H1H3330P + H1H3347P at various doses

| Group | Treatment | Dose (mg/kg × # doses) | # Animals |
|---|---|---|---|
| 1 | Uninfected control | — | 5 |
| 2 | Infected control | PBS × 4 | 10 |
| 3 | Negative Control (irrelevant) antibody | [100] × 4 | 14 |
| 4 | (H1H3330P + H1H3347P combination) | [50/50] × 4 | 14 |
| 5 | | [16/16] × 4 | 14 |
| 6 | | [5.5/5.5] × 4 | 14 |
| 7 | | 1.85/1.85 × 4 | 14 |

TABLE 9D

Trial 4: Acute model: Combination Treatments with H1H3330P + H1H3347P at various doses

| Group | Treatment | Dose (mg/kg × # doses) | # Animals |
|---|---|---|---|
| 1 | Uninfected control | — | 5 |
| 2 | Infected control | PBS × 4 | 10 |
| 3 | Negative Control (irrelevant) antibody | [100] × 4 | 14 |
| 4 | (H1H3330P + H1H3347P combination) | [20/20] × 4 | 14 |
| 5 | | [5/5] × 4 | 14 |
| 6 | Comparator anti-Toxin A and comparator anti-Toxin B | [20/20] × 4 | 14 |
| 7 | | [5/5] × 4 | 14 |

Animals were observed twice a day for the duration of the experiment. General observations included signs for mortality and morbidity, the presence of diarrhea ("wet tail") and overall appearance (activity, general response to handling, touch, ruffled fur). Animals judged to be in a moribund state were euthanized. Criteria used to assign a moribund state were extended periods (5 days) of weight loss, progression to an emaciated state, prolonged lethargy (more than 3 days), signs of paralysis, skin erosions or trauma, hunched posture, and a distended abdomen. Observations continued, with deaths or euthanasia recorded for a period up to 10 days for the acute model.

Results

Statistical analysis of data from hamster models was done using the Log-Rank (Mantel Cox) test. For pairwise comparisons the Bonferroni correction was applied to the critical P value.

Figure 2:
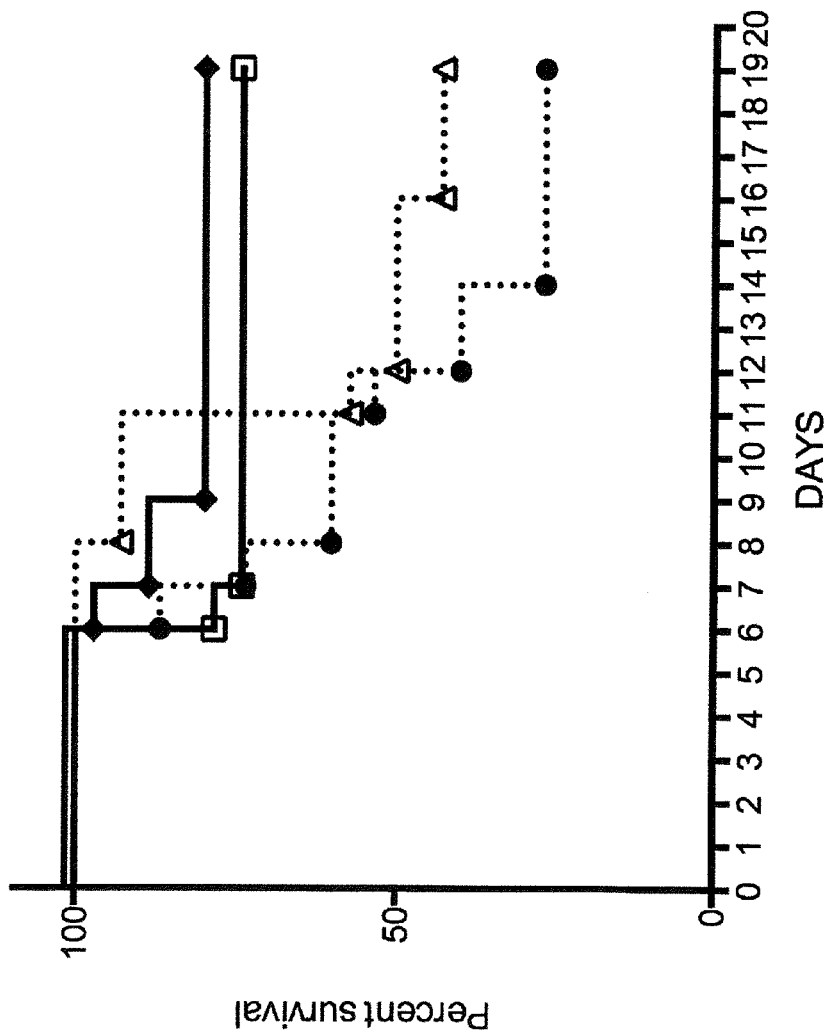
FIG. 2 is a graph showing results of hamster relapse assays as the percentage of hamsters surviving clindamycin and vancomycin treatment following *C. difficile* challenge and the effect of treatment with anti-toxin A and anti-toxin B mAbs. All antibodies were given subcutaneously once a day on days 3-6. Positive control antibodies are comparator antibodies, anti-Toxin A (control I) and anti-Toxin B (control II). Vancomycin was given as an oral dose at 10 mg/kg on days 1-3 to all animals. (● with dotted line: PBS control; Δ with dotted line: Negative isotype control at 10 mg/kg; □ with solid line: Control I/Control II at 5 mg/kg each (5/5); ◆ with solid line: H1H3330P/H1H3347P at 5 mg/kg each (5/5)).

In the first trial, which was a multi-dose study using a hamster relapse model, (see FIG. 2), combination treatment with H1H3330P plus H1H3347P, or combination treatment with the comparator antibodies, showed an increase in overall survival vs isotype control, or vancomycin alone, (74-78%; combination of anti-toxin A and anti-toxin B antibodies vs 27-43%; control arms). Specifically, by day 19, 27% of the hamsters receiving PBS alone survived; 43% receiving the isotype control survived; 74% receiving the anti-toxin A plus anti-toxin B comparator antibody combination survived; and 78% receiving the H1H3330P (anti-A antibody) plus H1H3347P (anti-B antibody) combination survived.

Figure 3:
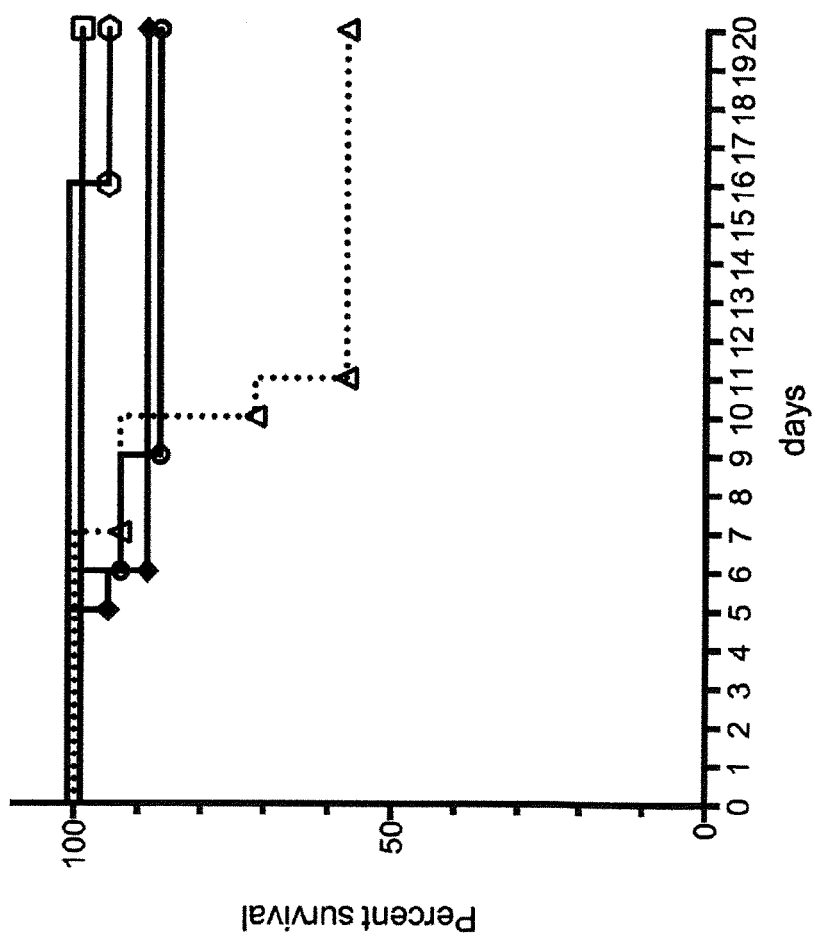
FIG. 3 is a graph showing results of hamster relapse assays as the percentage of hamsters surviving clindamycin and vancomycin treatment following *C. difficile* challenge and the effect of anti-toxin A and anti-toxin B mAbs. All antibodies were given subcutaneously once on day 3. Positive control antibodies are comparator antibodies, anti-Toxin A (control I) and anti-Toxin B (control II). Vancomycin was given as an oral dose at 10 mg/kg on days 1-3 to all animals. (Δ with dotted line: Negative isotype control at 10 mg/kg; □ with solid line: Control I/Control II at 5 mg/kg each (5/5); ◆ with solid line: H1H3330P/H1H3347P at 5 mg/kg each (5/5); ○ with solid line: Control I/Control II at 2 mg/kg each (2/2); ○ with solid line: H1H3330P/H1H3347P at 2 mg/kg each (2/2)).

In the second trial, which was a single-dose study using a hamster relapse model (see FIG. 3), combination treatment with either H1H3330P plus H1H3347P, or the comparator antibodies, increased survival as compared to the isotype control (negative control antibody), although there was no discrimination between the 2 mg/kg and 5 mg/kg doses.

Figure 4:
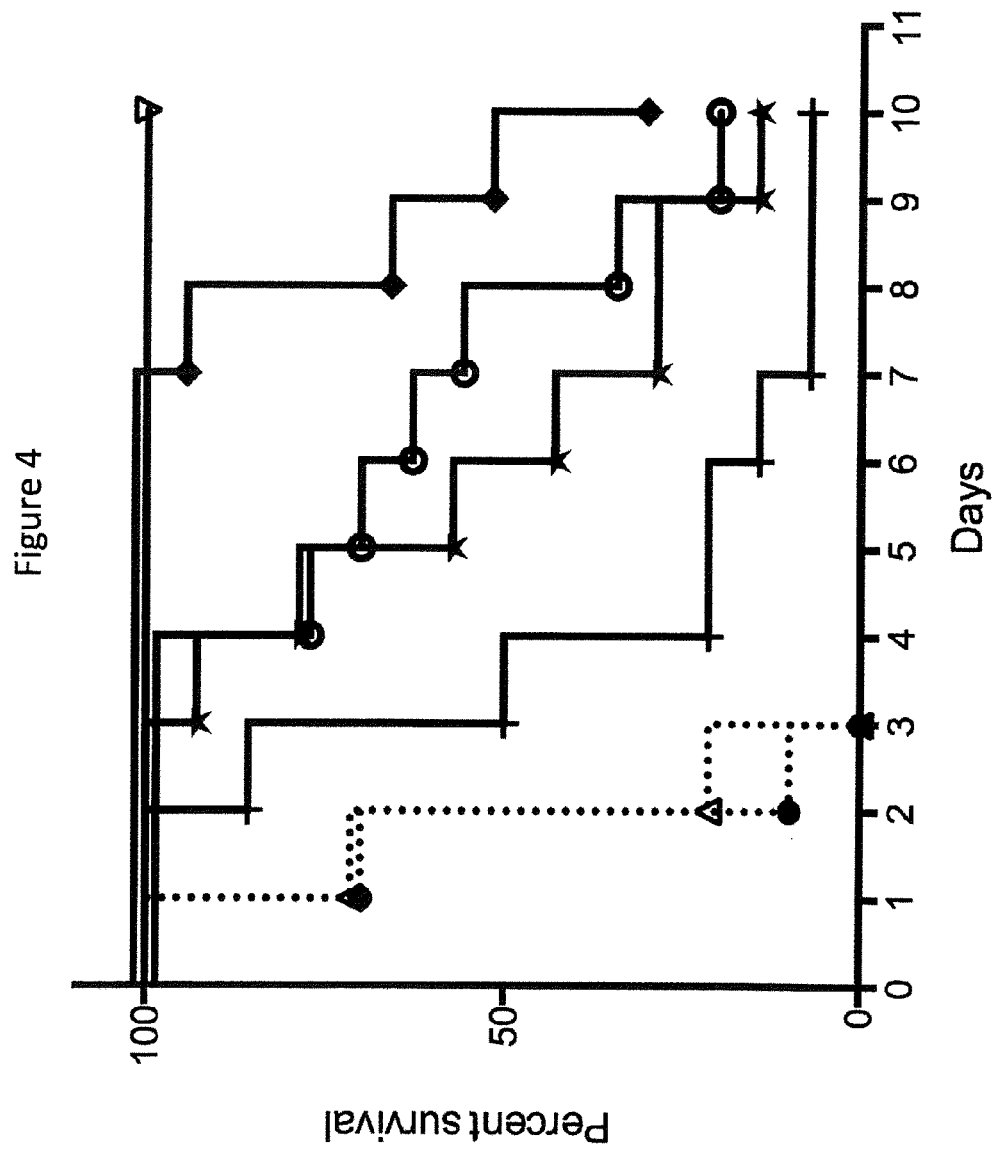
FIG. 4 is a graph showing survival results in an acute model of *C. difficile* infection in hamsters. Results are shown as the percentage of hamsters surviving *C. difficile* challenge (day 0) following clindamycin treatment (day −1). All antibodies were given subcutaneously on each of 4 days from day −3 to day 0. Antibodies were administered at 50 mg/kg each (50/50), 16.6 mg/kg each (16.6/16.6), 5.5 mg/kg each (5.5/5.5) and 1.85 mg/kg each (1.85/1.85). (∇ with solid line: Uninfected; ● with dotted line: PBS control; Δ with dotted line: Negative isotype control at 100 mg/kg; ◆ with solid line: H1H3330P/H1H3347P at 50 mg/kg each (50/50); ○ with solid line: H1H3330P/H1H3347P at 16.6 mg/kg each (16.6/16.6); □ with solid line: H1H3330P/H1H3347P at 5.5 mg/kg each (5.5/5.5); + with a solid line: H1H3330P/H1H3347P at 1.85 mg/kg each (1.85/1.85).

In the first acute model study in hamsters (See FIG. 4), treatment with the H1H3330P plus H1H3347P combination showed significant protection of the hamsters from death in a titratable manner compared to the negative controls ($p<0.0001$ for all groups vs isotype controls). The doses titrated from 50 mg/kg to 1.85 mg/kg (of each antibody given as a combination), with the high dose providing protection for all of the animals until day 7 compared to day 1 for the lowest dose.

Figure 5:
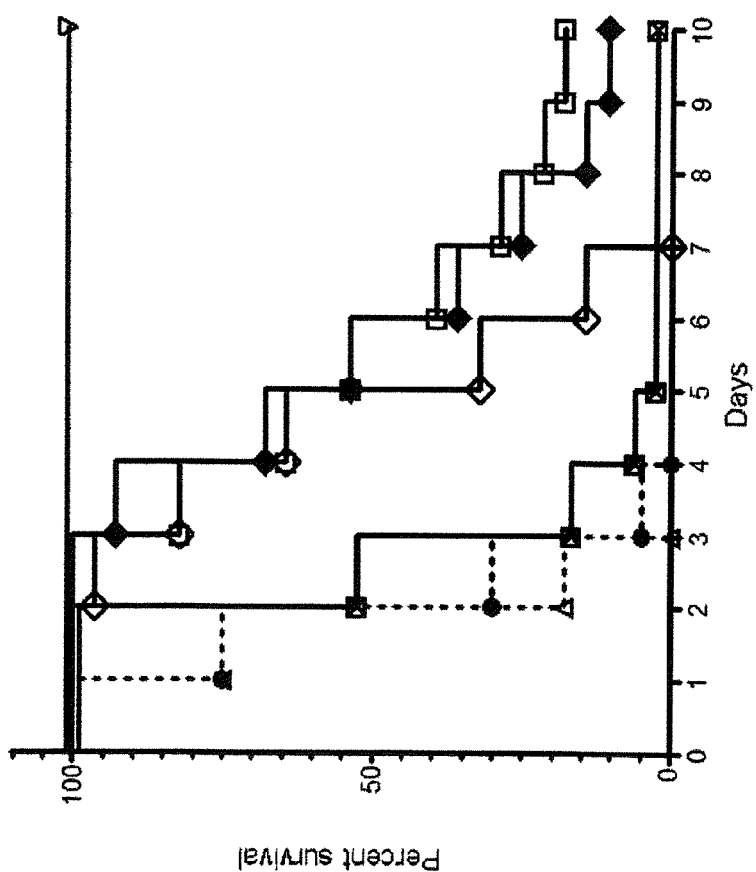
FIG. 5 is a graph showing survival results in an acute model of *C. difficile* infection in hamsters. Results are shown as the percentage of hamsters surviving *C. difficile* challenge (day 0) following clindamycin treatment (day −1). All antibodies were given subcutaneously on each of 4 days from day −3 to day 0. Antibodies were administered at 20 mg/kg each (20/20), or at 5 mg/kg each (5/5). (∇ with solid line: Uninfected; ● with dotted line: PBS control; Δ with dotted line: Negative isotype control at 40 mg/kg; □ with solid line: Control I/Control II at 20 mg/kg each (20/20); ⊠ with solid line: Control I/Control II at 5 mg/kg each (5/5); ◆ with solid line: H1H3330P/H1H3347P at 20 mg/kg each (20/20); ◇ with solid line: H1H3330P/H1H3347P at 5 mg/kg each (5/5)).

In further studies using the acute hamster model (see FIG. 5), combination treatment with either H1H3330P plus H1H3347P, or a combination of the comparator antibodies, significantly increased survival as compared to the isotype control (FIG. 5; Isotype control at 40 mg/kg vs Control I/Control II at 20 mg/kg each, $p<0.0001$; isotype control at 40 mg/kg vs Control I/Control II at 5 mg/kg each, $p=0.0003$; isotype control at 40 mg/kg vs H1H3330P/H1H3347P at 20 mg/kg each, $p<0.0001$; isotype control at 40 mg/kg vs H1H3330P/H1H3347P at 5 mg/kg each, $p<0.0001$). However, treatment with a combination of H1H3330P plus H1H3347P protected the hamsters from death in a manner superior to comparator antibody controls when tested at the low dose of 5 mg/kg of each antibody ($p<0.0001$), whereas there was no significant difference between the combination of H1H3330P plus H1H3347P vs the combination of the comparator antibodies at the higher dose of 20 mg/kg of each antibody ($p=0.73$). This result clearly demonstrates superiority at a low dose in the acute hamster model and suggests that doses of the H1H3330P plus H1H3347P antibodies could be effective in the clinic at lower concentrations compared to the comparator antibodies.

Example 10

The Effect of Anti-Toxin A and Anti-Toxin B Antibodies on Blocking the Cytotoxicity Induced by Culture Supernatant from Several Group BI Hypervirulent *C. difficile* Strains: Comparison with Comparator mAbs Patients infected with clinically-hypervirulent BI/NAP1/027 strains have lower cure rates than patients infected with non-BI strains when treated with either fidaxomicin or vancomycin (Petrella, L A, et al. (2012), Clinical Infectious Diseases, 55(3): 351-357). Furthermore, BI/NAP1/027 strains are associated with a higher CDI recurrence rate and higher expected mortality rate when compared to prototypic strains (Loo, V G, et al. (2005), N Engl J Med, 353:23; Petrella, L A, et al. (2012), Clinical Infectious Diseases, 55(3): 351-357. These hypervirulent strains are characterized by an increase in toxin A and B production, the presence of binary toxin and increased resistance to fluoroquinolones. The increase in toxin A and B production is most likely caused by a loss-of-function mutation in tcdC, a putative negative regulator of tcdA and tcdB expression, resulting in sustained toxin production throughout the lifecycle.

The ability of a 1:1 molar ratio mix of H1H3330P and H1H3347P to neutralize toxin from four clinically-isolated *C. difficile* BI/NAP1/027 strains was tested in a cell-based neutralization assay. The VA5 and VA17 clinically isolated hypervirulent strains were obtained from Case Western Reserve University, Cleveland, Ohio. The 6336 and 6443 clinically isolated hypervirulent strains were obtained from the Dept. of Veterans Affairs, Edward Hines, Jr. Hospital, Hines, Ill. Neutralization assays utilized Vero cells, a monkey kidney epithelial cell line, due to their susceptibility to both *C. difficile* toxins. Cells were incubated with varying amounts of antibody cocktail and a fixed amount of culture supernatant isolated from several *C. difficile* strains for 48 hours. Cytotoxicity was determined by addition of WST-1 reagent, a redox indicator that yields a colorimetric change when reduced; metabolic activity during cell growth reduces WST-1, resulting in increased absorbance at 450 nm.

Culture supernatant from several clinically isolated BI strains exhibited a wide range of cytotoxic activity on Vero cells, with $EC_{50}$ values for inducing cell cytotoxicity ranging from a 3700-fold dilution for the VA5 strain to 88200-fold dilution for the 6443 strain. A 1:1 molar ratio mix of H1H3330P and H1H3347P blocked cytotoxicity induced by culture supernatants from all group BI strains tested with a more than 34-fold better neutralization potency compared to a 1:1 molar ratio mix of comparator anti-Toxin A (control I; See U.S. Pat. No. 7,625,559 for clone 3D8 sequence) and comparator anti-Toxin B (control II; See U.S. Pat. No. 7,625,559 for clone 124-152 sequence). These data demonstrate that the H1H3330P/H1H3347P antibody pair was able to neutralize culture cytotoxicity with $IC_{50}$ values in the picomolar range (31-45 pM) for tested hypervirulent BI strains, compared to the comparator mAb cocktail ($IC_{50}$ range: 1200-1700 pM; see Table 10).

TABLE 10

| | | Neutralization Assay | | | |
|---|---|---|---|---|---|
| Strain | $EC_{50}$ (Fold Dilution) | [Supernatant] (Fold Dilution) | H1H3330P/ H1H3347P $IC_{50}$ (pM) | Comparator mAb 1/2 $IC_{50}$ (pM) | Fold pair/ control |
| VA5 | 6900 | 4700 | 36 | 1400 | 39 |
| VA17 | 3700 | 3000 | 31 | 1400 | 45 |
| 6336 | 15200 | 12100 | 45 | 1700 | 38 |
| 6443 | 88200 | 57500 | 35 | 1200 | 34 |

Example 11

Epitope Mapping of the Anti-Toxin A Antibody H1H3330P

The epitope of the C-term receptor-Binding Domain (CBD) of toxin A (SEQ ID:375) bound by H1H3330P was determined using mass spectrometry based proteomics. Briefly, the CBD of toxin A was subjected to trypsin digestion over a 12 hour period and the samples run on 10-14% gradient SDS-PAGE, followed by transfer to nitrocellulose membranes and Western blot analysis using either the H1H3330P antibody, or the control I antibody (See U.S. Pat. No. 7,625,559 for 3D8 antibody sequence) as primary antibodies. Further analysis of the peptide sequences that bound to the H1H3330P antibody was done using 2D electrophoresis followed by MALDI-TOF MS analysis. The procedures are described in greater detail below.

Limited Trypsin Digestion of Toxin A

Recombinant C-term receptor-Binding Domain (CBD) of toxin A (0.4 μg/μl in PBS) was added with sequence grade modified trypsin (Promega, Cat #V511C) at a 1:80 mass ratio and incubated at 37° C. for 0-12 hr. The enzyme was inactivated by adding 2 volumes of 1× Laemmli sample buffer and heated at 95° C. for 5 min. The samples were stored at −20° C. until analysis.

Western Blot Analysis

The extent of the proteolysis was first examined by 10-14% gradient SDS-PAGE. The amount of each sample loaded was equivalent to 1 μg initial CBD of Toxin A, and the separated proteins in the gel were visualized with SimplyBlue coomassie stain (Invitrogen, Cat# LC6065).

The samples digested for 0 hour and 12 hour were then selected for 10-14% gradient SDS-PAGE separation with an equivalent to 50 ng initial CBD of toxin A loaded for each sample. Separated proteins were transferred to a nitrocellose membrane, and probed with primary antibody H1H3330P or Control Antibody I at a concentration of 1 μg/ml in TBST (Tris-buffer saline solution containing 0.05% Tween-20) overnight at 4° C. followed by anti-human IgG HRP conjugated secondary antibody (Pierce, Cat #31412; at 1:15,000 dilution in TBST). Both H1H3330P & Control 1 antibodies had a human IgG1 constant domain. The membrane was incubated with chemiluminescence substrate (Perkin Elmer, Cat # NEL103E001EA) and the image was captured onto X-ray film.

2D Gel Electrophoresis

To determine which amino acids were represented in the protein band unique to Western blots performed using the H1H3330P antibody, a two-dimensional (2D) gel was performed using the 12 hour trypsin digest of the CBD of toxin A.

In-Gel Trypsin Digestion and Peptide Mapping by MALDI-TOF MS

The 2D-gel analysis revealed 4 protein spots, closely clustered in the pH (pI values~9) dimension, which composed the 50 kDa band that was visualized by Western blot using H1H3330P. The 4 protein spots with corresponding molecular weights of ~50 kDa from the 2D-gel using the 12 hour trypsin digestion were excised, destained by 50% acetonitrile, reduced by 65 mM DTT, and alkylated by 135 mM iodoacetamide. After dehydration by acetonitrile, 20 ul of 2.5 ng/μl sequence grade trypsin (Promega, Cat # V5111) was added to cover the gel bands and the in-gel digestion was carried out by overnight incubation at 37° C.

The resulting peptides were desalted by Ziptip C18 (Millipore, Cat# ZTC18S096) and analyzed by Bruker UltrafleXtreme MALDI-TOF-TOF MS. The spectrum was processed by FlexAnalysis software and internally calibrated with autolytic trypsin fragment peaks. The calibrated peak lists were searched against an in-house database containing the sequence of the CBD Toxin A at a mass accuracy of 10 ppm.

Results

The results showed that blotting with H1H3330P revealed a major protein band at around 50 kDa at 12 hours post trypsin digestion, while no protein band having a molecular weight of around 50 kDa was observed when blotting was carried out with the control 1 antibody at 12 hours post trypsin digestion.

To determine which amino acids were represented in the 50 kDa protein band, unique to Western blots performed using H1H3330P, a two-dimensional (2D) gel was performed using the 12 hour trypsin digest, as described above. As noted, 2D-gel analysis revealed 4 protein spots, closely clustered in the pH (pI values~9) dimension, which composed the 50 kDa band visualized by Western blot using H1H3330P. Mass spectrometry analysis of these 4 protein spots identified 17 matching peptides covering amino acid residues 468-863 of the CBD of toxin A (SEQ ID: 375). This fragment of toxin A (amino acids spanning residue 468 to 863) has a predicted molecular weight of 45 kDa and a predicted isoelectric point of 9.01 corresponding well to the values obtained from 2-D gel analysis.

This example illustrates that the anti-toxin A antibody H1H3330P has an epitope unique from that of Control 1 (3D8 in U.S. Pat. No. 7,625,559) and binds the CBD of toxin Δ within amino acids 468 to 863. Particular amino acid sequences were identified within this region which interacted with the H1H3330P antibody and these amino acid sequences were residues 468-488 of SEQ ID NO: 375, residues 510-530 of SEQ ID NO: 375, residues 602-610 of SEQ ID NO: 375, residues 644-703 of SEQ ID NO: 724-794 of SEQ ID NO: 375, residues 799-814 of SEQ ID NO: 375 and residues 858-863 of SEQ ID NO: 375.

What is claimed is:

1. An isolated antibody or antigen-binding fragment thereof that specifically binds to *Clostridium difficile* toxin A wherein the antibody, or antigen-binding fragment thereof comprises: (a) a HCVR having the amino acid sequence of SEQ ID NO: 146; and (b) a LCVR having the amino acid sequence of SEQ ID NO: 154.

2. A pharmaceutical composition comprising the antibody of claim 1 and a pharmaceutically acceptable carrier or diluent.

3. The pharmaceutical composition of claim 2, wherein the composition further comprises at least one antibody, or an antigen-binding fragment thereof that binds specifically to toxin B of *Clostridium difficile*.

4. The pharmaceutical composition of claim 3, wherein the antibody or an antigen-binding fragment thereof that specifically binds toxin B of *Clostridium difficile* comprises a HCVR having the amino acid sequence of SEQ ID NO: 274 and a LCVR having the amino acid sequence of SEQ ID NO: 282.

5. The pharmaceutical composition of claim 4, wherein the antibodies contained within the composition are effective at neutralizing toxins A and B from a hypervirulent strain of *Clostridium difficile*.

6. The pharmaceutical composition of claim 5, wherein the hypervirulent strain of *Clostridium difficile* is a BI/NAP1/027 strain.

7. The pharmaceutical composition of claim 6, wherein the BI/NAP1/027 strain is selected from VA5, VA17, 6336 and 6443.

* * * * *

SEQUENCE LISTING

<160> NUMBER OF SEQ ID NOS: 398

<210> SEQ ID NO 1
<211> LENGTH: 357
<212> TYPE: DNA
<213> ORGANISM: Artificial Sequence
<220> FEATURE:
<223> OTHER INFORMATION: Synthetic

<400> SEQUENCE: 1
gaggtgcaac tgttggagtc tgggggaggc ttggcacagc ctgggggtc cctgagactc      60 tcctgtgcag cctctggatt caactttggc acccatgaca tgagctgggt ccgccaggct     120
ccagggaagg gactagagtg ggtctcaggt cttacaagta ctggtggtag cgcttcctcc     180
gcagactccg tgaagggccg gttcaccatc tccagagaca attccaagaa tattctgtat     240
ttacaaatga acagcctgag agccgaggac acggccgtat attactgtgc gaaaacgttt     300
aactggaact cctactttga ctactggggc cagggaaccc tggtcaccgt ctcctca       357

<210> SEQ ID NO 2
<211> LENGTH: 119
<212> TYPE: PRT
<213> ORGANISM: Artificial Sequence
<220> FEATURE:
<223> OTHER INFORMATION: Synthetic

<400> SEQUENCE: 2

Glu Val Gln Leu Leu Glu Ser Gly Gly Gly Leu Ala Gln Pro Gly Gly
 1               5                  10                  15

Ser Leu Arg Leu Ser Cys Ala Ala Ser Gly Phe Asn Phe Gly Thr His
            20                  25                  30

Asp Met Ser Trp Val Arg Gln Ala Pro Gly Lys Gly Leu Glu Trp Val
        35                  40                  45

Ser Gly Leu Thr Ser Thr Gly Gly Ser Ala Ser Ser Ala Asp Ser Val
    50                  55                  60

Lys Gly Arg Phe Thr Ile Ser Arg Asp Asn Ser Lys Asn Ile Leu Tyr
65                  70                  75                  80

Leu Gln Met Asn Ser Leu Arg Ala Glu Asp Thr Ala Val Tyr Tyr Cys
                85                  90                  95

Ala Lys Thr Phe Asn Trp Asn Ser Tyr Phe Asp Tyr Trp Gly Gln Gly
            100                 105                 110

Thr Leu Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcaact ttggcaccca tgac                                             24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Asn Phe Gly Thr His Asp
 1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
cttacaagta ctggtggtag cgct                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Leu Thr Ser Thr Gly Gly Ser Ala
 1               5

<210> SEQ ID NO 7
<211> LENGTH: 36
<212> TYPE: DNA
<213> ORGANISM: Artificial Sequence
<220> FEATURE:
<223> OTHER INFORMATION: Synthetic

<400> SEQUENCE: 7
gcgaaaacgt ttaactggaa ctcctacttt gactac                             36

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Ala Lys Thr Phe Asn Trp Asn Ser Tyr Phe Asp Tyr
 1               5                  10

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9
gaaattgtgt tgacgcagtc tccaggcacc ctgtctttgt ctccagggga aagagccacc    60
ctctcctgca gggccagtca gagtattagc acctactact tagcctggta ccagcagaaa   120
cctgaccagc tcccaggct cctcatctat ggtacatcca gcagggccac tggcatccca   180
gacaggttca gtggcagtgg gtctgggaca gacttcactc tcaccatcag cagactggac   240
cctgaagatt ttgcagtgta ttactgtcaa cagtatggta actcactgta cacttttggc   300
caggggacca agctggagat caaa                                         324

<210> SEQ ID NO 10
<211> LENGTH: 108

```
<212> TYPE: PRT
<213> ORGANISM: Artificial Sequence
<220> FEATURE:
<223> OTHER INFORMATION: Synthetic

<400> SEQUENCE: 10

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Ile Ser Thr Tyr
            20                  25                  30

Tyr Leu Ala Trp Tyr Gln Gln Lys Pro Asp Gln Pro Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Asp
65                  70                  75                  80

Pro Glu Asp Phe Ala Val Tyr Tyr Cys Gln Gln Tyr Gly Asn Ser Leu
                85                  90                  95

Tyr Thr Phe Gly Gln Gly Thr Lys Leu Glu Ile Lys
            100                 105

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
cagagtatta gcacctacta c                                          21

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Gln Ser Ile Ser Thr Tyr Tyr
 1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ggtacatcc                                                         9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Gly Thr Ser
 1
```

```
<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacagtatg gtaactcact gtacact                                               27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Gly Asn Ser Leu Tyr Thr
 1               5

<210> SEQ ID NO 17
<211> LENGTH: 357
<212> TYPE: DNA
<213> ORGANISM: Artificial Sequence
<220> FEATURE:
<223> OTHER INFORMATION: Synthetic

<400> SEQUENCE: 17
caggtacaac tggtggaatc tgggggagac gtggttcagc ctggaggtc cctgagactc            60 tcctgtgcag catctggatt caccttcagt ggccacggca tgcactgggt ccgccaggct          120
ccaggcaagg gtctagagtg ggtggcactt atattgtatg atggaagtag tgaagactat          180
acagactccg tgaagggccg ctttaccgtc tccagagaca attccaagaa caccctgtat          240
ttgcaaatga acagtctgag agccgaagac acggctgtct attactgtgc gcgaggagt           300 attttaaatc gcccgtttga ttactggggc caggaaccc tggtcaccgt ctcctca             357

<210> SEQ ID NO 18
<211> LENGTH: 119
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Glu Ser Gly Gly Asp Val Val Gln Pro Gly Arg
 1               5                  10                  15

Ser Leu Arg Leu Ser Cys Ala Ala Ser Gly Phe Thr Phe Ser Gly His
             20                  25                  30

Gly Met His Trp Val Arg Gln Ala Pro Gly Lys Gly Leu Glu Trp Val
         35                  40                  45

Ala Leu Ile Leu Tyr Asp Gly Ser Ser Glu Asp Tyr Thr Asp Ser Val
     50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Ile Leu Asn Arg Pro Phe Asp Tyr Trp Gly Gln Gly
            100                 105                 110

Thr Leu Val Thr Val Ser Ser
            115
```

```
<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct tcagtggcca cggc                                              24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Ser Gly His Gly
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
atattgtatg atggaagtag tgaa                                              24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Leu Tyr Asp Gly Ser Ser Glu
1               5

<210> SEQ ID NO 23
<211> LENGTH: 36
<212> TYPE: DNA
<213> ORGANISM: Artificial Sequence
<220> FEATURE:
<223> OTHER INFORMATION: Synthetic

<400> SEQUENCE: 23
gcgcgaggga gtattttaaa tcgcccgttt gattac                                 36

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Ala Arg Gly Ser Ile Leu Asn Arg Pro Phe Asp Tyr
1               5                   10

<210> SEQ ID NO 25
<211> LENGTH: 339
```

```
<212> TYPE: DNA
<213> ORGANISM: Artificial Sequence
<220> FEATURE:
<223> OTHER INFORMATION: Synthetic

<400> SEQUENCE: 25
gacatcgtga tgacccagtc tccagactcc ctggctgtgt ctctgggcga gagggccacc      60
atcaactgca agtccagcca gagtatttta ttcagttcca acaataagat ctacttagct     120
tggttccagc agaaaccagg acagcctcct aaactactca tttactggac atctacccgg     180
gaatccgggg tccctgaccg attcagtggc agcgggtctg ggacagattt cactctcact     240
atcagtagtc tgcaggctga agatgtggca gtttactact gtcaacaata ttatactctt     300
ccattcactt tcggccctgg gaccaaagtg gatatcaaa                             339

<210> SEQ ID NO 26
<211> LENGTH: 113
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Ile Leu Phe Ser
             20                  25                  30

Ser Asn Asn Lys Ile Tyr Leu Ala Trp Phe Gln Gln Lys Pro Gly Gln
         35                  40                  45

Pro Pro Lys Leu Leu Ile Tyr Trp Thr Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Thr Leu Pro Phe Thr Phe Gly Pro Gly Thr Lys Val Asp Ile
            100                 105                 110

Lys

<210> SEQ ID NO 27
<211> LENGTH: 36
<212> TYPE: DNA
<213> ORGANISM: Artificial Sequence
<220> FEATURE:
<223> OTHER INFORMATION: Synthetic

<400> SEQUENCE: 27
cagagtattt tattcagttc aacaataag atctac                                 36

<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

Gln Ser Ile Leu Phe Ser Ser Asn Asn Lys Ile Tyr
 1               5                  10

<210> SEQ ID NO 29
```

```
<211> LENGTH: 9
<212> TYPE: DNA
<213> ORGANISM: Artificial Sequence
<220> FEATURE:
<223> OTHER INFORMATION: Synthetic

<400> SEQUENCE: 29 tggacatct                                                                  9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Trp Thr Ser
 1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caacaatatt atactcttcc attcact                                             27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Gln Tyr Tyr Thr Leu Pro Phe Thr
 1               5

<210> SEQ ID NO 33
<211> LENGTH: 357
<212> TYPE: DNA
<213> ORGANISM: Artificial Sequence
<220> FEATURE:
<223> OTHER INFORMATION: Synthetic

<400> SEQUENCE: 33
cagatacagc tggtggagtc tgggggaggc gtggtccagc ctggaaggtc cctgagactc          60
tcctgtgtag cctctgggtt caccctcagt ggacatggca tgcactgggt ccgccaggct         120
ccaggcaagg ggctggagtg ggtggcattt atatcatttg atggaggtca tcaagactac         180
acagacgccg cggagggccg attcaccatc tccagagaca attccaagaa cacgttgtat         240
ctggaaatgg tcagcctgag acctgcagac acggctatat attattgtgt gaaagggagc         300
gactcgtcgc gaggttttgg ctactggggc cggggaatcc tggtcaccgt ctcctca           357

<210> SEQ ID NO 34
<211> LENGTH: 119
<212> TYPE: PRT
<213> ORGANISM: Artificial Sequence
<220> FEATURE:
<223> OTHER INFORMATION: Synthetic

<400> SEQUENCE: 34
```

-continued

Gln Ile Gln Leu Val Glu Ser Gly Gly Val Val Gln Pro Gly Arg
1               5                   10                  15

Ser Leu Arg Leu Ser Cys Val Ala Ser Gly Phe Thr Leu Ser Gly His
            20                  25                  30

Gly Met His Trp Val Arg Gln Ala Pro Gly Lys Gly Leu Glu Trp Val
        35                  40                  45

Ala Phe Ile Ser Phe Asp Gly Gly His Gln Asp Tyr Thr Asp Ala Ala
    50                  55                  60

Glu Gly Arg Phe Thr Ile Ser Arg Asp Asn Ser Lys Asn Thr Leu Tyr
65                  70                  75                  80

Leu Glu Met Val Ser Leu Arg Pro Ala Asp Thr Ala Ile Tyr Tyr Cys
                85                  90                  95

Val Lys Gly Ser Asp Ser Ser Arg Gly Phe Gly Tyr Trp Gly Arg Gly
            100                 105                 110

Ile Leu Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
gggttcaccc tcagtggaca tggc                                      24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Leu Ser Gly His Gly
1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
atatcatttg atggaggtca tcaa                                      24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Ser Phe Asp Gly Gly His Gln
1               5

<210> SEQ ID NO 39
<211> LENGTH: 36
<212> TYPE: DNA

<213> ORGANISM: Artificial Sequence
<220> FEATURE:
<223> OTHER INFORMATION: Synthetic

<400> SEQUENCE: 39
gtgaaaggga gcgactcgtc gcgaggtttt ggctac                              36

<210> SEQ ID NO 40
<211> LENGTH: 12
<212> TYPE: PRT
<213> ORGANISM: Artificial Sequence
<220> FEATURE:
<223> OTHER INFORMATION: Synthetic

<400> SEQUENCE: 40

Val Lys Gly Ser Asp Ser Ser Arg Gly Phe Gly Tyr
 1               5                  10

<210> SEQ ID NO 41
<211> LENGTH: 339
<212> TYPE: DNA
<213> ORGANISM: Artificial Sequence
<220> FEATURE:
<223> OTHER INFORMATION: Synthetic

<400> SEQUENCE: 41
gacatcgtga tgacccagtc tccagactcc ctggctgtgt ctctgggcga gagggccacc     60
atcaactgca gtccagcca gagtgtttta ttcagttccg acaataagaa ctacttggct    120
tggtaccagc tgaaaccagg tcagcctcct cacctactta tttactgggc atctattcgt    180
gattccgggg tccctgaccg atttagtggc agcgggtctg ggacagattt cacgctcacc    240
atcagcagcc tgcaggctga ggatgtggca gtttactcct gtcatcaata ttatagtgct    300 ccactcaccct tcggcggagg gaccaaggtg gagatcaaa                          339

<210> SEQ ID NO 42
<211> LENGTH: 113
<212> TYPE: PRT
<213> ORGANISM: Artificial Sequence
<220> FEATURE:
<223> OTHER INFORMATION: Synthetic

<400> SEQUENCE: 42

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Phe Ser
            20                  25                  30

Ser Asp Asn Lys Asn Tyr Leu Ala Trp Tyr Gln Leu Lys Pro Gly Gln
        35                  40                  45

Pro Pro His Leu Leu Ile Tyr Trp Ala Ser Ile Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Ser Cys His Gln
                85                  90                  95

Tyr Tyr Ser Ala Pro Leu Thr Phe Gly Gly Thr Lys Val Glu Ile
                100                 105                 110

Lys

<210> SEQ ID NO 43
<211> LENGTH: 36

```
<212> TYPE: DNA
<213> ORGANISM: Artificial Sequence
<220> FEATURE:
<223> OTHER INFORMATION: Synthetic

<400> SEQUENCE: 43
cagagtgttt tattcagttc gacaataag aactac                                  36

<210> SEQ ID NO 44
<211> LENGTH: 12
<212> TYPE: PRT
<213> ORGANISM: Artificial Sequence
<220> FEATURE:
<223> OTHER INFORMATION: Synthetic

<400> SEQUENCE: 44

Gln Ser Val Leu Phe Ser Ser Asp Asn Lys Asn Tyr
 1               5                  10

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 tgggcatct                                                               9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Trp Ala Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
catcaatatt atagtgctcc actcacc                                           27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

His Gln Tyr Tyr Ser Ala Pro Leu Thr
 1               5

<210> SEQ ID NO 49
<211> LENGTH: 372
<212> TYPE: DNA
<213> ORGANISM: Artificial Sequence
<220> FEATURE:
<223> OTHER INFORMATION: Synthetic
```

<400> SEQUENCE: 49

```
gaggtgcagc tggtggagtc tgggggggac ttggtacaac ctggagggtc cctgagactc      60
tcctgtgcag cctctggagt caccttcagg acatatgaaa tgaattgggt ccgccaggct     120
ccagggaagg gactgagtg gatttcacac attagtagca gtggtgatat tatatactat     180
acaaagtctg tgaagggccg attcaccatc tccagagata cgccaagaa ctcactgttt     240
ctgcaaatga caagtctgag agccgaggac acggctgtat attactgtgc gagagaaagg     300
tacagtcaat acggttatta ttacttcgga atggatgtct ggggccaagg gaccacggtc     360
accgtctcct ca                                                         372
```

<210> SEQ ID NO 50
<211> LENGTH: 124
<212> TYPE: PRT
<213> ORGANISM: Artificial Sequence
<220> FEATURE:
<223> OTHER INFORMATION: Synthetic

<400> SEQUENCE: 50

```
Glu Val Gln Leu Val Glu Ser Gly Gly Asp Leu Val Gln Pro Gly Gly
 1               5                  10                  15

Ser Leu Arg Leu Ser Cys Ala Ala Ser Gly Val Thr Phe Arg Thr Tyr
            20                  25                  30

Glu Met Asn Trp Val Arg Gln Ala Pro Gly Lys Gly Leu Glu Trp Ile
        35                  40                  45

Ser His Ile Ser Ser Ser Gly Asp Ile Ile Tyr Tyr Thr Lys Ser Val
    50                  55                  60

Lys Gly Arg Phe Thr Ile Ser Arg Asp Asn Ala Lys Asn Ser Leu Phe
65                  70                  75                  80

Leu Gln Met Thr Ser Leu Arg Ala Glu Asp Thr Ala Val Tyr Tyr Cys
                85                  90                  95

Ala Arg Glu Arg Tyr Ser Gln Tyr Gly Tyr Tyr Tyr Phe Gly Met Asp
            100                 105                 110

Val Trp Gly Gln Gly Thr Thr Val Thr Val Ser Ser
        115                 120
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggagtcacct tcaggacata tgaa                                             24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

```
Gly Val Thr Phe Arg Thr Tyr Glu
 1               5
```

<210> SEQ ID NO 53
<211> LENGTH: 24

<212> TYPE: DNA
<213> ORGANISM: Artificial Sequence
<220> FEATURE:
<223> OTHER INFORMATION: Synthetic

<400> SEQUENCE: 53
attagtagca gtggtgatat tata                                            24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Ser Ser Gly Asp Ile Ile
 1               5

<210> SEQ ID NO 55
<211> LENGTH: 51
<212> TYPE: DNA
<213> ORGANISM: Artificial Sequence
<220> FEATURE:
<223> OTHER INFORMATION: Synthetic

<400> SEQUENCE: 55
gcgagagaaa ggtacagtca atacggttat tattacttcg gaatggatgt c              51

<210> SEQ ID NO 56
<211> LENGTH: 17
<212> TYPE: PRT
<213> ORGANISM: Artificial Sequence
<220> FEATURE:
<223> OTHER INFORMATION: Synthetic

<400> SEQUENCE: 56

Ala Arg Glu Arg Tyr Ser Gln Tyr Gly Tyr Tyr Tyr Phe Gly Met Asp
 1               5                  10                  15
Val

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccttccacc ctgtctgcat ctataggaga cagagtcacc      60
atcacttgcc gggccagtca gaatactgat aagtggatgg cctggtatca gcagaaagca     120
gggaaagccc ctaaactcct gatctataag gcgtctattt tagaaagtgg ggtcccttca     180
aggttcagcg gcagtggatc tgggacagaa ttcactctca ccatcagcag cctgcagcct     240
gatgattttg caacttatta ctgccaagaa tataatactt attttcgggc gttcggccaa     300
gggaccaagg tggaaaccag a                                               321

<210> SEQ ID NO 58
<211> LENGTH: 107
<212> TYPE: PRT
<213> ORGANISM: Artificial Sequence
<220> FEATURE:
<223> OTHER INFORMATION: Synthetic -continued

<400> SEQUENCE: 58

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Asn Thr Asp Lys Trp
            20                  25                  30

Met Ala Trp Tyr Gln Gln Lys Ala Gly Lys Ala Pro Lys Leu Leu Ile
        35                  40                  45

Tyr Lys Ala Ser Ile Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu Tyr Asn Thr Tyr Phe Arg
                85                  90                  95

Ala Phe Gly Gln Gly Thr Lys Val Glu Thr Arg
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagaatactg ataagtgg                                                     18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Asn Thr Asp Lys Trp
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 aaggcgtct                                                                9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Lys Ala Ser
1

<210> SEQ ID NO 63
<211> LENGTH: 27
<212> TYPE: DNA
<213> ORGANISM: Artificial Sequence
<220> FEATURE:

<223> OTHER INFORMATION: Synthetic

<400> SEQUENCE: 63
caagaatata atacttattt tcgggcg                                              27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Glu Tyr Asn Thr Tyr Phe Arg Ala
 1               5

<210> SEQ ID NO 65
<211> LENGTH: 372
<212> TYPE: DNA
<213> ORGANISM: Artificial Sequence
<220> FEATURE:
<223> OTHER INFORMATION: Synthetic

<400> SEQUENCE: 65
gacgtgcagc tggtggagtc tgggggagac tttgtacaac ctggagggtc cctgagactc      60
tcctgtgcag cctctggagt cgccttcaat gattatgaaa tgaattggat ccgccaggct     120
ccagggaaga gactggagtg gatttcacac attgatagta gtggtactat tatatattac     180
gcagactctg tgaagggccg attcaccatc tccagagaca cgccaagaa ctcactgttt      240 ctgcaaatgg acagtctgag agccgaggac acggctgttt attactgtgc gagagaaagg     300
tacagtcact acggatatta ctacttcggt atggatgtct ggggccaagg gaccacggtc     360
accgtctcct ca                                                          372

<210> SEQ ID NO 66
<211> LENGTH: 124
<212> TYPE: PRT
<213> ORGANISM: Artificial Sequence
<220> FEATURE:
<223> OTHER INFORMATION: Synthetic

<400> SEQUENCE: 66

Asp Val Gln Leu Val Glu Ser Gly Gly Asp Phe Val Gln Pro Gly Gly
 1               5                  10                  15

Ser Leu Arg Leu Ser Cys Ala Ala Ser Gly Val Ala Phe Asn Asp Tyr
            20                  25                  30

Glu Met Asn Trp Ile Arg Gln Ala Pro Gly Lys Arg Leu Glu Trp Ile
        35                  40                  45

Ser His Ile Asp Ser Ser Gly Thr Ile Ile Tyr Tyr Ala Asp Ser Val
    50                  55                  60

Lys Gly Arg Phe Thr Ile Ser Arg Asp Ser Ala Lys Asn Ser Leu Phe
65                  70                  75                  80

Leu Gln Met Asp Ser Leu Arg Ala Glu Asp Thr Ala Val Tyr Tyr Cys
                85                  90                  95

Ala Arg Glu Arg Tyr Ser His Tyr Gly Tyr Tyr Tyr Phe Gly Met Asp
            100                 105                 110

Val Trp Gly Gln Gly Thr Thr Val Thr Val Ser Ser
        115                 120

<210> SEQ ID NO 67

```
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggagtcgcct tcaatgatta tgaa                                          24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Val Ala Phe Asn Asp Tyr Glu
 1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
attgatagta gtggtactat tata                                          24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Asp Ser Ser Gly Thr Ile Ile
 1               5

<210> SEQ ID NO 71
<211> LENGTH: 51
<212> TYPE: DNA
<213> ORGANISM: Artificial Sequence
<220> FEATURE:
<223> OTHER INFORMATION: Synthetic

<400> SEQUENCE: 71
gcgagagaaa ggtacagtca ctacggatat tactacttcg gtatggatgt c            51

<210> SEQ ID NO 72
<211> LENGTH: 17
<212> TYPE: PRT
<213> ORGANISM: Artificial Sequence
<220> FEATURE:
<223> OTHER INFORMATION: Synthetic

<400> SEQUENCE: 72

Ala Arg Glu Arg Tyr Ser His Tyr Gly Tyr Tyr Tyr Phe Gly Met Asp
 1               5                  10                  15

Val

<210> SEQ ID NO 73
<211> LENGTH: 321
<212> TYPE: DNA
```

```
<213> ORGANISM: Artificial Sequence
<220> FEATURE:
<223> OTHER INFORMATION: Synthetic

<400> SEQUENCE: 73
gacatccaga tgacccagtc tccttccacc ctgtctgcat ctgtaggaga cagagtcacc    60
atcacttgcc gggccagtca gaatattgat aactggttgg cctggtatca gcagaaaaca   120
ggtaaagccc ctaacctcct gatctataag gcgtctactt tggaaagtgg ggtcccttca   180
aggttcagcg gcagtggatc tgggacagaa ttcactctca ccatcatcag cctgcagcct   240
gatgattttg caacttatta ctgccaagaa tataatactt attctcggac gttcggccaa   300
ggcaccaagg tggaaatcaa a                                             321

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Asn Ile Asp Asn Trp
            20                  25                  30

Leu Ala Trp Tyr Gln Gln Lys Thr Gly Lys Ala Pro Asn Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ile Ser Leu Gln Pro
65                  70                  75                  80

Asp Asp Phe Ala Thr Tyr Tyr Cys Gln Glu Tyr Asn Thr Tyr Ser Arg
                85                  90                  95

Thr Phe Gly Gln Gly Thr Lys Val Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
cagaatattg ataactgg                                                  18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Asn Ile Asp Asn Trp
 1               5

<210> SEQ ID NO 77
<211> LENGTH: 9
<212> TYPE: DNA
<213> ORGANISM: Artificial Sequence
```

```
<220> FEATURE:
<223> OTHER INFORMATION: Synthetic

<400> SEQUENCE: 77 aaggcgtct                                                                   9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Lys Ala Ser
 1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caagaatata atacttattc tcggacg                                              27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Glu Tyr Asn Thr Tyr Ser Arg Thr
 1               5

<210> SEQ ID NO 81
<211> LENGTH: 372
<212> TYPE: DNA
<213> ORGANISM: Artificial Sequence
<220> FEATURE:
<223> OTHER INFORMATION: Synthetic

<400> SEQUENCE: 81
gagatacaat tgatagagtc tgggggagac atggtacaac ctggagggtc cctgagactc         60
tcctgtgcag cctctggaat ctcccttaat agttatgaaa tgaattgggt ccgccagact        120
ccagggatgg ggctggagtg gatttcacac ataagtagta gtggaacttc tatatattat        180
gcaaactctg tgaagggccg attcaccata ttcagagaca cgccaagaa ctcactgttg         240 ctgcaaatga acagtctgag agccgaggac acggctattt attactgtgc aagagaaaga        300
tacgatcact ccgggtatta ctacctcgga atggatgtct ggggcctagg gaccacggtc        360
accgtctcgt ca                                                            372

<210> SEQ ID NO 82
<211> LENGTH: 124
<212> TYPE: PRT
<213> ORGANISM: Artificial Sequence
<220> FEATURE:
<223> OTHER INFORMATION: Synthetic

<400> SEQUENCE: 82
```

Glu Ile Gln Leu Ile Glu Ser Gly Gly Asp Met Val Gln Pro Gly Gly
1               5                   10                  15

Ser Leu Arg Leu Ser Cys Ala Ala Ser Gly Ile Ser Leu Asn Ser Tyr
            20                  25                  30

Glu Met Asn Trp Val Arg Gln Thr Pro Gly Met Gly Leu Glu Trp Ile
        35                  40                  45

Ser His Ile Ser Ser Ser Gly Thr Ser Ile Tyr Tyr Ala Asn Ser Val
    50                  55                  60

Lys Gly Arg Phe Thr Ile Phe Arg Asp Ser Ala Lys Asn Ser Leu Leu
65                  70                  75                  80

Leu Gln Met Asn Ser Leu Arg Ala Glu Asp Thr Ala Ile Tyr Tyr Cys
                85                  90                  95

Ala Arg Glu Arg Tyr Asp His Ser Gly Tyr Tyr Tyr Leu Gly Met Asp
            100                 105                 110

Val Trp Gly Leu Gly Thr Thr Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggaatctccc ttaatagtta tgaa                                         24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Ile Ser Leu Asn Ser Tyr Glu
1               5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
ataagtagta gtggaacttc tata                                         24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Ser Ser Ser Gly Thr Ser Ile
1               5

<210> SEQ ID NO 87
<211> LENGTH: 51
<212> TYPE: DNA
<213> ORGANISM: Artificial Sequence

```
<220> FEATURE:
<223> OTHER INFORMATION: Synthetic

<400> SEQUENCE: 87
gcaagagaaa gatacgatca ctccgggtat tactacctcg gaatggatgt c          51

<210> SEQ ID NO 88
<211> LENGTH: 17
<212> TYPE: PRT
<213> ORGANISM: Artificial Sequence
<220> FEATURE:
<223> OTHER INFORMATION: Synthetic

<400> SEQUENCE: 88

Ala Arg Glu Arg Tyr Asp His Ser Gly Tyr Tyr Tyr Leu Gly Met Asp
 1               5                  10                  15

Val

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccttccacc ctgtctgcat ctttaggaga cagagtcacc     60
atcacttgcc gggccagtca gaatattgat aactggatgg cctggtatca gcagaaagtt    120
gggaaagccc ctaaactctt gatatatagg gcgtctactt tagaaactgg ggtcccttca    180
aggttcggcg gcagtggatt tgggacagaa ttcactctca ccatcagcag cctgcagcct    240
ggtgattttg cgacttacta ctgccaagaa tataatagtt attttcggac gttcggccaa    300
gggaccaagg tggagatcaa a                                              321

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Thr Leu Ser Ala Ser Leu Gly
 1               5                  10                  15

Asp Arg Val Thr Ile Thr Cys Arg Ala Ser Gln Asn Ile Asp Asn Trp
            20                  25                  30

Met Ala Trp Tyr Gln Gln Lys Val Gly Lys Ala Pro Lys Leu Leu Ile
        35                  40                  45

Tyr Arg Ala Ser Thr Leu Glu Thr Gly Val Pro Ser Arg Phe Gly Gly
    50                  55                  60

Ser Gly Phe Gly Thr Glu Phe Thr Leu Thr Ile Ser Ser Leu Gln Pro
65                  70                  75                  80

Gly Asp Phe Ala Thr Tyr Tyr Cys Gln Glu Tyr Asn Ser Tyr Phe Arg
                85                  90                  95

Thr Phe Gly Gln Gly Thr Lys Val Glu Ile Lys
            100                 105

<210> SEQ ID NO 91
<211> LENGTH: 18
<212> TYPE: DNA
```

```
<213> ORGANISM: Artificial Sequence
<220> FEATURE:
<223> OTHER INFORMATION: Synthetic

<400> SEQUENCE: 91
cagaatattg ataactgg                                                 18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Asn Ile Asp Asn Trp
1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 agggcgtct                                                            9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Arg Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caagaatata atagttattt tcggacg                                       27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Glu Tyr Asn Ser Tyr Phe Arg Thr
1               5

<210> SEQ ID NO 97
<211> LENGTH: 372
<212> TYPE: DNA
<213> ORGANISM: Artificial Sequence
<220> FEATURE:
<223> OTHER INFORMATION: Synthetic
```

<400> SEQUENCE: 97

```
gaggtgcagc tggtggagtc tgggggaggc ttggtacagc ctgggggtc cctgagactc      60
tcctgtgcag cctctggatt caccttcagt agttacgaca tgcactgggt ccgccaagtt    120
ataggaaaag gtctggagtg gtctcagct attggtactg ttggtgacac atactatgca     180
ggctccgtga agggccgatt caccatctcc agagaaaatg ccaagaattc cttgtacctt    240
caaatgaaca gcctgagagc cggggacacg gctgtgtatt actgtgcaag agatcggggg    300
ggtgcgaata tttatagttt ctactacggt atggacgtct ggggccaagg gaccacggtc    360
accgtctcct ca                                                        372
```

<210> SEQ ID NO 98
<211> LENGTH: 124
<212> TYPE: PRT
<213> ORGANISM: Artificial Sequence
<220> FEATURE:
<223> OTHER INFORMATION: Synthetic

<400> SEQUENCE: 98

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Val Ile Gly Lys Gly Leu Glu Trp Val
        35                  40                  45

Ser Ala Ile Gly Thr Val Gly Asp Thr Tyr Tyr Ala Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Gly Gly Ala Asn Ile Tyr Ser Phe Tyr Tyr Gly Met Asp
            100                 105                 110

Val Trp Gly Gln Gly Thr Thr Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcacct tcagtagtta cgac                                            24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Phe Thr Phe Ser Ser Tyr Asp
 1               5
```

<210> SEQ ID NO 101
<211> LENGTH: 21
<212> TYPE: DNA

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
attggtactg ttggtgacac a                                           21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Gly Thr Val Gly Asp Thr
 1               5

<210> SEQ ID NO 103
<211> LENGTH: 54
<212> TYPE: DNA
<213> ORGANISM: Artificial Sequence
<220> FEATURE:
<223> OTHER INFORMATION: Synthetic

<400> SEQUENCE: 103
gcaagagatc gggggggtgc gaatatttat agtttctact acggtatgga cgtc       54

<210> SEQ ID NO 104
<211> LENGTH: 18
<212> TYPE: PRT
<213> ORGANISM: Artificial Sequence
<220> FEATURE:
<223> OTHER INFORMATION: Synthetic

<400> SEQUENCE: 104

Ala Arg Asp Arg Gly Gly Ala Asn Ile Tyr Ser Phe Tyr Tyr Gly Met
 1               5                  10                  15

Asp Val

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcctcc ctgtctgtat ctgtaggaga cagagtcacc    60
atcacttgcc gggcgagtca ggacattagc aattatttag cctggtatca gcagaaacca   120
gggaaagttc ctaagctcct gatctatgct gcatccactt tgcaatcagg ggtcccatct   180
cggttcagtg gcagtggatc tgggacagat tcactctcac catcagcag cctgcagcct    240 gaagatgttg caactatt ctgtcaaaag tataacagtg ccccatcac tttcggccct      300 gggaccaaag tggatatcaa acga                                         324

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

```
Asp Ile Gln Met Thr Gln Ser Pro Ser Ser Leu Ser Val Ser Val Gly
 1               5                  10                  15

Asp Arg Val Thr Ile Thr Cys Arg Ala Ser Gln Asp Ile Ser Asn Tyr
             20                  25                  30

Leu Ala Trp Tyr Gln Lys Pro Gly Lys Val Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Lys Tyr Asn Ser Ala Pro Phe
             85                  90                  95

Thr Phe Gly Pro Gly Thr Lys Val Asp Ile Lys Arg
                100                 105
```

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
caggacatta gcaattat                                                 18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

```
Gln Asp Ile Ser Asn Tyr
 1               5
```

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                            9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

```
Ala Ala Ser
 1
```

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caaaagtata acagtgcccc attcact   27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Lys Tyr Asn Ser Ala Pro Phe Thr
 1               5

<210> SEQ ID NO 113
<211> LENGTH: 393
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggc ttggtacagc ctgggggtc cctgagactc   60 tcctgtgcag cctctggatt caccttaac agttttgtca tgagctgggt ccgtcaggct  120
ccagggaagg ggctggagtg ggtctcagct attagtggtt atggtggtag cacatactac  180
gcagactcca tgaagggccg gttcaccgtc tccagagaca attccaagaa tacgctgtat  240
ctgcaaatga acagcctgag agccgaggac acggccgtat attactgtgc gaaagatcac  300
aaggatttct atgcttcggg gagttatttt aaccgggact actactacgg tatggacgtc  360
tggggccaag ggaccacggt caccgtctcc tca                               393

<210> SEQ ID NO 114
<211> LENGTH: 131
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Ser Phe
            20                  25                  30

Val Met Ser Trp Val Arg Gln Ala Pro Gly Lys Gly Leu Glu Trp Val
        35                  40                  45

Ser Ala Ile Ser Gly Tyr Gly Gly Ser Thr Tyr Tyr Ala Asp Ser Met
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Lys Asp Phe Tyr Ala Ser Gly Ser Tyr Phe Asn Arg
            100                 105                 110

Asp Tyr Tyr Tyr Gly Met Asp Val Trp Gly Gln Gly Thr Thr Val Thr
        115                 120                 125

Val Ser Ser
    130

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct ttaacagttt tgtc                                          24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Asn Ser Phe Val
 1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
attagtggtt atggtggtag caca                                          24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Ser Gly Tyr Gly Gly Ser Thr
 1               5

<210> SEQ ID NO 119
<211> LENGTH: 72
<212> TYPE: DNA
<213> ORGANISM: Artificial Sequence
<220> FEATURE:
<223> OTHER INFORMATION: Synthetic

<400> SEQUENCE: 119
gcgaaagatc acaaggattt ctatgcttcg gggagttatt ttaaccggga ctactactac   60
ggtatggacg tc                                                       72

<210> SEQ ID NO 120
<211> LENGTH: 24
<212> TYPE: PRT
<213> ORGANISM: Artificial Sequence
<220> FEATURE:
<223> OTHER INFORMATION: Synthetic

<400> SEQUENCE: 120

Ala Lys Asp His Lys Asp Phe Tyr Ala Ser Gly Ser Tyr Phe Asn Arg
 1               5                  10                  15

Asp Tyr Tyr Tyr Gly Met Asp Val
                20

<210> SEQ ID NO 121
<211> LENGTH: 324
<212> TYPE: DNA
<213> ORGANISM: Artificial Sequence
<220> FEATURE:
<223> OTHER INFORMATION: Synthetic

<400> SEQUENCE: 121

```
gacatccaga tgacccagtc tccttccacc ctgtctgcat ctgttggaga cagagtcacc    60
atcacttgcc gggccagtca gagtattagt agctggttgg cctggtatca gcagaaacca   120
gggaaagccc ctaaggtcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attctcggac gttcggccaa   300
gggaccaagg tggaaatcaa acga                                          324
```

<210> SEQ ID NO 122
<211> LENGTH: 108
<212> TYPE: PRT
<213> ORGANISM: Artificial Sequence
<220> FEATURE:
<223> OTHER INFORMATION: Synthetic

<400> SEQUENCE: 122

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Val Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Arg
                 85                  90                  95

Thr Phe Gly Gln Gly Thr Lys Val Glu Ile Lys Arg
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123

```
cagagtatta gtagctgg                                                  18
```

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

```
Gln Ser Ile Ser Ser Trp
  1               5
```

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 aaggcgtct                                                                     9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Lys Ala Ser
 1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
caacagtata atagttattc tcggacg                                                27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr Asn Ser Tyr Ser Arg Thr
 1               5

<210> SEQ ID NO 129
<211> LENGTH: 372
<212> TYPE: DNA
<213> ORGANISM: Artificial Sequence
<220> FEATURE:
<223> OTHER INFORMATION: Synthetic

<400> SEQUENCE: 129
gaggtgcagc tggtggagtc tgggggaggc ttggtacagc ctggggggtc cctgacactc     60
tcctgcgcag cctctagatt caccttcagt aactacgaca tgcactgggt ccgccaagcc    120
acaggaaaag gtctggagtg ggtctcagct attggtactg tcggtgacac atactatgca    180
ggctctgtga agggccgatt caccatctcc agagacgatg ccaagaattc cctttatctc    240
caaatgaaca gcctgagagc cggggacacg gctgtttatt actgtgcaag agatcggggg    300
ggtgcgggga cttatagttt ctattacggt atggacgtct ggggccaagg gaccacggtc    360
accgtctcct ca                                                       372

<210> SEQ ID NO 130
<211> LENGTH: 124
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Thr Phe Ser Asn Tyr
            20                  25                  30

Asp Met His Trp Val Arg Gln Ala Thr Gly Lys Gly Leu Glu Trp Val
        35                  40                  45

Ser Ala Ile Gly Thr Val Gly Asp Thr Tyr Tyr Ala Gly Ser Val Lys
    50                  55                  60

Gly Arg Phe Thr Ile Ser Arg Asp Asp Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Gly Gly Ala Gly Thr Tyr Ser Phe Tyr Tyr Gly Met Asp
            100                 105                 110

Val Trp Gly Gln Gly Thr Thr Val Thr Val Ser Ser
        115                 120

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
agattcacct tcagtaacta cgac                                              24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Arg Phe Thr Phe Ser Asn Tyr Asp
1               5

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
attggtactg tcggtgacac a                                                 21

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Ile Gly Thr Val Gly Asp Thr
1               5

<210> SEQ ID NO 135
<211> LENGTH: 54
<212> TYPE: DNA
<213> ORGANISM: Artificial Sequence
<220> FEATURE:
<223> OTHER INFORMATION: Synthetic

<400> SEQUENCE: 135
gcaagagatc gggggggtgc ggggacttat agtttctatt acggtatgga cgtc          54

<210> SEQ ID NO 136
<211> LENGTH: 18
<212> TYPE: PRT
<213> ORGANISM: Artificial Sequence
<220> FEATURE:
<223> OTHER INFORMATION: Synthetic

<400> SEQUENCE: 136

Ala Arg Asp Arg Gly Gly Ala Gly Thr Tyr Ser Phe Tyr Tyr Gly Met
1               5                   10                  15

Asp Val

<210> SEQ ID NO 137
<211> LENGTH: 324
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccatcctcc ctgtctgcat ctgtaggaga cagagtcacc     60
atcacttgcc gggcgagtca ggacattagc aattatttag cctggtatca gcagaaacca   120
gggaaagttc ctaaactcct gatctatgct gcttccactt tgcaatcagg ggtcccatct   180
cggttcagtg gtagtggatc tgggacagat ttcactctca ccgtcagcag cctgcagcct   240
gaagatgttg caacttatta ctgtcaaaag tataccagtg ccccattcac tttcggccct   300
gggaccaaag tggatatcaa acga                                          324

<210> SEQ ID NO 138
<211> LENGTH: 108
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Val Ser Ser Leu Gln Pro
65                  70                  75                  80

Glu Asp Val Ala Thr Tyr Tyr Cys Gln Lys Tyr Thr Ser Ala Pro Phe
                85                  90                  95

Thr Phe Gly Pro Gly Thr Lys Val Asp Ile Lys Arg
            100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
caggacatta gcaattat                                                   18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Asp Ile Ser Asn Tyr
 1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gctgcttcc                                                              9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Ala Ser
 1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caaaagtata ccagtgcccc attcact                                         27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Lys Tyr Thr Ser Ala Pro Phe Thr
 1               5

<210> SEQ ID NO 145
<211> LENGTH: 369

<212> TYPE: DNA
<213> ORGANISM: Artificial Sequence
<220> FEATURE:
<223> OTHER INFORMATION: Synthetic

<400> SEQUENCE: 145

```
caggtgcagc tggtggagtc tgggggaggc gtggtccagc ctggggggtc cctgagactc    60
tcctgtgcag cgtctggatt caccttcagt agctatgcca tgcactgggt ccgccaggct   120
ccaggcaagg gactggagtg gtggcaatt atatggtttg atggaagtaa tgaagattat   180
gcagactccg tgaagggccg attcaccatc tccagagaca attccaagaa catggtatat   240
ctgcaaataa cagcctgag agccgaggac acggctgtgt attactgtgc gagatctgcc   300
aactggaact acgaaggggg accctctttt gactactggg gccagggaac cctggtcacc   360
gtctcctca                                                          369
```

<210> SEQ ID NO 146
<211> LENGTH: 123
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ser Ser Tyr
            20                  25                  30
Ala Met His Trp Val Arg Gln Ala Pro Gly Lys Gly Leu Glu Trp Val
        35                  40                  45
Ala Ile Ile Trp Phe Asp Gly Ser Asn Glu Asp Tyr Ala Asp Ser Val
    50                  55                  60
Lys Gly Arg Phe Thr Ile Ser Arg Asp Asn Ser Lys Asn Met Val Tyr
65                  70                  75                  80
Leu Gln Ile Asn Ser Leu Arg Ala Glu Asp Thr Ala Val Tyr Tyr Cys
                85                  90                  95
Ala Arg Ser Ala Asn Trp Asn Tyr Glu Gly Gly Pro Leu Phe Asp Tyr
            100                 105                 110
Trp Gly Gln Gly Thr Leu Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147

```
ggattcacct tcagtagcta tgcc                                           24
```

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Thr Phe Ser Ser Tyr Ala
1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atatggtttg atggaagtaa tgaa                                          24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Trp Phe Asp Gly Ser Asn Glu
 1               5

<210> SEQ ID NO 151
<211> LENGTH: 48
<212> TYPE: DNA
<213> ORGANISM: Artificial Sequence
<220> FEATURE:
<223> OTHER INFORMATION: Synthetic

<400> SEQUENCE: 151
gcgagatctg ccaactggaa ctacgaaggg ggacccctct ttgactac                48

<210> SEQ ID NO 152
<211> LENGTH: 16
<212> TYPE: PRT
<213> ORGANISM: Artificial Sequence
<220> FEATURE:
<223> OTHER INFORMATION: Synthetic

<400> SEQUENCE: 152

Ala Arg Ser Ala Asn Trp Asn Tyr Glu Gly Gly Pro Leu Phe Asp Tyr
 1               5                  10                  15

<210> SEQ ID NO 153
<211> LENGTH: 324
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccatcctcc ctgtctgctt ctgtaggaga ccgagtcacc      60
atcacttgcc gggcaagtca gaccattagc acctttttaa attggtatca gcagaagcca     120
gggaaaggcc ctgaactcct gatctacact gcatccagtt tgcaaagtgg ggtcccatca     180
aggttcagtg gcagtggatc tgggacagat ttcgctctca ccatcagcag tctgcaacct     240
gaagattttg cgacttacta ctgtcaacag aattacaatg accctcccac cttcggccaa     300
gggacacgac tggagattaa acga                                            324

<210> SEQ ID NO 154
<211> LENGTH: 108
<212> TYPE: PRT
<213> ORGANISM: Artificial Sequence
<220> FEATURE:

<223> OTHER INFORMATION: Synthetic

<400> SEQUENCE: 154

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Thr Ile Ser Thr Phe
            20                  25                  30
Leu Asn Trp Tyr Gln Gln Lys Pro Gly Lys Gly Pro Glu Leu Leu Ile
        35                  40                  45
Tyr Thr Ala Ser Ser Leu Gln Ser Gly Val Pro Ser Arg Phe Ser Gly
 50                  55                  60
Ser Gly Ser Gly Thr Asp Phe Ala Leu Thr Ile Ser Ser Leu Gln Pro
 65                  70                  75                  80
Glu Asp Phe Ala Thr Tyr Tyr Cys Gln Gln Asn Tyr Asn Asp Pro Pro
                85                  90                  95
Thr Phe Gly Gln Gly Thr Arg Leu Glu Ile Lys Arg
            100                 105
```

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
cagaccatta gcaccttt                                             18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

```
Gln Thr Ile Ser Thr Phe
 1               5
```

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 actgcatcc                                                        9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

```
Thr Ala Ser
 1
```

<210> SEQ ID NO 159
<211> LENGTH: 27
<212> TYPE: DNA

```
<213> ORGANISM: Artificial Sequence
<220> FEATURE:
<223> OTHER INFORMATION: Synthetic

<400> SEQUENCE: 159
caacagaatt acaatgaccc tcccacc                                              27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Asn Tyr Asn Asp Pro Pro Thr
 1               5

<210> SEQ ID NO 161
<211> LENGTH: 348
<212> TYPE: DNA
<213> ORGANISM: Artificial Sequence
<220> FEATURE:
<223> OTHER INFORMATION: Synthetic

<400> SEQUENCE: 161
caggtgcagc tggtggagtc tgggggaggc ttggtcaagc ctggagggtc cctgacactc          60
tcctgtgtag cctctggatt caccttcact gactactaca ttagttggat ccgccaggct         120
ccggggaagg gactggagtg gatttcatac attggtactg gtggtgctgc aaatactac          180 gcagactctg ttaagggccg attcaccgtc tccagggaca cgccaagaa ctcactgtat          240 ctactaatga caacctgag agccgaggac acggccgtat attattgtgc gagagatctg          300
gggatctttg acttatgggg ccagggaacc ctggtcaccg tctcctca                      348

<210> SEQ ID NO 162
<211> LENGTH: 116
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Glu Ser Gly Gly Gly Leu Val Lys Pro Gly Gly
 1               5                  10                  15

Ser Leu Thr Leu Ser Cys Val Ala Ser Gly Phe Thr Phe Thr Asp Tyr
            20                  25                  30

Tyr Ile Ser Trp Ile Arg Gln Ala Pro Gly Lys Gly Leu Glu Trp Ile
        35                  40                  45

Ser Tyr Ile Gly Thr Gly Gly Ala Ala Lys Tyr Tyr Ala Asp Ser Val
    50                  55                  60

Lys Gly Arg Phe Thr Val Ser Arg Asp Asn Ala Lys Asn Ser Leu Tyr
65                  70                  75                  80

Leu Leu Met Asn Asn Leu Arg Ala Glu Asp Thr Ala Val Tyr Tyr Cys
                85                  90                  95

Ala Arg Asp Leu Gly Ile Phe Asp Leu Trp Gly Gln Gly Thr Leu Val
            100                 105                 110

Thr Val Ser Ser
        115

<210> SEQ ID NO 163
```

```
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggattcacct tcactgacta ctac                                          24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Thr Phe Thr Asp Tyr Tyr
1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
attggtactg gtggtgctgc caaa                                          24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Gly Thr Gly Gly Ala Ala Lys
1               5

<210> SEQ ID NO 167
<211> LENGTH: 27
<212> TYPE: DNA
<213> ORGANISM: Artificial Sequence
<220> FEATURE:
<223> OTHER INFORMATION: Synthetic

<400> SEQUENCE: 167
gcgagagatc tggggatctt tgactta                                       27

<210> SEQ ID NO 168
<211> LENGTH: 9
<212> TYPE: PRT
<213> ORGANISM: Artificial Sequence
<220> FEATURE:
<223> OTHER INFORMATION: Synthetic

<400> SEQUENCE: 168

Ala Arg Asp Leu Gly Ile Phe Asp Leu
1               5

<210> SEQ ID NO 169
<211> LENGTH: 327
<212> TYPE: DNA
<213> ORGANISM: Artificial Sequence
<220> FEATURE:
```

<223> OTHER INFORMATION: Synthetic

<400> SEQUENCE: 169

```
gaaattgtga tgacgcagtc tccagccacc ctgtctgtgt ctccagggga aagagccacc    60
ctctcctgta gggccagtca gagtgttagt agtagtttag cctggtacca ccagaaacct   120
ggccaggctc ccaggctcct catccatggt gtttccacca gggccactgg tatcccagcc   180
aggttcagtg gcactgggtc tgggacagaa ttcactctca ccatcagcag cctgcagtct   240
gaagattttg cagtttatta ctgtcaacag tatcataact ggcctccgta cacttttggc   300
caggggacca agctggagat caaacga                                       327
```

<210> SEQ ID NO 170
<211> LENGTH: 109
<212> TYPE: PRT
<213> ORGANISM: Artificial Sequence
<220> FEATURE:
<223> OTHER INFORMATION: Synthetic

<400> SEQUENCE: 170

```
Glu Ile Val Met Thr Gln Ser Pro Ala Thr Leu Ser Val Ser Pro Gly
 1               5                  10                  15
Glu Arg Ala Thr Leu Ser Cys Arg Ala Ser Gln Ser Val Ser Ser Ser
                20                  25                  30
Leu Ala Trp Tyr His Gln Lys Pro Gly Gln Ala Pro Arg Leu Leu Ile
            35                  40                  45
His Gly Val Ser Thr Arg Ala Thr Gly Ile Pro Ala Arg Phe Ser Gly
        50                  55                  60
Thr Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr His Asn Trp Pro Pro
                85                  90                  95
Tyr Thr Phe Gly Gln Gly Thr Lys Leu Glu Ile Lys Arg
            100                 105
```

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171

```
cagagtgtta gtagtagt                                                  18
```

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

```
Gln Ser Val Ser Ser Ser
 1               5
```

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 ggtgtttcc                                                                  9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Gly Val Ser
 1

<210> SEQ ID NO 175
<211> LENGTH: 30
<212> TYPE: DNA
<213> ORGANISM: Artificial Sequence
<220> FEATURE:
<223> OTHER INFORMATION: Synthetic

<400> SEQUENCE: 175
caacagtatc ataactggcc tccgtacact                                          30

<210> SEQ ID NO 176
<211> LENGTH: 10
<212> TYPE: PRT
<213> ORGANISM: Artificial Sequence
<220> FEATURE:
<223> OTHER INFORMATION: Synthetic

<400> SEQUENCE: 176

Gln Gln Tyr His Asn Trp Pro Pro Tyr Thr
 1               5                  10

<210> SEQ ID NO 177
<211> LENGTH: 363
<212> TYPE: DNA
<213> ORGANISM: Artificial Sequence
<220> FEATURE:
<223> OTHER INFORMATION: Synthetic

<400> SEQUENCE: 177
caggtgcagc tggtggagtc tgggggaggc gtggtccagc ctggggaggtc cctgagactc        60 tcctgtgcag cctctggatt caccttcagt agttttggca tgcactgggt ccgccaggct       120
ccaggcaagg ggctggagtg gtgtcaatg atatcaaccg atggaagtaa gaaaaattat       180
gcagactccg tgaagggccg attcaccatc accagagaca attcaaagaa cacgctgtat       240
ttggaaatga acagcctgag agctgaggac acggctgtgt attacggtgt gagagttggg       300
tactatgatt cggggagtta ttataactat tggggccagg gaaccctggt caccgtctcc       360
tca                                                                    363

<210> SEQ ID NO 178
<211> LENGTH: 121
<212> TYPE: PRT
<213> ORGANISM: Artificial Sequence
<220> FEATURE:
<223> OTHER INFORMATION: Synthetic

<400> SEQUENCE: 178

Gln Val Gln Leu Val Glu Ser Gly Gly Gly Val Val Gln Pro Gly Arg
 1               5                  10                  15

```
Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ser Met Ile Ser Thr Asp Gly Ser Lys Lys Asn Tyr Ala Asp Ser Val
    50                  55                  60

Lys Gly Arg Phe Thr Ile Thr Arg Asp Asn Ser Lys Asn Thr Leu Tyr
65                  70                  75                  80

Leu Glu Met Asn Ser Leu Arg Ala Glu Asp Thr Ala Val Tyr Tyr Gly
                85                  90                  95

Val Arg Val Gly Tyr Tyr Asp Ser Gly Ser Tyr Tyr Asn Tyr Trp Gly
                100                 105                 110

Gln Gly Thr Leu Val Thr Val Ser Ser
        115                 120
```

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggattcacct tcagtagttt tggc                                        24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

```
Gly Phe Thr Phe Ser Ser Phe Gly
1               5
```

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
atatcaaccg atggaagtaa gaaa                                        24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

```
Ile Ser Thr Asp Gly Ser Lys Lys
1               5
```

<210> SEQ ID NO 183
<211> LENGTH: 42
<212> TYPE: DNA
<213> ORGANISM: Artificial Sequence
<220> FEATURE:
<223> OTHER INFORMATION: Synthetic

<400> SEQUENCE: 183
gtgagagttg ggtactatga ttcggggagt tattataact at            42

<210> SEQ ID NO 184
<211> LENGTH: 14
<212> TYPE: PRT
<213> ORGANISM: Artificial Sequence
<220> FEATURE:
<223> OTHER INFORMATION: Synthetic

<400> SEQUENCE: 184

Val Arg Val Gly Tyr Tyr Asp Ser Gly Ser Tyr Tyr Asn Tyr
1               5                   10

<210> SEQ ID NO 185
<211> LENGTH: 324
<212> TYPE: DNA
<213> ORGANISM: Artificial Sequence
<220> FEATURE:
<223> OTHER INFORMATION: Synthetic

<400> SEQUENCE: 185
gacatccaga tgacccagtc tccatcttcc gtgtctgcat ctgtaggtga cagagtcacc    60
atcacttgtc gggcgagtca gggtattcgc agctggttag cctggtttca gcagagacca   120
gggaaagccc ctaacctcct gatctatgct gcatccagtt tgcaaagtgg ggtctcatcc   180
aggttcagcg gcagtggctc tgggacagaa ttcactctca gcatcagcag cctgcagcct   240
gaagattttg caacttacta ttgtcaacag gcttacagtt tccgctcac tttcggcgga   300 gggaccaagg tggagatcaa acga                                         324

<210> SEQ ID NO 186
<211> LENGTH: 108
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Phe Gln Gln Arg Pro Gly Lys Ala Pro Asn Leu Leu Ile
        35                  40                  45

Tyr Ala Ala Ser Ser Leu Gln Ser Gly Val Ser Ser Arg Phe Ser Gly
    50                  55                  60

Ser Gly Ser Gly Thr Glu Phe Thr Leu Ser Ile Ser Ser Leu Gln Pro
65                  70                  75                  80

Glu Asp Phe Ala Thr Tyr Tyr Cys Gln Gln Ala Tyr Ser Phe Pro Leu
                85                  90                  95

Thr Phe Gly Gly Gly Thr Lys Val Glu Ile Lys Arg
            100                 105

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
cagggtattc gcagctgg					18

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Gly Ile Arg Ser Trp
 1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gctgcatcc					9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Ala Ser
 1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacaggctt acagttttcc gctcact					27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Ala Tyr Ser Phe Pro Leu Thr
 1               5

<210> SEQ ID NO 193
<211> LENGTH: 348
<212> TYPE: DNA
<213> ORGANISM: Artificial Sequence
<220> FEATURE:
<223> OTHER INFORMATION: Synthetic

<400> SEQUENCE: 193
gaggtgcagc tggtggagtc tgggggaggc ttggtgcggc ctggggggtc cctgagactc					60

```
tcctgtgcag cctctggatt cacctttagg atctatgcca tgagctgggt ccgccaggct    120
ccagggaagg ggctggagtg ggtctcaggt attagtggta gtggtgataa tacatactat    180
acagactccg tgaagggccg gttcatcatc tccagagaca attccaagag cacgctgtat    240
ctgcaaatga acagcctgag agccgaagat acggccgtat attactgtgc gagagggtgg    300
gagttactga actactgggg ccagggaacc ctggtcaccg tctcctca                 348
```

<210> SEQ ID NO 194
<211> LENGTH: 116
<212> TYPE: PRT
<213> ORGANISM: Artificial Sequence
<220> FEATURE:
<223> OTHER INFORMATION: Synthetic

<400> SEQUENCE: 194

```
Glu Val Gln Leu Val Glu Ser Gly Gly Gly Leu Val Arg Pro Gly Gly
 1               5                  10                  15

Ser Leu Arg Leu Ser Cys Ala Ala Ser Gly Phe Thr Phe Arg Ile Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Asp Asn Thr Tyr Tyr Thr Asp Ser Val
    50                  55                  60

Lys Gly Arg Phe Ile Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Glu Leu Leu Asn Tyr Trp Gly Gln Gly Thr Leu Val
            100                 105                 110

Thr Val Ser Ser
        115
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195

```
ggattcacct ttaggatcta tgcc                                            24
```

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

```
Gly Phe Thr Phe Arg Ile Tyr Ala
 1               5
```

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197

```
attagtggta gtggtgataa taca                                            24
```

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Ser Gly Ser Gly Asp Asn Thr
1               5

<210> SEQ ID NO 199
<211> LENGTH: 27
<212> TYPE: DNA
<213> ORGANISM: Artificial Sequence
<220> FEATURE:
<223> OTHER INFORMATION: Synthetic

<400> SEQUENCE: 199

```
gcgagagggt gggagttact gaactac                                         27
```

<210> SEQ ID NO 200
<211> LENGTH: 9
<212> TYPE: PRT
<213> ORGANISM: Artificial Sequence
<220> FEATURE:
<223> OTHER INFORMATION: Synthetic

<400> SEQUENCE: 200

Ala Arg Gly Trp Glu Leu Leu Asn Tyr
1               5

<210> SEQ ID NO 201
<211> LENGTH: 324
<212> TYPE: DNA
<213> ORGANISM: Artificial Sequence
<220> FEATURE:
<223> OTHER INFORMATION: Synthetic

<400> SEQUENCE: 201

```
gacatccaga tgacccagtc tccatcctca ctgtctgcat ttgtaggaga cagagtcacc     60
atcacttgtc gggcgagtca ggacattagc aatcatttag cctggtttca gcagaaacca    120
gggaaagtcc ctaagtccct gatctatgct gcgtccagtt tgcaaagtgg ggtcccatca    180
aaattcagcg gcagtggatc tgggacagat tcactctcac ccatcagcag cctgcagcct    240
gaagattttg caactattta ctgccaacag tatggtcttt atcctcccac tttcggccct    300
gggaccaaag tggatatcaa acga                                           324
```

<210> SEQ ID NO 202
<211> LENGTH: 108
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Leu Ser Ala Phe Val Gly
1               5                   10                  15

Asp Arg Val Thr Ile Thr Cys Arg Ala Ser Gln Asp Ile Ser Asn His
            20                  25                  30

Leu Ala Trp Phe Gln Gln Lys Pro Gly Lys Val Pro Lys Ser Leu Ile

```
                35                  40                  45
Tyr Ala Ala Ser Ser Leu Gln Ser Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Leu Tyr Pro Pro
                 85                  90                  95

Thr Phe Gly Pro Gly Thr Lys Val Asp Ile Lys Arg
            100                 105
```

```
<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
caggacatta gcaatcat                                              18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Asp Ile Ser Asn His
 1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 gctgcgtcc                                                         9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Ala Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacagtatg gtctttatcc tcccact                                    27

<210> SEQ ID NO 208
<211> LENGTH: 9
```

<212> TYPE: PRT
<213> ORGANISM: Artificial Sequence
<220> FEATURE:
<223> OTHER INFORMATION: Synthetic

<400> SEQUENCE: 208

Gln Gln Tyr Gly Leu Tyr Pro Pro Thr
 1               5

<210> SEQ ID NO 209
<211> LENGTH: 348
<212> TYPE: DNA
<213> ORGANISM: Artificial Sequence
<220> FEATURE:
<223> OTHER INFORMATION: Synthetic

<400> SEQUENCE: 209

```
gaggtgcagc tggtggagtc tgggggaggc ttggtacagc cggggggtc cctgagactc    60 tcctgtgcag cctctggatt cacttttagc atctatgcca tgagctgggt ccgccaggct   120
ccagggaagg ggctggagtg ggtctcaggt attagtggta gtggtggtag aacatactac   180
gcagactccg ttaagggccg gttcaccatc tctagagaca attccaagaa cacgctgtat   240
ctgcaaatga acagcctgag agtcgaggac acggccgttt attactgtgc gagagggtgg   300
gagcttctta acttctgggg ccagggaacc ctggtcaccg tctcctca               348
```

<210> SEQ ID NO 210
<211> LENGTH: 116
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Trp Glu Leu Leu Asn Phe Trp Gly Gln Gly Thr Leu Val
            100                 105                 110

Thr Val Ser Ser
        115

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcactt ttagcatcta tgcc                                            24

```
<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Ile Tyr Ala
  1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
attagtggta gtggtggtag aaca                                        24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ser Gly Ser Gly Gly Arg Thr
  1               5

<210> SEQ ID NO 215
<211> LENGTH: 27
<212> TYPE: DNA
<213> ORGANISM: Artificial Sequence
<220> FEATURE:
<223> OTHER INFORMATION: Synthetic

<400> SEQUENCE: 215
gcgagagggt gggagcttct taacttc                                     27

<210> SEQ ID NO 216
<211> LENGTH: 9
<212> TYPE: PRT
<213> ORGANISM: Artificial Sequence
<220> FEATURE:
<223> OTHER INFORMATION: Synthetic

<400> SEQUENCE: 216

Ala Arg Gly Trp Glu Leu Leu Asn Phe
  1               5

<210> SEQ ID NO 217
<211> LENGTH: 324
<212> TYPE: DNA
<213> ORGANISM: Artificial Sequence
<220> FEATURE:
<223> OTHER INFORMATION: Synthetic

<400> SEQUENCE: 217
gacatccaga tgacccagtc tccatcctca ctgtctgcat ctgtaggaga cagagtcacc    60
atcacttgtc gggcgagtca gggcattagt aataatttag cctggtttca gcagaaacca   120
gggaaagccc ctaagtccct gatctatgct gcatccagtt tgaaaagtgg ggtcccatca   180
aagttcagcg gcagtggatc tgggacagat ttcactctca ccatcaacag cctgcagcct   240
```

```
gaagattttg caacttatta ctgccaccag tataatagtt atcctccac tttcggccct      300 gggaccaaag tggatatcaa acga                                            324
```

<210> SEQ ID NO 218
<211> LENGTH: 108
<212> TYPE: PRT
<213> ORGANISM: Artificial Sequence
<220> FEATURE:
<223> OTHER INFORMATION: Synthetic

<400> SEQUENCE: 218

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Asn
             20                  25                  30

Leu Ala Trp Phe Gln Gln Lys Pro Gly Lys Ala Pro Lys Ser Leu Ile
         35                  40                  45

Tyr Ala Ala Ser Ser Leu Lys Ser Gly Val Pro Ser Lys Phe Ser Gly
     50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys His Gln Tyr Asn Ser Tyr Pro Pro
                 85                  90                  95

Thr Phe Gly Pro Gly Thr Lys Val Asp Ile Lys Arg
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219

```
cagggcatta gtaataat                                                    18
```

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

```
Gln Gly Ile Ser Asn Asn
  1               5
```

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221

```
gctgcatcc                                                               9
```

<210> SEQ ID NO 222
<211> LENGTH: 3
<212> TYPE: PRT
<213> ORGANISM: Artificial Sequence
<220> FEATURE:

<223> OTHER INFORMATION: Synthetic

<400> SEQUENCE: 222

Ala Ala Ser
 1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
caccagtata atagttatcc tcccact                                          27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

His Gln Tyr Asn Ser Tyr Pro Pro Thr
 1               5

<210> SEQ ID NO 225
<211> LENGTH: 348
<212> TYPE: DNA
<213> ORGANISM: Artificial Sequence
<220> FEATURE:
<223> OTHER INFORMATION: Synthetic

<400> SEQUENCE: 225
gaggtgcagc tggtggagtc tgggggaggc ttggtgcagc ctggggggtc cctgagactc      60
tcctgtgcag tctctggatt cacctttagc atctatgcca tgagctgggt ccgccaggct     120
ccagggaagg ggctggagtg ggtctcagct attagtggta gtggtgataa acatactac      180 gcagactccg tgaagggccg gttcaccatc tccagagaca attccaagaa cacgctgtat     240
ctgcaaatga acagcctgag agccgaggac acggccgtat tttactgtgc gagagggtgg     300
gagctcctaa actactgggg ccagggaacc ctggtcaccg tctcctca                  348

<210> SEQ ID NO 226
<211> LENGTH: 116
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Ile Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Asp Lys Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Phe Tyr Cys
            85                  90                  95

Ala Arg Gly Trp Glu Leu Leu Asn Tyr Trp Gly Gln Gly Thr Leu Val
        100                 105                 110

Thr Val Ser Ser
        115

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcacct ttagcatcta tgcc                                              24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Phe Ser Ile Tyr Ala
1               5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagtggta gtggtgataa gaca                                              24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Gly Ser Gly Asp Lys Thr
1               5

<210> SEQ ID NO 231
<211> LENGTH: 27
<212> TYPE: DNA
<213> ORGANISM: Artificial Sequence
<220> FEATURE:
<223> OTHER INFORMATION: Synthetic

<400> SEQUENCE: 231
gcgagagggt gggagctcct aaactac                                           27

<210> SEQ ID NO 232
<211> LENGTH: 9
<212> TYPE: PRT
<213> ORGANISM: Artificial Sequence
<220> FEATURE:
<223> OTHER INFORMATION: Synthetic

<400> SEQUENCE: 232

Ala Arg Gly Trp Glu Leu Leu Asn Tyr
1               5

<210> SEQ ID NO 233
<211> LENGTH: 324
<212> TYPE: DNA
<213> ORGANISM: Artificial Sequence
<220> FEATURE:
<223> OTHER INFORMATION: Synthetic

<400> SEQUENCE: 233

```
gacatccaga tgacccagtc tccatcctca ctgtctgcat ctgtaggaga cagagtcacc    60
atcacttgtc gggcgagtct ggacattagt aatttttag cctggtttca gcagaaacca   120
gggacagccc ctaagtccct gatctattct gcatccagtt tgcggactgg ggtcccatca   180
aagttcagcg gcagtggatc tgggacagat ttcactctca ccatcagcag cctgcagcct   240
gaagattttg caacttatta ctgccagcag tatagttctt accctcccac tttcggccct   300
gggaccaaag tggatatcaa acga                                         324
```

<210> SEQ ID NO 234
<211> LENGTH: 108
<212> TYPE: PRT
<213> ORGANISM: Artificial Sequence
<220> FEATURE:
<223> OTHER INFORMATION: Synthetic

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Leu Asp Ile Ser Asn Phe
            20                  25                  30

Leu Ala Trp Phe Gln Gln Lys Pro Gly Thr Ala Pro Lys Ser Leu Ile
        35                  40                  45

Tyr Ser Ala Ser Ser Leu Arg Thr Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Pro
                85                  90                  95

Thr Phe Gly Pro Gly Thr Lys Val Asp Ile Lys Arg
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235

```
ctggacatta gtaattt                                                  18
```

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Leu Asp Ile Ser Asn Phe
1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 tctgcatcc                                                              9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Ser Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
cagcagtata gttcttaccc tcccact                                         27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Tyr Ser Ser Tyr Pro Pro Thr
1               5

<210> SEQ ID NO 241
<211> LENGTH: 348
<212> TYPE: DNA
<213> ORGANISM: Artificial Sequence
<220> FEATURE:
<223> OTHER INFORMATION: Synthetic

<400> SEQUENCE: 241
gaggtgcagc tggtggagtc tgggggaggc ttggtacagc cggggggtc cctgagactc      60 tcctgtgtag cctctggatt caactttaga atctatgcca tgagctgggt ccgccaggct    120
ccagggaagg ggccggagtg ggtctcaggt attagtggta gtggtgataa cacatactac    180
gcagcctccg tgaagggccg gttcaccgtc tccagagaca attccaagaa cacgctgtat    240
ctgcaaatga ccagcctgag agccgaggac acggccgtat tttactgtgc gagagggtgg    300
gagctcctaa actattgggg ccagggaacc ctggtcaccg tctcctca                 348

<210> SEQ ID NO 242
<211> LENGTH: 116

```
<212> TYPE: PRT
<213> ORGANISM: Artificial Sequence
<220> FEATURE:
<223> OTHER INFORMATION: Synthetic

<400> SEQUENCE: 242

Glu Val Gln Leu Val Glu Ser Gly Gly Gly Leu Val Gln Pro Gly Gly
 1               5                  10                  15

Ser Leu Arg Leu Ser Cys Val Ala Ser Gly Phe Asn Phe Arg Ile Tyr
            20                  25                  30

Ala Met Ser Trp Val Arg Gln Ala Pro Gly Lys Gly Pro Glu Trp Val
        35                  40                  45

Ser Gly Ile Ser Gly Ser Gly Asp Asn Thr Tyr Tyr Ala Ala Ser Val
    50                  55                  60

Lys Gly Arg Phe Thr Val Ser Arg Asp Asn Ser Lys Asn Thr Leu Tyr
65                  70                  75                  80

Leu Gln Met Thr Ser Leu Arg Ala Glu Asp Thr Ala Val Phe Tyr Cys
                85                  90                  95

Ala Arg Gly Trp Glu Leu Leu Asn Tyr Trp Gly Gln Gly Thr Leu Val
            100                 105                 110

Thr Val Ser Ser
        115

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcaact ttagaatcta tgcc                                           24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Asn Phe Arg Ile Tyr Ala
 1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
attagtggta gtggtgataa caca                                           24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Gly Ser Gly Asp Asn Thr
```

<210> SEQ ID NO 247
<211> LENGTH: 27
<212> TYPE: DNA
<213> ORGANISM: Artificial Sequence
<220> FEATURE:
<223> OTHER INFORMATION: Synthetic

<400> SEQUENCE: 247
gcgagagggt gggagctcct aaactat                                27

<210> SEQ ID NO 248
<211> LENGTH: 9
<212> TYPE: PRT
<213> ORGANISM: Artificial Sequence
<220> FEATURE:
<223> OTHER INFORMATION: Synthetic

<400> SEQUENCE: 248

Ala Arg Gly Trp Glu Leu Leu Asn Tyr
 1               5

<210> SEQ ID NO 249
<211> LENGTH: 324
<212> TYPE: DNA
<213> ORGANISM: Artificial Sequence
<220> FEATURE:
<223> OTHER INFORMATION: Synthetic

<400> SEQUENCE: 249
gacatccaga tgacccagtc tccatcctca ctgtctgcat ctgtaggaga cagagtcacc    60
atcacttgtc gggcgagtct ggacattggc aattttttag cctggtttca gcagaaacca   120
gggacagccc ctaagtccct gatctattct gcatccagtc tgcagactgg ggtcccatca   180
aagttcagcg gcagtggatc tgggacagat tcactctca ccatcagcag cctgcagcct   240
gaagattttg caacttatta ctgccaacag tataattctt atcctcccac tttcggccct   300
gggaccaaag tggatatcaa acga                                         324

<210> SEQ ID NO 250
<211> LENGTH: 108
<212> TYPE: PRT
<213> ORGANISM: Artificial Sequence
<220> FEATURE:
<223> OTHER INFORMATION: Synthetic

<400> SEQUENCE: 250

Asp Ile Gln Met Thr Gln Ser Pro Ser Ser Leu Ser Ala Ser Val Gly
 1               5                  10                  15

Asp Arg Val Thr Ile Thr Cys Arg Ala Ser Leu Asp Ile Gly Asn Phe
             20                  25                  30

Leu Ala Trp Phe Gln Gln Lys Pro Gly Thr Ala Pro Lys Ser Leu Ile
         35                  40                  45

Tyr Ser Ala Ser Ser Leu Gln Thr Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Pro
                 85                  90                  95

Thr Phe Gly Pro Gly Thr Lys Val Asp Ile Lys Arg
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
ctggacattg gcaatttt                                                   18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Leu Asp Ile Gly Asn Phe
 1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 tctgcatcc                                                              9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Ser Ala Ser
 1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
caacagtata attcttatcc tcccact                                         27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Tyr Asn Ser Tyr Pro Pro Thr
 1               5

<210> SEQ ID NO 257
<211> LENGTH: 348

```
<212> TYPE: DNA
<213> ORGANISM: Artificial Sequence
<220> FEATURE:
<223> OTHER INFORMATION: Synthetic

<400> SEQUENCE: 257
gaggtgcagc tggtggagtc tgggggaggc ttggtacagc cggggggtc cctgagactc      60 tcctgtgcag cctctggatt tacctttaaa atctatgcca tgagttgggt ccgccagggc    120
ccagggaagg ggctggagtg gtctcggct attagtggaa atggtgacaa aacatactat    180
acagactccg tgcagggccg gttcaccatc tccagagaca attccaagaa cacactcttt    240
ctccaaatga acagcctgag agccgaggac acggccatat attactgtgc gcgagggtgg    300
gaactgctaa attactgggg ccagggaacc ctggtcaccg tctcctca                  348

<210> SEQ ID NO 258
<211> LENGTH: 116
<212> TYPE: PRT
<213> ORGANISM: Artificial Sequence
<220> FEATURE:
<223> OTHER INFORMATION: Synthetic

<400> SEQUENCE: 258

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Lys Ile Tyr
            20                  25                  30

Ala Met Ser Trp Val Arg Gln Gly Pro Gly Lys Gly Leu Glu Trp Val
        35                  40                  45

Ser Ala Ile Ser Gly Asn Gly Asp Lys Thr Tyr Tyr Thr Asp Ser Val
    50                  55                  60

Gln Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Ile Tyr Tyr Cys
                85                  90                  95

Ala Arg Gly Trp Glu Leu Leu Asn Tyr Trp Gly Gln Gly Thr Leu Val
            100                 105                 110

Thr Val Ser Ser
        115

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
ggatttacct ttaaaatcta tgcc                                             24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Thr Phe Lys Ile Tyr Ala
 1               5
```

```
<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
attagtggaa atggtgacaa aaca                                          24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ser Gly Asn Gly Asp Lys Thr
 1               5

<210> SEQ ID NO 263
<211> LENGTH: 27
<212> TYPE: DNA
<213> ORGANISM: Artificial Sequence
<220> FEATURE:
<223> OTHER INFORMATION: Synthetic

<400> SEQUENCE: 263
gcgcgagggt gggaactgct aaattac                                       27

<210> SEQ ID NO 264
<211> LENGTH: 9
<212> TYPE: PRT
<213> ORGANISM: Artificial Sequence
<220> FEATURE:
<223> OTHER INFORMATION: Synthetic

<400> SEQUENCE: 264

Ala Arg Gly Trp Glu Leu Leu Asn Tyr
 1               5

<210> SEQ ID NO 265
<211> LENGTH: 324
<212> TYPE: DNA
<213> ORGANISM: Artificial Sequence
<220> FEATURE:
<223> OTHER INFORMATION: Synthetic

<400> SEQUENCE: 265
gacatccaga tgacccagtc tccatcctca ctgtctgcat ctataggaga cagagtcacc    60
atcacttgtc gggcgagtca ggacattagc aattctttag cctggtttca gcagaaacca   120
gggaaagccc ctaagtccct gatctatgct gcatccagtt tgcaaagtgg ggtcccatca   180
aggttcagcg gcagtggatc tgggacagat ttcactctca ccatctccag cctgcagcct   240
gaagattttg caacttatta ctgccaacaa tatattcctt tccctcccac tttcggccct   300
gggaccaaag tggatatcaa acga                                         324

<210> SEQ ID NO 266
<211> LENGTH: 108
<212> TYPE: PRT
<213> ORGANISM: Artificial Sequence
<220> FEATURE:
<223> OTHER INFORMATION: Synthetic
```

-continued

<400> SEQUENCE: 266

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Asp Ile Ser Asn Ser
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Pro Phe Pro Pro
                85                  90                  95

Thr Phe Gly Pro Gly Thr Lys Val Asp Ile Lys Arg
            100                 105

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267
caggacatta gcaattct                                                18

<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

Gln Asp Ile Ser Asn Ser
1               5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 gctgcatcc                                                           9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Ala Ala Ser
1

<210> SEQ ID NO 271
<211> LENGTH: 27
<212> TYPE: DNA
<213> ORGANISM: Artificial Sequence
<220> FEATURE:

<223> OTHER INFORMATION: Synthetic

<400> SEQUENCE: 271
caacaatata ttcctttccc tcccact                                           27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Gln Gln Tyr Ile Pro Phe Pro Pro Thr
 1               5

<210> SEQ ID NO 273
<211> LENGTH: 348
<212> TYPE: DNA
<213> ORGANISM: Artificial Sequence
<220> FEATURE:
<223> OTHER INFORMATION: Synthetic

<400> SEQUENCE: 273
gaggtgcagc tggtggagtc tgggggaggc tggtacagc cggggggtc cctgagactc       60 tcctgtgtag cttctggatt cacctttacc agctatgcca tgagctgggt ccgccaggct     120
ccagggaggg ggctgcagtg ggtctcagct attggtggta gtggtgatag tatatattac     180
gcagactccg tcaagggccg gttcaccatc tccagagaca actccaagaa tacgctgtat     240
ctgcaaatgg acagcctgag agccgaggac acggccgtat attactgtgc aagaggatgg     300
gagttactca attactgggg ccagggaacc ctggtcaccg tctcctca                 348

<210> SEQ ID NO 274
<211> LENGTH: 116
<212> TYPE: PRT
<213> ORGANISM: Artificial Sequence
<220> FEATURE:
<223> OTHER INFORMATION: Synthetic

<400> SEQUENCE: 274

Glu Val Gln Leu Val Glu Ser Gly Gly Gly Leu Val Gln Pro Gly Gly
 1               5                  10                  15

Ser Leu Arg Leu Ser Cys Val Ala Ser Gly Phe Thr Phe Thr Ser Tyr
             20                  25                  30

Ala Met Ser Trp Val Arg Gln Ala Pro Gly Arg Gly Leu Gln Trp Val
         35                  40                  45

Ser Ala Ile Gly Gly Ser Gly Asp Ser Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Tyr Cys
                 85                  90                  95

Ala Arg Gly Trp Glu Leu Leu Asn Tyr Trp Gly Gln Gly Thr Leu Val
            100                 105                 110

Thr Val Ser Ser
        115

<210> SEQ ID NO 275
<211> LENGTH: 24
<212> TYPE: DNA

```
<213> ORGANISM: Artificial Sequence
<220> FEATURE:
<223> OTHER INFORMATION: Synthetic

<400> SEQUENCE: 275
ggattcacct ttaccagcta tgcc                                          24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Phe Thr Ser Tyr Ala
1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
attggtggta gtggtgatag tata                                          24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Gly Gly Ser Gly Asp Ser Ile
1               5

<210> SEQ ID NO 279
<211> LENGTH: 27
<212> TYPE: DNA
<213> ORGANISM: Artificial Sequence
<220> FEATURE:
<223> OTHER INFORMATION: Synthetic

<400> SEQUENCE: 279
gcaagaggat gggagttact caattac                                       27

<210> SEQ ID NO 280
<211> LENGTH: 9
<212> TYPE: PRT
<213> ORGANISM: Artificial Sequence
<220> FEATURE:
<223> OTHER INFORMATION: Synthetic

<400> SEQUENCE: 280

Ala Arg Gly Trp Glu Leu Leu Asn Tyr
1               5

<210> SEQ ID NO 281
<211> LENGTH: 324
<212> TYPE: DNA
<213> ORGANISM: Artificial Sequence
<220> FEATURE:
<223> OTHER INFORMATION: Synthetic
```

<400> SEQUENCE: 281

```
gacatccaga tgacccagtc tccatcctca ctgtctgcat ctgtaggaga cagagtcacc    60
atcacttgtc gggcgagtca ggacattggc aatttttag cctggtttca gcagaaacca   120
gggaaagccc ctaagtccct gatctatgct gcatccagtt tgaaaagtgg ggtcccatca   180
aagatcagcg gcagtggatc tgggacagat ttcactctca ccatcaacag cctgcagcct   240
gaagattttg caacttatta ctgccaacag tataatattt accctcccac tttcggccct   300
gggaccaaag tggatatcaa acga                                          324
```

<210> SEQ ID NO 282
<211> LENGTH: 108
<212> TYPE: PRT
<213> ORGANISM: Artificial Sequence
<220> FEATURE:
<223> OTHER INFORMATION: Synthetic

<400> SEQUENCE: 282

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Gly Asn Phe
             20                  25                  30

Leu Ala Trp Phe Gln Gln Lys Pro Gly Lys Ala Pro Lys Ser Leu Ile
         35                  40                  45

Tyr Ala Ala Ser Ser Leu Lys Ser Gly Val Pro Ser Lys Ile Ser Gly
     50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Tyr Asn Ile Tyr Pro Pro
                 85                  90                  95

Thr Phe Gly Pro Gly Thr Lys Val Asp Ile Lys Arg
            100                 105
```

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283

```
caggacattg gcaatttt                                                  18
```

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

```
Gln Asp Ile Gly Asn Phe
  1               5
```

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 gctgcatcc                                                                    9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Ala Ala Ser
 1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
caacagtata atatttaccc tcccact                                               27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Tyr Asn Ile Tyr Pro Pro Thr
 1               5

<210> SEQ ID NO 289
<211> LENGTH: 360
<212> TYPE: DNA
<213> ORGANISM: Artificial Sequence
<220> FEATURE:
<223> OTHER INFORMATION: Synthetic

<400> SEQUENCE: 289
caggtacagc tgcagcagtc aggtccagga ctggtgaagc cctcgcagac cctctcactc            60
acctgtgcca tctccgggga cagtgtctct agcaacagtg ctgcttggaa ctggatcagg          120
cagtccccat cgagaggcct tgagtggctg ggaaggacat actacaggtc caagtggtat          180
catgattatg cttttttctgt gaaaagtcga atacttatca atccagacac atccaagaac         240
ctgttctccc tgcaagtgaa ctctgtgact cccgaggaca cggctgtgta ttactgtgca          300
agagataggc gatcctactt tgactactgg ggccagggaa ccctggtcac cgtctcctca          360

<210> SEQ ID NO 290
<211> LENGTH: 120
<212> TYPE: PRT
<213> ORGANISM: Artificial Sequence
<220> FEATURE:
<223> OTHER INFORMATION: Synthetic

<400> SEQUENCE: 290

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
                20                  25                  30

```
Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr His Asp Tyr Ala
 50                  55                  60

Phe Ser Val Lys Ser Arg Ile Leu Ile Asn Pro Asp Thr Ser Lys Asn
 65                  70                  75                  80

Leu Phe Ser Leu Gln Val Asn Ser Val Thr Pro Glu Asp Thr Ala Val
                 85                  90                  95

Tyr Tyr Cys Ala Arg Asp Arg Arg Ser Tyr Phe Asp Tyr Trp Gly Gln
                100                 105                 110

Gly Thr Leu Val Thr Val Ser Ser
        115                 120
```

<210> SEQ ID NO 291
<211> LENGTH: 30
<212> TYPE: DNA
<213> ORGANISM: Artificial Sequence
<220> FEATURE:
<223> OTHER INFORMATION: Synthetic

<400> SEQUENCE: 291
ggggacagtg tctctagcaa cagtgctgct    30

<210> SEQ ID NO 292
<211> LENGTH: 10
<212> TYPE: PRT
<213> ORGANISM: Artificial Sequence
<220> FEATURE:
<223> OTHER INFORMATION: Synthetic

<400> SEQUENCE: 292

```
Gly Asp Ser Val Ser Ser Asn Ser Ala Ala
 1               5                  10
```

<210> SEQ ID NO 293
<211> LENGTH: 27
<212> TYPE: DNA
<213> ORGANISM: Artificial Sequence
<220> FEATURE:
<223> OTHER INFORMATION: Synthetic

<400> SEQUENCE: 293
acatactaca ggtccaagtg gtatcat    27

<210> SEQ ID NO 294
<211> LENGTH: 9
<212> TYPE: PRT
<213> ORGANISM: Artificial Sequence
<220> FEATURE:
<223> OTHER INFORMATION: Synthetic

<400> SEQUENCE: 294

```
Thr Tyr Tyr Arg Ser Lys Trp Tyr His
 1               5
```

<210> SEQ ID NO 295
<211> LENGTH: 30
<212> TYPE: DNA
<213> ORGANISM: Artificial Sequence
<220> FEATURE:
<223> OTHER INFORMATION: Synthetic

<400> SEQUENCE: 295
gcaagagata ggcgatccta ctttgactac    30

<210> SEQ ID NO 296
<211> LENGTH: 10
<212> TYPE: PRT
<213> ORGANISM: Artificial Sequence
<220> FEATURE:
<223> OTHER INFORMATION: Synthetic

<400> SEQUENCE: 296

Ala Arg Asp Arg Arg Ser Tyr Phe Asp Tyr
 1               5                  10

<210> SEQ ID NO 297
<211> LENGTH: 324
<212> TYPE: DNA
<213> ORGANISM: Artificial Sequence
<220> FEATURE:
<223> OTHER INFORMATION: Synthetic

<400> SEQUENCE: 297
gaaattgtgt tgacacagtc tccagccacc ctgtctttgt ctccagggga aagagccacc      60
ctctcctgca gggccagtcg gagtgttagc agttccttag cctggtacca acagaaacct     120
ggccaggctc ccaggctcct catctatgat gcatccaaca gggccactgg catcccagcc     180
aggttcagtg gcggtgggtc tgggacagac ttcactctca ccatcagcag cctagagcct     240
gaagattttg cagtttatta ctgtcagcag cgtaacaact ggcctcccac ttttggccag     300
gggaccaagc tggagatcaa acga                                            324

<210> SEQ ID NO 298
<211> LENGTH: 108
<212> TYPE: PRT
<213> ORGANISM: Artificial Sequence
<220> FEATURE:
<223> OTHER INFORMATION: Synthetic

<400> SEQUENCE: 298

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Arg Ser Val Ser Ser Ser
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Gly Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Asn Trp Pro Pro
                85                  90                  95

Thr Phe Gly Gln Gly Thr Lys Leu Glu Ile Lys Arg
            100                 105

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
cggagtgtta gcagttcc                                                    18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Arg Ser Val Ser Ser Ser
 1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gatgcatcc                                                                9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Asp Ala Ser
 1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
cagcagcgta acaactggcc tcccact                                            27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Arg Asn Asn Trp Pro Pro Thr
 1               5

<210> SEQ ID NO 305
<211> LENGTH: 369
<212> TYPE: DNA
<213> ORGANISM: Artificial Sequence
<220> FEATURE:
<223> OTHER INFORMATION: Synthetic

<400> SEQUENCE: 305
gaggtgcagc tggtggagtc tgggggaggc ttggtacagc ctggcaggtc cctgagactc        60
tcctgtacag cctctggatt cgttttttgaa gattatgcca tgcactgggt ccggcaagct      120
ccagggaagg gcctggagtg ggtctcaggt attagttgga atagtggtag gataggctat      180

```
acggactctg tgaagggccg attcaccgtc tccagagaca acgccaagaa ctccttgtat    240
ctgcaaatga acagtctgac aactgaggac acggccttgt attattgtgc aaaagataaa    300
tcgccctcta agtggaactt actaggtatg gacgtctggg gccaagggac cacggtcacc    360
gtctcctca                                                           369
```

```
<210> SEQ ID NO 306
<211> LENGTH: 123
<212> TYPE: PRT
<213> ORGANISM: Artificial Sequence
<220> FEATURE:
<223> OTHER INFORMATION: Synthetic

<400> SEQUENCE: 306
```

```
Glu Val Gln Leu Val Glu Ser Gly Gly Gly Leu Val Gln Pro Gly Arg
 1               5                  10                  15

Ser Leu Arg Leu Ser Cys Thr Ala Ser Gly Phe Val Phe Glu Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Thr Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Thr Thr Glu Asp Thr Ala Leu Tyr Tyr Cys
                85                  90                  95

Ala Lys Asp Lys Ser Pro Ser Lys Trp Asn Leu Leu Gly Met Asp Val
           100                 105                 110

Trp Gly Gln Gly Thr Thr Val Thr Val Ser Ser
       115                 120
```

```
<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
ggattcgttt ttgaagatta tgcc                                           24
```

```
<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308
```

```
Gly Phe Val Phe Glu Asp Tyr Ala
 1               5
```

```
<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309
attagttgga atagtggtag gata                                           24
```

```
<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Ser Trp Asn Ser Gly Arg Ile
 1               5

<210> SEQ ID NO 311
<211> LENGTH: 48
<212> TYPE: DNA
<213> ORGANISM: Artificial Sequence
<220> FEATURE:
<223> OTHER INFORMATION: Synthetic

<400> SEQUENCE: 311
gcaaaagata aatcgccctc taagtggaac ttactaggta tggacgtc            48

<210> SEQ ID NO 312
<211> LENGTH: 16
<212> TYPE: PRT
<213> ORGANISM: Artificial Sequence
<220> FEATURE:
<223> OTHER INFORMATION: Synthetic

<400> SEQUENCE: 312

Ala Lys Asp Lys Ser Pro Ser Lys Trp Asn Leu Leu Gly Met Asp Val
 1               5                   10                  15

<210> SEQ ID NO 313
<211> LENGTH: 324
<212> TYPE: DNA
<213> ORGANISM: Artificial Sequence
<220> FEATURE:
<223> OTHER INFORMATION: Synthetic

<400> SEQUENCE: 313
gccatccaga tgacccagtc tccatcctcc ctgtctgcat ctgtaggaga cagagtcacc      60
atcacttgcc gggcaagtca ggacattaga aatgatttag ctggtttca gcagaaacca     120 gggagagccc ctaacctcct aatctttggt gcatccagtt tacaaagtgg ggtcccatca     180
aggttcagcg gcagtggatc tggcacagat ttcactctca ccatcagcgg cctgcagcct     240
gaagattttt caacttatta ctgtctacaa gattacactt acccattcac tttcggccct     300
gggaccaaag tggatatcaa acga                                           324

<210> SEQ ID NO 314
<211> LENGTH: 108
<212> TYPE: PRT
<213> ORGANISM: Artificial Sequence
<220> FEATURE:
<223> OTHER INFORMATION: Synthetic

<400> SEQUENCE: 314

Ala Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Ile Arg Asn Asp
                20                  25                  30

Leu Gly Trp Phe Gln Gln Lys Pro Gly Arg Ala Pro Asn Leu Leu Ile
            35                  40                  45
```

Phe Gly Ala Ser Ser Leu Gln Ser Gly Val Pro Ser Arg Phe Ser Gly
            50                  55                  60

Ser Gly Ser Gly Thr Asp Phe Thr Leu Thr Ile Ser Gly Leu Gln Pro
 65                  70                  75                  80

Glu Asp Phe Ser Thr Tyr Tyr Cys Leu Gln Asp Tyr Thr Tyr Pro Phe
                85                  90                  95

Thr Phe Gly Pro Gly Thr Lys Val Asp Ile Lys Arg
            100                 105

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
caggacatta gaaatgat                                                    18

<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

Gln Asp Ile Arg Asn Asp
 1               5

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 ggtgcatcc                                                               9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Gly Ala Ser
 1

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
ctacaagatt acacttaccc attcact                                          27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Leu Gln Asp Tyr Thr Tyr Pro Phe Thr
1               5

<210> SEQ ID NO 321
<211> LENGTH: 363
<212> TYPE: DNA
<213> ORGANISM: Artificial Sequence
<220> FEATURE:
<223> OTHER INFORMATION: Synthetic

<400> SEQUENCE: 321

```
caggtgcagc tggtgcagtc tggggctgag gtacagaagc ccggggcgtc agtgaaagtc    60
tcctgcaagg cttctggata caccttcacc gactactata ttcattgggt gcgacaggcc   120
cctggacaag gcttgagtg gatgggatgg atcaaccta aaactggtgg cacaaactat    180
gcaccgaagt tcagggcag ggtcaccatg accaggact cgtccatcat acagcctac     240
atggacttga ccagactgac ctctgacgac acggccgtgt tttactgtgc gagacgggga   300
tataatagta ggtggtccgt ttttgactac tggggccagg gaaccctggt caccgtctcc   360
tca                                                                 363
```

<210> SEQ ID NO 322
<211> LENGTH: 121
<212> TYPE: PRT
<213> ORGANISM: Artificial Sequence
<220> FEATURE:
<223> OTHER INFORMATION: Synthetic

<400> SEQUENCE: 322

Gln Val Gln Leu Val Gln Ser Gly Ala Glu Val Gln Lys Pro Gly Ala
1               5                   10                  15
Ser Val Lys Val Ser Cys Lys Ala Ser Gly Tyr Thr Phe Thr Asp Tyr
            20                  25                  30
Tyr Ile His Trp Val Arg Gln Ala Pro Gly Gln Gly Leu Glu Trp Met
        35                  40                  45
Gly Trp Ile Asn Pro Lys Thr Gly Gly Thr Asn Tyr Ala Pro Lys Phe
    50                  55                  60
Gln Gly Arg Val Thr Met Thr Arg Asp Ser Ser Ile Ile Thr Ala Tyr
65                  70                  75                  80
Met Asp Leu Thr Arg Leu Thr Ser Asp Asp Thr Ala Val Phe Tyr Cys
                85                  90                  95
Ala Arg Arg Gly Tyr Asn Ser Arg Trp Ser Val Phe Asp Tyr Trp Gly
            100                 105                 110
Gln Gly Thr Leu Val Thr Val Ser Ser
        115                 120

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323

```
ggatacacct tcaccgacta ctat                                          24
```

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

Gly Tyr Thr Phe Thr Asp Tyr Tyr
1               5

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
atcaacccta aaactggtgg caca                                            24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Asn Pro Lys Thr Gly Gly Thr
1               5

<210> SEQ ID NO 327
<211> LENGTH: 42
<212> TYPE: DNA
<213> ORGANISM: Artificial Sequence
<220> FEATURE:
<223> OTHER INFORMATION: Synthetic

<400> SEQUENCE: 327
gcgagacggg gatataatag taggtggtcc gtttttgact ac                        42

<210> SEQ ID NO 328
<211> LENGTH: 14
<212> TYPE: PRT
<213> ORGANISM: Artificial Sequence
<220> FEATURE:
<223> OTHER INFORMATION: Synthetic

<400> SEQUENCE: 328

Ala Arg Arg Gly Tyr Asn Ser Arg Trp Ser Val Phe Asp Tyr
1               5                   10

<210> SEQ ID NO 329
<211> LENGTH: 327
<212> TYPE: DNA
<213> ORGANISM: Artificial Sequence
<220> FEATURE:
<223> OTHER INFORMATION: Synthetic

<400> SEQUENCE: 329
gaaattgtgt tgacgcagtc tccaggcacc ctgtctttgt ctccagggga aagagccacc     60
ctctcctgta gggccagtca gagtgtttac agcaactact tagcctggta ccagcagaaa    120
cgtggcctgg ctcccaggct cctcatctat ggtgcatcca gcagggccac tggcatccca    180
gacaggttca gtggcagtgg gtctgggaca gacttcactc tcaccatcag cagactggag    240

```
cctgaagatt ttgcagtgta ttactgtcag cagcatggtg gctcaccggt cactttcggc    300
ggagggacca aggtggagat caaacga                                         327
```

<210> SEQ ID NO 330
<211> LENGTH: 109
<212> TYPE: PRT
<213> ORGANISM: Artificial Sequence
<220> FEATURE:
<223> OTHER INFORMATION: Synthetic

<400> SEQUENCE: 330

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Tyr Ser Asn
             20                  25                  30

Tyr Leu Ala Trp Tyr Gln Gln Lys Arg Gly Leu Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln His Gly Gly Ser Pro
                 85                  90                  95

Val Thr Phe Gly Gly Gly Thr Lys Val Glu Ile Lys Arg
                100                 105
```

<210> SEQ ID NO 331
<211> LENGTH: 21
<212> TYPE: DNA
<213> ORGANISM: Artificial Sequence
<220> FEATURE:
<223> OTHER INFORMATION: Synthetic

<400> SEQUENCE: 331

```
cagagtgttt acagcaacta c                                                21
```

<210> SEQ ID NO 332
<211> LENGTH: 7
<212> TYPE: PRT
<213> ORGANISM: Artificial Sequence
<220> FEATURE:
<223> OTHER INFORMATION: Synthetic

<400> SEQUENCE: 332

```
Gln Ser Val Tyr Ser Asn Tyr
  1               5
```

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333

```
ggtgcatcc                                                               9
```

<210> SEQ ID NO 334
<211> LENGTH: 3
<212> TYPE: PRT
<213> ORGANISM: Artificial Sequence
<220> FEATURE:

<223> OTHER INFORMATION: Synthetic

<400> SEQUENCE: 334

Gly Ala Ser
 1

<210> SEQ ID NO 335
<211> LENGTH: 27
<212> TYPE: DNA
<213> ORGANISM: Artificial Sequence
<220> FEATURE:
<223> OTHER INFORMATION: Synthetic

<400> SEQUENCE: 335
cagcagcatg gtggctcacc ggtcact                                          27

<210> SEQ ID NO 336
<211> LENGTH: 9
<212> TYPE: PRT
<213> ORGANISM: Artificial Sequence
<220> FEATURE:
<223> OTHER INFORMATION: Synthetic

<400> SEQUENCE: 336

Gln Gln His Gly Gly Ser Pro Val Thr
 1               5

<210> SEQ ID NO 337
<211> LENGTH: 366
<212> TYPE: DNA
<213> ORGANISM: Artificial Sequence
<220> FEATURE:
<223> OTHER INFORMATION: Synthetic

<400> SEQUENCE: 337
caggtgcagc tggtggagtc tgggggaggc gtggtccagc ctggggaggtc cctgagactc     60 tcctgtgaag cctctggatt caccttcagt agctatggca tgcactgggt ccgccaggct    120
ccaggcaacg ggctggagtg gatcgcagtt atatcatctg atggaaataa taaatattat    180
atagaatccg tgaagggccg attcaccatg tccagagaca attccaagaa cacgctgtat    240
ctgcaattga acagcctgag aactgaggac acggctgtgt attactgtgc gacttacaac    300
tggaacgacg acggggacgg ggttttttgac tactggggcc agggaaccct ggtcaccgtc    360
tcctca                                                                366

<210> SEQ ID NO 338
<211> LENGTH: 122
<212> TYPE: PRT
<213> ORGANISM: Artificial Sequence
<220> FEATURE:
<223> OTHER INFORMATION: Synthetic

<400> SEQUENCE: 338

Gln Val Gln Leu Val Glu Ser Gly Gly Gly Val Val Gln Pro Gly Arg
 1               5                  10                  15

Ser Leu Arg Leu Ser Cys Glu Ala Ser Gly Phe Thr Phe Ser Ser Tyr
             20                  25                  30

Gly Met His Trp Val Arg Gln Ala Pro Gly Asn Gly Leu Glu Trp Ile
         35                  40                  45

Ala Val Ile Ser Ser Asp Gly Asn Asn Lys Tyr Tyr Ile Glu Ser Val
     50                  55                  60

Lys Gly Arg Phe Thr Met Ser Arg Asp Asn Ser Lys Asn Thr Leu Tyr

```
            65                  70                  75                  80
Leu Gln Leu Asn Ser Leu Arg Thr Glu Asp Thr Ala Val Tyr Tyr Cys
                85                  90                  95
Ala Thr Tyr Asn Trp Asn Asp Asp Gly Asp Gly Val Phe Asp Tyr Trp
               100                 105                 110
Gly Gln Gly Thr Leu Val Thr Val Ser Ser
           115                 120
```

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggattcacct tcagtagcta tggc                                              24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Phe Thr Phe Ser Ser Tyr Gly
1               5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
atatcatctg atggaaataa taaa                                              24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Ser Ser Asp Gly Asn Asn Lys
1               5

<210> SEQ ID NO 343
<211> LENGTH: 45
<212> TYPE: DNA
<213> ORGANISM: Artificial Sequence
<220> FEATURE:
<223> OTHER INFORMATION: Synthetic

<400> SEQUENCE: 343
gcgacttaca actggaacga cgacggggac ggggtttttg actac               45

<210> SEQ ID NO 344
<211> LENGTH: 15
<212> TYPE: PRT
<213> ORGANISM: Artificial Sequence
<220> FEATURE:

<223> OTHER INFORMATION: Synthetic

<400> SEQUENCE: 344

Ala Thr Tyr Asn Trp Asn Asp Asp Gly Asp Gly Val Phe Asp Tyr
1               5                   10                  15

<210> SEQ ID NO 345
<211> LENGTH: 324
<212> TYPE: DNA
<213> ORGANISM: Artificial Sequence
<220> FEATURE:
<223> OTHER INFORMATION: Synthetic

<400> SEQUENCE: 345
gacatccaga tgacccagtc tccatcttcc gtgtctgcat ctgtaggaga cagagtcacc     60
atcacttgtc gggcgagtca gggtattagc aactggttag cctggtatca gcagaaacca    120
gggaaagccc ctaagctcct gatctatggt acatccagtt tgcaaagtgg ggtcccatca    180
aggttcagcg gcagtggatc tgggacagat ttcactctca ccatcagcag cctgcagcct    240
gaagattttg caacttacta ttgtcaacag gttaagagtt tcccgtacac ttttggccag    300
gggaccaagc tggagatcaa acga                                           324

<210> SEQ ID NO 346
<211> LENGTH: 108
<212> TYPE: PRT
<213> ORGANISM: Artificial Sequence
<220> FEATURE:
<223> OTHER INFORMATION: Synthetic

<400> SEQUENCE: 346

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Lys Ser Phe Pro Tyr
                85                  90                  95

Thr Phe Gly Gln Gly Thr Lys Leu Glu Ile Lys Arg
            100                 105

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347
cagggtatta gcaactgg                                                   18

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

Gln Gly Ile Ser Asn Trp
1               5

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 ggtacatcc                                                                          9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Gly Thr Ser
1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacaggtta agagtttccc gtacact                                                     27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Val Lys Ser Phe Pro Tyr Thr
1               5

<210> SEQ ID NO 353
<211> LENGTH: 354
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc ggggggaggc ttggtacagc ctggggggtc cctgagactc      60
tcctgtgcag cctctggatt cacctttagc agatatggca tgaactgggt ccgccaggct     120
ccagggaagg ggctggagtg gtctcagct attagtggta gtggtggtag cacataccac     180
gcagactccg tgaagggccg gttcaccatc tccagagaca attccaagaa cacactgtat    240
ctgcaaatga atagcctgag agccgcggac acggccatat atttctgtgc gtcttacaat    300
tggaacgacg gggtggacgt ctggggccaa gggaccacgg tcaccgtctc ctca          354

```
<210> SEQ ID NO 354
<211> LENGTH: 117
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Gly Met Asn Trp Val Arg Gln Ala Pro Gly Lys Gly Leu Glu Trp Val
        35                  40                  45

Ser Ala Ile Ser Gly Ser Gly Gly Ser Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Ala Asp Thr Ala Ile Tyr Phe Cys
                85                  90                  95

Ala Ser Tyr Asn Trp Asn Asp Gly Val Asp Val Trp Gly Gln Gly Thr
            100                 105                 110

Thr Val Thr Val Ser
        115

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355
ggattcacct ttagcagata tggc                                          24

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

Gly Phe Thr Phe Ser Arg Tyr Gly
 1               5

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
attagtggta gtggtggtag caca                                          24

<210> SEQ ID NO 358
<211> LENGTH: 8
<212> TYPE: PRT
<213> ORGANISM: Artificial Sequence
<220> FEATURE:
<223> OTHER INFORMATION: Synthetic

<400> SEQUENCE: 358
```

Ile Ser Gly Ser Gly Gly Ser Thr
1               5

<210> SEQ ID NO 359
<211> LENGTH: 33
<212> TYPE: DNA
<213> ORGANISM: Artificial Sequence
<220> FEATURE:
<223> OTHER INFORMATION: Synthetic

<400> SEQUENCE: 359
gcgtcttaca attggaacga cggggtggac gtc                                   33

<210> SEQ ID NO 360
<211> LENGTH: 11
<212> TYPE: PRT
<213> ORGANISM: Artificial Sequence
<220> FEATURE:
<223> OTHER INFORMATION: Synthetic

<400> SEQUENCE: 360

Ala Ser Tyr Asn Trp Asn Asp Gly Val Asp Val
1               5                   10

<210> SEQ ID NO 361
<211> LENGTH: 324
<212> TYPE: DNA
<213> ORGANISM: Artificial Sequence
<220> FEATURE:
<223> OTHER INFORMATION: Synthetic

<400> SEQUENCE: 361
gacatccaga tgacccagtc tccatcttcc gtgtctgcat ctataggaga cagggtcacc       60
atcacttgtc gggcgagtca gggtattagc aactggttag cctggtatca gcagaaacca      120
gggaaagccc ctaagctcct gatctatggt gcatccagtt tgcaaagtgg agtctcatca      180
aggttcagcg gcagtggatc tgggacagat ttcactctca ccatcatcag ccttcagcct      240
gaagattttg caacttacta ttgtcaacag gctaacagtt tcccgtacac ttttggccag      300
gggaccaagc tggagatcaa acga                                             324

<210> SEQ ID NO 362
<211> LENGTH: 108
<212> TYPE: PRT
<213> ORGANISM: Artificial Sequence
<220> FEATURE:
<223> OTHER INFORMATION: Synthetic

<400> SEQUENCE: 362

Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Ser Ser Arg Phe Ser Gly
    50                  55                  60

Ser Gly Ser Gly Thr Asp Phe Thr Leu Thr Ile Ile Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys Arg
            100                 105

<210> SEQ ID NO 363
<211> LENGTH: 18
<212> TYPE: DNA
<213> ORGANISM: Artificial Sequence
<220> FEATURE:
<223> OTHER INFORMATION: Synthetic

<400> SEQUENCE: 363
cagggtatta gcaactgg                                                 18

<210> SEQ ID NO 364
<211> LENGTH: 6
<212> TYPE: PRT
<213> ORGANISM: Artificial Sequence
<220> FEATURE:
<223> OTHER INFORMATION: Synthetic

<400> SEQUENCE: 364

Gln Gly Ile Ser Asn Trp
 1               5

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 ggtgcatcc                                                            9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Gly Ala Ser
 1

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
caacaggcta acagtttccc gtacact                                       27

<210> SEQ ID NO 368
<211> LENGTH: 9
<212> TYPE: PRT
<213> ORGANISM: Artificial Sequence
<220> FEATURE:
<223> OTHER INFORMATION: Synthetic

<400> SEQUENCE: 368

Gln Gln Ala Asn Ser Phe Pro Tyr Thr
 1               5

-continued

<210> SEQ ID NO 369
<211> LENGTH: 214
<212> TYPE: PRT
<213> ORGANISM: Artificial Sequence
<220> FEATURE:
<223> OTHER INFORMATION: Synthetic

<400> SEQUENCE: 369

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 370
<211> LENGTH: 452
<212> TYPE: PRT
<213> ORGANISM: Artificial Sequence
<220> FEATURE:
<223> OTHER INFORMATION: Synthetic

<400> SEQUENCE: 370

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Asn Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Glu Asp Tyr Thr Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

```
Ala Arg Trp Gly Met Val Arg Gly Val Ile Asp Val Phe Asp Ile Trp
                100                 105                 110
Gly Gln Gly Thr Val Val Thr Val Ser Ser Ala Ser Thr Lys Gly Pro
            115                 120                 125
Ser Val Phe Pro Leu Ala Pro Ser Ser Lys Ser Thr Ser Gly Gly Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 371
<211> LENGTH: 215
<212> TYPE: PRT
<213> ORGANISM: Artificial Sequence
<220> FEATURE:
<223> OTHER INFORMATION: Synthetic

<400> SEQUENCE: 371
```

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Thr
             85                  90                  95

Trp Thr Phe Gly Gln Gly Thr Lys Val Glu Ile Lys Arg Thr Val Ala
         100                 105                 110

Ala Pro Ser Val Phe Ile Phe Pro Pro Ser Asp Glu Gln Leu Lys Ser
         115                 120                 125

Gly Thr Ala Ser Val Val Cys Leu Leu Asn Asn Phe Tyr Pro Arg Glu
     130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
             165                 170                 175

Ser Ser Thr Leu Thr Leu Ser Lys Ala Asp Tyr Glu Lys His Lys Val
         180                 185                 190

Tyr Ala Cys Glu Val Thr His Gln Gly Leu Ser Ser Pro Val Thr Lys
     195                 200                 205

Ser Phe Asn Arg Gly Glu Cys
 210                 215

<210> SEQ ID NO 372
<211> LENGTH: 449
<212> TYPE: PRT
<213> ORGANISM: Artificial Sequence
<220> FEATURE:
<223> OTHER INFORMATION: Synthetic

<400> SEQUENCE: 372

Glu Val Gln Leu Val Gln Ser Gly Ala Glu Val Lys Lys Ser Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Phe Tyr Pro Gly Asp Ser Ser Thr Arg Tyr Ser Pro Ser Phe
     50                  55                  60

Gln Gly Gln Val Thr Ile Ser Ala Asp Lys Ser Val Asn Thr Ala Tyr
 65                  70                  75                  80

Leu Gln Trp Ser Ser Leu Lys Ala Ser Asp Thr Ala Met Tyr Tyr Cys
             85                  90                  95

Ala Arg Arg Arg Asn Trp Gly Asn Ala Phe Asp Ile Trp Gly Gln Gly
         100                 105                 110

Thr Met Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 373
<211> LENGTH: 213
<212> TYPE: PRT
<213> ORGANISM: Artificial Sequence
<220> FEATURE:
<223> OTHER INFORMATION: Synthetic

<400> SEQUENCE: 373

Asn Ile Val Met Thr Gln Ser Pro Lys Ser Met Ser Met Ser Val Gly
1               5                   10                  15

Glu Arg Val Thr Phe Asn Cys Arg Ala Ser Glu Asn Val Gly Thr Tyr
            20                  25                  30

Val Phe Trp Tyr Gln Gln Lys Pro Glu Gln Ser Pro Arg Leu Leu Ile
        35                  40                  45

Tyr Gly Ala Ser Asn Arg Tyr Thr Gly Val Pro Asp Arg Phe Thr Gly
```

```
                50              55              60
Ser Gly Ser Ala Thr Asp Phe Thr Leu Thr Ile Ser Gly Val Gln Ala
 65                  70                  75                  80

Glu Asp Leu Ala Asp Tyr His Cys Gly Gln Ser Tyr Arg His Leu Thr
                 85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Gly Glu Cys
    210

<210> SEQ ID NO 374
<211> LENGTH: 449
<212> TYPE: PRT
<213> ORGANISM: Artificial Sequence
<220> FEATURE:
<223> OTHER INFORMATION: Synthetic

<400> SEQUENCE: 374

Gln Val Gln Leu Gln Gln Pro Gly Ala Glu Leu Val Lys Pro Gly Ala
  1               5                  10                  15

Ser Val Arg Leu Ser Cys Lys Ala Gly Gly Tyr Thr Phe Thr Ser Tyr
                 20                  25                  30

Trp Leu His Trp Val Lys Gln Arg Pro Gly Gln Gly Leu Glu Trp Ile
             35                  40                  45

Gly Met Ile His Pro Asn Ser Gly Ser Tyr Asp Tyr Ser Glu Thr Phe
     50                  55                  60

Arg Thr Lys Ala Thr Leu Thr Val Asp Lys Ser Ser Asp Thr Ala Tyr
 65                  70                  75                  80

Met Gln Leu Thr Ser Leu Thr Ser Glu Asp Ser Ala Val Tyr Tyr Cys
                 85                  90                  95

Ala Arg Gly Gly Ser Asn Tyr Asp Ile Phe Ala Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
```

```
                195                 200                 205
Ser Thr Lys Val Asp Lys Ile Glu Pro Arg Gly Pro Thr Ile Lys
    210                 215                 220

Pro Cys Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys

<210> SEQ ID NO 375
<211> LENGTH: 863
<212> TYPE: PRT
<213> ORGANISM: Artificial Sequence
<220> FEATURE:
<223> OTHER INFORMATION: Synthetic

<400> SEQUENCE: 375

Phe Asn Leu Val Thr Gly Trp Gln Thr Ile Asn Gly Lys Lys Tyr Tyr
1               5                   10                  15

Phe Asp Ile Asn Thr Gly Ala Ala Leu Ile Ser Tyr Lys Ile Ile Asn
                20                  25                  30

Gly Lys His Phe Tyr Phe Asn Asn Asp Gly Val Met Gln Leu Gly Val
            35                  40                  45

Phe Lys Gly Pro Asp Gly Phe Glu Tyr Phe Ala Pro Ala Asn Thr Gln
        50                  55                  60

Asn Asn Asn Ile Glu Gly Gln Ala Ile Val Tyr Gln Ser Lys Phe Leu
65                  70                  75                  80

Thr Leu Asn Gly Lys Lys Tyr Tyr Phe Asp Asn Asp Ser Lys Ala Val
                85                  90                  95

Thr Gly Trp Arg Ile Ile Asn Asn Glu Lys Tyr Tyr Phe Asn Pro Asn
            100                 105                 110
```

```
Asn Ala Ile Ala Ala Val Gly Leu Gln Val Ile Asp Asn Asn Lys Tyr
            115                 120                 125

Tyr Phe Asn Pro Asp Thr Ala Ile Ile Ser Lys Gly Trp Gln Thr Val
        130                 135                 140

Asn Gly Ser Arg Tyr Tyr Phe Asp Thr Asp Thr Ala Ile Ala Phe Asn
145                 150                 155                 160

Gly Tyr Lys Thr Ile Asp Gly Lys His Phe Tyr Phe Asp Ser Asp Cys
                165                 170                 175

Val Val Lys Ile Gly Val Phe Ser Thr Ser Asn Gly Phe Glu Tyr Phe
                180                 185                 190

Ala Pro Ala Asn Thr Tyr Asn Asn Asn Ile Glu Gly Gln Ala Ile Val
            195                 200                 205

Tyr Gln Ser Lys Phe Leu Thr Leu Asn Gly Lys Lys Tyr Tyr Phe Asp
        210                 215                 220

Asn Asn Ser Lys Ala Val Thr Gly Trp Gln Thr Ile Asp Ser Lys Lys
225                 230                 235                 240

Tyr Tyr Phe Asn Thr Asn Thr Ala Glu Ala Ala Thr Gly Trp Gln Thr
                245                 250                 255

Ile Asp Gly Lys Lys Tyr Tyr Phe Asn Thr Asn Thr Ala Glu Ala Ala
                260                 265                 270

Thr Gly Trp Gln Thr Ile Asp Gly Lys Lys Tyr Tyr Phe Asn Thr Asn
            275                 280                 285

Thr Ala Ile Ala Ser Thr Gly Tyr Thr Ile Ile Asn Gly Lys His Phe
290                 295                 300

Tyr Phe Asn Thr Asp Gly Ile Met Gln Ile Gly Val Phe Lys Gly Pro
305                 310                 315                 320

Asn Gly Phe Glu Tyr Phe Ala Pro Ala Asn Thr Asp Ala Asn Asn Ile
                325                 330                 335

Glu Gly Gln Ala Ile Leu Tyr Gln Asn Glu Phe Leu Thr Leu Asn Gly
            340                 345                 350

Lys Lys Tyr Tyr Phe Gly Ser Asp Ser Lys Ala Val Thr Gly Trp Arg
        355                 360                 365

Ile Ile Asn Asn Lys Lys Tyr Tyr Phe Asn Pro Asn Asn Ala Ile Ala
        370                 375                 380

Ala Ile His Leu Cys Thr Ile Asn Asn Asp Lys Tyr Tyr Phe Ser Tyr
385                 390                 395                 400

Asp Gly Ile Leu Gln Asn Gly Tyr Ile Thr Ile Glu Arg Asn Asn Phe
            405                 410                 415

Tyr Phe Asp Ala Asn Asn Glu Ser Lys Met Val Thr Gly Val Phe Lys
            420                 425                 430

Gly Pro Asn Gly Phe Glu Tyr Phe Ala Pro Ala Asn Thr His Asn Asn
            435                 440                 445

Asn Ile Glu Gly Gln Ala Ile Val Tyr Gln Asn Lys Phe Leu Thr Leu
        450                 455                 460

Asn Gly Lys Lys Tyr Tyr Phe Asp Asn Asp Ser Lys Ala Val Thr Gly
465                 470                 475                 480

Trp Gln Thr Ile Asp Gly Lys Lys Tyr Tyr Phe Asn Leu Asn Thr Ala
                485                 490                 495

Glu Ala Ala Thr Gly Trp Gln Thr Ile Asp Gly Lys Lys Tyr Tyr Phe
            500                 505                 510

Asn Leu Asn Thr Ala Glu Ala Ala Thr Gly Trp Gln Thr Ile Asp Gly
            515                 520                 525
```

Lys Lys Tyr Tyr Phe Asn Thr Asn Thr Phe Ile Ala Ser Thr Gly Tyr
    530                 535                 540

Thr Ser Ile Asn Gly Lys His Phe Tyr Phe Asn Thr Asp Gly Ile Met
545                 550                 555                 560

Gln Ile Gly Val Phe Lys Gly Pro Asn Gly Phe Glu Tyr Phe Ala Pro
                565                 570                 575

Ala Asn Thr His Asn Asn Asn Ile Glu Gly Gln Ala Ile Leu Tyr Gln
            580                 585                 590

Asn Lys Phe Leu Thr Leu Asn Gly Lys Lys Tyr Tyr Phe Gly Ser Asp
        595                 600                 605

Ser Lys Ala Val Thr Gly Leu Arg Thr Ile Asp Gly Lys Lys Tyr Tyr
    610                 615                 620

Phe Asn Thr Asn Thr Ala Val Ala Val Thr Gly Trp Gln Thr Ile Asn
625                 630                 635                 640

Gly Lys Lys Tyr Tyr Phe Asn Thr Asn Thr Ser Ile Ala Ser Thr Gly
                645                 650                 655

Tyr Thr Ile Ile Ser Gly Lys His Phe Tyr Phe Asn Thr Asp Gly Ile
            660                 665                 670

Met Gln Ile Gly Val Phe Lys Gly Pro Asp Gly Phe Glu Tyr Phe Ala
        675                 680                 685

Pro Ala Asn Thr Asp Ala Asn Asn Ile Glu Gly Gln Ala Ile Arg Tyr
    690                 695                 700

Gln Asn Arg Phe Leu Tyr Leu His Asp Asn Ile Tyr Tyr Phe Gly Asn
705                 710                 715                 720

Asn Ser Lys Ala Ala Thr Gly Trp Val Thr Ile Asp Gly Asn Arg Tyr
                725                 730                 735

Tyr Phe Glu Pro Asn Thr Ala Met Gly Ala Asn Gly Tyr Lys Thr Ile
            740                 745                 750

Asp Asn Lys Asn Phe Tyr Phe Arg Asn Gly Leu Pro Gln Ile Gly Val
        755                 760                 765

Phe Lys Gly Ser Asn Gly Phe Glu Tyr Phe Ala Pro Ala Asn Thr Asp
    770                 775                 780

Ala Asn Asn Ile Glu Gly Gln Ala Ile Arg Tyr Gln Asn Arg Phe Leu
785                 790                 795                 800

His Leu Leu Gly Lys Ile Tyr Tyr Phe Gly Asn Asn Ser Lys Ala Val
                805                 810                 815

Thr Gly Trp Gln Thr Ile Asn Gly Lys Val Tyr Tyr Phe Met Pro Asp
            820                 825                 830

Thr Ala Met Ala Ala Ala Gly Gly Leu Phe Glu Ile Asp Gly Val Ile
        835                 840                 845

Tyr Phe Phe Gly Val Asp Gly Val Lys Ala Pro Gly Ile Tyr Gly
    850                 855                 860

<210> SEQ ID NO 376
<211> LENGTH: 516
<212> TYPE: PRT
<213> ORGANISM: Artificial Sequence
<220> FEATURE:
<223> OTHER INFORMATION: Synthetic

<400> SEQUENCE: 376

Asn Leu Ile Thr Gly Phe Val Thr Val Gly Asp Asp Lys Tyr Tyr Phe
1               5                   10                  15

Asn Pro Ile Asn Gly Gly Ala Ala Ser Ile Gly Glu Thr Ile Ile Asp
            20                  25                  30

-continued

```
Asp Lys Asn Tyr Tyr Phe Asn Gln Ser Gly Val Leu Gln Thr Gly Val
             35                  40                  45
Phe Ser Thr Glu Asp Gly Phe Lys Tyr Phe Ala Pro Ala Asn Thr Leu
 50                  55                  60
Asp Glu Asn Leu Glu Gly Glu Ala Ile Asp Phe Thr Gly Lys Leu Ile
 65                  70                  75                  80
Ile Asp Glu Asn Ile Tyr Tyr Phe Asp Asp Asn Tyr Arg Gly Ala Val
                 85                  90                  95
Glu Trp Lys Glu Leu Asp Gly Glu Met His Tyr Phe Ser Pro Glu Thr
                100                 105                 110
Gly Lys Ala Phe Lys Gly Leu Asn Gln Ile Gly Asp Tyr Lys Tyr Tyr
             115                 120                 125
Phe Asn Ser Asp Gly Val Met Gln Lys Gly Phe Val Ser Ile Asn Asp
 130                 135                 140
Asn Lys His Tyr Phe Asp Asp Ser Gly Val Met Lys Val Gly Tyr Thr
145                 150                 155                 160
Glu Ile Asp Gly Lys His Phe Tyr Phe Ala Glu Asn Gly Glu Met Gln
                165                 170                 175
Ile Gly Val Phe Asn Thr Glu Asp Gly Phe Lys Tyr Phe Ala His His
             180                 185                 190
Asn Glu Asp Leu Gly Asn Glu Glu Gly Glu Glu Ile Ser Tyr Ser Gly
             195                 200                 205
Ile Leu Asn Phe Asn Asn Lys Ile Tyr Tyr Phe Asp Asp Ser Phe Thr
             210                 215                 220
Ala Val Val Gly Trp Lys Asp Leu Glu Asp Gly Ser Lys Tyr Tyr Phe
225                 230                 235                 240
Asp Glu Asp Thr Ala Glu Ala Tyr Ile Gly Leu Ser Leu Ile Asn Asp
                245                 250                 255
Gly Gln Tyr Tyr Phe Asn Asp Asp Gly Ile Met Gln Val Gly Phe Val
             260                 265                 270
Thr Ile Asn Asp Lys Val Phe Tyr Phe Ser Asp Ser Gly Ile Ile Glu
             275                 280                 285
Ser Gly Val Gln Asn Ile Asp Asp Asn Tyr Phe Tyr Ile Asp Asp Asn
 290                 295                 300
Gly Ile Val Gln Ile Gly Val Phe Asp Thr Ser Asp Gly Tyr Lys Tyr
305                 310                 315                 320
Phe Ala Pro Ala Asn Thr Val Asn Asp Asn Ile Tyr Gly Gln Ala Val
                325                 330                 335
Glu Tyr Ser Gly Leu Val Arg Val Gly Glu Asp Val Tyr Tyr Phe Gly
             340                 345                 350
Glu Thr Tyr Thr Ile Glu Thr Gly Trp Ile Tyr Asp Met Glu Asn Glu
             355                 360                 365
Ser Asp Lys Tyr Tyr Phe Asn Pro Glu Thr Lys Lys Ala Cys Lys Gly
 370                 375                 380
Ile Asn Leu Ile Asp Asp Ile Lys Tyr Tyr Phe Asp Glu Lys Gly Ile
385                 390                 395                 400
Met Arg Thr Gly Leu Ile Ser Phe Glu Asn Asn Tyr Tyr Phe Asn
                405                 410                 415
Glu Asn Gly Glu Met Gln Phe Gly Tyr Ile Asn Ile Glu Asp Lys Met
             420                 425                 430
Phe Tyr Phe Gly Glu Asp Gly Val Met Gln Ile Gly Val Phe Asn Thr
             435                 440                 445
Pro Asp Gly Phe Lys Tyr Phe Ala His Gln Asn Thr Leu Asp Glu Asn
```

```
            450                 455                 460
Phe Glu Gly Glu Ser Ile Asn Tyr Thr Gly Trp Leu Asp Leu Asp Glu
465                 470                 475                 480

Lys Arg Tyr Tyr Phe Thr Asp Glu Tyr Ile Ala Ala Thr Gly Ser Val
                485                 490                 495

Ile Ile Asp Gly Glu Tyr Tyr Phe Asp Pro Asp Thr Ala Gln Leu
            500                 505                 510

Val Ile Ser Glu
        515

<210> SEQ ID NO 377
<211> LENGTH: 8133
<212> TYPE: DNA
<213> ORGANISM: Clostridium difficile

<400> SEQUENCE: 377
atgtctttaa tatctaaaga agagttaata aaactcgcat atagcattag accaagagaa      60
aatgagtata aaactatact aactaattta gacgaatata ataagttaac acaaacaat    120
aatgaaaata atatttaca attaaaaaaa ctaaatgaat caattgatgt ttttatgaat    180
aaatataaaa cttcaagcag aaatagagca ctctctaatc taaaaaaaga tatattaaaa    240
gaagtaattc ttattaaaaa ttccaataca agccctgtag aaaaaaattt acattttgta    300
tggataggtg gagaagtcag tgatattgct cttgaataca taaaacaatg gctgatatt    360
aatgcagaat ataatattaa actgtggtat gatagtgaag cattcttagt aaatacacta    420
aaaaaggcta tagttgaatc ttctaccact gaagcattac agctactaga ggaagagatt    480
caaaatcctc aatttgataa tatgaaattt tacaaaaaaa ggatggaatt tatatatgat    540
agacaaaaaa ggtttataaa ttattataaa tctcaaatca ataaacctac agtacctaca    600
atagatgata ttataaagtc tcatctagta tctgaatata tagagatga  actgtatta    660
gaatcatata gaacaaattc tttgagaaaa ataaatagta atcatgggat agatatcagg    720
gctaatagtt tgtttacaga acaagagtta ttaaatatt  atagtcagga gttgttaaat    780
cgtggaaatt tagctgcagc atctgacata gtaagattat tagccctaaa aaattttggc    840
ggagtatatt tagatgttga tatgcttcca ggtattcact ctgatttatt taaaacaata    900
tctagaccta gctctattgg actagaccgt tgggaaatga taaaattaga ggctattatg    960
aagtataaaa aatatataaa taattataca tcagaaaact ttgataaact tgatcaacaa   1020
ttaaagata attttaaact cattatagaa agtaaaagtg aaaaatctga gatatttct    1080
aaattagaaa atttaaatgt atctgatctt gaaattaaaa tagctttcgc tttaggcagt   1140
gttataaatc aagccttgat atcaaaacaa ggttcatatc ttactaacct agtaataga a   1200
caagtaaaaa atagatatca attttaaac caacaccta  acccagccat agagtctgat   1260
aataacttca cagatactac taaaattttt catgattcat tatttaattc agctaccgca   1320
gaaaactcta tgttttaac aaaaatagca ccatacttac aagtaggttt tatgccagaa   1380
gctcgctcca caataagttt aagtggtcca ggagcttatg cgtcagctta ctatgatttc   1440
ataaatttac aagaaaatac tatagaaaaa actttaaaag catcagattt aatagaatt    1500
aaattcccag aaaataatct atctcaattg acagaacaag aaataaatag tctatggagc   1560
tttgatcaag caagtgcaaa atatcaattt gagaaatatg taagagatta tactggtgga   1620
tctctttctg aagacaatgg ggtagacttt aataaaaata ctgccctcga caaaactat    1680
ttattaaata taaaaattcc atcaaacaat gtagaagaag ctggaagtaa aaattatgtt   1740
```

```
cattatatca tacagttaca aggagatgat ataagttatg aagcaacatg caatttattt    1800
tctaaaaatc ctaaaaatag tattattata caacgaaata tgaatgaaag tgcaaaaagc    1860 tacttttaa gtgatgatgg agaatctatt ttagaattaa ataaatatag gatacctgaa    1920
agattaaaaa ataaggaaaa agtaaaagta acctttattg gacatggtaa agatgaattc    1980
aacacaagcg aatttgctag attaagtgta gattcacttt ccaatgagat aagttcattt    2040
ttagatacca taaaattaga tatatcacct aaaaatgtag aagtaaactt acttggatgt    2100
aatatgttta gttatgattt taatgttgaa gaaacttatc ctgggaagtt gctattaagt    2160
attatggaca aaattacttc cactttacct gatgtaaata aaaattctat tactatagga    2220
gcaaatcaat atgaagtaag aattaatagt gagggaagaa aagaacttct ggctcactca    2280
ggtaaatgga taaataaaga agaagctatt atgagcgatt tatctagtaa agaatacatt    2340 tttttgatt ctatagataa taagctaaaa gcaaagtcca agaatattcc aggattagca    2400
tcaatatcag aagatataaa aacattatta cttgatgcaa gtgttagtcc tgatacaaaa    2460
tttattttaa ataatcttaa gcttaatatt gaatcttcta ttggtgatta catttattat    2520
gaaaaattag agcctgttaa aaatataatt cacaattcta tagatgattt aatagatgag    2580
ttcaatctac ttgaaaatgt atctgatgaa ttatatgaat taaaaaaatt aaataatcta    2640
gatgagaagt atttaatatc ttttgaagat atctcaaaaa ataattcaac ttactctgta    2700
agatttatta acaaaagtaa tggtgagtca gtttatgtag aaacagaaaa agaaatttt    2760 tcaaaatata gcgaacatat tacaaaagaa ataagtacta aaagaatag tataattaca    2820 gatgttaatg gtaattttatt ggataatata cagttagatc atacttctca agttaataca    2880
ttaaacgcag cattctttat tcaatcatta atagattata gtagcaataa agatgtactg    2940
aatgatttaa gtacctcagt taaggttcaa ctttatgctc aactatttag tacaggttta    3000
aatactatat atgactctat ccaattagta aatttaatat caaatgcagt aaatgatact    3060
ataaatgtac tacctacaat aacagagggg atacctattg tatctactat attagacgga    3120
ataaacttag gtgcagcaat taaggaatta ctagacgaac atgaccccatt actaaaaaaa    3180 gaattagaag ctaaggtggg tgttttagca ataaatatgt cattatctat agctgcaact    3240
gtagcttcaa ttgttggaat aggtgctgaa gttactattt tcttattacc tatagctggt    3300
atatctgcag gaataccttc attagttaat aatgaattaa tattgcatga taaggcaact    3360
tcagtggtaa actatttaa tcatttgtct gaatctaaaa aatatggccc tcttaaaaca    3420
gaagatgata aaatttagt tcctattgat gatttagtaa tatcagaaat agatttaat    3480 aataattcga taaaactagg aacatgtaat atattagcaa tggagggggg atcaggacac    3540
acagtgactg gtaatataga tcacttttc tcatctccat ctataagttc tcatattcct    3600
tcattatcaa tttattctgc aataggtata gaaacagaaa atctagattt ttcaaaaaaa    3660
ataatgatgt tacctaatgc tccttcaaga gtgttttggt gggaaactgg agcagttcca    3720
ggtttaagat cattggaaaa tgacggaact agattacttg attcaataag agatttatac    3780
ccaggtaaat tttactggag attctatgct tttttcgatt atgcaataac tacattaaaa    3840
ccagtttatg aagacactaa tattaaaatt aaactagata agatactag aaacttcata    3900 atgccaacta taactactaa cgaaattaga aacaaattat cttattcatt tgatggagca    3960
ggaggaactt actctttatt attatcttca tatccaatat caacgaatat aaattttatct    4020 aaagatgatt tatggatatt taatattgat aatgaagtaa gagaaatatc tatagaaaat    4080
```

```
ggtactatta aaaaaggaaa gttaataaaa gatgttttaa gtaaaattga tataaataaa    4140
aataaactta ttataggcaa tcaaacaata gattttttcag gcgatataga taataaagat   4200
agatatatat tcttgacttg tgagttagat gataaaatta gtttaataat agaaataaat   4260
cttgttgcaa aatcttatag tttgttattg tctggggata aaaattattt gatatccaat   4320
ttatctaata ttattgagaa aatcaatact ttaggcctag atagtaaaaa tatagcgtac   4380
aattacactg atgaatctaa taataaatat tttggagcta tatctaaaac aagtcaaaaa   4440
agcataatac attataaaaa agacagtaaa aatatattag aattttataa tgacagtaca   4500
ttagaattta acagtaaaga ttttattgct gaagatataa atgtatttat gaagatgat    4560 attaatacta taacaggaaa atactatgtt gataataata ctgataaaag tatagatttc   4620
tctatttctt tagttagtaa aaatcaagta aaagtaaatg gattatattt aaatgaatcc   4680
gtatactcat cttaccttga ttttgtgaaa aattcagatg gacaccataa tacttctaat   4740
tttatgaatt tatttttgga caatataagt ttctggaaat tgtttgggtt tgaaaatata   4800
aattttgtaa tcgataaata ctttacccct gttggtaaaa ctaatcttgg atatgtagaa   4860
tttatttgtg acaataataa aaatatagat atatatttg gtgaatggaa aacatcgtca   4920
tctaaaagca ctatatttag cggaaatggt agaaatgttg tagtagagcc tatatataat   4980
cctgatacgg gtgaagatat atctacttca ctagattttt cctatgaacc tctctatgga   5040
atagatagat atatcaataa agtattgata gcacctgatt tatatacaag tttaataaat   5100
attaatacca attattattc aaatgagtac taccctgaga ttatagttct taacccaaat   5160
acattccaca aaaagtaaa tataaattta gatagttctt cttttgagta taaatggtct   5220
acagaaggaa gtgacttat tttagttaga tacttagaag aaagtaataa aaaaatatta   5280
caaaaaataa gaatcaaagg tatcttatct aatactcaat catttaataa aatgagtata   5340
gattttaaag atattaaaaa actatcatta ggatatataa tgagtaattt taaatcattt   5400
aattctgaaa atgaattaga tagagatcat ttaggattta aaataataga taataaaact   5460
tattactatg atgaagatag taaattagtt aaaggattaa tcaatataaa taattcatta   5520
ttctattttg atcctataga atttaactta gtaactggat ggcaaactat caatggtaaa   5580
aaatattatt ttgatataaa tactggagca gctttaatta gttataaaat tattaatggt   5640
aaacactttt atttttaataa tgatggtgtg atgcagttgg gagtatttaa aggacctgat   5700
ggatttgaat attttgcacc tgccaatact caaaataata acatagaagg tcaggctata   5760
gtttatcaaa gtaaattctt aactttgaat ggcaaaaaat attattttga taatgactca   5820
aaagcagtca ctggatggag aattattaac aatgagaaat attactttaa tcctaataat   5880
gctattgctg cagtcggatt gcaagtaatt gacaataata agtattattt caatcctgac   5940
actgctatca tctcaaaagg ttggcagact gttaatggta gtagatacta ctttgatact   6000
gataccgcta ttgcctttaa tggttataaa actattgatg gtaaacactt ttattttgat   6060
agtgattgtg tagtgaaaat aggtgtgttt agtacctcta atggatttga atattttgca   6120
cctgctaata cttataataa taacatagaa ggtcaggcta tagtttatca agtaaattc    6180 ttaactttga atggtaaaaa atattacttt gataataact caaaagcagt taccggatgg   6240
caaactattg atagtaaaaa atattacttt aatactaaca ctgctgaagc agctactgga   6300
tggcaaacta ttgatggtaa aaaatattac tttaatacta acactgctga agcagctact   6360
ggatggcaaa ctattgatgg taaaaaatat tactttaata ctaacactgc tatagcttca   6420
actggttata caattattaa tggtaaacat ttttattttta atactgatgg tattatgcag   6480
```

| | | | | | |
|---|---|---|---|---|---|
| ataggagtgt | ttaaaggacc | taatggattt | gaatatttg | cacctgctaa | tacggatgct | 6540 |
| aacaacatag | aaggtcaagc | tatactttac | caaaatgaat | tcttaacttt | gaatggtaaa | 6600 |
| aaatattact | ttggtagtga | ctcaaaagca | gttactggat | ggagaattat | aacaataag | 6660 |
| aaatattact | ttaatcctaa | taatgctatt | gctgcaattc | atctatgcac | tataaataat | 6720 |
| gacaagtatt | actttagtta | tgatggaatt | cttcaaaatg | gatatattac | tattgaaaga | 6780 |
| aataatttct | attttgatgc | taataatgaa | tctaaaatgg | taacaggagt | atttaaagga | 6840 |
| cctaatggat | ttgagtattt | tgcacctgct | aatactcaca | ataataacat | agaaggtcag | 6900 |
| gctatagttt | accagaacaa | attcttaact | ttgaatggca | aaaatatta | ttttgataat | 6960 |
| gactcaaaag | cagttactgg | atggcaaacc | attgatggta | aaaatatta | ctttaatctt | 7020 |
| aacactgctg | aagcagctac | tggatggcaa | actattgatg | gtaaaaaata | ttactttaat | 7080 |
| cttaacactg | ctgaagcagc | tactggatgg | caaactattg | atggtaaaaa | atattacttt | 7140 |
| aatactaaca | ctttcatagc | ctcaactggt | tatacaagta | ttaatggtaa | acattttat | 7200 |
| tttaatactg | atggtattat | gcagatagga | gtgtttaaag | gacctaatgg | atttgaatac | 7260 |
| tttgcacctg | ctaatactca | taataataac | atagaaggtc | aagctatact | ttaccaaaat | 7320 |
| aaattcttaa | ctttgaatgg | taaaaaatat | tactttggta | gtgactcaaa | agcagttacc | 7380 |
| ggattgcgaa | ctattgatgg | taaaaaatat | tactttaata | ctaacactgc | tgttgcagtt | 7440 |
| actggatggc | aaactattaa | tggtaaaaaa | tactacttta | atactaacac | ttctatagct | 7500 |
| tcaactggtt | atacaattat | tagtggtaaa | cattttatt | ttaatactga | tggtattatg | 7560 |
| cagataggag | tgtttaaagg | acctgatgga | tttgaatact | ttgcacctgc | taatacagat | 7620 |
| gctaacaata | tagaaggtca | agctatacgt | tatcaaaata | gattcctata | tttacatgac | 7680 |
| aatatatatt | attttggtaa | taattcaaaa | gcagctactg | gtttgggtaa | cattgatggt | 7740 |
| aatagatatt | acttcgagcc | taatacagct | atgggtgcga | atggttataa | aactattgat | 7800 |
| aataaaaatt | tttactttag | aaatggttta | cctcagatag | gagtgtttaa | agggtctaat | 7860 |
| ggatttgaat | actttgcacc | tgctaatacg | gatgctaaca | atatagaagg | tcaagctata | 7920 |
| cgttatcaaa | atagattcct | acatttactt | ggaaaaatat | attactttgg | taataattca | 7980 |
| aaagcagtta | ctggatggca | aactattaat | ggtaaagtat | attactttat | gcctgatact | 8040 |
| gctatggctg | cagctggtgg | acttttcgag | attgatggtg | ttatatattt | ctttggtgtt | 8100 |
| gatggagtaa | aagcccctgg | gatatatggc | taa | | | 8133 |

```
<210> SEQ ID NO 378
<211> LENGTH: 2710
<212> TYPE: PRT
<213> ORGANISM: Clostridium difficile

<400> SEQUENCE: 378

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
                20                  25                  30

Tyr Asn Lys Leu Thr Thr Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80
```

-continued

```
Glu Val Ile Leu Ile Lys Asn Ser Asn Thr Ser Pro Val Glu Lys Asn
                 85                  90                  95
Leu His Phe Val Trp Ile Gly Gly Glu Val Ser Asp Ile Ala Leu Glu
                100                 105                 110
Tyr Ile Lys Gln Trp Ala Asp Ile Asn Ala Glu Tyr Asn Ile Lys Leu
                115                 120                 125
Trp Tyr Asp Ser Glu Ala Phe Leu Val Asn Thr Leu Lys Lys Ala Ile
            130                 135                 140
Val Glu Ser Ser Thr Thr Glu Ala Leu Gln Leu Leu Glu Glu Glu Ile
145                 150                 155                 160
Gln Asn Pro Gln Phe Asp Asn Met Lys Phe Tyr Lys Lys Arg Met Glu
                165                 170                 175
Phe Ile Tyr Asp Arg Gln Lys Arg Phe Ile Asn Tyr Tyr Lys Ser Gln
                180                 185                 190
Ile Asn Lys Pro Thr Val Pro Thr Ile Asp Asp Ile Ile Lys Ser His
                195                 200                 205
Leu Val Ser Glu Tyr Asn Arg Asp Glu Thr Val Leu Glu Ser Tyr Arg
            210                 215                 220
Thr Asn Ser Leu Arg Lys Ile Asn Ser Asn His Gly Ile Asp Ile Arg
225                 230                 235                 240
Ala Asn Ser Leu Phe Thr Glu Gln Glu Leu Leu Asn Ile Tyr Ser Gln
                245                 250                 255
Glu Leu Leu Asn Arg Gly Asn Leu Ala Ala Ala Ser Asp Ile Val Arg
                260                 265                 270
Leu Leu Ala Leu Lys Asn Phe Gly Gly Val Tyr Leu Asp Val Asp Met
            275                 280                 285
Leu Pro Gly Ile His Ser Asp Leu Phe Lys Thr Ile Ser Arg Pro Ser
290                 295                 300
Ser Ile Gly Leu Asp Arg Trp Glu Met Ile Lys Leu Glu Ala Ile Met
305                 310                 315                 320
Lys Tyr Lys Lys Tyr Ile Asn Asn Tyr Thr Ser Glu Asn Phe Asp Lys
                325                 330                 335
Leu Asp Gln Gln Leu Lys Asp Asn Phe Lys Leu Ile Ile Glu Ser Lys
            340                 345                 350
Ser Glu Lys Ser Glu Ile Phe Ser Lys Leu Glu Asn Leu Asn Val Ser
            355                 360                 365
Asp Leu Glu Ile Lys Ile Ala Phe Ala Leu Gly Ser Val Ile Asn Gln
            370                 375                 380
Ala Leu Ile Ser Lys Gln Gly Ser Tyr Leu Thr Asn Leu Val Ile Glu
385                 390                 395                 400
Gln Val Lys Asn Arg Tyr Gln Phe Leu Asn Gln His Leu Asn Pro Ala
                405                 410                 415
Ile Glu Ser Asp Asn Asn Phe Thr Asp Thr Thr Lys Ile Phe His Asp
                420                 425                 430
Ser Leu Phe Asn Ser Ala Thr Ala Glu Asn Ser Met Phe Leu Thr Lys
            435                 440                 445
Ile Ala Pro Tyr Leu Gln Val Gly Phe Met Pro Glu Ala Arg Ser Thr
450                 455                 460
Ile Ser Leu Ser Gly Pro Gly Ala Tyr Ala Ser Ala Tyr Tyr Asp Phe
465                 470                 475                 480
Ile Asn Leu Gln Glu Asn Thr Ile Glu Lys Thr Leu Lys Ala Ser Asp
                485                 490                 495
```

```
Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
            515                 520                 525

Gln Phe Glu Lys Tyr Val Arg Asp Tyr Thr Gly Gly Ser Leu Ser Glu
            530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Val Glu Ala Gly Ser
            565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
            595                 600                 605

Ile Ile Gln Arg Asn Met Asn Glu Ser Ala Lys Ser Tyr Phe Leu Ser
            610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
            645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
            675                 680                 685

Ser Pro Lys Asn Val Glu Val Asn Leu Leu Gly Cys Asn Met Phe Ser
690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
            725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
            755                 760                 765

Ala Ile Met Ser Asp Leu Ser Ser Lys Glu Tyr Ile Phe Phe Asp Ser
            770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Asp Ala Ser Val Ser
            805                 810                 815

Pro Asp Thr Lys Phe Ile Leu Asn Asn Leu Lys Leu Asn Ile Glu Ser
            820                 825                 830

Ser Ile Gly Asp Tyr Ile Tyr Tyr Glu Lys Leu Glu Pro Val Lys Asn
            835                 840                 845

Ile Ile His Asn Ser Ile Asp Asp Leu Ile Asp Glu Phe Asn Leu Leu
            850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
            885                 890                 895

Thr Tyr Ser Val Arg Phe Ile Asn Lys Ser Asn Gly Glu Ser Val Tyr
            900                 905                 910

Val Glu Thr Glu Lys Glu Ile Phe Ser Lys Tyr Ser Glu His Ile Thr
```

-continued

```
            915                 920                 925
Lys Glu Ile Ser Thr Ile Lys Asn Ser Ile Ile Thr Asp Val Asn Gly
    930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
            980                 985                 990

Ala Gln Leu Phe Ser Thr Gly Leu Asn Thr Ile Tyr Asp Ser Ile Gln
            995                 1000                1005

Leu Val Asn Leu Ile Ser Asn Ala Val Asn Asp Thr Ile Asn Val Leu
        1010                1015                1020

Pro Thr Ile Thr Glu Gly Ile Pro Ile Val Ser Thr Ile Leu Asp Gly
1025                1030                1035                1040

Ile Asn Leu Gly Ala Ala Ile Lys Glu Leu Leu Asp Glu His Asp Pro
            1045                1050                1055

Leu Leu Lys Lys Glu Leu Glu Ala Lys Val Gly Val Leu Ala Ile Asn
            1060                1065                1070

Met Ser Leu Ser Ile Ala Ala Thr Val Ala Ser Ile Val Gly Ile Gly
        1075                1080                1085

Ala Glu Val Thr Ile Phe Leu Leu Pro Ile Ala Gly Ile Ser Ala Gly
        1090                1095                1100

Ile Pro Ser Leu Val Asn Asn Glu Leu Ile Leu His Asp Lys Ala Thr
1105                1110                1115                1120

Ser Val Val Asn Tyr Phe Asn His Leu Ser Glu Ser Lys Lys Tyr Gly
            1125                1130                1135

Pro Leu Lys Thr Glu Asp Asp Lys Ile Leu Val Pro Ile Asp Asp Leu
            1140                1145                1150

Val Ile Ser Glu Ile Asp Phe Asn Asn Asn Ser Ile Lys Leu Gly Thr
            1155                1160                1165

Cys Asn Ile Leu Ala Met Glu Gly Gly Ser Gly His Thr Val Thr Gly
    1170                1175                1180

Asn Ile Asp His Phe Phe Ser Ser Pro Ser Ile Ser Ser His Ile Pro
1185                1190                1195                1200

Ser Leu Ser Ile Tyr Ser Ala Ile Gly Ile Glu Thr Glu Asn Leu Asp
            1205                1210                1215

Phe Ser Lys Lys Ile Met Met Leu Pro Asn Ala Pro Ser Arg Val Phe
            1220                1225                1230

Trp Trp Glu Thr Gly Ala Val Pro Gly Leu Arg Ser Leu Glu Asn Asp
        1235                1240                1245

Gly Thr Arg Leu Leu Asp Ser Ile Arg Asp Leu Tyr Pro Gly Lys Phe
        1250                1255                1260

Tyr Trp Arg Phe Tyr Ala Phe Phe Asp Tyr Ala Ile Thr Thr Leu Lys
1265                1270                1275                1280

Pro Val Tyr Glu Asp Thr Asn Ile Lys Ile Lys Leu Asp Lys Asp Thr
            1285                1290                1295

Arg Asn Phe Ile Met Pro Thr Ile Thr Thr Asn Glu Ile Arg Asn Lys
            1300                1305                1310

Leu Ser Tyr Ser Phe Asp Gly Ala Gly Gly Thr Tyr Ser Leu Leu Leu
        1315                1320                1325

Ser Ser Tyr Pro Ile Ser Thr Asn Ile Asn Leu Ser Lys Asp Asp Leu
        1330                1335                1340
```

```
Trp Ile Phe Asn Ile Asp Asn Glu Val Arg Glu Ile Ser Ile Glu Asn
1345                1350                1355                1360

Gly Thr Ile Lys Lys Gly Lys Leu Ile Lys Asp Val Leu Ser Lys Ile
            1365                1370                1375

Asp Ile Asn Lys Asn Lys Leu Ile Ile Gly Asn Gln Thr Ile Asp Phe
        1380                1385                1390

Ser Gly Asp Ile Asp Asn Lys Asp Arg Tyr Ile Phe Leu Thr Cys Glu
            1395                1400                1405

Leu Asp Asp Lys Ile Ser Leu Ile Ile Glu Ile Asn Leu Val Ala Lys
        1410                1415                1420

Ser Tyr Ser Leu Leu Ser Gly Asp Lys Asn Tyr Leu Ile Ser Asn
1425                1430                1435                1440

Leu Ser Asn Thr Ile Glu Lys Ile Asn Thr Leu Gly Leu Asp Ser Lys
                1445                1450                1455

Asn Ile Ala Tyr Asn Tyr Thr Asp Glu Ser Asn Asn Lys Tyr Phe Gly
            1460                1465                1470

Ala Ile Ser Lys Thr Ser Gln Lys Ser Ile Ile His Tyr Lys Lys Asp
        1475                1480                1485

Ser Lys Asn Ile Leu Glu Phe Tyr Asn Asp Ser Thr Leu Glu Phe Asn
        1490                1495                1500

Ser Lys Asp Phe Ile Ala Glu Asp Ile Asn Val Phe Met Lys Asp Asp
1505                1510                1515                1520

Ile Asn Thr Ile Thr Gly Lys Tyr Tyr Val Asp Asn Asn Thr Asp Lys
            1525                1530                1535

Ser Ile Asp Phe Ser Ile Ser Leu Val Ser Lys Asn Gln Val Lys Val
            1540                1545                1550

Asn Gly Leu Tyr Leu Asn Glu Ser Val Tyr Ser Ser Tyr Leu Asp Phe
        1555                1560                1565

Val Lys Asn Ser Asp Gly His His Asn Thr Ser Asn Phe Met Asn Leu
1570                1575                1580

Phe Leu Asp Asn Ile Ser Phe Trp Lys Leu Phe Gly Phe Glu Asn Ile
1585                1590                1595                1600

Asn Phe Val Ile Asp Lys Tyr Phe Thr Leu Val Gly Lys Thr Asn Leu
                1605                1610                1615

Gly Tyr Val Glu Phe Ile Cys Asp Asn Asn Lys Asn Ile Asp Ile Tyr
            1620                1625                1630

Phe Gly Glu Trp Lys Thr Ser Ser Ser Lys Ser Thr Ile Phe Ser Gly
        1635                1640                1645

Asn Gly Arg Asn Val Val Glu Pro Ile Tyr Asn Pro Asp Thr Gly
        1650                1655                1660

Glu Asp Ile Ser Thr Ser Leu Asp Phe Ser Tyr Glu Pro Leu Tyr Gly
1665                1670                1675                1680

Ile Asp Arg Tyr Ile Asn Lys Val Leu Ile Ala Pro Asp Leu Tyr Thr
            1685                1690                1695

Ser Leu Ile Asn Ile Asn Thr Asn Tyr Tyr Ser Asn Glu Tyr Tyr Pro
        1700                1705                1710

Glu Ile Ile Val Leu Asn Pro Asn Thr Phe His Lys Lys Val Asn Ile
        1715                1720                1725

Asn Leu Asp Ser Ser Ser Phe Glu Tyr Lys Trp Ser Thr Glu Gly Ser
        1730                1735                1740

Asp Phe Ile Leu Val Arg Tyr Leu Glu Glu Ser Asn Lys Lys Ile Leu
1745                1750                1755                1760
```

-continued

Gln Lys Ile Arg Ile Lys Gly Ile Leu Ser Asn Thr Gln Ser Phe Asn
            1765                1770                1775

Lys Met Ser Ile Asp Phe Lys Asp Ile Lys Leu Ser Leu Gly Tyr
       1780                1785                1790

Ile Met Ser Asn Phe Lys Ser Phe Asn Ser Glu Asn Glu Leu Asp Arg
            1795                1800                1805

Asp His Leu Gly Phe Lys Ile Ile Asp Asn Lys Thr Tyr Tyr Tyr Asp
            1810                1815                1820

Glu Asp Ser Lys Leu Val Lys Gly Leu Ile Asn Ile Asn Asn Ser Leu
1825                1830                1835                1840

Phe Tyr Phe Asp Pro Ile Glu Phe Asn Leu Val Thr Gly Trp Gln Thr
                 1845                1850                1855

Ile Asn Gly Lys Lys Tyr Tyr Phe Asp Ile Asn Thr Gly Ala Ala Leu
            1860                1865                1870

Thr Ser Tyr Lys Ile Ile Asn Gly Lys His Phe Tyr Phe Asn Asn Asp
       1875                1880                1885

Gly Val Met Gln Leu Gly Val Phe Lys Gly Pro Asp Gly Phe Glu Tyr
       1890                1895                1900

Phe Ala Pro Ala Asn Thr Gln Asn Asn Asn Ile Glu Gly Gln Ala Ile
1905                1910                1915                1920

Val Tyr Gln Ser Lys Phe Leu Thr Leu Asn Gly Lys Lys Tyr Tyr Phe
            1925                1930                1935

Asp Asn Asn Ser Lys Ala Val Thr Gly Trp Arg Ile Ile Asn Asn Glu
            1940                1945                1950

Lys Tyr Tyr Phe Asn Pro Asn Asn Ala Ile Ala Ala Val Gly Leu Gln
            1955                1960                1965

Val Ile Asp Asn Asn Lys Tyr Tyr Phe Asn Pro Asp Thr Ala Ile Ile
       1970                1975                1980

Ser Lys Gly Trp Gln Thr Val Asn Gly Ser Arg Tyr Tyr Phe Asp Thr
1985                1990                1995                2000

Asp Thr Ala Ile Ala Phe Asn Gly Tyr Lys Thr Ile Asp Gly Lys His
            2005                2010                2015

Phe Tyr Phe Asp Ser Asp Cys Val Val Lys Ile Gly Val Phe Ser Thr
            2020                2025                2030

Ser Asn Gly Phe Glu Tyr Phe Ala Pro Ala Asn Thr Tyr Asn Asn Asn
            2035                2040                2045

Ile Glu Gly Gln Ala Ile Val Tyr Gln Ser Lys Phe Leu Thr Leu Asn
            2050                2055                2060

Gly Lys Lys Tyr Tyr Phe Asp Asn Asn Ser Lys Ala Val Thr Gly Leu
2065                2070                2075                2080

Gln Thr Ile Asp Ser Lys Lys Tyr Tyr Phe Asn Thr Asn Thr Ala Glu
            2085                2090                2095

Ala Ala Thr Gly Trp Gln Thr Ile Asp Gly Lys Lys Tyr Tyr Phe Asn
            2100                2105                2110

Thr Asn Thr Ala Glu Ala Ala Thr Gly Trp Gln Thr Ile Asp Gly Lys
            2115                2120                2125

Lys Tyr Tyr Phe Asn Thr Asn Thr Ala Ile Ala Ser Thr Gly Tyr Thr
            2130                2135                2140

Ile Ile Asn Gly Lys His Phe Tyr Phe Asn Thr Asp Gly Ile Met Gln
2145                2150                2155                2160

Ile Gly Val Phe Lys Gly Pro Asn Gly Phe Glu Tyr Phe Ala Pro Ala
            2165                2170                2175

Asn Thr Asp Ala Asn Asn Ile Glu Gly Gln Ala Ile Leu Tyr Gln Asn

-continued

```
                2180                2185                2190
Glu Phe Leu Thr Leu Asn Gly Lys Lys Tyr Tyr Phe Gly Ser Asp Ser
            2195                2200                2205
Lys Ala Val Thr Gly Trp Arg Ile Ile Asn Asn Lys Lys Tyr Tyr Phe
            2210                2215                2220
Asn Pro Asn Asn Ala Ile Ala Ala Ile His Leu Cys Thr Ile Asn Asn
2225                2230                2235                2240
Asp Lys Tyr Tyr Phe Ser Tyr Asp Gly Ile Leu Gln Asn Gly Tyr Ile
            2245                2250                2255
Thr Ile Glu Arg Asn Asn Phe Tyr Phe Asp Ala Asn Asn Glu Ser Lys
            2260                2265                2270
Met Val Thr Gly Val Phe Lys Gly Pro Asn Gly Phe Glu Tyr Phe Ala
            2275                2280                2285
Pro Ala Asn Thr His Asn Asn Asn Ile Glu Gly Gln Ala Ile Val Tyr
            2290                2295                2300
Gln Asn Lys Phe Leu Thr Leu Asn Gly Lys Lys Tyr Tyr Phe Asp Asn
2305                2310                2315                2320
Asp Ser Lys Ala Val Thr Gly Trp Gln Thr Ile Asp Gly Lys Lys Tyr
            2325                2330                2335
Tyr Phe Asn Leu Asn Thr Ala Glu Ala Ala Thr Gly Trp Gln Thr Ile
            2340                2345                2350
Asp Gly Lys Lys Tyr Tyr Phe Asn Leu Asn Thr Ala Glu Ala Ala Thr
            2355                2360                2365
Gly Trp Gln Thr Ile Asp Gly Lys Lys Tyr Tyr Phe Asn Thr Asn Thr
            2370                2375                2380
Phe Ile Ala Ser Thr Gly Tyr Thr Ser Ile Asn Gly Lys His Phe Tyr
2385                2390                2395                2400
Phe Asn Thr Asp Gly Ile Met Gln Ile Gly Val Phe Lys Gly Pro Asn
            2405                2410                2415
Gly Phe Glu Tyr Phe Ala Pro Ala Asn Thr Asp Ala Asn Asn Ile Glu
            2420                2425                2430
Gly Gln Ala Ile Leu Tyr Gln Asn Lys Phe Leu Thr Leu Asn Gly Lys
            2435                2440                2445
Lys Tyr Tyr Phe Gly Ser Asp Ser Lys Ala Val Thr Gly Leu Arg Thr
            2450                2455                2460
Ile Asp Gly Lys Lys Tyr Tyr Phe Asn Thr Asn Thr Ala Val Ala Val
2465                2470                2475                2480
Thr Gly Trp Gln Thr Ile Asn Gly Lys Lys Tyr Tyr Phe Asn Thr Asn
            2485                2490                2495
Thr Ser Ile Ala Ser Thr Gly Tyr Thr Ile Ile Ser Gly Lys His Phe
            2500                2505                2510
Tyr Phe Asn Thr Asp Gly Ile Met Gln Ile Gly Val Phe Lys Gly Pro
            2515                2520                2525
Asp Gly Phe Glu Tyr Phe Ala Pro Ala Asn Thr Asp Ala Asn Asn Ile
            2530                2535                2540
Glu Gly Gln Ala Ile Arg Tyr Gln Asn Arg Phe Leu Tyr Leu His Asp
2545                2550                2555                2560
Asn Ile Tyr Tyr Phe Gly Asn Asn Ser Lys Ala Ala Thr Gly Trp Val
            2565                2570                2575
Thr Ile Asp Gly Asn Arg Tyr Tyr Phe Glu Pro Asn Thr Ala Met Gly
            2580                2585                2590
Ala Asn Gly Tyr Lys Thr Ile Asp Asn Lys Asn Phe Tyr Phe Arg Asn
            2595                2600                2605
```

```
Gly Leu Pro Gln Ile Gly Val Phe Lys Gly Ser Asn Gly Phe Glu Tyr
    2610                2615                2620

Phe Ala Pro Ala Asn Thr Asp Ala Asn Asn Ile Glu Gly Gln Ala Ile
2625                2630                2635                2640

Arg Tyr Gln Asn Arg Phe Leu His Leu Leu Gly Lys Ile Tyr Tyr Phe
                2645                2650                2655

Gly Asn Asn Ser Lys Ala Val Thr Gly Trp Gln Thr Ile Asn Gly Lys
            2660                2665                2670

Val Tyr Tyr Phe Met Pro Asp Thr Ala Met Ala Ala Ala Gly Gly Leu
        2675                2680                2685

Phe Glu Ile Asp Gly Val Ile Tyr Phe Phe Gly Val Asp Gly Val Lys
    2690                2695                2700

Ala Pro Gly Ile Tyr Gly
2705                2710
```

<210> SEQ ID NO 379
<211> LENGTH: 7101
<212> TYPE: DNA
<213> ORGANISM: Clostridium difficile

<400> SEQUENCE: 379

```
atgagtttag ttaatagaaa acagttagaa aaaatggcaa atgtaagatt tcgtactcaa      60
gaagatgaat atgttgcaat attggatgct ttagaagaat atcataatat gtcagagaat     120
actgtagtcg aaaaatattt aaaattaaaa gatataaata gtttaacaga tatttatata     180
gatacatata aaaaatctgg tagaaataaa gccttaaaaa aatttaagga atatctagtt     240
acagaagtat tagagctaaa gaataataat ttaactccag ttgagaaaaa tttacatttt     300
gtttggattg gaggtcaaat aaatgacact gctattaatt atataaatca atggaaagat     360
gtaaatagtg attataatgt taatgttttt tatgatagta atgcattttt gataaacaca     420
ttgaaaaaaa ctgtagtaga atcagcaata aatgatacac ttgaatcatt tagagaaaac     480
ttaaatgacc ctagatttga ctataataaa ttcttcagaa aacgtatgga aataatttat     540
gataaacaga aaaatttcat aaactactat aaagctcaaa gagaagaaaa tcctgaactt     600
ataattgatg atattgtaaa gacatatctt tcaaatgagt attcaaagga gatagatgaa     660
cttaatacct atattgaaga atccttaaat aaaattacac agaatagtgg aaatgatgtt     720
agaaactttg aagaatttaa aaatggagag tcattcaact tatatgaaca agagttggta     780
gaaaggtgga atttagctgc tgcttctgac atattaagaa tatctgcatt aaaagaaatt     840
ggtggtatgt atttagatgt tgatatgtta ccaggaatac aaccagactt atttgagtct     900
atagagaaac ctagttcagt aacagtggat ttttgggaaa tgacaaagtt agaagctata     960
atgaaataca aagaatatat accagaatat acctcagaac attttgacat gttagacgaa    1020
gaagttcaaa gtagttttga atctgttcta gcttctaagt cagataaatc agaaatattc    1080
tcatcacttg gtgatatgga ggcatcacca ctagaagtta aaattgcatt taatagtaag    1140
ggtattataa atcaagggct aatttctgtg aaagactcat attgtagcaa tttaatagta    1200
aaacaaatcg agaatagata taaaatattg aataatagtt taaatccagc tattagcgag    1260
gataatgatt ttaatactac aacgaatacc tttattgata gtataatggc tgaagctaat    1320
gcagataatg gtagatttat gatggaacta ggaaagtatt taagagttgg tttcttccca    1380
gatgttaaaa ctactattaa cttaagtggc cctgaagcat atgcggcagc ttatcaagat    1440
ttattaatgt ttaaagaagg cagtatgaat atccatttga tagaagctga tttaagaaac    1500
```

```
tttgaaatct ctaaaactaa tatttctcaa tcaactgaac aagaaatggc tagcttatgg   1560
tcatttgacg atgcaagagc taaagctcaa tttgaagaat ataaaaggaa ttattttgaa   1620
ggttctcttg gtgaagatga taatcttgat ttttctcaaa atatagtagt tgacaaggag   1680
tatcttttag aaaaaatatc ttcattagca agaagttcag agagaggata tatacactat   1740
attgttcagt tacaaggaga taaaattagt tatgaagcag catgtaactt atttgcaaag   1800
actccttatg atagtgtact gtttcagaaa aatatagaag attcagaaat tgcatattat   1860
tataatcctg gagatggtga aatacaagaa atagacaagt ataaaattcc aagtataatt   1920
tctgatagac ctaagattaa attaacattt attggtcatg gtaaagatga atttaatact   1980
gatatatttg caggttttga tgtagattca ttatccacag aaatagaagc agcaatagat   2040
ttagctaaag aggatatttc tcctaagtca atagaaataa atttattagg atgtaatatg   2100
tttagctact ctatcaacgt agaggagact tatcctggaa aattattact taaagttaaa   2160
gataaaatat cagaattaat gccatctata agtcaagact ctattatagt aagtgcaaat   2220
caatatgaag ttagaataaa tagtgaagga agaagagaat tattggatca ttctggtgaa   2280
tggataaata aagaagaaag tattataaag gatatttcat caaagaataa tatatcattt   2340
aatcctaaag aaaataaaat tacagtaaaa tctaaaaatt tacctgagct atctacatta   2400
ttacaagaaa ttagaaataa ttctaattca agtgatattg aactagaaga aaaagtaatg   2460
ttaacagaat gtgagataaa tgttatttca aatatagata cgcaaattgt tgaggaaagg   2520
attgaagaag ctaagaattt aacttctgac tctattaatt atataaaaga tgaatttaaa   2580
ctaatagaat ctatttctga tgcactatgt gacttaaaac aacagaatga attagaagat   2640
tctcatttta tatcttttga ggacatatca gagactgatg agggatttag tataagattt   2700
attaataaag aaactggaga atctatattt gtagaaactg aaaaaacaat attctctgaa   2760
tatgctaatc atataactga agagatttct aagataaaag gtactatatt tgatactgta   2820
aatggtaagt tagtaaaaaa agtaaattta gatactacac acgaagtaaa tactttaaat   2880
gctgcatttt ttatacaatc attaataaga tataatagtt ctaaagaatc tcttagtaat   2940
ttaagtgtag caatgaaagt ccaagtttac gctcaattat ttagtactgg tttaaatact   3000
attacagatg cagccaaagt tgttgaatta gtatcaactg cattagatga aactatagac   3060
ttacttccta cattatctga aggattacct ataattgcaa ctattataga tggtgtaagt   3120
ttaggtgcag caatcaaaga gctaagtgaa acgagtgacc cattattaag acaagaaata   3180
gaagctaaga taggtataat ggcagtaaat ttaacaacag ctacaactgc aatcattact   3240
tcatctttgg ggatagctag tggatttagt atacttttag ttcctttagc aggaatttca   3300
gcaggtatac caagcttagt aaacaatgaa cttgtacttc gagataaggc aacaaaggtt   3360
gtagattatt ttaaacatgt ttcattagtt gaaactgaag gagtatttac tttattagat   3420
gataaaataa tgatgccaca agatgattta gtgtatatcag aaatagattt taataataat   3480
tcaatagttt taggtaaatg tgaaatctgg agaatggaag gtggttcagg tcatactgta   3540
actgatgata tagatcactt cttttcagca ccatcaataa catatagaga gcccacactta   3600 tctatatatg acgtattgga agtacaaaaa gaagaacttg atttgtcaaa agatttaatg   3660
gtattaccta atgctccaaa tagagtattt gcttgggaaa caggatggac accaggttta   3720
agaagcttag aaaatgatgg cacaaaaactg ttagaccgta taagagataa ctatgaaggt   3780
gagttttatt ggagatattt tgcttttata gctgatgctt aataacaac attaaaacca   3840
```

```
agatatgaag atactaatat aagaataaat ttagatagta atactagaag tttttatagtt      3900 ccaataataa ctacagaata tataagagaa aaattatcat attctttcta tggttcagga      3960
ggaacttatg cattgtctct ttctcaatat aatatgggta taaatataga attaagtgaa      4020
agtgatgttt ggattataga tgttgataat gttgtgagag atgtaactat agaatctgat      4080
aaaattaaaa aaggtgattt aatagaaggt attttatcta cactaagtat tgaagagaat      4140
aaaattatct taaatagcca tgagattaat ttttctggtg aggtaaatgg aagtaatgga      4200
tttgtttctt taacattttc aattttagaa ggaataaatg caattataga agttgattta      4260
ttatctaaat catataaatt acttatttct ggcgaattaa aaatattgat gttaaattca      4320
aatcatattc aacagaaaat agattatata ggattcaata gcgaattaca gaaaaatata      4380
ccatatagct ttgtagatag tgaaggaaaa gagaatggtt ttattaatgg ttcaacaaaa      4440
gaaggtttat ttgtatctga attacctgat gtagttctta taagtaaggt ttatatggat      4500
gatagtaagc cttcatttgg atattatagt aataatttga aagatgtcaa agttataact      4560
aaagataatg ttaatatatt aacaggttat tatcttaagg atgatataaa aatctctctt      4620
tctttgactc tacaagatga aaaaactata agttaaaata gtgtgcattt agatgaaagt      4680
ggagtagctg agattttgaa gttcatgaat agaaaaggta atacaaatac ttcagattct      4740
ttaatgagct ttttagaaag tatgaatata aaaagtattt tcgttaattt cttacaatct      4800
aatattaagt ttatattaga tgctaatttt ataataagtg gtactacttc tattggccaa      4860
tttgagttta tttgtgatga aaatgataat atacaaccat atttcattaa gtttaataca      4920
ctagaaacta attatacttt atatgtagga aatagacaaa atatgatagt ggaaccaaat      4980
tatgatttag atgattctgg agatatatct tcaactgtta tcaatttctc tcaaaagtat      5040
ctttatggaa tagacagttg tgttaataaa gttgtaattt caccaaatat ttatacagat      5100
gaaataaata taacgcctgt atatgaaaca aataatactt atccagaagt tattgtatta      5160
gatgcaaatt atataaatga aaaaataaat gttaatatca atgatctatc tatacgatat      5220
gtatggagta atgatggtaa tgattttatt cttatgtcaa ctagtgaaga aaataaggtg      5280
tcacaagtta aaataagatt cgttaatgtt tttaaagata agactttggc aaataagcta      5340
tcttttaact ttagtgataa acaagatgta cctgtaagtg aaataatctt atcatttaca      5400
ccttcatatt atgaggatgg attgattggc tatgatttgg gtctagtttc tttatataat      5460
gagaaatttt atattaataa ctttggaatg atggtatctg gattaatata tattaatgat      5520
tcattatatt attttaaacc accagtaaat aatttgataa ctggatttgt gactgtaggc      5580
gatgataaat actactttaa tccaattaat ggtggagctg cttcaattgg agagacaata      5640
attgatgaca aaaattatta tttcaaccaa agtggagtgt tacaaacagg tgtatttagt      5700
acagaagatg gatttaaata ttttgcccca gctaatacac ttgatgaaaa cctagaagga      5760
gaagcaattg attttactgg aaaattaatt attgacgaaa atatttatta ttttgatgat      5820
aattatagag gagctgtaga atggaaagaa ttagatggtg aaatgcacta ttttagccca      5880
gaaacaggta agcttttaa aggtctaaat caaataggtg attataaata ctatttcaat      5940
tctgatggag ttatgcaaaa aggatttgtt agtataaatg ataataaaca ctattttgat      6000
gattctggtg ttatgaaagt aggttacact gaaatagatg gcaagcattt ctactttgct      6060
gaaaacggag aaatgcaaat aggagtattt aatacagaag atggatttaa atattttgct      6120
catcataatg aagatttagg aaatgaagaa ggtgaagaaa tctcatattc tggtatatta      6180
aatttcaata ataaaattta ctattttgat gattcattta cagctgtagt tggatggaaa      6240
```

```
gatttagagg atggttcaaa gtattatttt gatgaagata cagcagaagc atatataggt    6300
ttgtcattaa taaatgatgg tcaatattat tttaatgatg atggaattat gcaagttgga    6360
tttgtcacta taaatgataa agtcttctac ttctctgact ctggaattat agaatctgga    6420
gtacaaaaca tagatgacaa ttatttctat atagatgata atggtatagt tcaaattggt    6480
gtatttgata cttcagatgg atataaatat tttgcacctg ctaatactgt aaatgataat    6540
atttacggac aagcagttga atatagtggt ttagttagag ttggtgaaga tgtatattat    6600
tttggagaaa catatacaat tgagactgga tggatatatg atatggaaaa tgaaagtgat    6660
aaatattatt tcaatccaga aactaaaaaa gcatgcaaag gtattaattt aattgatgat    6720
ataaaatatt attttgatga agggcata atgagaacgg gtcttatatc atttgaaaat     6780
aataattatt actttaatga gaatggtgaa atgcaatttg gttatataaa tatagaagat    6840
aagatgttct attttggtga agatggtgtc atgcagattg gagtatttaa tacaccagat    6900
ggatttaaat actttgcaca tcaaaatact tggatgagaa attttgaggg agaatcaata    6960
aactatactg gttggttaga tttagatgaa aagagatatt attttacaga tgaatatatt    7020
gcagcaactg gttcagttat tattgatggt gaggagtatt attttgatcc tgatacagct    7080
caattagtga ttagtgaata g                                              7101
```

<210> SEQ ID NO 380
<211> LENGTH: 2366
<212> TYPE: PRT
<213> ORGANISM: Clostridium difficile

<400> SEQUENCE: 380

```
Met Ser Leu Val Asn Arg Lys Gln Leu Glu Lys Met Ala Asn Val Arg
 1               5                  10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
```

```
            210                 215                 220
Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
                    260                 265                 270

Arg Ile Ser Ala Leu Lys Glu Ile Gly Met Tyr Leu Asp Val Asp
                275                 280                 285

Met Leu Pro Gly Ile Gln Pro Asp Leu Phe Glu Ser Ile Glu Lys Pro
            290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
                340                 345                 350

Lys Ser Asp Lys Ser Glu Ile Phe Ser Ser Leu Gly Asp Met Glu Ala
                355                 360                 365

Ser Pro Leu Glu Val Lys Ile Ala Phe Asn Ser Lys Gly Ile Ile Asn
            370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
                420                 425                 430

Asp Ser Ile Met Ala Glu Ala Asn Ala Asp Asn Gly Arg Phe Met Met
            435                 440                 445

Glu Leu Gly Lys Tyr Leu Arg Val Gly Phe Phe Pro Asp Val Lys Thr
            450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Asp Ala Arg Ala Lys
            515                 520                 525

Ala Gln Phe Glu Glu Tyr Lys Arg Asn Tyr Phe Glu Gly Ser Leu Gly
            530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
                580                 585                 590

Ala Ala Cys Asn Leu Phe Ala Lys Thr Pro Tyr Asp Ser Val Leu Phe
            595                 600                 605

Gln Lys Asn Ile Glu Asp Ser Glu Ile Ala Tyr Tyr Tyr Asn Pro Gly
            610                 615                 620

Asp Gly Glu Ile Gln Glu Ile Asp Lys Tyr Lys Ile Pro Ser Ile Ile
625                 630                 635                 640
```

```
Ser Asp Arg Pro Lys Ile Lys Leu Thr Phe Ile Gly His Gly Lys Asp
            645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
            675                 680                 685

Lys Ser Ile Glu Ile Asn Leu Leu Gly Cys Asn Met Phe Ser Tyr Ser
            690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
            725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
            755                 760                 765

Ile Lys Asp Ile Ser Ser Lys Glu Tyr Ile Ser Phe Asn Pro Lys Glu
            770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
            805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
            835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
            885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
            930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
            965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
            995                 1000                1005

Glu Leu Val Ser Thr Ala Leu Asp Glu Thr Ile Asp Leu Leu Pro Thr
            1010                1015                1020

Leu Ser Glu Gly Leu Pro Ile Ile Ala Thr Ile Ile Asp Gly Val Ser
1025                1030                1035                1040

Leu Gly Ala Ala Ile Lys Glu Leu Ser Glu Thr Ser Asp Pro Leu Leu
            1045                1050                1055
```

```
Arg Gln Glu Ile Glu Ala Lys Ile Gly Ile Met Ala Val Asn Leu Thr
            1060                1065                1070

Thr Ala Thr Thr Ala Ile Ile Thr Ser Ser Leu Gly Ile Ala Ser Gly
        1075                1080                1085

Phe Ser Ile Leu Leu Val Pro Leu Ala Gly Ile Ser Ala Gly Ile Pro
        1090                1095                1100

Ser Leu Val Asn Asn Glu Leu Val Leu Arg Asp Lys Ala Thr Lys Val
1105                1110                1115                1120

Val Asp Tyr Phe Lys His Val Ser Leu Val Glu Thr Glu Gly Val Phe
                1125                1130                1135

Thr Leu Leu Asp Asp Lys Ile Met Met Pro Gln Asp Asp Leu Val Ile
            1140                1145                1150

Ser Glu Ile Asp Phe Asn Asn Asn Ser Ile Val Leu Gly Lys Cys Glu
        1155                1160                1165

Ile Trp Arg Met Glu Gly Gly Ser Gly His Thr Val Thr Asp Asp Ile
        1170                1175                1180

Asp His Phe Phe Ser Ala Pro Ser Ile Thr Tyr Arg Glu Pro His Leu
1185                1190                1195                1200

Ser Ile Tyr Asp Val Leu Glu Val Gln Lys Glu Glu Leu Asp Leu Ser
        1205                1210                1215

Lys Asp Leu Met Val Leu Pro Asn Ala Pro Asn Arg Val Phe Ala Trp
        1220                1225                1230

Glu Thr Gly Trp Thr Pro Gly Leu Arg Ser Leu Glu Asn Asp Gly Thr
        1235                1240                1245

Lys Leu Leu Asp Arg Ile Arg Asp Asn Tyr Glu Gly Glu Phe Tyr Trp
        1250                1255                1260

Arg Tyr Phe Ala Phe Ile Ala Asp Ala Leu Ile Thr Thr Leu Lys Pro
1265                1270                1275                1280

Arg Tyr Glu Asp Thr Asn Ile Arg Ile Asn Leu Asp Ser Asn Thr Arg
            1285                1290                1295

Ser Phe Ile Val Pro Ile Ile Thr Glu Tyr Ile Arg Glu Lys Leu
        1300                1305                1310

Ser Tyr Ser Phe Tyr Gly Ser Gly Gly Thr Tyr Ala Leu Ser Leu Ser
        1315                1320                1325

Gln Tyr Asn Met Gly Ile Asn Ile Glu Leu Ser Glu Ser Asp Val Trp
        1330                1335                1340

Ile Ile Asp Val Asp Asn Val Val Arg Asp Val Thr Ile Glu Ser Asp
1345                1350                1355                1360

Lys Ile Lys Lys Gly Asp Leu Ile Glu Gly Ile Leu Ser Thr Leu Ser
            1365                1370                1375

Ile Glu Glu Asn Lys Ile Ile Leu Asn Ser His Glu Ile Asn Phe Ser
        1380                1385                1390

Gly Glu Val Asn Gly Ser Asn Gly Phe Val Ser Leu Thr Phe Ser Ile
        1395                1400                1405

Leu Glu Gly Ile Asn Ala Ile Ile Glu Val Asp Leu Leu Ser Lys Ser
        1410                1415                1420

Tyr Lys Leu Leu Ile Ser Gly Glu Leu Lys Ile Leu Met Leu Asn Ser
1425                1430                1435                1440

Asn His Ile Gln Gln Lys Ile Asp Tyr Ile Gly Phe Asn Ser Glu Leu
            1445                1450                1455

Gln Lys Asn Ile Pro Tyr Ser Phe Val Asp Ser Glu Gly Lys Glu Asn
        1460                1465                1470

Gly Phe Ile Asn Gly Ser Thr Lys Glu Gly Leu Phe Val Ser Glu Leu
```

```
                  1475                1480                1485

Pro Asp Val Val Leu Ile Ser Lys Val Tyr Met Asp Asp Ser Lys Pro
    1490                1495                1500

Ser Phe Gly Tyr Tyr Ser Asn Asn Leu Lys Asp Val Lys Val Ile Thr
1505                1510                1515                1520

Lys Asp Asn Val Asn Ile Leu Thr Gly Tyr Tyr Leu Lys Asp Asp Ile
                1525                1530                1535

Lys Ile Ser Leu Ser Leu Thr Leu Gln Asp Glu Lys Thr Ile Lys Leu
            1540                1545                1550

Asn Ser Val His Leu Asp Glu Ser Gly Val Ala Glu Ile Leu Lys Phe
        1555                1560                1565

Met Asn Arg Lys Gly Asn Thr Asn Thr Ser Asp Ser Leu Met Ser Phe
    1570                1575                1580

Leu Glu Ser Met Asn Ile Lys Ser Ile Phe Val Asn Phe Leu Gln Ser
1585                1590                1595                1600

Asn Ile Lys Phe Ile Leu Asp Ala Asn Phe Ile Ile Ser Gly Thr Thr
                1605                1610                1615

Ser Ile Gly Gln Phe Glu Phe Ile Cys Asp Glu Asn Asp Asn Ile Gln
            1620                1625                1630

Pro Tyr Phe Ile Lys Phe Asn Thr Leu Glu Thr Asn Tyr Thr Leu Tyr
        1635                1640                1645

Val Gly Asn Arg Gln Asn Met Ile Val Glu Pro Asn Tyr Asp Leu Asp
    1650                1655                1660

Asp Ser Gly Asp Ile Ser Ser Thr Val Ile Asn Phe Ser Gln Lys Tyr
1665                1670                1675                1680

Leu Tyr Gly Ile Asp Ser Cys Val Asn Lys Val Val Ile Ser Pro Asn
                1685                1690                1695

Ile Tyr Thr Asp Glu Ile Asn Ile Thr Pro Val Tyr Glu Thr Asn Asn
            1700                1705                1710

Thr Tyr Pro Glu Val Ile Val Leu Asp Ala Asn Tyr Ile Asn Glu Lys
        1715                1720                1725

Ile Asn Val Asn Ile Asn Asp Leu Ser Ile Arg Tyr Val Trp Ser Asn
    1730                1735                1740

Asp Gly Asn Asp Phe Ile Leu Met Ser Thr Ser Glu Glu Asn Lys Val
1745                1750                1755                1760

Ser Gln Val Lys Ile Arg Phe Val Asn Val Phe Lys Asp Lys Thr Leu
                1765                1770                1775

Ala Asn Lys Leu Ser Phe Asn Phe Ser Asp Lys Gln Asp Val Pro Val
            1780                1785                1790

Ser Glu Ile Ile Leu Ser Phe Thr Pro Ser Tyr Tyr Glu Asp Gly Leu
        1795                1800                1805

Ile Gly Tyr Asp Leu Gly Leu Val Ser Leu Tyr Asn Glu Lys Phe Tyr
    1810                1815                1820

Ile Asn Asn Phe Gly Met Met Val Ser Gly Leu Ile Tyr Ile Asn Asp
1825                1830                1835                1840

Ser Leu Tyr Tyr Phe Lys Pro Pro Val Asn Asn Leu Ile Thr Gly Phe
                1845                1850                1855

Val Thr Val Gly Asp Asp Lys Tyr Tyr Phe Asn Pro Ile Asn Gly Gly
            1860                1865                1870

Ala Ala Ser Ile Gly Glu Thr Ile Ile Asp Asp Lys Asn Tyr Tyr Phe
        1875                1880                1885

Asn Gln Ser Gly Val Leu Gln Thr Gly Val Phe Ser Thr Glu Asp Gly
    1890                1895                1900
```

```
Phe Lys Tyr Phe Ala Pro Ala Asn Thr Leu Asp Glu Asn Leu Glu Gly
1905                1910                1915                1920

Glu Ala Ile Asp Phe Thr Gly Lys Leu Ile Ile Asp Glu Asn Ile Tyr
                1925                1930                1935

Tyr Phe Asp Asp Asn Tyr Arg Gly Ala Val Glu Trp Lys Glu Leu Asp
            1940                1945                1950

Gly Glu Met His Tyr Phe Ser Pro Glu Thr Gly Lys Ala Phe Lys Gly
            1955                1960                1965

Leu Asn Gln Ile Gly Asp Tyr Lys Tyr Tyr Phe Asn Ser Asp Gly Val
            1970                1975                1980

Met Gln Lys Gly Phe Val Ser Ile Asn Asp Asn Lys Tyr Tyr Phe Asp
1985                1990                1995                2000

Asp Ser Gly Val Met Lys Val Gly Tyr Thr Glu Ile Asp Gly Lys His
                2005                2010                2015

Phe Tyr Phe Ala Glu Asn Gly Glu Met Gln Ile Gly Val Phe Asn Thr
                2020                2025                2030

Glu Asp Gly Phe Lys Tyr Phe Ala His His Asn Glu Asp Leu Gly Asn
            2035                2040                2045

Glu Glu Gly Glu Glu Ile Ser Tyr Ser Gly Ile Leu Asn Phe Asn Asn
            2050                2055                2060

Lys Ile Tyr Tyr Phe Asp Asp Ser Phe Thr Ala Val Val Gly Trp Lys
2065                2070                2075                2080

Asp Leu Glu Asp Gly Ser Lys Tyr Tyr Phe Asp Glu Asp Thr Ala Glu
                2085                2090                2095

Ala Tyr Ile Gly Leu Ser Leu Ile Asn Asp Gly Gln Tyr Tyr Phe Asn
                2100                2105                2110

Asp Asp Gly Ile Met Gln Val Gly Phe Val Thr Ile Asn Asp Lys Val
            2115                2120                2125

Phe Tyr Phe Ser Asp Ser Gly Ile Ile Glu Ser Gly Val Gln Asn Ile
            2130                2135                2140

Asp Asp Asn Tyr Phe Tyr Ile Asp Asp Asn Gly Ile Val Gln Ile Gly
2145                2150                2155                2160

Val Phe Asp Thr Ser Asp Gly Tyr Lys Tyr Phe Ala Pro Ala Asn Thr
                2165                2170                2175

Val Asn Asp Asn Ile Tyr Gly Gln Ala Val Glu Tyr Ser Gly Leu Val
                2180                2185                2190

Arg Val Gly Glu Asp Val Tyr Tyr Phe Gly Glu Thr Tyr Thr Ile Glu
            2195                2200                2205

Thr Gly Trp Ile Tyr Asp Met Glu Asn Glu Ser Asp Lys Tyr Tyr Phe
            2210                2215                2220

Asn Pro Glu Thr Lys Lys Ala Cys Lys Gly Ile Asn Leu Ile Asp Asp
2225                2230                2235                2240

Ile Lys Tyr Tyr Phe Asp Glu Lys Gly Ile Met Arg Thr Gly Leu Ile
                2245                2250                2255

Ser Phe Glu Asn Asn Asn Tyr Tyr Phe Asn Glu Asn Gly Glu Met Gln
                2260                2265                2270

Phe Gly Tyr Ile Asn Ile Glu Asp Lys Met Phe Tyr Phe Gly Glu Asp
            2275                2280                2285

Gly Val Met Gln Ile Gly Val Phe Asn Thr Pro Asp Gly Phe Lys Tyr
            2290                2295                2300

Phe Ala His Gln Asn Thr Leu Asp Glu Asn Phe Glu Gly Glu Ser Ile
2305                2310                2315                2320
```

```
Asn Tyr Thr Gly Trp Leu Asp Leu Asp Glu Lys Arg Tyr Tyr Phe Thr
            2325                2330                2335

Asp Glu Tyr Ile Ala Ala Thr Gly Ser Val Ile Ile Asp Gly Glu Glu
        2340                2345                2350

Tyr Tyr Phe Asp Pro Asp Thr Ala Gln Leu Val Ile Ser Glu
    2355                2360                2365

<210> SEQ ID NO 381
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly
<220> FEATURE:
<221> NAME/KEY: VARIANT
<222> LOCATION: (2)...(2)
<223> OTHER INFORMATION: Xaa = Phe,  Val, or Ile
<220> FEATURE:
<221> NAME/KEY: VARIANT
<222> LOCATION: (3)...(3)
<223> OTHER INFORMATION: Xaa = Thr, Ala, or Ser
<220> FEATURE:
<221> NAME/KEY: VARIANT
<222> LOCATION: (4)...(4)
<223> OTHER INFORMATION: Xaa = Phe or Leu
<220> FEATURE:
<221> NAME/KEY: VARIANT
<222> LOCATION: (5)...(5)
<223> OTHER INFORMATION: Xaa = Ser, Arg, or Asn
<220> FEATURE:
<221> NAME/KEY: VARIANT
<222> LOCATION: (6)...(6)
<223> OTHER INFORMATION: Xaa = Gly, Thr, Asp, or Ser
<220> FEATURE:
<221> NAME/KEY: VARIANT
<222> LOCATION: (7)...(7)
<223> OTHER INFORMATION: Xaa = His, or Tyr
<220> FEATURE:
<221> NAME/KEY: VARIANT
<222> LOCATION: (8)...(8)
<223> OTHER INFORMATION: Xaa = Gly, or Glu

<400> SEQUENCE: 381

Xaa Xaa Xaa Xaa Xaa Xaa Xaa Xaa
 1               5

<210> SEQ ID NO 382
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile
<220> FEATURE:
<221> NAME/KEY: VARIANT
<222> LOCATION: (2)...(2)
<223> OTHER INFORMATION: Xaa = Leu, Ser, or Asp
<220> FEATURE:
<221> NAME/KEY: VARIANT
<222> LOCATION: (3)...(3)
<223> OTHER INFORMATION: Xaa = Tyr, Phe, or Ser
<220> FEATURE:
<221> NAME/KEY: VARIANT
<222> LOCATION: (4)...(4)
<223> OTHER INFORMATION: Xaa = Asp, or Ser
<220> FEATURE:
<221> NAME/KEY: VARIANT
```

```
<222> LOCATION: (5)...(5)
<223> OTHER INFORMATION: Xaa = Gly
<220> FEATURE:
<221> NAME/KEY: VARIANT
<222> LOCATION: (6)...(6)
<223> OTHER INFORMATION: Xaa = Ser, Gly, Asp, or Thr
<220> FEATURE:
<221> NAME/KEY: VARIANT
<222> LOCATION: (7)...(7)
<223> OTHER INFORMATION: Xaa = Ser, His, or Ile
<220> FEATURE:
<221> NAME/KEY: VARIANT
<222> LOCATION: (8)...(8)
<223> OTHER INFORMATION: Xaa = Glu, Gln, or Ile

<400> SEQUENCE: 382

Xaa Xaa Xaa Xaa Xaa Xaa Xaa Xaa
 1               5

<210> SEQ ID NO 383
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala, or Val
<220> FEATURE:
<221> NAME/KEY: VARIANT
<222> LOCATION: (2)...(2)
<223> OTHER INFORMATION: Xaa = Lys, or Arg
<220> FEATURE:
<221> NAME/KEY: VARIANT
<222> LOCATION: (3)...(3)
<223> OTHER INFORMATION: Xaa = Gly, or Glu
<220> FEATURE:
<221> NAME/KEY: VARIANT
<222> LOCATION: (4)...(4)
<223> OTHER INFORMATION: Xaa = Ser, or Arg
<220> FEATURE:
<221> NAME/KEY: VARIANT
<222> LOCATION: (5)...(5)
<223> OTHER INFORMATION: Xaa = Ile, Asp, or Tyr
<220> FEATURE:
<221> NAME/KEY: VARIANT
<222> LOCATION: (6)...(6)
<223> OTHER INFORMATION: Xaa = Leu, Ser, or Asp
<220> FEATURE:
<221> NAME/KEY: VARIANT
<222> LOCATION: (7)...(7)
<223> OTHER INFORMATION: Xaa = Asn, Ser, Gln, or His
<220> FEATURE:
<221> NAME/KEY: VARIANT
<222> LOCATION: (8)...(8)
<223> OTHER INFORMATION: Xaa = Arg, Tyr, or Ser
<220> FEATURE:
<221> NAME/KEY: VARIANT
<222> LOCATION: (9)...(9)
<223> OTHER INFORMATION: Xaa = Pro, or Gly
<220> FEATURE:
<221> NAME/KEY: VARIANT
<222> LOCATION: (10)...(10)
<223> OTHER INFORMATION: Xaa = Phe, or Tyr
<220> FEATURE:
<221> NAME/KEY: VARIANT
<222> LOCATION: (11)...(11)
<223> OTHER INFORMATION: Xaa = Asp, Gly, or Tyr
<220> FEATURE:
<221> NAME/KEY: VARIANT
<222> LOCATION: (12)...(12)
<223> OTHER INFORMATION: Xaa = Tyr
<220> FEATURE:
<221> NAME/KEY: VARIANT
<222> LOCATION: (13)...(13)
<223> OTHER INFORMATION: Xaa = Phe, Leu, or absent
```

```
<220> FEATURE:
<221> NAME/KEY: VARIANT
<222> LOCATION: (14)...(14)
<223> OTHER INFORMATION: Xaa = Gly, or absent
<220> FEATURE:
<221> NAME/KEY: VARIANT
<222> LOCATION: (15)...(15)
<223> OTHER INFORMATION: Xaa = Met, or absent
<220> FEATURE:
<221> NAME/KEY: VARIANT
<222> LOCATION: (16)...(16)
<223> OTHER INFORMATION: Xaa = Asp, or absent
<220> FEATURE:
<221> NAME/KEY: VARIANT
<222> LOCATION: (17)...(17)
<223> OTHER INFORMATION: Xaa = Val, or absent

<400> SEQUENCE: 383

Xaa Xaa Xaa Xaa Xaa Xaa Xaa Xaa Xaa Xaa Xaa Xaa Xaa Xaa Xaa Xaa
 1               5                  10                  15

Xaa

<210> SEQ ID NO 384
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Ser, or Glu
<220> FEATURE:
<221> NAME/KEY: VARIANT
<222> LOCATION: (3)...(3)
<223> OTHER INFORMATION: Xaa = Ile, Val, or Thr
<220> FEATURE:
<221> NAME/KEY: VARIANT
<222> LOCATION: (4)...(4)
<223> OTHER INFORMATION: Xaa = Leu, or Asp
<220> FEATURE:
<221> NAME/KEY: VARIANT
<222> LOCATION: (5)...(5)
<223> OTHER INFORMATION: Xaa = Phe, Lys, or Asn
<220> FEATURE:
<221> NAME/KEY: VARIANT
<222> LOCATION: (6)...(6)
<223> OTHER INFORMATION: Xaa = Ser, or Trp
<220> FEATURE:
<221> NAME/KEY: VARIANT
<222> LOCATION: (7)...(7)
<223> OTHER INFORMATION: Xaa = Ser, or absent
<220> FEATURE:
<221> NAME/KEY: VARIANT
<222> LOCATION: (8)...(8)
<223> OTHER INFORMATION: Xaa = Asn, Asp, or absent
<220> FEATURE:
<221> NAME/KEY: VARIANT
<222> LOCATION: (9)...(9)
<223> OTHER INFORMATION: Xaa = Asn, or absent
<220> FEATURE:
<221> NAME/KEY: VARIANT
<222> LOCATION: (10)...(10)
<223> OTHER INFORMATION: Xaa = Lys, or absent
<220> FEATURE:
<221> NAME/KEY: VARIANT
<222> LOCATION: (11)...(11)
<223> OTHER INFORMATION: Xaa = Ile, Asn, or absent
<220> FEATURE:
<221> NAME/KEY: VARIANT
<222> LOCATION: (12)...(12)
<223> OTHER INFORMATION: Xaa = Tyr, or absent
```

<400> SEQUENCE: 384

Xaa Xaa Xaa Xaa Xaa Xaa Xaa Xaa Xaa Xaa Xaa Xaa
 1               5                   10

<210> SEQ ID NO 385
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Trp, Lys, or Arg
<220> FEATURE:
<221> NAME/KEY: VARIANT
<222> LOCATION: (2)...(2)
<223> OTHER INFORMATION: Xaa = Ala or Thr
<220> FEATURE:
<221> NAME/KEY: VARIANT
<222> LOCATION: (3)...(3)
<223> OTHER INFORMATION: Xaa = Ser

<400> SEQUENCE: 385

Xaa Xaa Xaa
 1

<210> SEQ ID NO 386
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln or His
<220> FEATURE:
<221> NAME/KEY: VARIANT
<222> LOCATION: (2)...(2)
<223> OTHER INFORMATION: Xaa = Gln, or Glu
<220> FEATURE:
<221> NAME/KEY: VARIANT
<222> LOCATION: (3)...(3)
<223> OTHER INFORMATION: Xaa = Tyr
<220> FEATURE:
<221> NAME/KEY: VARIANT
<222> LOCATION: (4)...(4)
<223> OTHER INFORMATION: Xaa = Tyr, or Asn
<220> FEATURE:
<221> NAME/KEY: VARIANT
<222> LOCATION: (5)...(5)
<223> OTHER INFORMATION: Xaa = Thr, or Ser
<220> FEATURE:
<221> NAME/KEY: VARIANT
<222> LOCATION: (6)...(6)
<223> OTHER INFORMATION: Xaa = Leu, Ala, or Tyr
<220> FEATURE:
<221> NAME/KEY: VARIANT
<222> LOCATION: (7)...(7)
<223> OTHER INFORMATION: Xaa = Pro, Phe, or Ser
<220> FEATURE:
<221> NAME/KEY: VARIANT
<222> LOCATION: (8)...(8)
<223> OTHER INFORMATION: Xaa = Leu, Phe, or Arg
<220> FEATURE:
<221> NAME/KEY: VARIANT
<222> LOCATION: (9)...(9)
<223> OTHER INFORMATION: Xaa = Thr, or Ala

<400> SEQUENCE: 386

Xaa Xaa Xaa Xaa Xaa Xaa Xaa Xaa Xaa
 1               5

```
<210> SEQ ID NO 387
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly,  or Arg
<220> FEATURE:
<221> NAME/KEY: VARIANT
<222> LOCATION: (2)...(2)
<223> OTHER INFORMATION: Xaa = Phe
<220> FEATURE:
<221> NAME/KEY: VARIANT
<222> LOCATION: (3)...(3)
<223> OTHER INFORMATION: Xaa = Asn, or Thr
<220> FEATURE:
<221> NAME/KEY: VARIANT
<222> LOCATION: (4)...(4)
<223> OTHER INFORMATION: Xaa = Phe
<220> FEATURE:
<221> NAME/KEY: VARIANT
<222> LOCATION: (5)...(5)
<223> OTHER INFORMATION: Xaa = Gly, Ser, Asn, or Thr
<220> FEATURE:
<221> NAME/KEY: VARIANT
<222> LOCATION: (6)...(6)
<223> OTHER INFORMATION: Xaa = Thr, Ser, Asn, or Asp
<220> FEATURE:
<221> NAME/KEY: VARIANT
<222> LOCATION: (7)...(7)
<223> OTHER INFORMATION: Xaa = His, Tyr, or Phe
<220> FEATURE:
<221> NAME/KEY: VARIANT
<222> LOCATION: (8)...(8)
<223> OTHER INFORMATION: Xaa = Asp, Val, Ala, or Tyr

<400> SEQUENCE: 387

Xaa Xaa Xaa Xaa Xaa Xaa Xaa Xaa
 1               5

<210> SEQ ID NO 388
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Leu, or Ile
<220> FEATURE:
<221> NAME/KEY: VARIANT
<222> LOCATION: (2)...(2)
<223> OTHER INFORMATION: Xaa = Thr, Gly, Ser, or Trp
<220> FEATURE:
<221> NAME/KEY: VARIANT
<222> LOCATION: (3)...(3)
<223> OTHER INFORMATION: Xaa = Ser, Thr, Gly, or Phe
<220> FEATURE:
<221> NAME/KEY: VARIANT
<222> LOCATION: (4)...(4)
<223> OTHER INFORMATION: Xaa = Thr, Val, Tyr, Val, Asp, or Gly
<220> FEATURE:
<221> NAME/KEY: VARIANT
<222> LOCATION: (5)...(5)
<223> OTHER INFORMATION: Xaa = Gly
<220> FEATURE:
<221> NAME/KEY: VARIANT
<222> LOCATION: (6)...(6)
<223> OTHER INFORMATION: Xaa = Gly, Asp, Ser, or Ala
<220> FEATURE:
<221> NAME/KEY: VARIANT
```

```
<222> LOCATION: (7)...(7)
<223> OTHER INFORMATION: Xaa = Ser, Thr, Asn, or Ala
<220> FEATURE:
<221> NAME/KEY: VARIANT
<222> LOCATION: (8)...(8)
<223> OTHER INFORMATION: Xaa = Ala, Thr, Glu, Lys, or absent

<400> SEQUENCE: 388

Xaa Xaa Xaa Xaa Xaa Xaa Xaa Xaa
 1               5

<210> SEQ ID NO 389
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala
<220> FEATURE:
<221> NAME/KEY: VARIANT
<222> LOCATION: (2)...(2)
<223> OTHER INFORMATION: Xaa = Lys, or Arg
<220> FEATURE:
<221> NAME/KEY: VARIANT
<222> LOCATION: (3)...(3)
<223> OTHER INFORMATION: Xaa = Thr, Asp, or Ser
<220> FEATURE:
<221> NAME/KEY: VARIANT
<222> LOCATION: (4)...(4)
<223> OTHER INFORMATION: Xaa = Phe, Arg, His, Ala, or Leu
<220> FEATURE:
<221> NAME/KEY: VARSPLIC
<222> LOCATION: (5)...(5)
<223> OTHER INFORMATION: Xaa = Asn, Gly, or Lys
<220> FEATURE:
<221> NAME/KEY: VARIANT
<222> LOCATION: (6)...(6)
<223> OTHER INFORMATION: Xaa = Trp, Gly, Asp, or Ile
<220> FEATURE:
<221> NAME/KEY: VARIANT
<222> LOCATION: (7)...(7)
<223> OTHER INFORMATION: Xaa = Asn, Ala, or Phe
<220> FEATURE:
<221> NAME/KEY: VARIANT
<222> LOCATION: (8)...(8)
<223> OTHER INFORMATION: Xaa = Ser, Asn, Tyr, Gly, or Asp
<220> FEATURE:
<221> NAME/KEY: VARIANT
<222> LOCATION: (9)...(9)
<223> OTHER INFORMATION: Xaa = Tyr, Ile, Ala, Thr, Glu, or Leu
<220> FEATURE:
<221> NAME/KEY: VARIANT
<222> LOCATION: (10)...(10)
<223> OTHER INFORMATION: Xaa = Phe, Tyr,  Ser, Gly, or absent
<220> FEATURE:
<221> NAME/KEY: VARIANT
<222> LOCATION: (11)...(11)
<223> OTHER INFORMATION: Xaa = Asp. Ser, Gly, or absent
<220> FEATURE:
<221> NAME/KEY: VARIANT
<222> LOCATION: (12)...(12)
<223> OTHER INFORMATION: Xaa = Tyr, Phe, Ser, Pro, or absent
<220> FEATURE:
<221> NAME/KEY: VARIANT
<222> LOCATION: (13)...(13)
<223> OTHER INFORMATION: Xaa = Tyr, Leu, or absent
<220> FEATURE:
<221> NAME/KEY: VARIANT
<222> LOCATION: (14)...(14)
<223> OTHER INFORMATION: Xaa = Tyr, Phe, or absent
<220> FEATURE:
<221> NAME/KEY: VARIANT
<222> LOCATION: (15)...(15)
<223> OTHER INFORMATION: Xaa = Gly, Asn, Asp, or absent
```

```
<220> FEATURE:
<221> NAME/KEY: VARIANT
<222> LOCATION: (16)...(16)
<223> OTHER INFORMATION: Xaa = Met, Arg, Tyr, or absent
<220> FEATURE:
<221> NAME/KEY: VARIANT
<222> LOCATION: (17)...(17)
<223> OTHER INFORMATION: Xaa = Asp, or absent
<220> FEATURE:
<221> NAME/KEY: VARIANT
<222> LOCATION: (18)...(18)
<223> OTHER INFORMATION: Xaa = Tyr, Val, or absent
<220> FEATURE:
<221> NAME/KEY: VARIANT
<222> LOCATION: (19)...(19)
<223> OTHER INFORMATION: Xaa = Tyr, or absent
<220> FEATURE:
<221> NAME/KEY: VARIANT
<222> LOCATION: (20)...(20)
<223> OTHER INFORMATION: Xaa = Tyr, or absent
<220> FEATURE:
<221> NAME/KEY: VARIANT
<222> LOCATION: (21)...(21)
<223> OTHER INFORMATION: Xaa = Gly, or absent
<220> FEATURE:
<221> NAME/KEY: VARIANT
<222> LOCATION: (22)...(22)
<223> OTHER INFORMATION: Xaa = Met, or absent
<220> FEATURE:
<221> NAME/KEY: VARIANT
<222> LOCATION: (23)...(23)
<223> OTHER INFORMATION: Xaa = Asp, or absent
<220> FEATURE:
<221> NAME/KEY: VARIANT
<222> LOCATION: (24)...(24)
<223> OTHER INFORMATION: Xaa = Val, or absent

<400> SEQUENCE: 389

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa
            20

<210> SEQ ID NO 390
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Ser, Asp, or Thr
<220> FEATURE:
<221> NAME/KEY: VARIANT
<222> LOCATION: (3)...(3)
<223> OTHER INFORMATION: Xaa = Ile, or Val
<220> FEATURE:
<221> NAME/KEY: VARIANT
<222> LOCATION: (4)...(4)
<223> OTHER INFORMATION: Xaa = Ser
<220> FEATURE:
<221> NAME/KEY: VARIANT
<222> LOCATION: (5)...(5)
<223> OTHER INFORMATION: Xaa = Thr, Asn, or Ser
<220> FEATURE:
<221> NAME/KEY: VARIANT
<222> LOCATION: (6)...(6)
<223> OTHER INFORMATION: Xaa = Tyr, Trp, Phe, or Ser
<220> FEATURE:
<221> NAME/KEY: VARIANT
<222> LOCATION: (7)...(7)
```

<223> OTHER INFORMATION: Xaa = Tyr, or absent

<400> SEQUENCE: 390

Xaa Xaa Xaa Xaa Xaa Xaa Xaa
 1               5

<210> SEQ ID NO 391
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly, Ala, Lys, or Thr
<220> FEATURE:
<221> NAME/KEY: VARIANT
<222> LOCATION: (2)...(2)
<223> OTHER INFORMATION: Xaa = Ala, Thr, or Val
<220> FEATURE:
<221> NAME/KEY: VARIANT
<222> LOCATION: (3)...(3)
<223> OTHER INFORMATION: Xaa = Ser

<400> SEQUENCE: 391

Xaa Xaa Xaa
 1

<210> SEQ ID NO 392
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln or absent
<220> FEATURE:
<221> NAME/KEY: VARIANT
<222> LOCATION: (2)...(2)
<223> OTHER INFORMATION: Xaa = Gln, Lys, or absent
<220> FEATURE:
<221> NAME/KEY: VARIANT
<222> LOCATION: (3)...(3)
<223> OTHER INFORMATION: Xaa = Tyr, Asn, or absent
<220> FEATURE:
<221> NAME/KEY: VARIANT
<222> LOCATION: (4)...(4)
<223> OTHER INFORMATION: Xaa = Gly, Asn, Thr, Tyr, His, or absent
<220> FEATURE:
<221> NAME/KEY: VARIANT
<222> LOCATION: (5)...(5)
<223> OTHER INFORMATION: Xaa = Asn, Ser, or absent
<220> FEATURE:
<221> NAME/KEY: VARIANT
<222> LOCATION: (6)...(6)
<223> OTHER INFORMATION: Xaa = Ser, Ala, Tyr, Asp, Trp, or absent
<220> FEATURE:
<221> NAME/KEY: VARIANT
<222> LOCATION: (7)...(7)
<223> OTHER INFORMATION: Xaa = Leu, Pro, Ser, or absent
<220> FEATURE:
<221> NAME/KEY: VARIANT
<222> LOCATION: (8)...(8)
<223> OTHER INFORMATION: Xaa = Tyr, Phe, Arg, Pro, or absent
<220> FEATURE:
<221> NAME/KEY: VARIANT
<222> LOCATION: (9)...(9)
<223> OTHER INFORMATION: Xaa = Thr, Tyr, or absent
<220> FEATURE:
<221> NAME/KEY: VARIANT
<222> LOCATION: (10)...(10)
<223> OTHER INFORMATION: Xaa = Thr

<400> SEQUENCE: 392

Xaa Xaa Xaa Xaa Xaa Xaa Xaa Xaa Xaa Xaa
1               5                   10

<210> SEQ ID NO 393
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly
<220> FEATURE:
<221> NAME/KEY: VARIANT
<222> LOCATION: (2)...(2)
<223> OTHER INFORMATION: Xaa = Phe, Asp, or Tyr
<220> FEATURE:
<221> NAME/KEY: VARIANT
<222> LOCATION: (3)...(3)
<223> OTHER INFORMATION: Xaa = Thr, Asn, Ser, or Val
<220> FEATURE:
<221> NAME/KEY: VARIANT
<222> LOCATION: (4)...(4)
<223> OTHER INFORMATION: Xaa = Phe, or Val
<220> FEATURE:
<221> NAME/KEY: VARIANT
<222> LOCATION: (5)...(5)
<223> OTHER INFORMATION: Xaa = Ser, Arg, Lys, Glu, or Thr
<220> FEATURE:
<221> NAME/KEY: VARIANT
<222> LOCATION: (6)...(6)
<223> OTHER INFORMATION: Xaa = Ser, Ile, Asp, or Arg
<220> FEATURE:
<221> NAME/KEY: VARIANT
<222> LOCATION: (7)...(7)
<223> OTHER INFORMATION: Xaa = Phe, Tyr, or Asn
<220> FEATURE:
<221> NAME/KEY: VARIANT
<222> LOCATION: (8)...(8)
<223> OTHER INFORMATION: Xaa = Gly, Ala, Ser, or Tyr
<220> FEATURE:
<221> NAME/KEY: VARIANT
<222> LOCATION: (9)...(9)
<223> OTHER INFORMATION: Xaa = Ala, or absent
<220> FEATURE:
<221> NAME/KEY: VARIANT
<222> LOCATION: (10)...(10)
<223> OTHER INFORMATION: Xaa = Ala or absent

<400> SEQUENCE: 393

Xaa Xaa Xaa Xaa Xaa Xaa Xaa Xaa Xaa Xaa
1               5                   10

<210> SEQ ID NO 394
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile, or Thr
<220> FEATURE:
<221> NAME/KEY: VARIANT
<222> LOCATION: (2)...(2)
<223> OTHER INFORMATION: Xaa = Ser, Gly, Tyr, or Asn
<220> FEATURE:
<221> NAME/KEY: VARIANT
<222> LOCATION: (3)...(3)
<223> OTHER INFORMATION: Xaa = Thr, Gly, Tyr, Trp, Pro, or Ser
<220> FEATURE:

-continued

```
<221> NAME/KEY: VARIANT
<222> LOCATION: (4)...(4)
<223> OTHER INFORMATION: Xaa = Asp, Ser, Asn, Arg, Lys, or Asp
<220> FEATURE:
<221> NAME/KEY: VARIANT
<222> LOCATION: (5)...(5)
<223> OTHER INFORMATION: Xaa = Gly, Ser, or Thr
<220> FEATURE:
<221> NAME/KEY: VARIANT
<222> LOCATION: (6)...(6)
<223> OTHER INFORMATION: Xaa = Ser, Asp, Gly, Lys, or Asn
<220> FEATURE:
<221> NAME/KEY: VARIANT
<222> LOCATION: (7)...(7)
<223> OTHER INFORMATION: Xaa = Lys, Arg, Asn, Ser, Trp, or Gly
<220> FEATURE:
<221> NAME/KEY: VARIANT
<222> LOCATION: (8)...(8)
<223> OTHER INFORMATION: Xaa = Lys, Thr, Ile, or Tyr
<220> FEATURE:
<221> NAME/KEY: VARIANT
<222> LOCATION: (9)...(9)
<223> OTHER INFORMATION: Xaa = His, or absent

<400> SEQUENCE: 394

Xaa Xaa Xaa Xaa Xaa Xaa Xaa Xaa Xaa
 1               5

<210> SEQ ID NO 395
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: xaa = Ala, or Val
<220> FEATURE:
<221> NAME/KEY: VARIANT
<222> LOCATION: (2)...(2)
<223> OTHER INFORMATION: Xaa = Arg, Lys, Thr, or Ser
<220> FEATURE:
<221> NAME/KEY: VARIANT
<222> LOCATION: (3)...(3)
<223> OTHER INFORMATION: Xaa = Val, Gly, Asp, Arg, or Tyr
<220> FEATURE:
<221> NAME/KEY: VARIANT
<222> LOCATION: (4)...(4)
<223> OTHER INFORMATION: Xaa = Gly, Trp, Arg, Lys, or Asn
<220> FEATURE:
<221> NAME/KEY: VARIANT
<222> LOCATION: (5)...(5)
<223> OTHER INFORMATION: Xaa = Glu, Tyr, Arg, Ser, or Trp
<220> FEATURE:
<221> NAME/KEY: VARIANT
<222> LOCATION: (6)...(6)
<223> OTHER INFORMATION: Xaa = Leu, Tyr, Ser, Pro, or Asn
<220> FEATURE:
<221> NAME/KEY: VARIANT
<222> LOCATION: (7)...(7)
<223> OTHER INFORMATION: Xaa = Leu, Asp, Tyr, Ser, or Asp
<220> FEATURE:
<221> NAME/KEY: VARIANT
<222> LOCATION: (8)...(8)
<223> OTHER INFORMATION: Xaa = Asn, Ser, Phe, Lys, Arg, Asp, or Gly
<220> FEATURE:
<221> NAME/KEY: VARIANT
<222> LOCATION: (9)...(9)
<223> OTHER INFORMATION: Xaa = Tyr, Gly, Phe, Asp, Trp, or Val
<220> FEATURE:
<221> NAME/KEY: VARIANT
<222> LOCATION: (10)...(10)
<223> OTHER INFORMATION: Xaa = Ser, Tyr, Asn, Asp, or absent
<220> FEATURE:
<221> NAME/KEY: VARIANT
<222> LOCATION: (11)...(11)
```

```
<223> OTHER INFORMATION: Xaa = Tyr, Leu, Val, Gly, or absent
<220> FEATURE:
<221> NAME/KEY: VARIANT
<222> LOCATION: (12)...(12)
<223> OTHER INFORMATION: Xaa = Tyr, Leu, Phe, Val, or absent
<220> FEATURE:
<221> NAME/KEY: VARIANT
<222> LOCATION: (13)...(13)
<223> OTHER INFORMATION: Xaa = Asn, Gly, Asp, Phe, or absent
<220> FEATURE:
<221> NAME/KEY: VARIANT
<222> LOCATION: (14)...(14)
<223> OTHER INFORMATION: Xaa = Tyr, Met, Asp, or absent
<220> FEATURE:
<221> NAME/KEY: VARIANT
<222> LOCATION: (15)...(15)
<223> OTHER INFORMATION: Xaa = Asp, Tyr, or absent
<220> FEATURE:
<221> NAME/KEY: VARIANT
<222> LOCATION: (16)...(16)
<223> OTHER INFORMATION: Xaa = Val, or absent

<400> SEQUENCE: 395

Xaa Xaa Xaa Xaa Xaa Xaa Xaa Xaa Xaa Xaa Xaa Xaa Xaa Xaa Xaa Xaa
 1               5                  10                  15

<210> SEQ ID NO 396
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln, Leu, or Arg
<220> FEATURE:
<221> NAME/KEY: VARIANT
<222> LOCATION: (2)...(2)
<223> OTHER INFORMATION: Xaa = Gly, Asp, or Ser
<220> FEATURE:
<221> NAME/KEY: VARIANT
<222> LOCATION: (3)...(3)
<223> OTHER INFORMATION: Xaa = Ile, or Val
<220> FEATURE:
<221> NAME/KEY: VARIANT
<222> LOCATION: (4)...(4)
<223> OTHER INFORMATION: Xaa = Arg, Ser, Gly, or Tyr
<220> FEATURE:
<221> NAME/KEY: VARIANT
<222> LOCATION: (5)...(5)
<223> OTHER INFORMATION: Xaa = Ser, or Asn
<220> FEATURE:
<221> NAME/KEY: VARIANT
<222> LOCATION: (6)...(6)
<223> OTHER INFORMATION: Xaa = Trp, His, Asn, Phe, Ser, or Asp
<220> FEATURE:
<221> NAME/KEY: VARIANT
<222> LOCATION: (7)...(7)
<223> OTHER INFORMATION: Xaa = Tyr, or absent

<400> SEQUENCE: 396

Xaa Xaa Xaa Xaa Xaa Xaa Xaa
 1               5

<210> SEQ ID NO 397
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala, Ser, Asp, or Gly
```

```
<220> FEATURE:
<221> NAME/KEY: VARIANT
<222> LOCATION: (2)...(2)
<223> OTHER INFORMATION: Xaa = Ala, or Thr
<220> FEATURE:
<221> NAME/KEY: VARIANT
<222> LOCATION: (3)...(3)
<223> OTHER INFORMATION: Xaa = Ser

<400> SEQUENCE: 397

Xaa Xaa Xaa
 1

<210> SEQ ID NO 398
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln, His, or Leu
<220> FEATURE:
<221> NAME/KEY: VARIANT
<222> LOCATION: (2)...(2)
<223> OTHER INFORMATION: Xaa = Gln
<220> FEATURE:
<221> NAME/KEY: VARIANT
<222> LOCATION: (3)...(3)
<223> OTHER INFORMATION: Xaa = Ala, Tyr, Arg, Asp, His, or Val
<220> FEATURE:
<221> NAME/KEY: VARIANT
<222> LOCATION: (4)...(4)
<223> OTHER INFORMATION: Xaa = Tyr, Gly, Asn, Ser, Ile, or Lys
<220> FEATURE:
<221> NAME/KEY: VARIANT
<222> LOCATION: (5)...(5)
<223> OTHER INFORMATION: Xaa = Ser, Leu, Pro, Ile, Asn, Thr, or Gly
<220> FEATURE:
<221> NAME/KEY: VARIANT
<222> LOCATION: (6)...(6)
<223> OTHER INFORMATION: Xaa = Phe, Tyr, Trp, or Ser
<220> FEATURE:
<221> NAME/KEY: VARIANT
<222> LOCATION: (7)...(7)
<223> OTHER INFORMATION: Xaa = Pro
<220> FEATURE:
<221> NAME/KEY: VARIANT
<222> LOCATION: (8)...(8)
<223> OTHER INFORMATION: Xaa = Leu, Pro, Phe, Val, or Tyr
<220> FEATURE:
<221> NAME/KEY: VARIANT
<222> LOCATION: (9)...(9)
<223> OTHER INFORMATION: Xaa = Thr

<400> SEQUENCE: 398

Xaa Xaa Xaa Xaa Xaa Xaa Xaa Xaa Xaa
 1               5
```